(12) United States Patent
Michejda et al.

(10) Patent No.: US 8,912,146 B2
(45) Date of Patent: Dec. 16, 2014

(54) DERIVATIVES OF APF AND METHODS OF USE

(75) Inventors: Christopher Michejda, North Potomac, MD (US); Maria Michejda, legal representative, North Potomac, MD (US); Susan K. Keay, Ellicott City, MD (US); Zoltan Szekely, Frederick, MD (US); Piotr Kaczmarek, Cambridge, MA (US)

(73) Assignees: University of Maryland, Baltimore, Baltimore, MD (US); The Department of Health and Human Services, Washington, DC (US); The United States of America as Represented by the Department of Veterans Affairs, Washington, DC (US)

( * ) Notice: Subject to any disclaimer, the term of this patent is extended or adjusted under 35 U.S.C. 154(b) by 770 days.

(21) Appl. No.: 13/059,292

(22) PCT Filed: Aug. 18, 2009

(86) PCT No.: PCT/US2009/054207
§ 371 (c)(1),
(2), (4) Date: Nov. 3, 2011

(87) PCT Pub. No.: WO2010/022089
PCT Pub. Date: Feb. 25, 2010

(65) Prior Publication Data
US 2012/0094933 A1 Apr. 19, 2012

Related U.S. Application Data

(60) Provisional application No. 61/089,698, filed on Aug. 18, 2008, provisional application No. 61/142,407, filed on Jan. 5, 2009, provisional application No. 61/161,349, filed on Mar. 18, 2009.

(51) Int. Cl.
*A61K 38/14* (2006.01)
(52) U.S. Cl.
CPC .................................. *A61K 38/14* (2013.01)
USPC ....................................................... 514/19.2
(58) Field of Classification Search
CPC ..................................................... A61K 38/14
See application file for complete search history.

(56) References Cited

U.S. PATENT DOCUMENTS

| | | | |
|---|---|---|---|
| 5,523,290 A | 6/1996 | LeBoeuf et al. | |
| 5,811,393 A | 9/1998 | Klagsbrun et al. | 514/12 |
| 5,916,871 A | 6/1999 | Johnson | 514/8 |
| 5,962,645 A | 10/1999 | Keay et al. | 530/350 |
| 6,156,522 A | 12/2000 | Keay et al. | 435/7.1 |
| 6,232,289 B1 | 5/2001 | Keay et al. | 514/2 |
| 6,376,197 B1 | 4/2002 | Keay et al. | 435/7.1 |
| 2002/0016443 A1 | 2/2002 | Keay et al. | 530/350 |
| 2005/0096263 A1 | 5/2005 | Keay et al. | 514/8 |
| 2005/0272703 A1 | 12/2005 | Wallner et al. | 514/64 |
| 2006/0194738 A1 | 8/2006 | Fong et al. | 514/16 |
| 2009/0148505 A1* | 6/2009 | Keay et al. | 424/450 |

FOREIGN PATENT DOCUMENTS

WO    WO-2008/014484 A1    1/2008

OTHER PUBLICATIONS

Barachi Jr. et al., "Studies of the antiproliferative factor from the interstitial cystitis patients and its potential as an anticancer agent," ASP Hawaii abstract, 2009.
Barachi Jr., "Studies of the antiproliferative factor from interstitial cystitis patients and its potential as an anticancer agent," presented at American Society of Pharmacognosy 50th Anniversary, Jun. 28, 2009.
Kaczmarek et al., "A preliminary SAR study for the carbohydrate segment of the antiproliferative factor from interstitial cystitis patients," abstract from NIH & FDA Glycosciences Research Day, 2009.
Kaczmarek et al., "Antiproliferative factor: On the road to a cure for interstitial cystitis and a new class of anti-cancer drugs," poster presented at National Institute of Health, 2008.
Kaczmarek et al., "SAR study for the carbohydrate segment of the antiproliferative factor from interstitial cystitis patients," poster presented at ACT spring meeting in Mar. 2009.
Kaczmarek et al., "Synthetic analogs of the antiproliferative factor from the Bladders of the interstitial cystitis patients are potent inhibitors of the urothelial carcinoma cells in vitro," poster presented in San Diego on Jan. 31, 2007.
Kaczmarek et al., "The antiproliferative factor from interstitial cystitis patients—structure-activity relationship studies," abstract presented at NCI Spring Fest, 2009.
Kaczmarek et al., "The antiproliferative factor from interstitial cystitis patients—structure-activity relationship studies," poster presented at NCI Spring Fest on Feb. 24, 2009.
Kaczmarek et al., "Two faces of antiproliferative factor from interstitial cystitis patients structure-activity relationship studies," poster presented, 2009.
Kaczmarek, "The antiproliferative factor from interstitial cystitis patients structure-activity relationship studies," presentation presented in Apr. 2009.
Keay et al., "Inhibition of antiproliferative factor (APF) activity in bladder epithelial cells by two synthetic APF derivatives," poster presented on Apr. 16, 2009.
Keay et al., "The frizzled 8-related antiproliferative factor from IC patients inhibits bladder and kidney carcinoma cell proliferation in vitro," poster presented NCI-EOS Prague meeting in Nov. 2006.
Koch et al., "Inhibition of carcinoma and melanoma cell proliferation in vitro by a novel frizzled 8 protein-related antiproliferative factor (APF)," abstract submitted to AACR on Dec. 2, 2008.

(Continued)

*Primary Examiner* — Christina Bradley

(57) ABSTRACT

Derivatives of bladder epithelial antiproliferative factor and methods of using them are disclosed. In specific embodiments, the glycopeptide compositions are useful for the treatment and/or prevention of medical conditions, including cancer. In other embodiments, there are compositions and methods related to treatment of bladder conditions. In particular embodiments, the glycopeptide comprises D-pipecolic acid or L-pipecolic acid.

7 Claims, 136 Drawing Sheets

(56) References Cited

OTHER PUBLICATIONS

Koch et al., "Inhibition of carcinoma and melanoma cell proliferation in vitro by a novel frizzled 8 protein-related antiproliferative factor (APF)," poster presented on Apr. 8, 2009.

Shahjee et al., "CKAP4/p63 mediates antiproliferative factor (APF) inhibition of Akt/GSK3 signaling in T24 bladder carcinoma cell," abstract submitted to AACR on Dec. 1, 2008.

Kim, Jayoung, et al; "p53 Mediates Interstitial Cystitis Antiproliferative Factor (APF)-Induced Growth Inhibition of Human Urothelial Cells"; FEBS Letters, 2007, vol. 581, pp. 3795-3799.

Auger et al., "Purification and Partial Characterization of a Hepatocyte Antiproliferative, Glycopeptide," *Journal of Cellular Biochemistry*, 40:439-451, 1989.

Barchi et al., "Short and sweet: evolution of a small glycopeptide from a bladder disorder to an anticancer lead," *Molecular Interventions*, 9(1):14-17, 2009.

Beier-Holgersen, "The in vitro cytotoxicity of urine from patients with interstitial cystitis," *Journal of Urology*, 151:206-207, 1994.

Campbell et al., *Laboratory Techniques in Biochemistry and Molecular Biology*, 13:1-32, 1986.

Hsieh et al., "Biochemical characterization of Wnt-Frizzled interactions using a soluble, biologically active vertebrate Wnt protein," *Proc. Natl. Acad. Sci. USA*, 96:3546-3551, 1999.

Janeway et al., *Immunobiology*, Section 2-7, 1997.

Kaczmarek et al., "Structure-activity relationship studies for the peptide portion of the bladder epithelial cell antiproliferative factor from interstitial cystitis patients," *J Med Chem.*, 51(19):5974-5983, 2008.

Keay et al., "An antiproliferative factor from interstitial cystitis patients is a frizzled 8 protein-related sialoglycopeptide," *Proceedings of the National Academy of Sciences USA*, 101(32):11803-11808, 2004.

Keay et al., "Bladder Epithelial Cells from Patients with Interstitial Cystitis Produce an Inhibitor of Heparin-Binding Epidermal Growth Factor-Like Growth Factor Production," *The Journal of Urology*, 164:2112-2118, 2000.

Keay et al., "Changes in human bladder epithelial cell gene expression asscoiated with interstitial cystitis or antiproliferative factor treatment," *Physiol. Genomics*, 14:107-115, 2003.

Keay et al., "Current and future directions in diagnostic markers in interstitial cystitis," *Intern'l J. of Urology*, 10:S27-230, 2003.

Keay et al., "Decreased in Vitro Proliferation of Bladder Epithelial Cells from Patients with Interstitial Cystitis," *The Journal of Urology*, 61:1278-1284, 2003.

Keay et al., "Normalization of proliferation and paracellular permeability of bladder epithelial cells from interstitial cystitis patients by a synthetic inhibitor of antiproliferative factor," *FASEB*, 22:1120, 2008.

Keay et al., "Sensitivity and specificity of antiproliferative factor, heparin-binding epidermal growth factor-like growth factor, and epidermal growth factor as urine markers for interstitial cystitis," *Urology*, 57:9-14, 2001.

Office Action issued in Australian Application No. 2004264853, issued Jan. 14, 2010.

Office Action issued in Japanese Application No. 2006-517828, issued Mar. 12, 2010.

Office Action issued in U.S. Appl. No. 10/992,586, mailed Aug. 31, 2005.

Office Action issued in U.S. Appl. No. 10/992,586, mailed Apr. 11, 2006.

Office Action issued in U.S. Appl. No. 10/992,586, mailed Jan. 6, 2006.

Office Action issued in U.S. Appl. No. 10/992,586, mailed Nov. 3, 2006.

Office Action issued in U.S. Appl. No. 11/743,865, mailed Feb. 22, 2011.

Office Action issued in U.S. Appl. No. 11/743,865, mailed Jul. 9, 2010.

Office Action issued in U.S. Appl. No. 11/743,865, mailed Oct. 1, 2009.

Office Action issued in U.S. Appl. No. 11/955,755, mailed Feb. 22, 2011.

Office Action issued in U.S. Appl. No. 11/955,755, mailed Jul. 20, 2010.

Office Action issued in U.S. Appl. No. 11/955,755, mailed Mar. 25, 2010.

Parson et al., "Role of Toxic Urine in Interstitial Cystitis," *Journal of Urology*, 143:373A, 1990.

PCT International Preliminary Report on Patentability issued in International Application No. PCT/US2009/054207, mailed Mar. 3, 2011.

PCT International Search Report and Written Opinion issued in International Application No. PCT/US2010/045863, mailed Dec. 14, 2010.

PCT International Search Report and Written Opinion issued in International Application No. PCT/US2009/054207, mailed Apr. 26, 2010.

Rashid et al., "Interstitial cystitis antiproliferative factor (APF) as a cell-cycle modulator," *BMC Urology*, 4(3):1-5, 2004.

Regan et al., "Heme oxygenase-1 induction protects murine cortical astrocytes from hemoglobin toxicity," *Neurosci. Lett.*, 282(1-2):1-4, 2000.

Saitoh et al., "Molecular cloning and characterization of human Frizzled-8 gene on chromosome 10p11.2," *Int J Oncol.*, 18(5):991-6, 2001.

Supplemental European Search Report issued in European Application No. 04777402, dated Feb. 21, 2008.

Zhang et al., "Comparison of APF Activity and Epithelial Growth Factor Levels in Urine from Chinese, African-American, and White American Patients with Intestitial Cystitis," *Urology*, 61:897-901, 2003.

\* cited by examiner

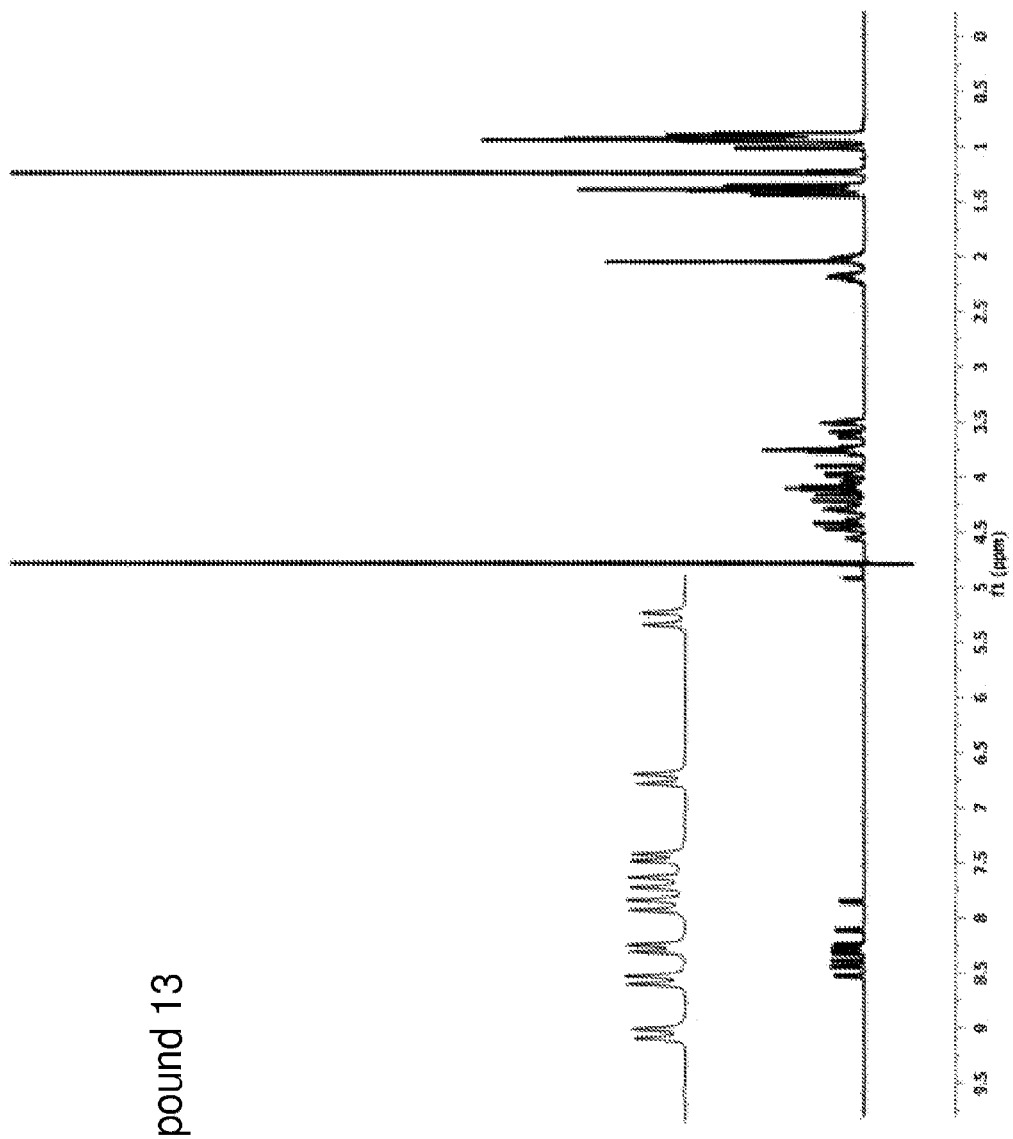

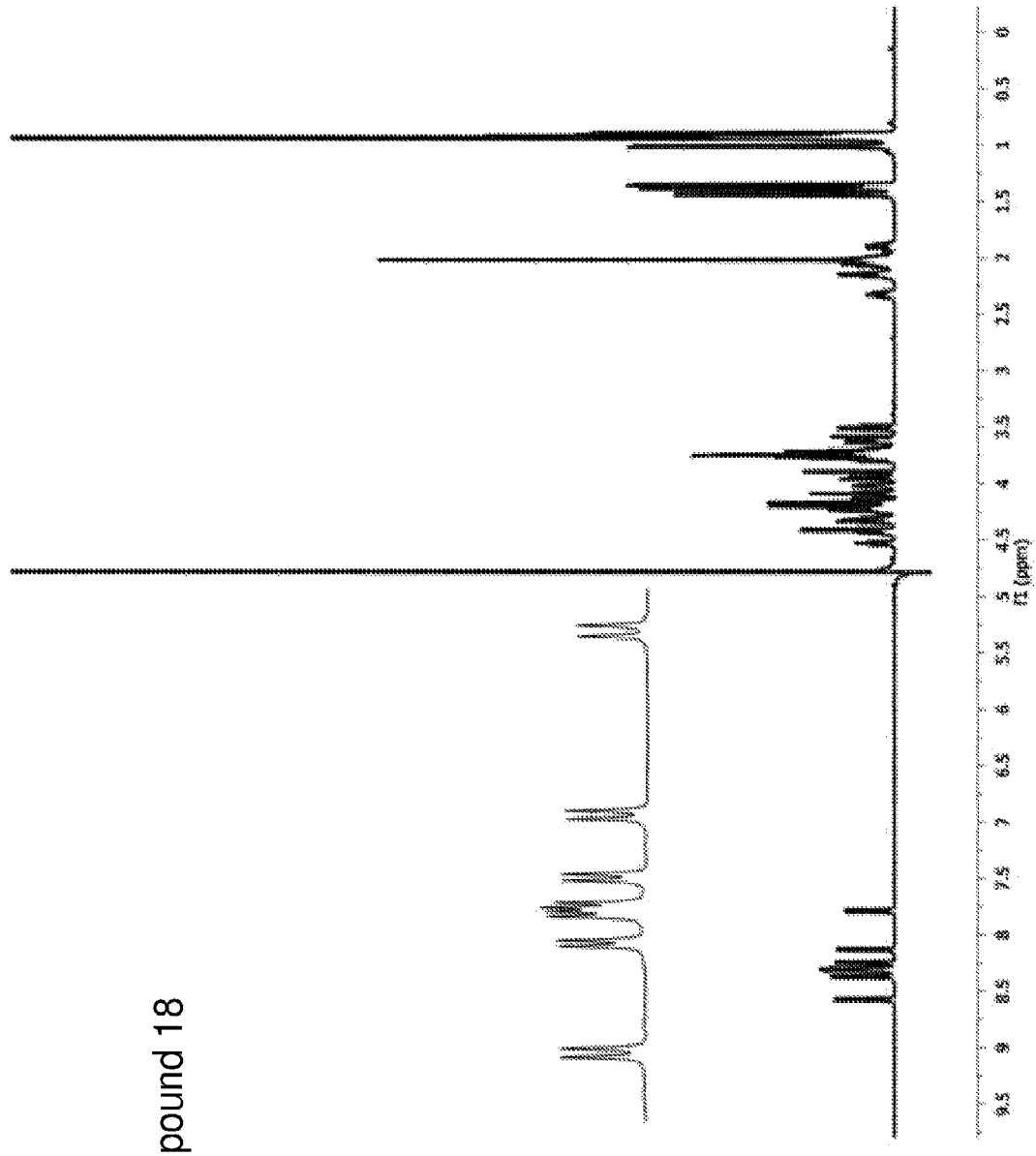

Compound 19

Compound 20

Compound 24

Compound 32

Compound 36

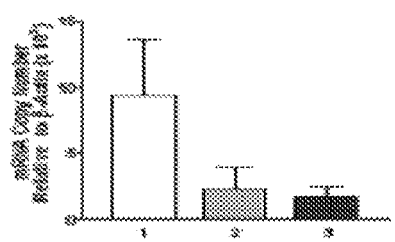
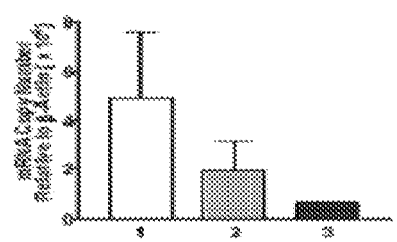
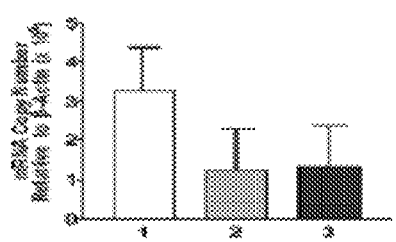
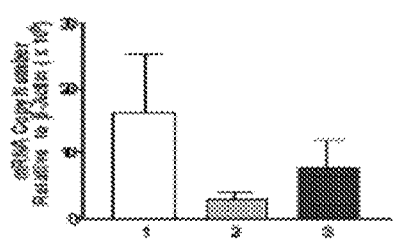
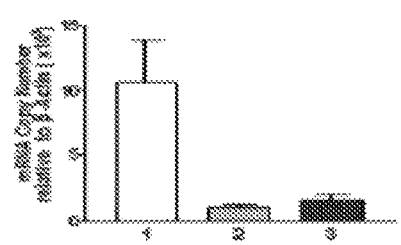
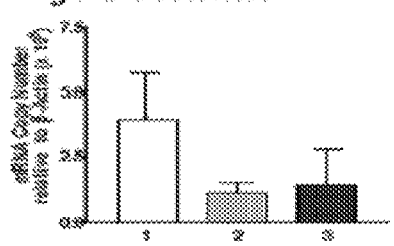
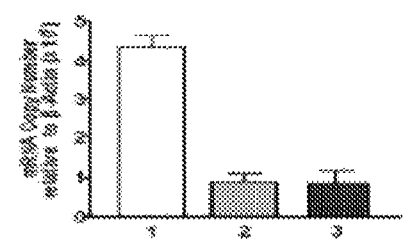
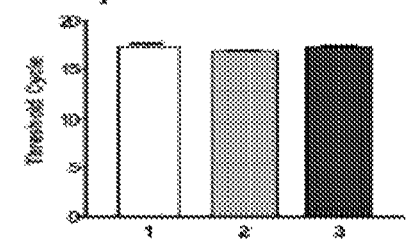
30 Day D-Proline APF Treated
FIG. 43 ial Application Ser. No. 61/142,407, filed Jan. 5, 2009; and U.S. Provisional Application Ser. No. 61/161,349, filed Mar. 18, 2009, all of which applications are incorporated by reference herein in their entirety.

SEQUENCE LISTING

```
<160> NUMBER OF SEQ ID NOS: 49

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1
```

Thr Val Pro Ala Ala Val Val Val Ala
1               5

<210> SEQ ID NO 2
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 2
accgtgcccg ccgcggtggt ggtcgcc                                          27

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Ser Val Pro Ala Ala Val Val Val Ala
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Thr Val Pro Ala Ala Val Val Leu Ala
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Ser Leu Pro Ala Ala Val Val Val Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Thr Leu Pro Ala Ala Val Val Val Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 7

Ala Ala Val Val Val Ala

```
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Thr Val Pro Ala Ala Gly Gly Gly Ala
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 9

Thr Val Pro Ala Ala Val Val Val Ala Lys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Ala Val Val Val Ala
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 11

Ala Xaa Xaa Xaa Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 12

Gly Xaa Xaa Xaa Gly
1               5

<210> SEQ ID NO 13
<211> LENGTH: 5
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 13

Ser Xaa Xaa Xaa Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is D-pipecolic acid

<400> SEQUENCE: 14

Thr Val Xaa Ala Ala Val Val Val Ala
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is L-pipecolic acid

<400> SEQUENCE: 15

Thr Val Xaa Ala Ala Val Val Val Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is D-pipecolic acid or L-pipecolic acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 16

Thr Val Xaa Ala Ala Xaa Xaa Xaa Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Ala Val Val Val Ala Ala Pro Val Thr
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 18

Thr Val Pro Ala Ala Ala Ala Ala
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 19

Thr Val Pro Ala Ala Val Val Val
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 20

Thr Val Pro Ala Ala Val Val
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 21

Thr Val Pro Ala Ala Arg Arg Arg
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is Psi-Me,Me proline

<400> SEQUENCE: 22

Thr Leu Ser Xaa Ala Ala Val Val Val Ala
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: misc_feature
<222> LOCATION: (3)..(3)
<223> OTHER INFORMATION: Xaa is trans-4-hydroxyproline

<400> SEQUENCE: 23

Thr Val Xaa Ala Ala Val Val Val Ala
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is azetidine 2-carboxylic acid

<400> SEQUENCE: 24

Thr Val Xaa Ala Ala Val Val Val Ala
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (10)..(10)
<223> OTHER INFORMATION: Xaa is acetylated lysine

<400> SEQUENCE: 25

Thr Val Pro Ala Ala Val Val Val Ala Xaa
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (10)..(10)
<223> OTHER INFORMATION: Xaa is lysine with N(epsilon) - attached dansyl
      group

<400> SEQUENCE: 26

Thr Val Pro Ala Ala Val Val Val Ala Xaa
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is D-proline

<400> SEQUENCE: 27

Thr Val Xaa Ala Ala Val Val Val Ala
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is acetylated threonine

<400> SEQUENCE: 28

Xaa Val Pro Ala Ala Val Val Val Ala
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 29

Tyr Thr Val Pro Ala Ala Val Val Val Ala
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Thr Tyr Pro Ala Ala Val Val Val Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is L-pipecolic acid

<400> SEQUENCE: 31

Ser Val Xaa Ala Ala Val Val Val Ala
1               5

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is Psi-Me,Me proline

<400> SEQUENCE: 32

Thr Val Ser Xaa Ala Ala Val Val Val Ala
1               5                   10

<210> SEQ ID NO 33
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 33

Thr Val Ala Ala Ala Val Val Val Ala
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is O-t-butyryl-trans-4-hydroxyproline

<400> SEQUENCE: 34

Thr Val Xaa Ala Ala Val Val Val Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is N-methylalanine

<400> SEQUENCE: 35

Thr Val Xaa Ala Ala Val Val Val Ala
1               5

<210> SEQ ID NO 36
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is 12-aminododecanoic acid

<400> SEQUENCE: 36

Thr Val Pro Xaa
1

<210> SEQ ID NO 37
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 37

Thr Val Pro Ala Ala
1               5

<210> SEQ ID NO 38
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 38

Thr Val Pro Ala Ala Val Val Ala Val
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 39

Thr Val Pro Ala Ala Val Val Val Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 40

Thr Val Pro Ala Val Val Val Val Ala
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 41

Thr Val Pro Ala Ser Val Val Val Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 42

Thr Val Pro Ala Gly Val Val Val Gly
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (7)..(7)
<223> OTHER INFORMATION: Xaa is D-valine

<400> SEQUENCE: 43

Thr Val Pro Ala Ala Val Xaa Val Ala
1               5

<210> SEQ ID NO 44
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 44

Thr Val Pro Ala Ala Ile Val Ile Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (9)..(9)
<223> OTHER INFORMATION: Xaa is carboxyamidylated alanine

<400> SEQUENCE: 45

Thr Val Pro Ala Ala Val Val Val Xaa
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 46

Thr Val Pro Ala Ala Val Val Val Ala Cys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 47

Thr Val Pro Ala Ala Val Val Val Ala Glu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 48

Thr Val Pro Ala Ala Val Val Val Ala Lys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (10)..(10)
<223> OTHER INFORMATION: Xaa is t-butyl protected glutamate
```

```
<400> SEQUENCE: 49

Thr Val Pro Ala Ala Val Val Val Ala Xaa
1               5                   10
```

DERIVATIVES OF APF AND METHODS OF USE

STATEMENT REGARDING FEDERALLY SPONSORED RESEARCH OR DEVELOPMENT

This invention was made with government support under Grant Number DK52596 awarded by the National Institutes of Health and VA Merit Review Funding awarded by the U.S. Department of Veterans Affairs. The United States Government has certain rights in the invention.

The present invention is a national phase application filed under 35 USC §371 from PCT/US2009/054207, filed Aug. 18, 2009, which claims priority to U.S. Provisional Application Ser. No. 61/089,698, filed Aug. 18, 2008; U.S. Provisional Application Ser. No. 61/142,407, filed Jan. 5, 2009; and U.S. Provisional Application Ser. No. 61/161,349, filed Mar. 18, 2009, all of which applications are incorporated by reference herein in their entirety.

FIELD OF THE INVENTION

The present invention is directed at least to the fields of biochemistry, cell biology, chemistry, molecular biology, and medicine, including cancer therapy and/or prevention and/or bladder disorder therapy and/or prevention. More specifically, in some cases the present invention addresses compounds having growth inhibitory activity. The present invention relates to the treatment of any disease involving uncontrolled cell proliferation, such as cancer and other maladies. In other cases, the present invention relates to inhibition of antiproliferative factors.

BACKGROUND OF THE INVENTION

The present invention concerns embodiments related to bladder disorder treatment and/or prevention and other embodiments related to cancer treatment and/or prevention.

Bladder Disorders

Approximately one million people in the United States suffer from the bladder disorder interstitial cystitis, which is a chronic painful urinary bladder condition characterized by thinning or ulceration of the bladder epithelial lining (Curhan et al., 1999).

Cystoscopic abnormalities seen in the bladder of patients with this disorder include petechial hemorrhages called "glomerulations" and ulcers that extend into the lamina propria (Hunner's ulcers) (Johansson and Fall, 1990; Skoluda et al., 1974). The most consistent histologic abnormalities include denudation or thinning of the bladder epithelium to 1-2 cell layers (Johansson and Fall, 1990; Skoluda et al., 1974; Tomaszewski et al., 2001). These findings suggest that interstitial cystitis may be caused by an inhibition of normal bladder epithelial cell proliferation, resulting in a loss of epithelial barrier integrity with subsequent exposure of sensory nerve cells in the bladder wall to urinary.

The isolation of an antiproliferative factor ("APF") peptide that is made uniquely by bladder epithelial cells from interstitial cystitis patients (Keay et al., 2001; Keay et al., 2000) and profoundly inhibits normal bladder epithelial cell growth (Keay et al., 2003) was previously described. U.S. Pat. No. 5,962,645, incorporated by reference herein in its entirety, teaches a purified human antiproliferative factor (APF) isolated from the urine of patients with interstitial cystitis wherein the APF is characterized by a molecular weight of about 1.7 kDa determined by mass spectrometry on a sample in an aqueous acetonitrile solution and a pI range of about 1.38-3.5, and the APF is capable of inhibiting normal human bladder epithelial (HBE) and bladder carcinoma cell proliferation. Picomolar quantities of HPLC-purified APF were able to induce several changes in normal bladder epithelial cells in vitro, including significantly decreased rates of proliferation (Keay et al., 2003) and decreased production of a growth factor required for log-phase growth of bladder epithelial cells (heparin-binding epidermal growth factor-like growth factor, or HB-EGF) (Keay et al., 2000; Keay et al., 2003).

Cancer

Cancer continues to be a significant health problem worldwide, and therapies for cancer are in demand. A therapeutic and/or preventative regimen for cancer could include a natural antiproliferative factor, or synthetic analog thereof. The naturally-occuring antiproliferative factor is present in individuals with interstitial cystitis (IC), a devastating disease of the urinary bladder that is characterized by thinning or even focal obliteration of the bladder epithelium. In fact, urine from IC patients has been shown to contain an antiproliferative factor (APF) that decreases $^3$H-thymidine incorporation by human bladder epithelial cells (Keay et al., 1996). A variety of techniques including total synthesis were previously used to identify APF as a nonapeptide (TVPAAVVVA; SEQ ID NO:1) containing a 2,3-sialylated core 1 α-O-linked disaccharide (Galβ1-3GalNAc, the Thomsen-Friedenreich antigen, or "TF$_{ag}$") linked to the N-terminal threonine residue (i.e., Neu5Acα2-3Galβ1-3GalNAcα-O-TVPAAVVVA (SEQ ID NO:1), FIG. 2) (Keay et al., 2004). The peptide sequence of APF is identical to a segment of the 6th transmembrane domain of the frizzled-8 protein, a Wnt ligand receptor (Keay et al., 2004; Saitoh et al., 2001).

Early studies indicated that purified native APF increased E-cadherin expression and decreased proliferation of bladder epithelial cells in vitro (Keay et al., 2003), and both native and synthetic APF were shown to inhibit the proliferation of normal bladder epithelial as well as cells derived from urothelial carcinomas at picomolar to low nanomolar concentrations (Keay et al., 2004; Keay et al., 2006). Therefore, APF, and other derivatives, including more efficacious synthetic derivatives, represent an innovative group of anti-tumor agents with a novel mode of action.

Other and further objects, features, and advantages will be apparent from the following description of the presently preferred embodiments of the invention, which are given for the purpose of disclosure.

SUMMARY OF THE INVENTION

In general, the present invention provides derivatives of endogenous antiproliferative factor (APF) and methods of use therefore. In certain embodiments, the derivatives have anti-proliferation activity, whereas in other embodiments the derivatives lack anti-proliferation activity. For APF derivatives that have anti-proliferation activity, embodiments of the present invention encompass one or more methods and/or compositions that concern therapy and/or prevention of a proliferation disorder, such as cancer or restenosis, for example. For APF derivatives that lack anti-proliferation activity, in certain cases these may be APF antagonists, and embodiments of the present invention encompass one or more methods and/or compositions that concern therapy and/or prevention of one or more epithelial disorders, including bladder disorders.

In certain cases, the present invention is directed to one or more methods and/or compositions that concern cancer therapy and/or prevention. The invention also concerns use of these compounds for the treatment and/or prevention of a proliferation disorder, such as cancer, restenosis, or nonmalignant abnormally increased cell proliferation (e.g., hypertrophic scars, polycystic kidney disease, polycystic liver disease, and/or pulmonary fibrosis).

In certain cases, the present invention is directed to methods of treating cancer comprising administering an effective amount of derivatives of APF to an individual in need of such treatment. Any kind of cancer may be treated, such as kidney, bladder, lung, breast, prostate, brain, stomach, colon, spleen, liver, pancreatic, melanoma, head and neck, thyroid, uterine, cervical, ovarian, gall bladder, and so forth. In specific embodiments, though, the invention is useful for treating cancers of epithelial origin, such as bladder or prostate cancer, comprising co-administering an effective amount of derivatives of APF to a patient in need of such treatment. In additional aspects of the invention, the derivative of APF improves, facilitates, or assists in overcoming resistance or improving sensitivity to a cancer therapy selected from the group of chemotherapy, radiotherapy, surgery gene therapy, and/or immunotherapy.

In an additional embodiment, there is a method of treating a hyperplasia, comprising the step of administering a therapeutically effective amount of a derivative of APF. In a specific embodiment, the method further comprises an additional therapy for the hyperplasia, such as an epithelial hyperplasia or a fibroblast hyperplasia.

In particular embodiments, the present invention is directed to methods of treating epithelial hyperplasia or malignancies of epithelial origin comprising administering an effective amount of a derivative of APF to an individual in need of such treatment.

In certain aspects, the present invention is directed to methods of treating fibroblast hyperplasia or malignancy comprising administering an effective amount of a derivative of APF to an individual in need of such treatment.

The present invention is directed to methods of treating lymphoreticular malignancies or solid tumors comprising administering an effective amount of a derivative of APF to an individual in need of such treatment, in particular cases.

In some embodiments, certain compounds of the present invention also have antiangiogenic properties and are contemplated for use in methods of treatments benefiting from inhibiting or slowing the formation and/or differentiation of blood vessels, such as blood vessels that feed a tumor. In an additional embodiment, there is a method of inhibiting angiogenesis in an individual, comprising administering to the individual a therapeutically effective amount of an APF derivative composition.

In an additional embodiment of the present invention, there is a method of treating cancer, comprising the step of administering a therapeutically effective amount of an APF derivative composition. In specific embodiments, the cancer comprises an epithelial cancer, such as bladder cancer, kidney cancer, lung cancer, pancreatic cancer, breast cancer, ovarian cancer, melanoma, colon cancer, or prostate cancer. In an additional specific embodiment, the method further comprises an additional cancer therapy, such as surgery, chemotherapy, radiation, gene therapy, immunotherapy, or a combination thereof.

In another embodiment, there is a method of enhancing cancer treatment of an individual, comprising administering to the individual a therapeutically effective amount of an APF derivative composition. Administration of the composition may enhance chemotherapy, radiotherapy, immunotherapy, gene therapy, or a combination thereof. The composition may be administered prior to the cancer treatment being enhanced, concomitant with the cancer treatment being enhanced, subsequent to the cancer treatment being enhanced, or a combination thereof.

In another embodiment of the present invention, there is a method of treating a bladder disorder, comprising the step of administering a therapeutically effective amount of an APF derivative composition. In a specific embodiment, the method further comprises an additional bladder disorder therapy. In a specific embodiment, the bladder disorder comprises bladder cancer. In an additional specific embodiment, the method further comprises an additional cancer therapy, such as surgery, chemotherapy, radiation, gene therapy, immunotherapy, or a combination thereof.

In particular embodiments of the invention, there is a method of treating a bladder disorder in an individual, comprising the step of administering to the individual a therapeutically effective amount of an isolated or synthesized composition comprising a derivative of urinary bladder antiproliferative factor having one to six sugar moieties, wherein at least one sugar moiety is linked to a peptide moiety of about two to about fifteen amino acid residues, wherein the peptide moiety comprises D-proline or D-pipecolic acid. In specific embodiments, the bladder disorder is interstitial cystitis, chronic pelvic pain syndrome, irritable bladder syndrome, urethral syndrome, painful bladder syndrome, or chronic nonbacterial prostatitis. In specific cases, the individual has one or more symptoms selected from the group consisting of abdominal pain, urethral pain, vaginal pain, pain with sexual intercourse, urgency, bladder pressure, bladder spasms, increased day frequency of urination, and increased night frequency of urination. In certain cases, the method further comprises an additional bladder disorder treatment, such as an additional interstitial cystitis treatment.

The present invention encompasses isolated derivatives of endogenous APF, synthetic derivatives of APF, or mixtures thereof, including, in some cases, mixtures with the endogenous APF.

In an embodiment of the present invention, there is an isolated or synthesized composition comprising a derivative of APF having one or more sugar moieties, wherein at least one sugar moiety is linked to a hydrophobic moiety. The APF derivative composition comprises a sialoglycopeptide, in specific embodiments, although in alternative embodiments it comprises a glycopeptide or a peptide.

The APF derivative composition may be further defined as comprising a sugar moiety and a peptide. Particular peptide moieties include any suitable structure, although in specific embodiments they may be linear, cyclical, branched, or a combination thereof, for example. In further specific embodiments, the peptide moiety comprises homology to at least part of a frizzled polypeptide, such as having homology to at least part of a transmembrane domain of frizzled 8. In other specific embodiments, the peptide component of APF derivative comprises total or substantially total homology to at least part of the putative sixth transmembrane domain of frizzled 8, a G-protein coupled receptor whose natural ligand is Wnt, an important regulator of cell proliferation. An example of a secreted frizzled related protein is described in U.S. Pat. No. 6,600,018, which is incorporated by reference herein in its entirety.

In one embodiment of the present invention, there is an isolated or synthesized composition comprising a derivative of APF having one to six sugar moieties, wherein at least one sugar moiety is linked to a peptide moiety of about two to fifteen amino acid residues, wherein the peptide moiety comprises D-proline, D-pipecolic acid, or L-pipecolic acid. In a specific embodiment, a peptide of the present invention comprises one or more of an amino acid selected from the group consisting of threonine, valine, alanine, serine, and leucine. In a particular aspect of the invention, one of the residues of the peptide is a linking amino acid, and in another aspect the linking amino acid comprises a heteroatom covalently linked to one of the sugar moieties. In certain embodiments, the linking amino acid is a serine, threonine, or cysteine. In specific cases, the composition is further defined as comprising two sugar residues and nine amino acids, wherein the linking amino acid is a serine, a threonine or a cysteine. In particular aspects, the amino acid that is third from the N-terminus of the peptide is proline, D-proline, D-pipecolic acid, or L-pipecolic acid.

In certain embodiments, the peptide comprises an amino acid mimetic. For example, the peptide may comprise a mimetic of threonine, valine, proline, alanine, serine, or leucine. In certain embodiments, the proline mimetics of the present invention comprise a heterocyclic group, wherein the "heterocyclic group" includes an unsubstituted or substituted stable 3- to 7-membered monocyclic or 7- to 10-membered bicyclic heterocyclic ring and that consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom that affords a stable structure. The hetercyclic group may be saturated or unsaturated.

Non-limiting specific examples of heterocyclic groups include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, and tetrahydroisoquinolinyl.

Moreoever, proline mimetics of the present invention include but are not limited to, D-proline, D-pipecolic acid, L-pipecolic acid, hydroxyproline, O-t-butyryl-trans-4-hydroxyproline, pipecolic acid, nipecotic acid, isonipecotic acid, and other chemical derivatives of piperidine wherein piperdine comprises at least one polar substituent (such as a carboxylic acid, ketone, amine, amide, sulfonic, sulfuric, nitric oxide) those illustrated in FIGS. 11 and 12, and 7-azaindoline. In particular aspects, the amino acid that is third from the N-terminus of the peptide is D-pipecolic acid, L-pipecolic acid, or D-proline. Pipecolic acid is also known in the art as piperidine-2-carboxylic acid or homoproline.

In particular embodiments of the invention, the peptide moiety comprises one or more amino acid mimetics that confer a resistance to proteolytic cleavage to the peptide moiety. In some embodiments, the amino acid mimetic comprises a non-natural stereochemistry (such as a dextrarotary (D) amino acid at one or more of the amino acids in the peptide moiety), and/or amino acid analogues including, but not limited to, L-pipecolic acid, D-pipecolic acid, hydroxyproline, tert-butylhydroxyproline, alanine, N-alkyl amino acid wherein the alkyl is methyl, ethyl, propyl, isopropyl, butyl, or tert-butyl, or the proline mimetics disclosed herein. In certain aspects, any of the amino acids, amino acid mimetics, synthetic amino acids, non-natural amino acids, amino acid analogues, amino acid derivatives, and so forth may be in the D or levorotary (L) configuration. In particular embodiments of the invention, the peptide moiety comprises one or more agents, such as amino acid derivatives, that allow the peptide or a fragment thereof to be protease-resistant. In some embodiments, the peptide comprises L-pipecolic acid or D-pipecolic acid, whereas in other embodiments the peptide comprises hydroxyproline, O-t-butyryl-trans-4-hydroxyproline, alanine, or N-methyl alanine, D-proline, for example. In certain aspects of the invention, APF derivatives having one or more altered amino acids (compared to the conventional 20 amino acids) have at least some resistance to one or more proteases, including, for example, compounds 2, 3, 5, 6, 11, 12, 13, 14, 15, 18, 21, 23, 25, 26, 29, 30, 31, 34, and 35 described herein.

In specific embodiments, the peptide moiety of the APF derivatives of the present invention comprises SEQ ID NO:14 (TVXAAVVVA, wherein X is D-pipecolic acid); SEQ ID NO:15 (TVXAAVVVA, wherein X is L-pipecolic acid); or SEQ ID NO:16 (TVX$_1$AAX$_2$X$_3$X$_4$A, wherein X$_1$ is D-pipecolic acid or L-pipecolic acid or D-proline and X$_2$, X$_3$, and X$_4$ comprise any natural or synthetic amino acid). In some embodiments, the peptide moiety of the APF derivatives of the present invention comprises TVXAAVVVA, wherein X is D-proline (SEQ ID NO:27). In specific embodiments, the peptide moiety of the APF derivative comprises SVXAAVVVA, wherein X is L-pipecolic acid or D-pipecolic acid (SEQ ID NO:31).

In specific embodiments of the present invention, the peptide moiety of APF derivative is modified from TVPAAVVVA (SEQ ID NO:1), wherein one or more of the following characteristics are comprised therein: 1) threonine is replaced with serine; 2) the proline is replaced with a proline mimetic such as, for example, L-pipecolic acid, D-proline, D-pipecolic acid, hydroxyproline, O-t-butyryl-trans-4-hydroxyproline, nipecotic acid, isonipecotic acid, 7-azaindoline, one of the mimetics of FIG. 11 or 12, and a piperidine derivative that comprises at least one carboxylic acid, ketone, amine, amide, sulfonic, sulfuric, or nitric oxide; 3) the peptide moiety is eight or nine amino acids in length, and in specific embodiments wherein the peptide is eight amino acids, it is the C-terminal amino acid that is lacking compared to SEQ ID NO:1; 4) the peptide moiety is eight or nine amino acids in length wherein one or more of the valines are replaced with alanine; and/or 5) at least the three C-terminal amino acids are hydrophobic.

In specific embodiments, the APF derivatives comprise a peptide portion that has one or more of the following characteristics: 1) at least eight (8) N-terminal natural or unnatural amino acids; 2) a trans conformation for the Pro-Ala peptide bond; 3) alanine or glycine in position 5; 4) valine, leucine and/or isoleucine independently in positions 6, 7, and/or 8; 5) proline or proline mimetic in position 3. With respect to the proline mimetic at position 3 of the peptide moiety, any compound that structurally affords a rigidity to the peptide moiety substantially similar to proline at position 3 is contemplated.

The peptide moiety of the composition is further defined as comprising a naturally occurring amino acid, an unnatural amino acid, a derivative of a naturally occurring amino acid, a derivative of an unnatural amino acid, a modified amino acid, a backbone-modifying amino acid, or a mixture thereof. The peptide moiety is further defined as comprising one or more backbone-modifying amino acids that comprise reduced peptide bonds. Modified amino acids may be further defined as a methylated amino acid, an acetylated amino acid, a beta amino acid, or an amino acid mimetic. In some embodiments of the invention, one or more or all of the amino acids are D (dextrorotary) form. Further and in other specific embodiments, the amino acids are in reverse order from the naturally occurring peptide. For example, the peptide may comprise AVVVAAPVT (SEQ ID NO:17), wherein each of the amino acids are L-, or D- or a combination thereof. In further specific embodiments, the peptide comprises an amino acid wherein an L-threonine, L-serine, L-cysteine, L-glutamate, L-aspartate, L-arginine, L-lysine, L-histidine, L-phenylalanine, or L-tryptophan (or other heteroatom-containing structure) links to the sugar moiety. In specific embodiments, an L-sugar is linked to the D-threonine in SEQ ID NO:17.

In particular embodiments, the composition is further defined as comprising about one to about six sugar moieties; and a peptide moiety of about two to about fifteen amino acid residues, wherein one of the residues is a linking amino acid, and wherein the peptide is linked to at least one of the sugar moieties at a heteroatom of the linking amino acid, which may be polar, such as a serine, a threonine, a cysteine, a lysine, an arginine, or a tyrosine. Thus, it is contemplated that the heteroatom linked to the sugar moiety is an oxygen, nitrogen and/or a sulfur atom. In further specific embodiments, the composition comprises three sugar residues and nine amino acids, wherein the linking amino acid is a serine or a threonine. In yet other specific embodiments, the composition comprises two sugar residues and nine amino acids (or 2, 3, 4, 5, 6, 7, 8, 10, 11, 12, 13, 14, or 15 amino acids).

In particular aspects of the invention, the peptide moiety of APF facilitates association with a membrane, such as being inserted, linked, bound, intercalated, or otherwise associated thereto, or, alternatively, by binding to a membrane surface receptor, and the sugar moiety of native APF comprises a high level of the functional activity of the molecule. In one particular embodiment of the invention, CKAP4 is a receptor for APF derivatives.

Certain compounds of the present invention comprise a peptide moiety, which may be characterized by having a terminal subunit having a polar chemical characteristic and/or a heteroatom therein. The subunits of the peptide may include naturally-occurring amino acid residues, unnatural amino acids, derivatives of amino acids, such as methylated amino acids, peptidomimetic components and/or any combination thereof.

In certain embodiments, the peptide moiety may comprise less than about 50%, about 50% homology to at least part of frizzled 8, about 55% homology, about 60% homology, about 65% homology, about 70% homology, about 75% homology, about 80% homology, about 85% homology, about 90% homology, about 95% homology, or 100% homology. A skilled artisan is aware, however, that in those embodiments involving, for example, peptide mimetics sequence homology is not used to determine functionality, but rather chemical characteristics of hydrophobicity and physical and chemical similarities (i.e. polarity, steric bulk, hydrogen boding capabilities).

In one specific aspect of the invention, the APF molecules of the present invention are acidic, heat stable sialoglycopeptides comprising 9 amino acid residues (such as, for example, TVPAAVVVA, SEQ ID NO:1; SVPAAVVVA, SEQ ID NO:3; TVPAAVVLA, SEQ ID NO:4; SLPAAVVVA, SEQ ID NO:5; TVXAAVVVA SEQ ID NO:14, wherein X is D-pipecolic acid; TVXAAVVVA, SEQ ID NO:15, wherein X is L-pipecolic acid; or TVX$_1$AAX$_2$X$_3$X$_4$A, SEQ ID NO:16, wherein X$_1$ is D-pipecolic acid or L-pipecolic acid or D-proline and X$_2$, X$_3$, and X$_4$ comprise any amino acid; or TVX-AAVVVA, wherein X is D-proline (SEQ ID NO:27), covalently linked through the N-terminal threonine, serine, or cysteine, for example, to an N-acetylgalactosamine or N-acetylglucosamine residue that is linked via an α or β configuration to galactose, and sialylated on the galactose moiety via 2,3 linkage. The anomeric configuration of the glycosyl bond is alpha in particular embodiments, although it may be beta in alternative embodiments.

Alternatively, the APF derivatives of the present invention are acidic, heat stable sialoglycopeptides comprising between 5 and 8 natural or unnatural amino acids covalently linked through the N-terminal threonine, serine, or cysteine, for example, to an N-acetylgalactosamine or N-acetylglucosamine residue that is linked via an α or β configuration to galactose, and sialylated on the galactose moiety via 2,3 linkage. The anomeric configuration of the glycosyl bond is alpha in particular embodiments, although it may be beta in alternative embodiments.

In one embodiment, the APF compound comprises a sugar moiety having one or more sugars, wherein the sugars are referred to herein as a first sugar, a second sugar, a third sugar, and so forth. Although any of the sugars may be covalently linked to a peptide, for example, in specific embodiments the third sugar is covalently linked to a peptide, such as one having a sequence essentially as set forth in SEQ ID NOS:1, 3, 4, 5, 14, 15, or 16. The sugar moiety may include naturally-occurring sugars, synthetic sugars, derivatives thereof including sugar mimetic components, and/or any combination thereof.

In preferred embodiments, the sugar molecule includes one or more of a sialic acid, galactose, glucose, N-acetylglucosamine, and/or N-acetylgalactosamine, for example. In certain embodiment, the sialic acid molecule is covalently linked to the galactose or glucose through a (2, 3), a (2, 6), a (2, 8), and/or a (2,9) linkage. A skilled artisan is aware of the nomenclature used in sugar/carbohydrate chemistry to identify the atom at the locations specified. Alternatively, the galactose or glucose is covalently linked to the N-acetylgalactosamine or N-acetylglucosamine molecule through a 1→3, a 1→6 or a 1→4 linkage. In a further preferred embodiment, the N-acetylgalactosamine or N-acetylglucosamine sugar molecule is linked to the hydrophobic moiety in the alpha configuration.

The sugar moiety comprises a naturally occurring sugar, a synthetic sugar, a derivative of a naturally occurring sugar, or a derivative of a synthetic sugar. More specifically, at least one sugar moiety is an amino sugar such as a sialic acid (N-acetylneuraminic acid) molecule, and in some embodiments, the amino sugar is linked to at least another (second) sugar via a (2,3) linkage, a (2,6) linkage, a (2,8) linkage, or a (2,9) linkage. The linkage between at least one sugar moiety and a peptide moiety is a covalent linkage; the linkage between a sugar moiety and a lipid moiety is a covalent linkage; and other linkages described herein may be covalent. Alternatively, at least one sugar moiety is a hexose moiety (such as galactose, glucose, or mannose) linked to an N-acetylated hexose (such as N-acetyl galactosamine or N-acetyl glucosamine).

In specific embodiments involving more than one sugar moiety, the linkage between one sugar moiety and another sugar moiety is a 1→3 linkage, a 1→4 linkage, or a 1→6 linkage. In other embodiments, the linkage between at least one sugar moiety and a hydrophobic moiety, such as a peptide or a lipid, is in the alpha or beta configuration.

In certain embodiments of the present invention, the inventive compound comprises an isolated glycopeptide APF molecule or analog thereof. The APF molecule of the present invention reduces or fully inhibits cell proliferation, in certain aspects. In specific embodiments, the cell being proliferated is a cancer cell. In a particular aspect of the invention, exposure of a cell to APF provides a block in cell cycling in primarily the G2 and/or M phase of the cell cycle block and/or the production of polyploidy. In another embodiment, APF provides a G1 block. As such, APF affects cell cycle distribution, which in particular embodiments contributes at least in part to the pathogenesis of cancer. In further embodiments, exposure of one or more cells to APF results in inhibition of proliferation of the one or more cells, which may comprise a cell cycle block at any point in the cell cycle, although in particular embodiments the block is primarily in G2 or M phase.

In certain embodiments of the present invention, the derivative of APF inhibits the effects of endogenous APF, and, in at least some cases, thereby stimulates abnormally slow cell proliferation.

Also contemplated are derivatives of APF in which the peptide having a sequence essentially as set forth in SEQ ID NO:1 is a fragment thereof, wherein the fragment is 1 to about 8 amino acids of SEQ ID NO:1, including 2, 3, 4, 5, 6, 7, or 8 amino acids. Analogous fragments are contemplated for SEQ ID NO:3, SEQ ID NO:4, SEQ ID NO:5, SEQ ID NO:14, SEQ ID NO:15, or SEQ ID NO:16, for example. It is further contemplated that the peptide moiety may be a nonapeptide or longer than a nonapeptide, such as having 10 or more amino acids in the peptide moiety, or having 15 or more amino acids in the peptide moiety.

The peptide moiety may be 2, 3, 4, 5, 6, 7, 8, 9, 10, 11, 12, 13, 14, or 15 amino acids in length, in some aspects of the invention, and may comprise SEQ ID NO:1, SEQ ID NO:3, SEQ ID NO:4, SEQ ID NO:5, SEQ ID NO:14, SEQ ID NO:15, or SEQ ID NO:16, for example.

In specific embodiments of the present invention, the APF composition may be further defined as: (a) Sialic acid-galactose-Nacetylgalactosamine-threonine-valine-proline-alanine-alanine-valine-valine-valine-alanine; (b) Sialic acid-galactose-Nacetylglucosamine-threonine-valine-proline-alanine-alanine-valine-valine-valine-alanine; or (c) Sialic acid-galactose-Nacetylglucosamine-serine-leucine-proline-alanine-alanine-valine-valine-valine-alanine. In alternative embodiments, the compositions may lack the sialic acid molecule.

The composition of (a) may be further defined as having one (or one or more) of the following: the sialic acid is linked to galactose via a 2,3 linkage; the galactose is linked to the N-acetylgalactosamine via a 1,3 linkage; and/or the N-acetylgalactosamine is linked to threonine via an O linkage in an alpha or beta configuration.

The composition of (b) may be further defined as having one (or one or more) of the following: the sialic acid is linked to galactose via a 2,3 linkage; the galactose is linked to the N-acetylglucosamine via a 1,4 linkage; and/or the N-acetylglucosamine is linked to threonine via an O linkage in an alpha or beta configuration.

The composition of (c) may be further defined as having one (or one or more) of the following: the sialic acid is linked to galactose via a 2,3 linkage; the galactose is linked to the N-acetylglucosamine via a 1,4 linkage; and/or the N-acetylglucosamine is linked to serine via an O linkage in an alpha or beta configuration.

In other embodiments of the present invention, there is an isolated peptide selected from the group consisting of SEQ ID NO:1; SEQ ID NO:3; SEQ ID NO:4; SEQ ID NO:5, SEQ ID NO:14, SEQ ID NO:15, or SEQ ID NO:16, or a functional derivative thereof. The functional derivative thereof may be further defined as comprising a conservative substitution at one or more amino acids of the peptide. The conservative substitution may be further defined as a substitution at serine, threonine, proline, or a combination thereof. In specific embodiments, the conservative substitution comprises a hydrophobic conservative substitution, such as a substitution at one or more alanines, one or more valines, one or more prolines; or a combination thereof. In specific embodiments, a function of peptides of the invention contemplated here is for use as a standard in a kit (such as to quantify APF in samples; as an antiproliferative factor; and/or as a means for inducing antibody production).

Compositions comprising the APF compounds of the present invention are contemplated. The compositions may further comprise a delivery agent, such as a liposome; encapsulated cell; conjugated molecules, such as antibodies (Safavy et al., 2003), other peptides, and a variety of non-peptide conjugates (including folate and polyethylene glycol; Aronov et al., 2003); drugs, such as geldanamycin (Mandler et al., 2004) or insulin (Ou et al., 2003); liposomes (Heath and Martin, 1986); lactosaminated human albumin (Di Stefano et al., 2003); polyethylene glycol (PEG) (Aronov et al., 2003); nanoparticles, such as colloidal gold; or other molecules that bind to cell surface receptors to facilitate cellular interaction with or uptake of the APF compounds.

The composition may be comprised in a pharmaceutically acceptable excipient. The composition may also reversibly arrest cell proliferation. In specific embodiments, the composition is further defined as comprising activity for arresting cell cycling primarily in G2 or M phase or both.

It is contemplated that among the derivatives of APF are natural precursors or metabolites of APF. Further, natural or synthetic APF or their derivatives may be labeled with a detectable molecule such as, for example, a fluorescent, colorimetric, or radioactive moiety. Examples of fluorescent moieties include dansyl, fluorescein, and rhodamine. In all cases, the compounds of the present invention alter cellular functions in a manner similar to or identical to the alterations affected by native APF. In particular aspects of the invention, derivatives of APF comprise anticellular proliferation activity, including for cancer cells.

An APF composition of the present invention may be further defined as comprising a label, such as a fluorescent moiety, a colorimetric moiety, or a radioactive moiety. In certain embodiments, the label is attached to at least one of the one or more sugar moieties, such as sialic acid, glucose, galactose, N-acetylgalactosamine or N-acetylglucosamine. Alternatively, the label is attached any suitable atom in a peptide, such as within at least one of the amino acids making up the peptide moiety, such as at a heteroatom in a serine, threonine, or cysteine amino acid subunit, or attached to the carboxyl group at the carboxyl end of the peptide. Alternatively, the label is attached to at least one of the atoms of the lipid moiety such as at a double bond in an unsaturated fatty acid (i.e., oleic acid and the like), or at a polar head group of a lipid (alcohol).

Oligonucleotides that encode the nonapeptide of SEQ ID NO:1 or biologically functional derivatives thereof, such as the peptides of SEQ ID NO:3, SEQ ID NO:4, SEQ ID NO:5, SEQ ID NO:14, SEQ ID NO:15, or SEQ ID NO:16, for example, and/or precursors of APF are also contemplated herein. An exemplary oligonucleotide that encodes SEQ ID NO:1 is SEQ ID NO:2. However, given the limited choices of triplet nucleotides per given codon for a particular amino acid, a skilled artisan recognizes that a polynucleotide encoding a peptide of the invention, exemplary embodiments of which include SEQ ID NO:1, SEQ ID NO:3, SEQ ID NO:4, SEQ ID NO:5, SEQ ID NO:14, SEQ ID NO:15, or SEQ ID NO:16, are limited in number and are well within the scope of the invention. This is particularly true given the further subset of codons available for encoding hydrophobic amino acids, which are preferably comprised in at least part of the peptide moiety of the APF molecule.

In additional embodiments of the present invention, there is an isolated polynucleotide encoding SEQ ID NO:1, which may be further defined as SEQ ID NO:2.

The polynucleotides may be further defined as having one or more of the following: a codon for threonine selected from the group consisting of ACA, ACC, ACG, and ACU; a codon for one or more valines selected from the group consisting of GUA, GUC, GUG, and GUU; a codon for proline selected from the group consisting of CCA, CCC, CCG, and CCU; and a codon for one or more alanines selected from the group consisting of GCA, GCC, GCG, and GCU.

In another embodiment, there is an isolated polynucleotide encoding SEQ ID NO:3, such as one further defined as having one or more of the following: a codon for serine selected from the group consisting of AGC, AGU, UCA, UCC, UCG, and UCU; a codon for one or more valines selected from the group consisting of GUA, GUC, GUG, or GUU; a codon for proline selected from the group consisting of CCA, CCC, CCG, or CCU; and a codon for one or more alanines selected from the group consisting of GCA, GCC, GCG, or GCU.

In an additional embodiment, there is an isolated polynucleotide encoding SEQ ID NO:4, such as one further defined as having one or more of the following: a codon for threonine selected from the group consisting of ACA, ACC, ACG, and ACU; a codon for one or more valines selected from the group consisting of GUA, GUC, GUG, and GUU; a codon for proline selected from the group consisting of CCA, CCC, CCG, and CCU; a codon for one or more alanines selected from the group consisting of GCA, GCC, GCG, and GCU; and a codon for leucine selected from the group consisting of UUA, UUG, CUA, CUC, CUG, and CUU.

In another embodiment of the present invention, there is an isolated polynucleotide encoding SEQ ID NO:5, such as one further defined as having one or more of the following: a codon for serine selected from the group consisting of AGC, AGU, UCA, UCC, UCG, and UCU; a codon for leucine selected from the group consisting of UUA, UUG, CUA, CUC, CUG, and CUU; a codon for proline selected from the group consisting of CCA, CCC, CCG, and CCU; a codon for one or more alanines selected from the group consisting of GCA, GCC, GCG, and GCU; and a codon for one or more valines selected from the group consisting of GUA, GUC, GUG, and GUU.

In additional embodiments of the present invention, there is a kit, comprising the APF derivative composition housed in a suitable container. There may be a kit for treating and/or preventing cancer or a bladder condition in an individual.

In specific embodiments, certain derivatives having D-proline or D-pipecolic acid in the peptide moiety are used to abolish the activity of endogenous APF and, in certain cases, are used as antagonists of APF.

In one embodiment of the invention, there is a composition comprising a derivative of antiproliferative factor (APF) having one to six sugar moieties, wherein at least one sugar moiety is linked to a peptide moiety of about two to fifteen amino acid resides, wherein said peptide moiety comprises a proline mimetic selected from the group consisting of D-proline, D-pipecolic acid, L-pipecolic acid, hydroxyproline, O-t-butyryl-trans-4-hydroxyproline, N-methylalanine, nipecotic acid, isonipecotic acid, 7-azaindoline, one of the mimetics of FIG. 11 or 12, and a piperidine derivative that comprises at least one carboxylic acid, ketone, amine, amide, sulfonic, sulfuric, or nitric oxide. In a specific embodiment, the proline mimetic comprises D-pipecolic acid or L-pipecolic acid. In another specific embodiment, the peptide comprises one or more of an amino acid selected from the group consisting of threonine, valine, alanine, serine, and leucine. In some cases, the linkage between the sugar and the peptide is in alpha configuration. In particular aspects, the amino acid that is third from the N-terminus of the peptide is D-pipecolic acid or L-pipecolic acid.

In some embodiments, there is a pharmaceutical composition comprising the APF derivative composition and one or more pharmaceutically acceptable excipients.

In another embodiment of the invention, there is a composition comprising a derivative of APF, wherein the composition comprises two sugars and a peptide having a proline mimetic and no more than 15 amino acids in length, wherein the sugars are β-galactose and N-acetyl galactosamine, wherein the N-acetyl galactosamine is linked to the peptide in the alpha configuration. In other embodiments, there is a kit comprising the APF derivative composition.

In one embodiment, there is a method of treating a bladder disorder in an individual, comprising the step of administering to the individual a therapeutically effective amount of an APF derivative composition, wherein the composition lacks anti-proliferation activity. In a specific embodiment, the bladder disorder is interstitial cystitis.

In some embodiments, there is a method of treating a proliferation disorder in an individual, comprising the step of administering to the individual a therapeutically effective amount of an APF derivative composition, wherein the composition has anti-proliferation activity.

In particular cases, there is a composition comprising a derivative of APF having at least one sugar and a peptide moiety having modifications compared to TVPAAVVVA (SEQ ID NO:1), wherein the modifications comprise one or more of the following: 1) threonine is replaced with serine; 2) the proline is replaced with a proline mimetic selected from the group consisting of D-proline, D-pipecolic acid, L-pipecolic acid, hydroxyproline, O-t-butyryl-trans-4-hydroxyproline, N-methylalanine, nipecotic acid, isonipecotic acid, 7-azaindoline, one of the mimetics of FIG. 11 or 12, and a piperidine derivative that comprises at least one carboxylic acid, ketone, amine, amide, sulfonic, sulfuric, or nitric oxide; 3) eight or nine amino acids in length wherein when the peptide is 8 amino acids, the C-terminal amino acid is lacking compared to SEQ ID NO:1; 4) eight or nine amino acids in length wherein one or more of the valines are replaced with alanine; and 5) at least the three C-terminal amino acids are hydrophobic, such as hydrophobic amino acids are selected from the group consisting of leucine, alanine, and valine.

In some embodiments, there is an antiproliferative factor (APF) peptide or fragment thereof comprising a TVP*AAVVVA amino acid sequence having proliferative modulatory activity, wherein the antiproliferative factor (APF) has one to six sugar moieties, wherein at least one sugar moiety is linked to a peptide moiety of about two to fifteen amino acid resides, wherein the P* derivative comprises a proline mimetic selected from the group consisting of D-proline, D-pipecolic acid, L-pipecolic acid, hydroxyproline, O-t-butyryl-trans-4-hydroxyproline, nipecotic acid, isonipecotic acid, 7-azaindoline, one of the mimetics of FIG. 11 or 12, and a piperidine derivative that comprises at least one carboxylic acid, ketone, amine, amide, sulfonic, sulfuric, or nitric oxide.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 43 shows the effect of 30 day treatment on mRNA expression for various cell proteins, where the white bar (1) is the D-proline treated sample, the gray bar (2) is a peptide-control-treated sample, and the black bar (3) is an untreated cell control sample.

DETAILED DESCRIPTION OF THE INVENTION

Figure 1:
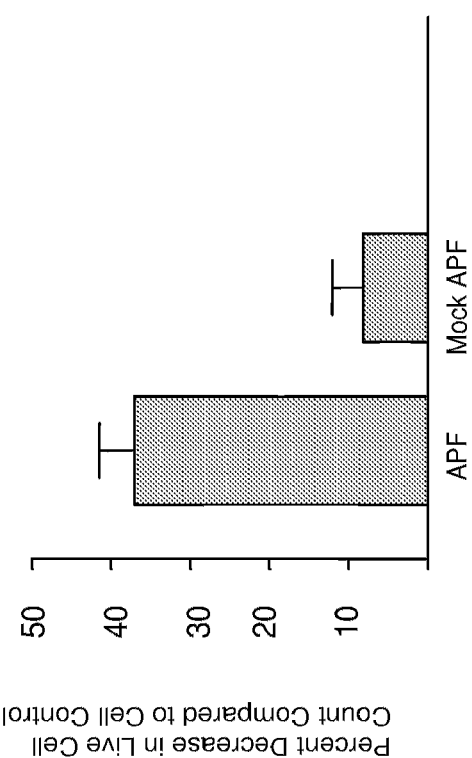
FIG. 1 shows HPLC-purified APF antiproliferative activity against LNCaP prostate cancer cells in vitro.

This application incorporates by reference herein in their entirety the following documents: U.S. Provisional Patent Application Ser. No. 60/484,010, filed Jul. 1, 2003; U.S. Provisional Patent Application Ser. No. 60/515,850, filed Oct. 29, 2003; U.S. Provisional Patent Application Ser. No. 60/569,363, filed May 7, 2004; U.S. Nonprovisional patent application Ser. No. 10/882,586, filed Jul. 1, 2004, now abandoned; PCT Internation Patent Application Serial No. PCT/US2004/021239, filed Jul. 1, 2004; U.S. Nonprovisional patent application Ser. No. 11/743,865, filed May 3, 2007; U.S. Nonprovisional patent application Ser. No. 11/955,755, filed Dec. 13, 2007, and a U.S. CIP Application Serial No. Unknown entitled "Derivatives of APF and Methods of Use" and filed concomitantly with the present application on Aug. 18, 2009.

I. DEFINITIONS

As used herein the specification, "a" or "an" may mean one or more. As used herein in the claim(s), when used in conjunction with the word "comprising", the words "a" or "an" may mean one or more than one. As used herein "another" may mean at least a second or more. In some cases, the claims may encompass subject matter that consists of an element(s) or consists essentially of an element(s).

The term "alpha configuration" α as used herein refers to structural relationships in carbohydrate chemistry, wherein the anomeric group is in the axial configuration when the conformational formulation of the pyranose ring is used. Conversely, the term "beta configuration" β refers to that arrangement in which the anomeric group is equatorial.

The term "backbone-modifying amino acid" is known in the art and is discussed as follows. Normal peptide or protein backbone is formed from polymerization of alpha amino acids, which have the amino group on the carbon adjacent to the carboxyl group. This produces a polymer in which the repeating unit is —[NHCH(R)C(O)]—, wherein R is the sidechain that makes each amino acid different, but the repeating unit that forms the back bone is as shown. If the amino group is moved to a different carbon, for example the beta-carbon of alanine, if an abnormal side group is added, and/or if the amino acid is changed to the D isomer, the backbone is no longer natural but still has many of the properties of peptides. Proteolytic enzymes do not recognize altered backbones. Beta-alanine, hydroxyproline, acetylated lysine, or gamma-butyric acid are common backbone altering amino acids. They are not naturally found in peptides or proteins.

The term "bladder disorder" as used herein refers to an abnormal condition of the urinary bladder.

The term "conservative substitution" as used herein refers to replacing an amino acid in a peptide or polypeptide with a different amino acid of a similar chemical nature. For example, a nonpolar amino acid may be conservatively substituted with another nonpolar amino acid. In specific embodiments, a hydrophobic amino acid may be substituted with another hydrophobic amino acid.

The terms "APF derivative" refers to a peptide mimetic having at least about 85% amino acid sequence identity to TVPAAVVVA (SEQ ID NO:1). In specific embodiments, the terms "APF derivative," or "derivative of APF" or "APF derivative composition", which all may be used interchangeably and are interchangeable with the term "APF analog" as used herein refers to a compound, such as a synthetic compound, that is formed from the structure of the endobiotic APF (Neu5Acα2-3Galβ1-3GalNAcα-O-TVPAAVVVA; SEQ ID NO:1) by removing, adding or replacing a specific atom, group of atoms, amino acid, group of amino acids, or sugar moiety, for example. In specific embodiments, the derivative of APF has anti-proliferation activity, whereas in other cases the derivative of APF lacks anti-proliferation activity. In specific cases, the derivative comprises proliferation modulatory activity, wherein the derivative of APF has anti-proliferation activity or the derivative of APF reduces or abolishes APF activity or is an APF antagonist. One of skill in the art recognizes how to determine whether a particular derivative of APF has anti-proliferation activity based at least on the disclosure provided herein.

The term "epithelial cancer" as used herein refers to a cancer in a tissue originating from epithelial cells of the tissue. For example, epithelial cancer may comprise urinary bladder; kidney, adrenal glands, ureter; lung; heart; gastrointestinal tract (including the stomach, small intestine, large intestine, rectum, liver, pancreas and gall bladder); spleen; male reproductive tract, including the seminal vesicles, prostate, bulbourethral gland, vas deferens, epididymis, testes, and penis; female reproductive tract, including the ovaries, Fallopian tubes, uterus, cervix, and vagina; kidneys; adrenal glands; thymus; thyroid; skin; bone (including synovium); ocular tissues (including cornea, retina, and lens); cochlea; breast tissue; lymph nodes; oral mucosa (including gingival), salivary gland, parotid gland; skin (including keratinocytes and melanocytes), and nasopharygeal mucosa (including sinus mucosa), for example.

The term "heteroatom" as used herein refers to an atom in an organic molecule that is other than carbon or hydrogen.

The term "hydrophobic" as used herein refers to lacking affinity for water.

The term "hydrophobic amino acid" as used herein refers to amino acids that are unable to form hydrogen bonds with water because they have no, or very small, electrical charges in their structure. In aqueous solution, hydrophobic amino acids disrupt the hydrogen bonding structure that is formed among water molecules, given that they are unable to contribute to it. Hydrophobic amino acids vary in size, and the majority of hydrophobic amino acids have a side chain that is purely hydrocarbon. Other things being equal, a larger hydrophobic side chain will be more strongly hydrophobic than a smaller one. Specific examples of hydrophobic amino acids include those that comprise aliphatic hydrocarbon side chains, such as alanine, valine, leucine, or isoleucine; aromatic side chains, such as phenylalanine or tryptophan; sulfur-comprising side chains, such as methionine; and/or imino acids, such as proline, for example. In particular embodiments, hydrophobic amino acids are considered to be alanine, valine, leucine, and isoleucine.

The term "hyperplasia" as used herein refers to the abnormal proliferation of normal cells in normal arrangement in a tissue. Hyperplasia can lead to abnormal tissue architecture, however, as in keloid scar formation, or polycystic kidney or liver disease where hyperplasia of the epithelium results in cyst formation; in prostatic hyperplasia, hyperplasia of the epithelium contributes to increased size of the prostate and decreased size of lumens within the tubules of that organ.

The term "mimetic" as used herein refers to a composition that arises from modification of an existing molecule in order to alter that molecule's properties, such as its stability or biological activity, for example. In certain cases, the mimetic is a proline mimetic, and in specific cases, the proline mimetic comprises a similar structure to proline. In particular cases, the proline mimetic imparts the same bend in a peptide that occurs with proline.

The term "peptide" as used herein refers to a compound made up of a single chain of D- or L-amino acids or a mixture of D- and L-amino acids joined by peptide bonds. Generally, the peptides used herein contain at least two amino acid residues and are less than about 50 amino acids in length. D-amino acids are represented herein by a lower-case one-letter amino acid symbol (e.g., r for D-arginine), whereas L-amino acids are represented by an upper case one-letter amino acid symbol (e.g., R for L-arginine). The peptides may be cyclical, linear, branched, or a combination thereof. In particular cases, APF derivative comprises a well-defined three-dimensional structure.

The term "peptide mimetic" refers to a compound that is capable of mimicking or antagonizing the biological actions of an endogenous peptide. A peptide mimetic may include non-peptidic structural elements, unnatural peptides, synthesized organic molecules, naturally occurring organic molecules, and components thereof. In one embodiment, a peptide mimetic is an APF derivative.

"Polypeptide" as used herein refers to a polymer of at least two amino acid residues and which contains one or more peptide bonds. "Polypeptide" encompasses peptides and proteins, regardless of whether the polypeptide has a well-defined conformation.

The term "protein" as used herein refers to a compound that is composed of amino acids linked by peptide bonds, but in contrast to peptides, is larger and has a well-defined conformation, such as a well-defined three-dimensional conformation. Proteins, as opposed to peptides, generally consist of chains of 50 or more amino acids.

The term "purified" as used herein, is intended to refer to an analyte purified to any degree relative to its naturally-obtainable state, i.e., in this case, relative to its purity within a eukaryotic cell or within a fluid such as cell medium or supernatant, or a biological fluid such as urine, serum, or plasma.

A "subunit," as used herein, is a monomeric unit that is joined to form a larger polymeric compound. The set of amino acids are an example of subunits. Each amino acid shares a common backbone (—C—C—N—), and the different amino acids differ in their sidechains. The backbone is repeated in a polypeptide. A subunit represents the shortest repeating pattern of elements in a polymer backbone. For example, two amino acids of a peptide are not considered one subunit because two amino acids would not have the shortest repeating pattern of elements in the polymer backbone.

The term "terminal amino acid" as used herein refers to the amino acid on the end of a linear peptide of an APF molecule, and may refer to a N-terminal amino acid or a C-terminal amino acid.

The terms "therapeutic agent", "therapeutic composition", and "therapeutic substance" refer, without limitation, to any composition that can be used to the benefit of an organism including but not limited to a mammalian organism. Such agents may take the form of ions, small organic molecules, peptides, proteins or polypeptides, glycopeptides (and other modified peptides), oligonucleotides, and oligosaccharides, for example.

The term "therapeutically effective amount" as used herein refers to the amount of a composition utilized alone or in combination with another compound for a therapeutic purpose that results in ameliorating at least one symptom or objective finding (sign) of the medical condition being treated. A skilled artisan recognizes that the invention is useful for providing less than a complete cure, so long as one or more symptoms or signs are alleviated. For example, in treating a bladder condition, a therapeutically effective amount would include the amount that facilitates any or all of the following: decrease (or by inhibition, an increase) in cell proliferation; reduction in pain, urgency, or frequency of urination; reduction in the amount, degree and/or intensity of thinning and/or ulceration of the bladder epithelial lining; and so forth.

The term "urinary bladder" as used herein refers to a distensible membranous sac that serves for the temporary retention of the urine of an individual. Normally it resides in the pelvis in front of the rectum, and it receives the urine from the two ureters, discharging it at intervals into the urethra through an orifice closed by a sphincter. The organ is lined with transitional hypoblastic epithelium.

The term "antiproliferative factor" as used herein refers to an endogenous antiproliferative factor as described herein that is associated primarily with the urinary bladder. It may be associated with a cell of the bladder, such as with an epithelial cell, and this then may be referred to as a "urinary bladder epithelial cell antiproliferative factor". The factor may be identified within one or more bladder epithelial cells or it may be identified following secretion from one or more cells, or both. In addition, or alternative to, the factor may be suspended in urine within a bladder or in urine excreted therefrom, or both. Such an association of the factor with the urinary bladder may permit the detection of the APF as diagnostic for a bladder condition, such as interstitial cystitis, for example. Although in some embodiments APF is located in the urinary bladder, in alternative embodiments the APF molecule is also associated with serum, plasma, or other tissue. In particular cases, the term "antiproliferative factor" as used herein refers to the naturally occuring antiproliferative factor from bladder epithelial cells, as described in U.S. Nonprovisional patent application Ser. No. 10/882,586, filed Jul. 1, 2004.

II. CERTAIN EMBODIMENTS OF THE PRESENT INVENTION

In certain embodiments of the invention, there are compositions and methods related to cancer therapy and/or prevention and/or bladder condition therapy and/or prevention. In particular aspects, the compositions and methods are related to compounds similar in structure to the naturally occurring APF from bladder epithelial cells and that have anti-cell proliferation activity. In other aspects, the compositions and methods are related to compounds similar in structure to the naturally occurring APF from bladder epithelial cells and that have anti-APF activity or are otherwise useful for bladder disorder treatment and/or prevention.

In specific embodiments, the APF derivatives comprise a peptide portion that has one or more of the following characteristics: 1) at least 8 N-terminal amino acids; 2) a trans conformation for the Pro-Ala peptide bond; 3) alanine in position 5; 4) valines in positions 6, 7, and/or 8; 5) the conformation allowed by proline or pipecolic acid in position 3; 6) a particular arrangement of methyl groups on the two N-terminal amino acids; 7) an amino acid no bulkier than alanine in the 9th position; 8) a free N-terminal amino group; and 9) a free C-terminal carboxy group. In specific embodiments, the position that is third from the N-terminus is D- or L-pipecolic acid or is D- or L-proline.

In particular embodiments of the invention, the peptide moiety comprises one or more agents that allow the peptide or a fragment thereof to be protease-resistant. In some embodiments, the peptide comprises pipecolic acid, whereas in other embodiments the peptide comprises hydroxyproline, O-t-butyryl-trans-4-hydroxyproline, O-t-butyryl-hydroxyglutamate N-methyl alanine, or acetylated lysine.

In certain aspects, any of the amino acids, amino acid mimetics, synthetic amino acids, non-natural amino acids, amino acid analogues, amino acid derivatives, and so forth may be in the D or levorotary (L) configuration.

III. ANTIPROLIFERATIVE FACTOR (APF) AND DERIVATIVES THEREOF

In some cases, the present invention encompasses compositions based on the APF from bladder epithelial cells and methods of using them, or in some cases it encompasses derivatives of APF and methods of using them. In one embodiment, the naturally occuring APF comprises a glycopeptide that inhibits proliferation of bladder epithelial cells, skin fibroblasts, and other epithelial cells including prostate cells, and in some embodiments is generated by bladder epithelial cells, such as those associated with interstitial cystitis. In specific embodiments, APF is described in U.S. Nonprovisional patent application Ser. No. 10/882,586, now abandoned, and in particular embodiments is provided in FIG. 4 therein.

In certain embodiments, one or more moieties of naturally occuring APF is modified, including, for example, the sugar moiety, the peptide moiety, or the linkage therebetween. In certain cases, the sugar moiety is modified to change the identity and/or number of the sugar(s). In specific aspects, the peptide moiety is modified to change the identity and/or number of amino acids. For example, the proline in the naturally occuring APF may be altered to a proline mimetic. In specific cases, the proline in the naturally occuring APF may be altered to D-pipecolic acid or L-pipecolic acid. In particular embodiments, the linkage between the sugar moiety and peptide moiety is alpha, as with natural APF, although in specific embodiments the linkage is a beta configuration.

Thus, in specific embodiments, APF compositions related to the present invention at least comprise about one to about six sugar residues; and a peptide of about two to about fifteen amino acid residues, wherein the peptide-linked to one of the sugar moieties at a linking amino acid, wherein the linking amino acid comprises a heteroatom that serves as the linking portion of the linking amino acid. More specifically, the linking amino acid comprises a serine, a threonine, or a cysteine. In other specific embodiments, the compositions of the present invention comprises two or three sugar residues and nine amino acids and the linking amino acid is a threonine or serine.

In one particular aspect of the invention, an APF derivative composition may comprise in part a hydrophobic moiety, such as a peptide, for example one including SEQ ID NO:1, SEQ ID NO:3, or SEQ ID NO:4, SEQ ID NO:5, SEQ ID NO:14, SEQ ID NO:15, or SEQ ID NO:16, or a lipid. The peptide may comprise at least part of a transmembrane domain, and in particular embodiments it comprises part of frizzled 8, such as a transmembrane domain of frizzled 8. In specific embodiments, the peptide is hydrophobic.

The glycoprotein comprising a galactose covalently linked to an N-acetylglucosamine or an N-acetylgalactosamine covalently linked to a peptide of SEQ ID NO:1 or variants thereof is provided herein. The term "variants thereof" includes peptidomimetics of various types (Ahn et al., 2002). The peptides may comprise any suitable amino acids, such as L-amino acids, D-amino acids, N-methylated amino acids, or a combination thereof, as well as peptidomimetic compounds such as unnatural amino acids or other "peptide-like" organic constructs that mimic the specific structural elements of a linear, cyclic, or branched peptide that correspond to active peptides. The sugar moieties may be natural, synthetic, carbohydratemimetic, or a mixture thereof may be used in a composition. Glycopeptidomimetic compounds where the sugars are carbohydratemimetic moieties or the peptide components are peptidomimetic moieties, or a combination of the two, are encompassed in the invention. In specific embodiments, the sugars of the present invention include amino sugars.

In a particular aspect of the invention, the APF from which the derivative is generated or modeled therefrom has a molecular mass of 1482.8 and comprises nine amino acids and three sugar moieties in the following order: (a) Sialic acid-galactose-N-acetylgalactosamine-threonine-valine-proline-alanine-alanine-valine-valine-valine-alanine; or (b) Sialic acid-galactose-Nacetylglucosamine-threonine-valine-proline-alanine-alanine-valine-valine-valine-alanine; or (c) Sialic acid-galactose-N-acetylglucosamine-serine-leucine-proline-alanine-alanine-valine-valine-valine-alanine. The composition may be further defined as having one or more of the following: the sialic acid in (a) is linked to galactose via a 2,3 linkage; the sialic acid in (b) is linked to galactose via a 2,3 linkage; the sialic acid in (c) is linked to galactose via a 2,3 linkage; the galactose in (a) is linked to the N-acetylgalactosamine via a 1,3 linkage; the galactose in (b) is linked to the N-acetylglucosamine via a 1,4 linkage; the galactose in (c) is linked to the N-acetylglucosamine via a 1,4 linkage; the N-acetylglucosamine is linked to serine via an O linkage in an alpha configuration; or the N-acetylgalactosamine is linked to threonine or serine via an O linkage in an alpha configuration.

It is contemplated that the compounds of the present invention may be modified so as to improve certain characteristics, such as solubility by adding a water soluble unit. The term "water soluble unit" means any functional group imparting water solubility, including, but not limited to, $SO_3-$, $PO_3^{2-}$, $CH_2COO^-$, a quaternary ammonium group attached via an ester or alkyl linkage such as $C=O(CH_2)_x$ $NAlk_3$ or $(CH_2)_x$ $NAlk_3$ where $Alk_3$ represents three alkyl groups that are independently C1-C4 alkyl and x is 1-4, $(CH_2CH_2O)_n$ $CH_2CH_2OX$ (n=1-3) wherein X may be H or $CH_3$, i.e., PEG or MeO-PEG. The counterion for water soluble units bearing a charge include, but are not limited to, metals such as alkali and alkaline earth metals, and halogens.

Certain compounds of the present invention comprise a threonine, a serine, or a cysteine at the N-terminus or any functional equivalent. Non-limiting examples of functional equivalents include a synthetic derivative having a primary or secondary or tertiary alcohol, an ester, a carboxylic acid, an ether, a thiol, a thiolate, or any functional group enabling for covalent linkage with a sugar molecule, provided the molecule retains biological function.

Other functionalities contemplated in "derivatives" of the present invention include isomers of any of the sugars or amino acids, whether positional, structural, or stereoisomers, for example. Other substituents known to those skilled in the chemical arts may be provided, so long as the biological function of the molecule (anti-cell proliferation activity, for example) is retained.

IV. THERAPEUTIC AND/OR PREVENTATIVE EMBODIMENTS

A skilled artisan recognizes that the APF derivative compositions of the present invention may be addressed in a variety of ways to provide therapy and/or prevention for cancer or therapy and/or prevention of bladder disorder.

The composition may be delivered by any suitable means, although in specific embodiments it is delivered via catheter. The composition may be delivered, for example, orally, intravenously, topically, subcutaneously, transcutaneously, intramuscularly, intra-articularly, parenterally, peritoneally, intranasally, intravesically, vaginally, rectally, or by inhalation, for example. In other specific embodiments, the composition is comprised in a pharmaceutically acceptable excipient, such as an aqueous or non-aqueous liquid or a combination thereof. In particular aspects of the invention, it is administered in a non-aqueous excipient due to the hydrophobic nature of the peptide moiety. It may be delivered alone or in a carrier, such as a liposome, encapsulated cell, viral vector, nanoparticles, biodegradable gel or polymer, implanted osmotic pump, or other suitable devices.

The methods and compositions may be employed for any type of cancer, including bladder, lung, kidney, adrenal, breast, prostate, brain, stomach, blood, colon, spleen, liver, pancreatic, melanoma, head and neck, thyroid, uterine, ovarian, cervical, gall bladder, and so forth. In specific embodiments, the compositions are employed for invasive cancer, metastatic cancer, cancer resistant to one or more therapies, and so forth. In particular aspects, the compositions of the present invention render sensitive a cancer that is resistant to one or more therapies.

In a particular embodiment, an APF composition of the present invention may be administered to an individual with any kind of cancer, including epithelial cancers. In specific embodiments, there is a malignancy of the bladder epithelium, which may be referred to herein as bladder cancer. In specific embodiments, there is a cancer therapy additional to the APF treatment, such as gene therapy, chemotherapy, radiation, surgery, immunotherapy, or a combination thereof.

V. BLADDER DISORDERS

Although the present invention may be useful for any medical condition for which APF provides therapy, in specific embodiments the present invention is useful for one or more bladder disorders. Although the term "bladder disorder" refers to any abnormal condition of the urinary bladder, in specific embodiments the bladder disorder comprises interstitial cystitis, bladder cancer, either as a primary or secondary cancer, chronic pelvic pain syndrome, irritable bladder syndrome, urethral syndrome, painful bladder syndrome, chronic nonbacterial prostatitis, and other bladder conditions, for example.

In specific embodiments of the present invention, there are methods and compositions related to interstitial cystitis. Typical symptoms of interstitial cystitis include pain, which can be in the abdominal, urethral or vaginal area and is also frequently associated with sexual intercourse; urgency, which includes the sensation of having to urinate immediately and may also be accompanied by pressure and/or spasms; and increased frequency of urination, which can be day and/or night frequency of urination.

Diagnosis of intersitial cystitis is heretofore performed using cystoscopy, and hydro-distention and biopsies are normally performed at the same time. Examination by cytoscopy of a typical bladder having interstitial cystitis may identify submucosal pinpoint hemorrhages (glomerulations), thinning of the epithelium and/or Hunner's ulcers; in some cases, inflammation may also be present. Thus, there is considerable pain when urine enters into the bladder of an IC patient, making it very difficult for patients with interstitial cystitis to be able to hold urine in their bladder, due to the burning, stinging and pain.

Current therapies include oral medications, such as pentosan polysulfate (Elmiron®), amitriptyline (Elavil®), hydroxyzine (Atarax®), gabapentin (Neurontin®), oxybutynin (Ditropan®), fluoxetine (Prozac®), heparin, DMSO, lidocaine, and cimetidine (Tagamet®). Other agents in development are PD-299685 (Pfizer®), suplatast tosilate (Taiho®), URG-101 (Urigen®), heparin, tipelukast (MediciNova®), and TTI-1612 (Trilium).

In specific embodiments of the invention, therapeutic agents associated with the present invention are used either alone or in conjunction with one or more of these or similar medications. In specific embodiments, the patients also suffer with various other syndromes including fibromyalgia, urethral syndrome, vulvodynia, irritable bowel syndrome, chronic fatigue syndrome, allergies, and other auto-immune disorders, such as scleroderma.

VI. PHARMACEUTICAL COMPOSITIONS

The present invention is also directed to pharmaceutical compositions for use in treating treating and/or preventing cancer or hyperplasias or for use in treatment and/or prevention of bladder disorder.

Such methods generally involve administering a pharmaceutical composition comprising an effective amount of the APF derivatives of the present invention.

Where the invention is directed to treating with the compounds of the present invention, administration of the compounds of the invention with a suitable pharmaceutical excipient as necessary can be carried out via any of the accepted modes of administration. The compounds may be comprised in a pharmaceutically acceptable excipient, which may be considered as a molecular entity and/or composition that does not produce an adverse, allergic and/or other untoward reaction when administered to an animal, as appropriate. It includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated.

In particular embodiments of the invention, the derivative of APF is utilized with a compound having anesthetic properties, including, for example, a topical anesthetic. In some cases, the topical anesthetic is useful for intravesical administration via catheter. Specific examples of topical anesthetic include benzocaine, butamben, dibucaine, lidocaine, oxybuprocaine, pramoxine, proparacaine, proxymetacaine, and tetracaine, for example.

Thus, administration can be, for example, intravenous, topical, subcutaneous, transcutaneous, intramuscular, oral, intra-articular, parenteral, peritoneal, intranasal, intravesical, vaginal, rectal, or by inhalation. Suitable sites of administration thus include, but are not limited to, skin, bronchial, gastrointestinal, anal, vaginal, eye, bladder, and ear. The formulations may take the form of solid, semi-solid, lyophilized powder, or liquid dosage forms, such as, for example, tablets, pills, polymer depots, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., REMINGTON'S PHARMACEUTICAL SCIENCES, 18TH ED., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Remington's Pharmaceutical Sciences, supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person. However, it is possible that an effective dose of APF, especially if administered directly into the bladder, may be outside of this range.

Stability of the conjugate can be further controlled by chemical alterations, including D amino acid residues in the polypeptide chain as well as other peptidomimetic moieties. Furthermore, stability of the conjugates could also be enhanced by unnatural carbohydrate residues.

VII. COMBINATION TREATMENTS

In certain cases, the APF derivatives of the present invention are administered in addition to another treatment for the medical condition being treated. For example, another cancer therapy may be employed for those APF derivatives that inhibit cell proliferation, and another bladder disorder therapy may be employed for those APF derivatives that treat and/or prevent bladder disorder.

Cancer

In order to increase the effectiveness of an APF derivative composition for the treatment of cancer in an individual, such as a patient, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy, for example, by combining it with other cancer therapies. In the context of the present invention, it is contemplated that APF derivative composition therapy could be used similarly in conjunction with chemotherapeutic, radiotherapeutic, surgical, or immunotherapeutic intervention, in addition to other pro-apoptotic or cell cycle regulating agents.

Alternatively, the APF derivative treatment may precede, follow, or both the other agent treatment by intervals ranging from minutes to weeks. In embodiments where the APF derivative composition and the other agent are applied separately to a cell of the individual, one would generally ensure that a significant period of time did not expire between the time of each delivery, such that the APF composition and the other agent would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, for example, wherein the APF derivative treatment is "A" and the secondary agent, such as radio- or chemotherapy, is "B":

A/B/A  B/A/B  B/B/A  A/A/B  A/B/B  B/A/A  A/B/B/B  B/A/B/B
B/B/B/A  B/B/A/B  A/A/B/B  A/B/A/B  A/B/B/A  B/B/A/A
B/A/B/A  B/A/A/B  A/A/A/B  B/A/A/A  A/B/A/A  A/A/B/A

Administration of the APF derivative compositions of the present invention to a patient will follow general protocols for the administration of chemotherapeutics, taking into account the toxicity, if any, of the molecule. It is expected that the treatment cycles would be repeated as necessary. It also is contemplated that various standard therapies, as well as surgical intervention, may be applied in combination with the described anti-hyperproliferative cell therapy.

a. Chemotherapy

A skilled artisan recognizes that in addition to the APF derivative treatment described herein for the purpose of inhibiting cell growth, other chemotherapeutic agents are useful in the treatment of neoplastic disease. Examples of such chemotherapeutic agents include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, pemetrexid, docetaxel, gemcitabine, navelbine, farnesyl-protein tansferase inhibitors, transplatinum, 5-fluorouracil, paclitaxel, vincristine, vinblastine, vinflunine, retaspimycin, and methotrexate, or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. In embodiments directed to cancer of the urinary bladder, immunotherapy encompasses but is not limited to treatment with Bacille Calmette-Guérin, for example.

Immunotherapy, thus, could be used as part of a combined therapy, in conjunction with APF therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Genes

In yet another embodiment, the secondary treatment is a secondary gene therapy in which a second therapeutic polynucleotide is administered before, after, or at the same time as an APF molecule, having a combined anti-hyperproliferative effect on target tissues. A variety of proteins are encompassed within the invention, including inhibitors of cellular proliferation, such as tumor suppressors, including p53; and/or regulators of programmed cell death, such as Bcl-2.

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, growth factor receptor antagonists, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy. Examples of growth factor receptor antagonists include but are not limited to cetuximab, bevacizumab, sorafenib, cediranib, sunitinib, vandetanib, axitinib, gefitinib, and erlotinib.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Bladder Disorder

In order to increase the effectiveness of an APF derivative composition for the treatment of bladder disorder in an individual, such as a patient, it may be desirable to combine these compositions with other agents effective in the treatment of the bladder disorder. In specific embodiments, such a treatment comprises pentosan polysulfate (Elmiron®), amitriptyline (Elavil®), hydroxyzine (Atarax®), gabapentin (Neurontin®), oxybutynin (Ditropan®), fluoxetine (Prozac®), heparin, DMSO, lidocaine, and cimetidine (Tagamet®). Other agents in development are PD-299685 (Pfizer®), suplatast tosilate (Taiho®), URG-101 (Urigen®), heparin, tipelukast (MediciNova®), and TTI-1612 (Trilium).

VIII. NUCLEIC ACID-BASED EXPRESSION SYSTEMS

In some embodiments of the invention, one or more suitable vectors are employed for transfecting the polynucleotide encoding the APF derivative backbone peptide into one or more cells. The skilled artisan recognizes how to obtain the appropriate sequence that encodes the peptide based on the example herein of SEQ ID NO:2 that encodes SEQ ID NO:1 peptide.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

5. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

8. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with 13 galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

9. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may include a viral vector that encodes one or more APF derivative peptide compositions or other components such as, for example, an immunomodulator or adjuvant. Non-limiting examples of virus vectors that may be used to deliver a nucleic acid of the present invention are described below.

10. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

11. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the [INVENTION] vaccines of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

12. Retroviral Vectors

Retroviruses have promise as nucleic acid delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding an APF peptide) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

13. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

B. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

C. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

IX. KITS

Therapeutic kits associated with the compositions of the present invention comprise another aspect of the present invention. Such kits will generally contain, in suitable container means, an APF derivative molecule of the present invention. The kit may have a single container means that contains the APF derivative composition or it may have distinct container means for the APF derivative composition and other reagents that may be included within such kits.

The components of the kit may be provided as liquid solution(s), or as dried powder(s). When the components are provided in a liquid solution, the liquid solution is an aqueous or non-aqueous solution, with a sterile aqueous or non-aqueous solution being particularly preferred. When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the composition may be placed, and preferably suitably aliquoted. Where a second agent is provided, the kit will also generally contain a second vial or other container into which this agent may be placed. The kits of the present invention will also typically include a means for containing the agent containers in close confinement for commercial sale. Such containers may include injection or blow-molded plastic containers into which the desired vials are retained, for example.

In certain aspects, the kit further comprises one or more reagents or apparatuses for diagnosis of cancer or bladder condition and/or one or more additional reagents for treatment of cancer or bladder disorder.

X. METHODS OF MANUFACTURING APF DERIVATIVES

APF and derivatives of APF may be generated in a variety of methods. The following describes exemplary methods for manufacturing particular compositions of the present invention, and it is known in the art how to make particular manipulations of these methods to obtain other APF derivative compounds. Although the present invention generally concerns derivatives of APF, in specific embodiments naturally occurring APF is isolated by methods known in the art (see at least Keay et al., 2000). For example, APF may be harvested from the supernatant of explanted patient bladder epithelial cells and purified using molecular weight fractionation, ion exchange chromatography, hydrophobic interaction chromatography, and reversed-phase high-performance liquid chromatography (HPLC), as described (Keay et al., 2000).

Manufacturing derivatives of APF may occur using a variety of techniques, but this section describes particular embodiments of doing so, as follows.

In certain embodiments, the synthesis of the peptides is carried out by solid phase methods on the Nautilus 2400 synthesizer (Argonaut Technologies, Foster City, Calif.) utilizing standard Fmoc chemistry on alanyl 2-chlorotrityl resin (Calbiochem-Novobiochem). Fmoc-protected amino acids (Anaspec Inc., San Jose, Calif.) were coupled utilizing N-{(dimethylamino)-1H-1,2,3-triazolo[4,5-b]pyridin-1-ylmethylene}-N-methylmethanaminium hexafluorophosphate N-oxide (HATU) (Sigma-Aldrich, Milwaukee, Wis.) and 1-hydroxy-7-azabenzotriazole (HOAt) (Anaspec, Inc.) reagents. All other reagents were purchased from Sigma-Aldrich. All intermediates and the final products were verified by mass spectrometry.

Fmoc protected O-α-(N-acetyllactosamine)-L-Threonine. Fmoc-L-Thr (Calbiochem-Novabiochem) was converted to phenacyl ester and glycosylated with 2-azido-1-α-bromo-hexa-O-acetyl-2-deoxylactose in the presence of silver triflate according to a slight modification of the procedure by Leuck and Kunz (Leuck and Kunz, 1997). The reaction was carried out a −40° C. that ensured >98% selectivity for the α-anomer. The anomeric purity was determined by proton NMR spectroscopy. The phenacyl ester was de-protected by zinc/acetic acid/acetic anhydride, which also resulted in the simultaneous reduction of the azido group and acetylation of the resulting amino group (Svarovsky and Barchi, 2003). The final product was purified by preparative, reverse phase (C8 column) HPLC.

Fmoc protected O-β-(N-acetyllactosamine)-L-Threonine. The procedure for production of the β anomer was identical to that for production of the α anomer except that the glycosylation of threonine by 2-azido-1-α-bromo-hexa-O-acetyl-2-deoxylactose was carried out at −20° C. The product generated by this procedure was a mixture of the α (90%) and β (10%) anomers, which were readily separated by silica gel flash chromatography using an ethyl acetate/hexanes gradient.

Fmoc protected O-α-[Galβ(1→3)GalNAc]-L-Threonine. The synthetic procedure was similar to the method used to produce the Fmoc protected O-α-(N-acetyllactosamine)-L-Threonine. Fmoc-L-Threonine phenacyl ester was glycosylated by the trichloroacetimidate-disaccharide donor in the presence of boron trifluoride diethyl etherate, following the procedure published by Qiu et al. (Qiu et al., 1996) with slight modifications. The conversion of the azido group and the deprotection of the phenacyl ester were identical to the procedures used in the Fmoc protected O-α-(N-acetyllactosamine)-L-Threonine synthesis.

General method for glycopeptide synthesis. The glycosylated Fmoc-protected threonine was activated by HATU/HOAt and added to the growing peptide chain in presence of Hunig's base for a prolonged coupling time (16 hours). The glycopeptide was cleaved from the resin with a mixture of trifluoroacetic acid, water, tri-isopropylsilane (90:5:5 v/v/v), the solvent was removed in vacuo, and the residue was dried under high vacuum. The crude, dry glycopeptide was dissolved in anhydrous methanol and treated with sodium methoxide powder for 30 min. When HPLC-MS indicated the complete removal of the acetyl groups, the reaction was stopped with acetic acid and evaporated to dryness. The crude deacetylated product was purified by preparative HPLC using a C8 reverse phase column.

Sialylation of N-terminal threonine hexosamine residue. The N-acetylhexosamine derivatives of the peptides were sialylated enzymatically using recombinant rat α-2,3 (N) sialyltransferase (EMD Biosciences, Inc., La Jolla, Calif.) and CMP-N-acetyl neuraminic acid substrate (Sigma) in 250 mM MOPS buffer pH 7.4. All crude glycopeptides were purified by reverse phase HPLC on a C8 column, and the purified peptides were analyzed by mass spectrometry.

Synthesis of APF derivatives. The synthesis of the peptide segments of the glycopeptides were carried out in 0.1 mM scale by solid-phase methods by using standard Fmoc chemistry on 2ClTrt resin. Protected amino acids (0.5 mmol) were coupled using HATU (0.5 mmol) and HOAt (0.5 mmol) reagents in the presence of DIPEA (1.0 mmol). The Fmoc group was removed with 20% piperidine in NMP, and a mixture of BEP/HOAt/DIPEA (0.05 mmol/0.05 mmol/0.15 mmol) in NMP was used for coupling of Fmoc-Thr(Ac$_4$Galβ1-3Ac$_2$GalNAcα-O—)—OH or Fmoc-Ser(Ac$_4$Galβ1-3Ac$_2$GalNAcα-O—)—OH (0.05 mmol) to the peptide chain. Acetyl groups were removed on the solid support using 10% hydrazine monohydrate in MeOH (Arya et al., 2002) and each glycopeptide was cleaved from the resin with TFA/DCM/H$_2$O (50/49/1) or TFA/H$_2$O (95/5). All intermediates and the final products were verified by HPLC-MS; purity of >95% was confirmed for all compounds by HPLC trace analysis at 227 nm (see Supporting Information). Glycopeptides were purified by RP-HPLC on either a C$_8$ or C$_{18}$ column with gradient elution with H$_2$O (0.1% TFA) and MeCN (0.1% TFA).

Synthesis of Glycopeptide 5. The glycopeptide was synthesized using the general procedure described above. After the attachment of Fmoc-Thr(Ac4Galβ1-3Ac2GalNAcα-O—)—OH, the Fmoc group was removed with 20% piperidine in NMP and the deprotected amino group was acetylated using Ac$_2$O/DIPEA (2:5) in DCM.

Synthesis of Glycopeptide 9. The synthesis of glycopeptide 9 was performed using the same general procedure described above with the exception that the Val-Ser(ΨPMe, Me pro) segment was coupled as a dipeptide unit. To protect the pseudoproline unit, the glycopeptide was cleaved from the resin using a TFE/DCM (2/8) mixture.

Synthesis of Glycopeptide 13. The general procedure described above was used to synthesize 13, which was then cleaved from the resin using a TFE/DCM (2:8) mixture to maintain the protective groups on the Hyp moiety.

Synthesis of Glycopeptide 14. The glycopeptide was synthesized as described above with the exception that coupling of the amino acid that precedes the N-methyl amino acid in the sequence was repeated twice.

Synthesis of Glycopeptide 29. This compound was synthesized using the general procedure described above except that it was performed on a Rink Amide resin. Prior to the first coupling step, the Fmoc group was removed with 20% piperidine in NMP.

Synthesis of Glycopeptide 35. After the acylation of the 2ClTrt resin with Dde-Lys(Fmoc)-OH, the Fmoc group was removed and the deprotected amino group was acetylated using a Ac$_2$O(2 mmol)/DIPEA(5 mmol) mixture in dry DCM. The Dde group was then removed with 2% hydrazine in DMF, and synthesis of the remaining glycopeptide was performed using the general method described above.

Synthesis of Cyclic Glycopeptide 36. Ac$_4$Galβ1-3Ac$_2$GalNAcα-O-TVPAAVVVA (SEQ ID NO:1) was synthesized using the general procedure described above on 2ClTrt resin. The Fmoc group was removed with 20% piperidine in NMP and the glycopeptide was cleaved off using TFA/DCM/H$_2$O (50/49/1). After HPLC purification of the crude glycopeptide, 30 mg (0.02 mmol) was dissolved in 2:1 DCM/DMF (45 ml) and stirred for 24 h in the presence of PyAOP/HOAt/DIPEA (0.1 mmol/0.1 mmol/0.1 mmol). The formation of 33 was then confirmed by HPLC-MS. Following evaporation of the solvent, the glycopeptide was dissolved in H$_2$O/MeCN and lyophilized. After additional HPLC purification the glycopeptide was dissolved in 10% hydrazine monohydrate in MeOH. All acetyl groups were then removed, the solution was neutralized with AcOH and evaporated. The dry glycopeptide was then dissolved in AcOH/H$_2$O/MeCN and lyophilized. Further HPLC purification led to pure 36 (5.5 mg, 23% yield).

XI. EXAMPLES

The following examples are included to demonstrate preferred embodiments of the invention. It should be appreciated by those of skill in the art that the techniques disclosed in the examples which follow present techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Therapeutic Embodiments with APF

In certain embodiments, prostate cancer cells (such as the exemplary LNCaP cells) are treated with APF compositions. LNCaP cells were plated at $2\times10^4$ cells per well of a 24 well tissue culture plate in DMEM medium containing 10% fetal bovine serum, 1% L-glutamine, 1% antibiotic/antimycotic solution, and grown at 37° C. in a 5% $CO_2$ atmosphere. The next day the medium was changed to DMEM containing the same additives except without fetal bovine serum, after which HPLC-purified APF or an equivalent amount of mock APF was added to each well. Live cell counts were performed on Day 3 of incubation by trypan blue exclusion. Values are the percent decrease in cell count compared to cell control given medium alone, and are given as the mean of triplicate wells; vertical lines are the standard deviation. The cells were sensitive to the antiproliferative activity of native purified APF (FIG. 1).

The APF composition may be delivered to the individual by any suitable means. In specific embodiments of the present invention, the APF composition is comprised as an oral medication and/or is delivered via a catheter, orally, intravenously, topically, subcutaneously, transcutaneously, intramuscularly, intraarticularly, parenterally, peritoneally, intranasally, intravesically, vaginally, rectally, or by inhalation, for example. A sufficient amount may be delivered directly to bladder tissue or it may be delivered systemically. A sufficient amount is one that ameliorates when given alone or in combination with other agents or other types of therapy at least one symptom or objective finding of the bladder cancer, and a skilled artisan recognizes standard methods to determine such an amount.

Example 2

Structure-Activity Relationship Studies for the Peptide Portion of Antiproliferative Factor The present example concerns exemplary comprehensive structure-activity relationship (SAR) studies on the peptide portion of antiproliferative factor (APF). For example, glycopeptide derivatives were synthesized by solid-phase methods using standard Fmoc chemistry and purified by RP-HPLC; all intermediate and final products were verified by HPLC-MS and NMR analysis. Antiproliferative activity of each derivative was determined by inhibition of $^3$H-thymidine incorporation in primary normal human bladder epithelial cells. Structural components of the peptide segment of APF that proved to be important for biological activity included the presence of at least 8 of the 9 N-terminal amino acids, a negative charge in the C-terminal amino acid, a free amino group at the N-terminus, maintenance of a specific amino acid sequence in the C-terminal tail, and trans conformation for the peptide bonds. These data provide exemplary guidelines for particular APF analogues as therapeutic agents, particularly for cancer treatment and/or prevention.

A variety of techniques including total synthesis were previously used to identify APF as a nonapeptide (TVPAAV-VVA; SEQ ID NO:1) containing a 2,3-sialylated core 1 α-O-linked disaccharide (Galβ1-3Gal NAc, the Thomsen-Friedenreich antigen, or "$TF_{ag}$") linked to the N-terminal threonine residue (i.e., Neu5Acα2-3Galβ1-3GalNAcα-O-TVPAAVVVA (SEQ ID NO:1)) (Keay et al., 2004). Preliminary SAR information obtained during the original complete characterization and synthesis of APF indicated that the terminal sialic acid residue is not necessary for activity, but that the α-linked TF-disaccharide of the peptide is required (i.e., Galβ1-3GalNAcβ-O-TVPAAVVVA (SEQ ID NO:1) and the nonglycosylated nonapeptide were completely inactive) (Keay et al., 2004). Additional extensive SAR studies on the peptide portion of the APF molecule are provided to characterize certain structural elements that are useful for antiproliferative activity. The synthesis of congeners (for which the term "congener" may be used interchangeably with the term "derivative") comprising structural modifications to the peptide portion of APF (TVPAAVVVA; SEQ ID NO:1), and the effects of these modifications on the biological activity of APF, are presented.

It was determined whether changes to certain structural aspects of the peptide segment influenced the biological activity of APF by systematically replacing or modifying amino acids residues from the N-to-C termini of the sequence. Derivatives are grouped based on amino acid substitutions or modifications made in 3 separate segments of APF: the N-terminal Thr-Val segment (Table 1), the Pro-Ala segment (Table 2), and the C-terminal tail (AVVVA; SEQ ID NO:10) segment (Tables 3-5). L-amino acids were used for the synthesis of all derivatives unless otherwise indicated.

TABLE 1

Substitutions or modifications of the N-terminus (Thr$^1$-Val$^2$)

| No | Derivative |
| --- | --- |
| 1 | 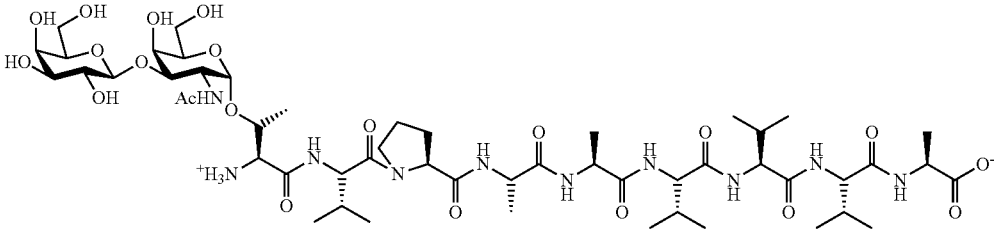<br>Galβ1-3GalNAcα-O-TVPAAVVVA |

TABLE 1-continued
Substitutions or modifications of the N-terminus (Thr¹-Val²)
2 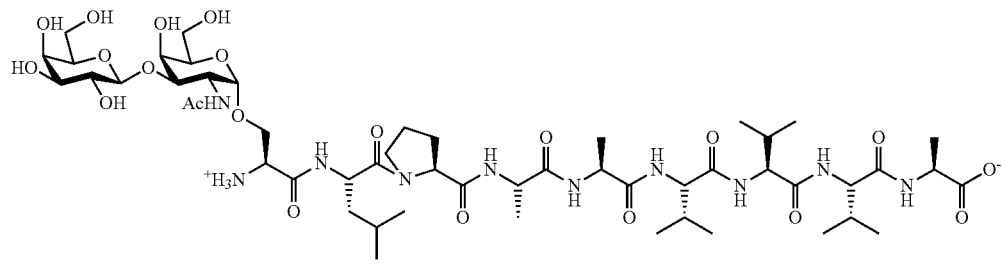
Galβ1-3GalNAcα-O-SLPAAVVVA
3 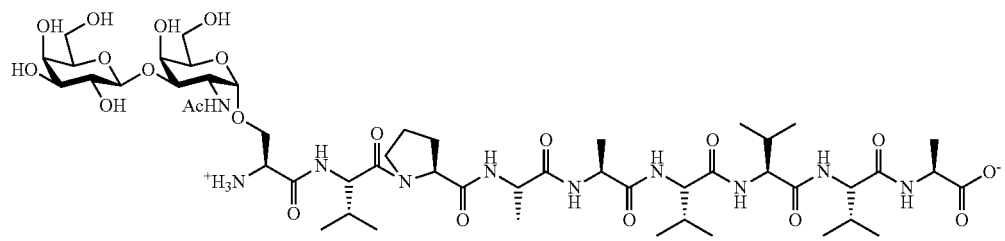
Galβ1-3GalNAcα-O-SVPAAVVVA
4 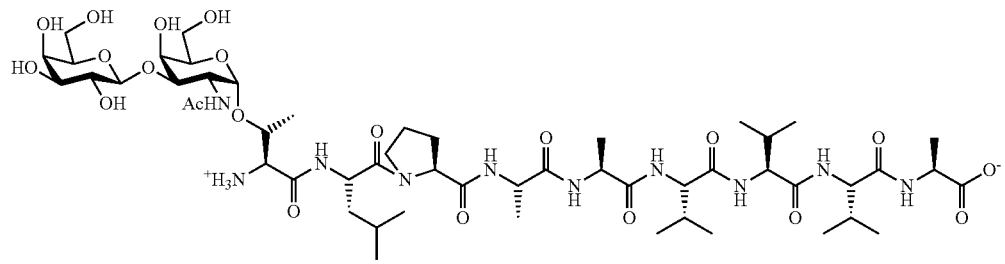
Galβ1-3GalNAcα-O-TLPAAVVVA
5 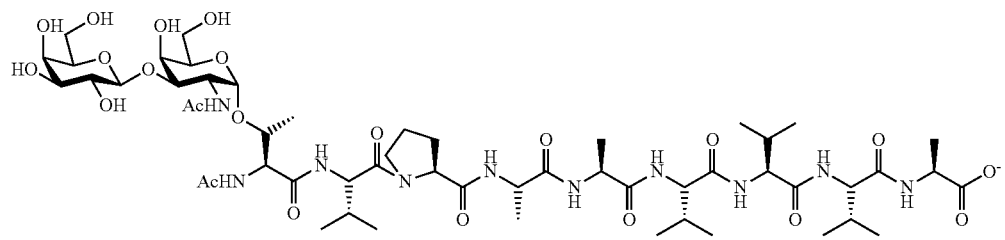
Ac-T(Galβ1-3GalNAcα-O-)VPAAVVVA
6 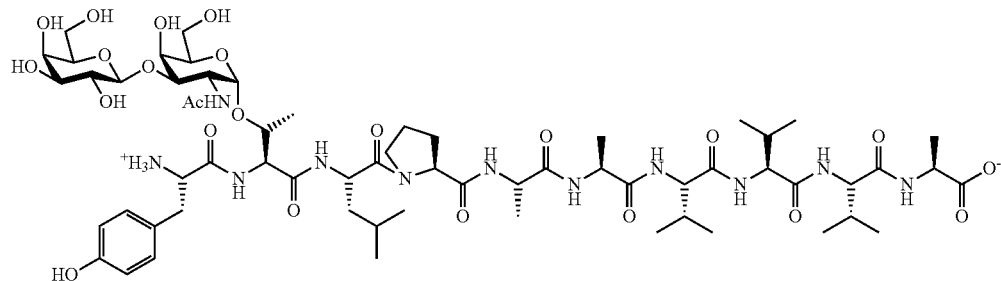
YT(Galβ1-3GalNAcα-O-)VPAAVVVA TABLE 1-continued Substitutions or modifications of the N-terminus (Thr[1]-Val[2])

7 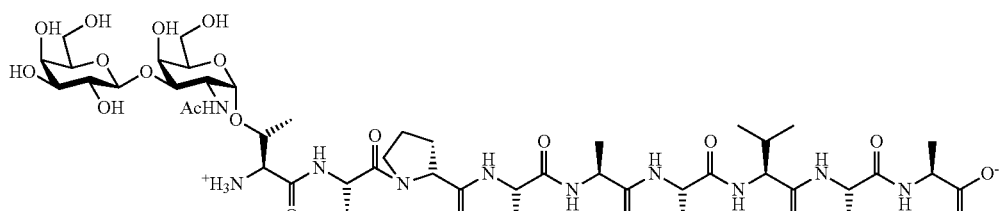

Galβ1-3GalNAcα-O-TYPAAVVVA

| No | SEQ ID NO: of peptide of Derivative | % of activity [a] | P value [b] |
|---|---|---|---|
| 1 | 1 | * | * |
| 2 | 5 | 1% | <0.001 |
| 3 | 3 | 0.01% | <0.001 |
| 4 | 6 | inactive | |
| 5 | 28 | 0.7% | <0.001 |
| 6 | 29 | 1% | <0.001 |
| 7 | 30 | inactive | |

[a] Due to the variability of the primary normal bladder epithelial cell response in the biological assay, the activity of each congener was normalized to the activity of 1 run simultaneously on the same plate according to the equation:

$$\% = \frac{\overline{IC_{50}}(APF)}{\overline{IC_{50}}(\text{derivative})} \cdot 100\%;$$

the average $IC_{50}$ value of 1 was ~1 nM. Percent of activity is expressed relative to 1 which served as a standard control on each plate. Derivatives with no significant activity at <25 μM concentration (the cut-off limit for the biological assay) were considered to be inactive.
[b] NS = not significant at p > 0.05

TABLE 2

Substitutions or modifications of the Pro[3]-Ala[4] segment

| No | Derivative |
|---|---|
| 8 | 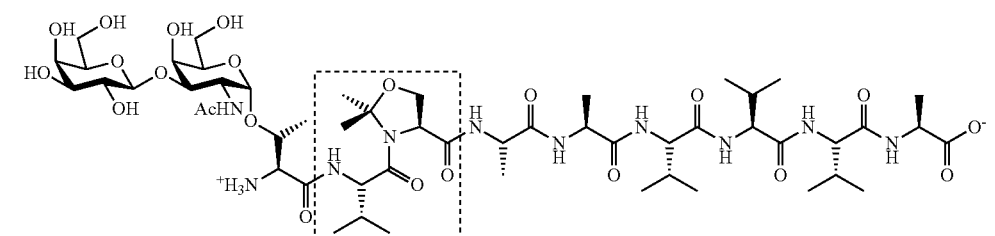 |

Galβ1-3GalNAcα-O-TV-D-Pro-AAVVVA

9 pseudo proline dipeptide

Galβ1-3GalNAcα-O-TVS(ψ$^{Me,Me}$pro)AAVVVA

TABLE 2-continued
Substitutions or modifications of the Pro³-Ala⁴ segment
10 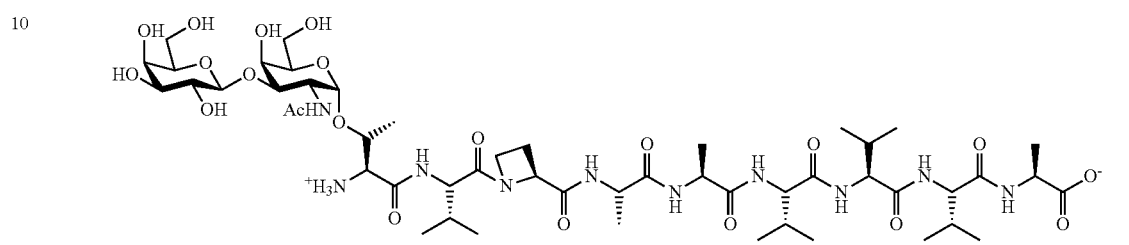
Galβ1-3GalNAcα-O-TV-Aze-AAVVVA
11 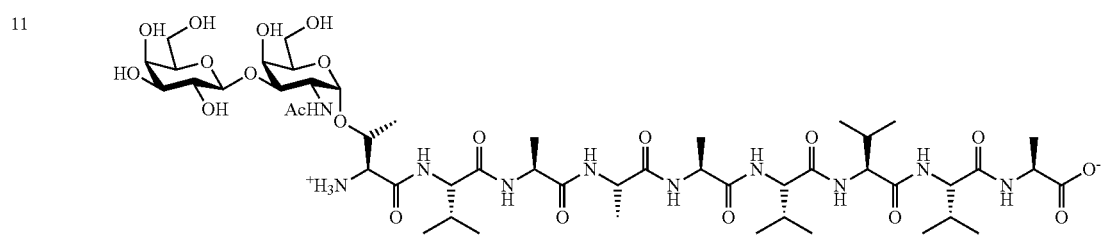
Galβ1-3GalNAcα-O-TVAAAVVVA
12 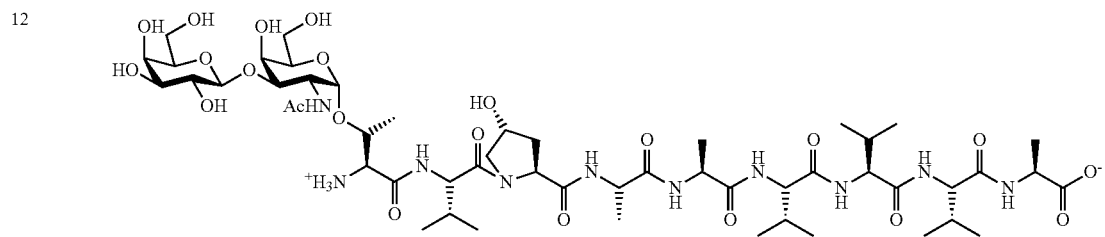
Galβ1-3GalNAcα-O-TV-Hyp-AAVVVA
13 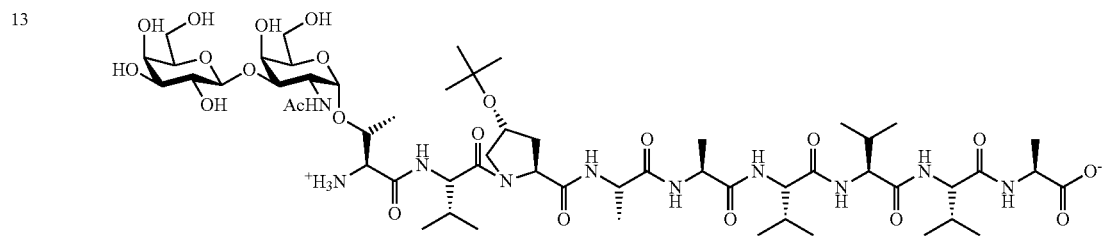
Galβ1-3GalNAcα-O-TV-Hyp(ᵗBu)-AAVVVA
14 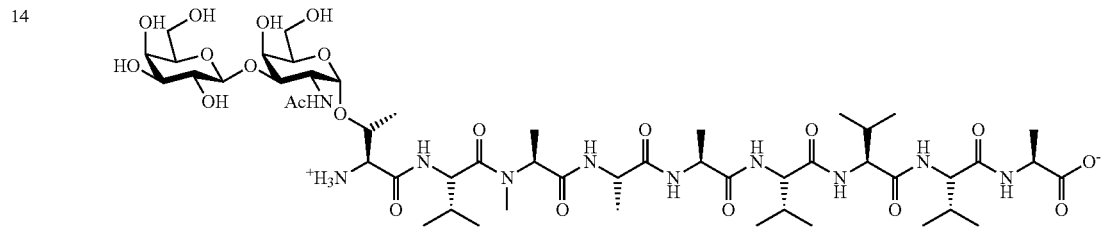
Galβ1-3GalNAcα-O-TV-N-MeAla-AAVVVA TABLE 2-continued Substitutions or modifications of the Pro³-Ala⁴ segment 15 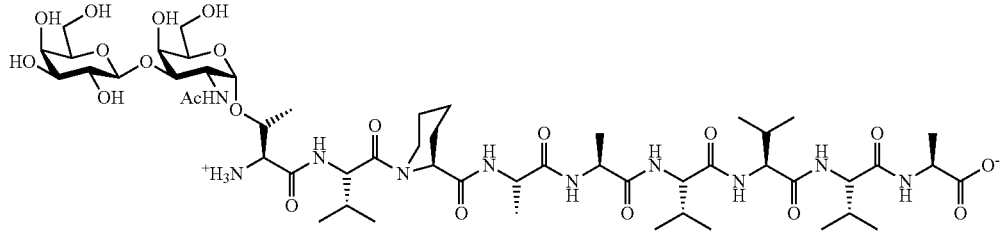

Galβ1-3GalNAcα-O-TV-Pip-AAVVVA

| No | SEQ ID NO: of peptide of Derivative | % of activity [a] | P value [b] |
|---|---|---|---|
| 8 | 27 | inactive | |
| 9 | 32 | inactive | |
| 10 | 24 | inactive | |
| 11 | 33 | 0.3% | <0.001 |
| 12 | 23 | 0.3% | <0.001 |
| 13 | 34 | 0.2% | <0.001 |
| 14 | 35 | 0.05% | <0.001 |
| 15 | 15 | 100% | NS |

[a] Due to the variability of the primary normal bladder epithelial cell response in the biological assay, the activity of each congener was normalized to the activity of 1 run simultaneously on the same plate according to the equation:

$$\% = \frac{IC_{50}(APF)}{IC_{50}(derivative)} \cdot 100\%;$$

the average $IC_{50}$ value of 1 was ~1 nM. Percent of activity is expressed relative to 1 which served as a standard control on each plate. Derivatives with no significant activity at <25 μM concentration (the cut-off limit for the biological assay) were considered to be inactive.
[b] NS = not significant at p > 0.05.

TABLE 3

Substitution of AAVVVA (SEQ ID NO: 7) with 12-aminododecanoic acid and truncated glycopeptides

| No | Derivative |
|---|---|
| 16 | 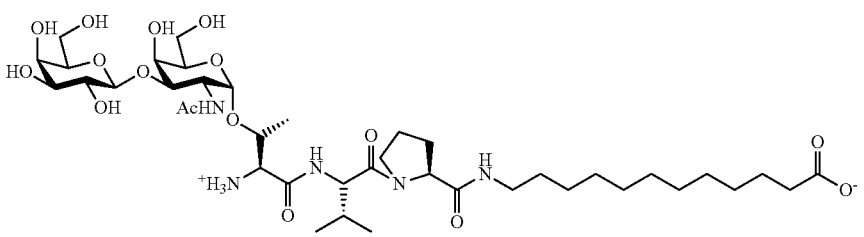<br>Galβ1-3GalNAcα-O-TVP-12-Ado |
| 17 | 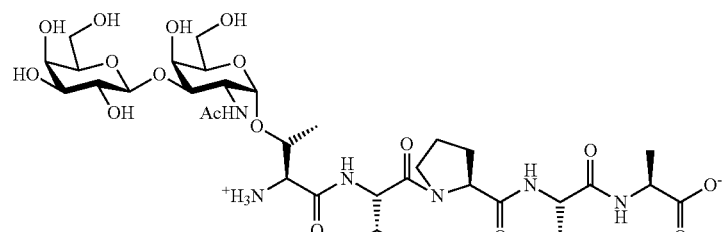<br>Galβ1-3GalNAcα-O-TVPAA |

TABLE 3-continued

Substitution of AAVVVA (SEQ ID NO: 7) with 12-aminododecanoic acid and truncated glycopeptides 18 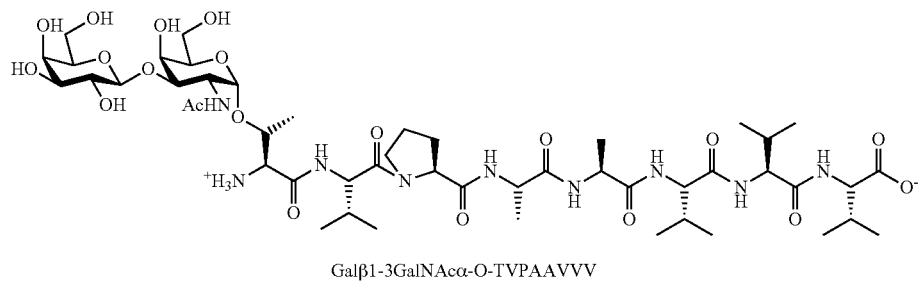

Galβ1-3GalNAcα-O-TVPAAVVV

19 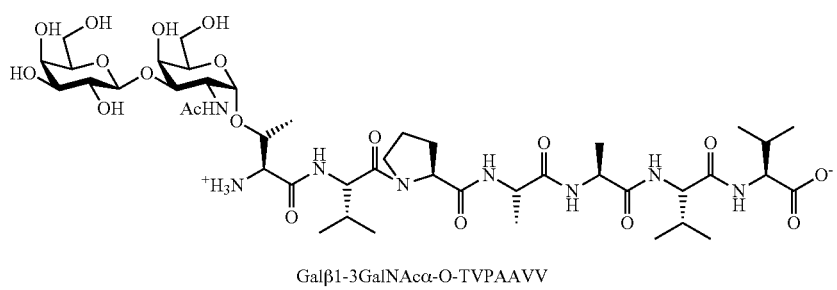

Galβ1-3GalNAcα-O-TVPAAVV

| No | SEQ ID NO: of peptide of Derivative | % of activity [a] | P value [b] |
|---|---|---|---|
| 16 | 36 | inactive | |
| 17 | 37 | inactive | |
| 18 | 19 | 100% | NS |
| 19 | 20 | inactive | |

[a] Due to the variability of the primary normal bladder epithelial cell response in the biological assay, the activity of each congener was normalized to the activity of 1 run simultaneously on the same plate according to the equation:

$$\% = \frac{\overline{IC_{50}}(APF)}{\overline{IC_{50}}(derivative)} \cdot 100\%;$$

the average $IC_{50}$ value of 1 was ~1 nM. Percent of activity is expressed relative to 1 which served as a standard control on each plate. Derivatives with no significant activity at <25 μM concentration (the cut-off limit for the biological assay) were considered to be inactive.

[b] NS = not significant at p > 0.05.

TABLE 4

Substitutions of C-terminal amino acids 5-9 (AVVVA; SEQ ID NO: 10)

| No | Derivative |
|---|---|

20 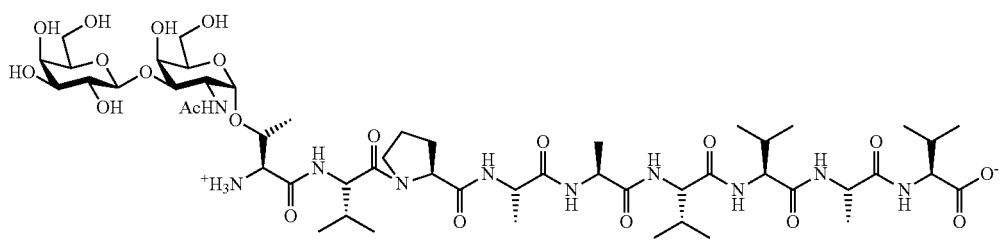

Galβ1-3GalNAcα-O-TVPAAVVAV

TABLE 4-continued
Substitutions of C-terminal amino acids 5-9 (AVVVA; SEQ ID NO: 10)
21 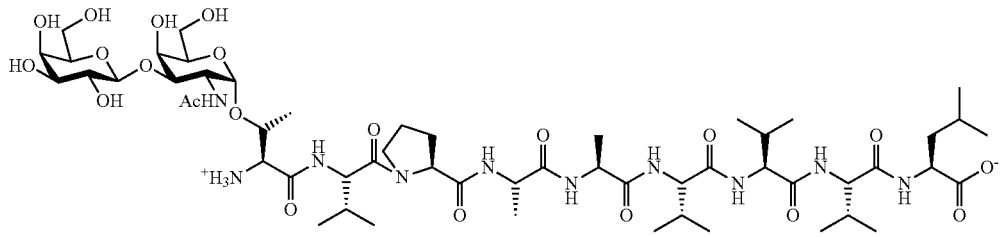
Galβ1-3GalNAcα-O-TVPAAVVVL
22 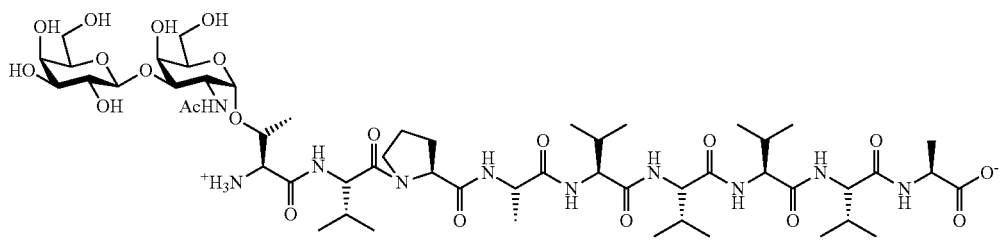
Galβ1-3GalNAcα-O-TVPAVVVVA
23 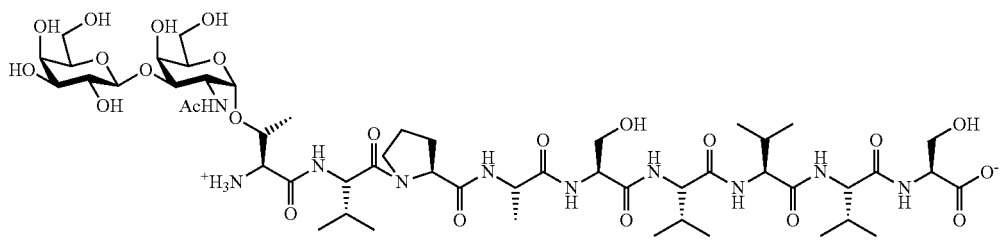
Galβ1-3GalNAcα-O-TVPASVVVS
24 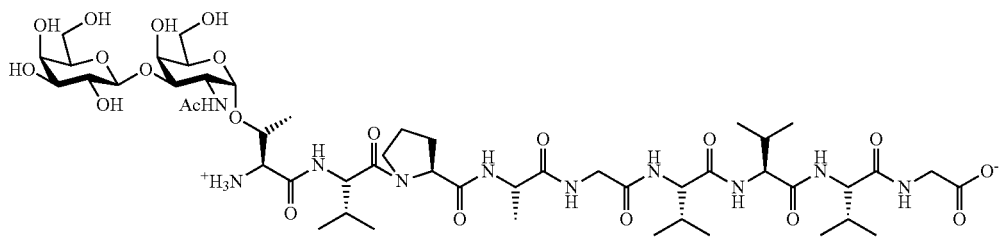
Galβ1-3GalNAcα-O-TVPAGVVVG
25 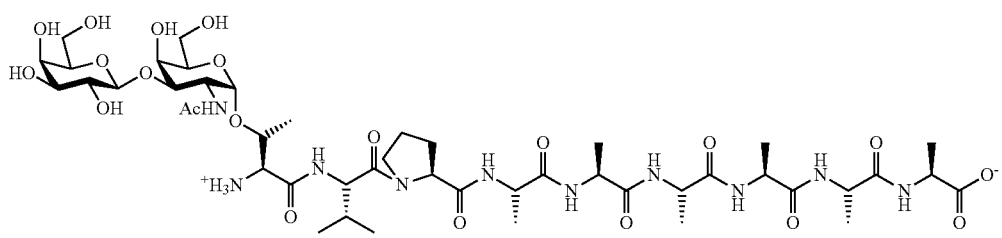
Galβ1-3GalNAcα-O-TVPAAAAAA

TABLE 4-continued

Substitutions of C-terminal amino acids 5-9 (AVVVA; SEQ ID NO: 10)

26 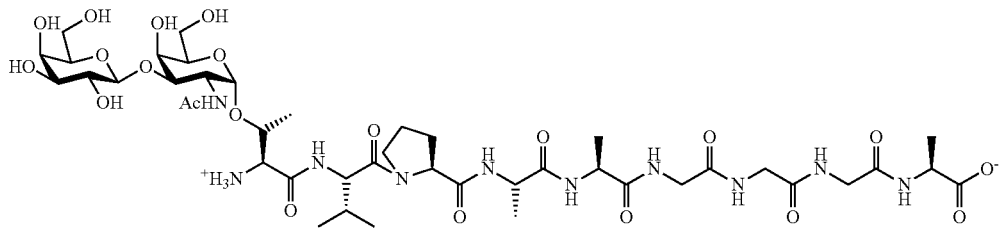

Galβ1-3GalNAcα-O-TVPAAGGGA

27 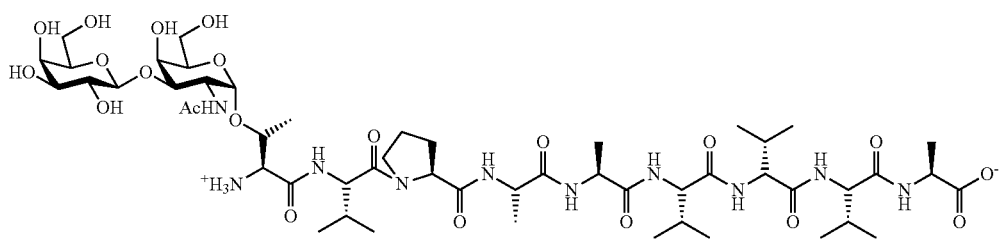

Galβ1-3GalNAcα-O-TVPAAV-D-Val-VA

28 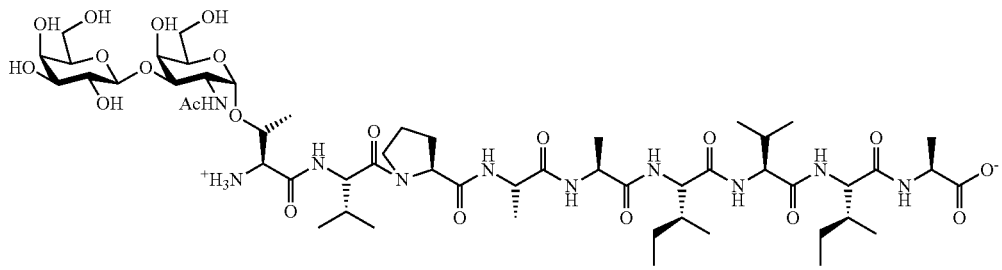

Galβ1-3GalNAcα-O-TVPAAIVIA

| No | SEQ ID NO: of peptide of Derivative | % of activity [a] | P value [b] |
|---|---|---|---|
| 20 | 38 | inactive | |
| 21 | 39 | 0.01% | <0.001 |
| 22 | 40 | inactive | |
| 23 | 41 | 0.2% | <0.001 |
| 24 | 42 | inactive | |
| 25 | 18 | 1% | <0.001 |
| 26 | 8 | 0.01% | <0.001 |
| 27 | 43 | inactive | |
| 28 | 44 | inactive | |

[a] Due to the variability of the primary normal bladder epithelial cell response in the biological assay, the activity of each congener was normalized to the activity of 1 run simultaneously on the same plate according to the equation:

$$\% = \frac{IC_{50}(APF)}{IC_{50}(derivative)} \cdot 100\%;$$

the average $IC_{50}$ value of 1 was ~1 nM. Percent of activity is expressed relative to 1 which served as a standard control on each plate. Derivatives with no significant activity at <25 μM concentration (the cut-off limit for the biological assay) were considered to be inactive.
[b] NS = not significant at p > 0.05.

TABLE 5

Modifications of the C-terminus

| No | Derivative | SEQ ID NO: of peptide of Derivative | % of activity[a] | P value[b] |
|---|---|---|---|---|
| 29 | Galβ1-3GalNAcα-O-TVPAAVVVA-CONH$_2$ | 45 | 0.3% | <0.001 |
| 30 | Galβ1-3GalNAcα-O-TVPAAVVVAC | 46 | 1% | <0.001 |

TABLE 5-continued

Modifications of the C-terminus

| No | Derivative | SEQ ID NO: of peptide of Derivative | % of activity [a] | P value [b] |
|---|---|---|---|---|
| 31 | Galβ1-3GalNAcα-O-TVPAAVVVAK(Dansyl) | 26 | 100% | NS |
| 32 | Galβ1-3GalNAcα-O-TVPAAVVVAE | 47 | inactive | |

TABLE 5-continued

Modifications of the C-terminus

| No | Derivative | SEQ ID NO: of peptide of Derivative | % of activity[a] | P value[b] |
|---|---|---|---|---|
| 33 | Galβ1-3GalNAcα-O-TVPAAVVVAK | 48 | inactive | |
| 34 | Galβ1-3GalNAcα-O-TVPAAVVVAE(O^tBu) | 49 | 0.01% | <0.001 |

TABLE 5-continued

Modifications of the C-terminus

| No | Derivative | SEQ ID NO: of peptide of Derivative | % of activity [a] | P value [b] |
|---|---|---|---|---|
| 35 | Galβ1-3GalNAcα-O-TVPAAVVVAK(Ac) | 25 | 0.05% | <0.001 |
| 36 | cyclo(1-9)Galβ1-3GalNAcα-O-TVPAAVVVA | 1 | inactive | |

[a] Due to the variability of the primary normal bladder epithelial cell response in the biological assay, the activity of each congener was normalized to the activity of 1 run simultaneously on the same plate according to the equation:

$$\% = \frac{IC_{50}(APF)}{IC_{50}(derivative)} \cdot 100\%;$$

the average $IC_{50}$ value of 1 was ~1 nM. Percent of activity is expressed relative to 1 which served as a standard control on each plate. Derivatives with no significant activity at <25 μM concentration (the cut-off limit for the biological assay) were considered to be inactive.

[b] NS = not significant at p > 0.05.

Figure 2:
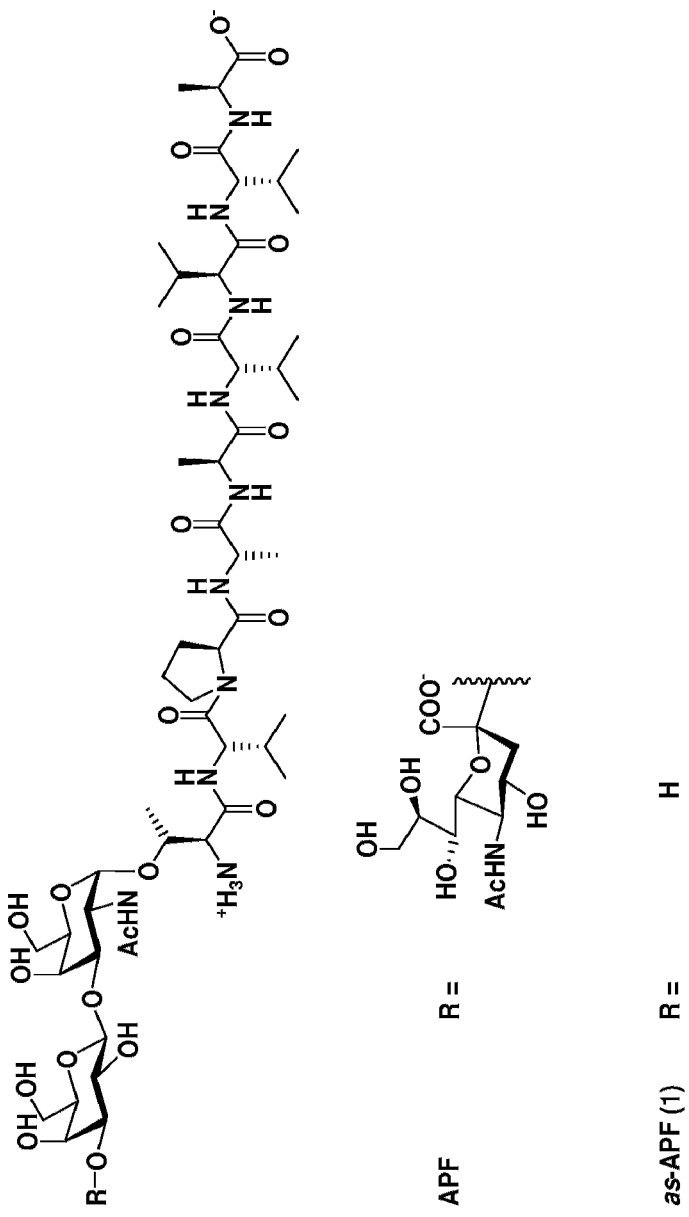
FIG. 2 provides structures of APF and as-APF.

It was previously determined that the endobiotic factor (Neu5Acα2-3Galβ1-3GalNAcα-O-TVPAAVVVA (SEQ ID NO:1), FIG. 2), the nonsialylated analogue (Galβ1-3GalNAcα-O-TVPAAVVVA (SEQ ID NO:1), 1), the sialylated compound with a lactosamine unit in place of the $TF_{ag}$ disaccharide α-O-linked to threonine (Neu5Ac α 2-3Galβ1-4-GlcNAcα-O-TVPAAVVVA (SEQ ID NO:1)), the sialylated compound with a lactosamine unit and substitution of the first two amino acids Thr-Val with Ser-Leu (Neu5Acα2-3Galβ1-4GlcNAcα-O-SLPAAVVVA; SEQ ID NO:3), and the same compound in nonsialylated form (Galβ1-4GlcNAcα-O-SLPAAVVVA; SEQ ID NO:3), are all essentially equipotent in biological antiproliferation assays. Based on these results, activity for each analogue described herein was compared simultaneously to activity of the most synthetically accessible of these analogs, the nonsialylated form of the endobiotic (Galβ1-3GalNAcα-O-TVPAAVVVA (SEQ ID NO:1), 1) hereafter referred to as asialo-APF, or "as-APF".

Modifications to the N-Terminus ($Thr^1$-$Val^2$)

Figure 3:
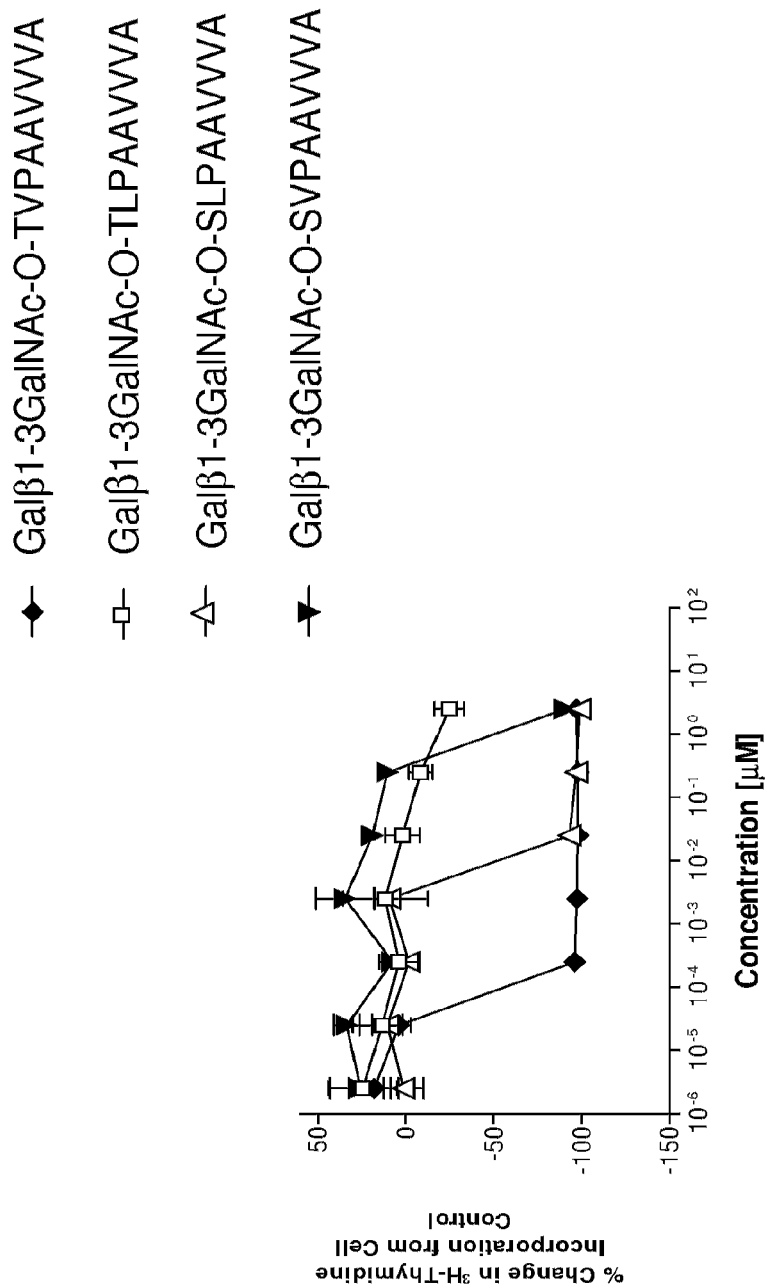
FIG. 3 shows antiproliferative activity of specific APF derivatives (modifications to the N terminus). Inhibition of tritiated thymidine incorporation by primary normal bladder epithelial cells was determined for each derivative at the concentrations indicated. Experiments were run in triplicate on two separate occasions. Data are expressed as the mean percent change in thymidine incorporation relative to a cell control treated with diluent (acetonitrile: $H_2O$ at 1:1) alone; bars indicate standard error of the mean for all six data points, wherein TVPAAVVVA is SEQ ID NO:1; TLPAAVVVA is SEQ ID NO:6; SVPAAVVVA is SEQ ID NO:3; and SLPAAVVVA is SEQ ID NO:5.

The threonine-valine in 1 was replaced with serine-leucine, an "isosteric" substitution that maintained identical atomic mass while essentially "transferring" a methylene unit from the N-terminal threonine to $Val^2$ (2, Table 1), resulting in a derivative similar to the Galβ1-4GlcNAcα-O-SLPAAVVVA (SEQ ID NO:3) derivative described previously (Keay et al., 2004). This modification resulted in two orders of magnitude loss of potency (Table 1) (FIG. 3). In comparison, simple removal of the threonine methyl group in this location (i.e., the lone substitution of $Thr^1$ with Ser, 3) resulted in even greater (4 orders of magnitude) loss of activity as compared to the parent as-APF molecule 1, and the lone substitution of $Val^2$ with Leu (4) resulted in inactivation (Table 1) (FIG. 3). These results indicate that the number and positioning of methyl groups in this location are useful for as-APF activity.

Certain other minor modifications to the N-terminal two amino acids also affected as-APF activity (Table 1). For example, acetylation of the N-terminal threonine (5), and extension of the peptide sequence with Tyr (a preceding amino acid in the sequence of frizzled-8 protein, (Saitoh et al., 2001) 6) both resulted in approximately 2 orders of magnitude loss of potency, providing evidence for the utility of the threonine amino group, in a specific embodiment. Interestingly, replacement of $Val^2$ with Tyr (7) resulted in complete inactivation of as-APF, indicating that the sidechain of the amino acid in this location is useful for activity, in a particular aspect.

Modifications to $Pro^3$-$Ala^4$

Figure 4:
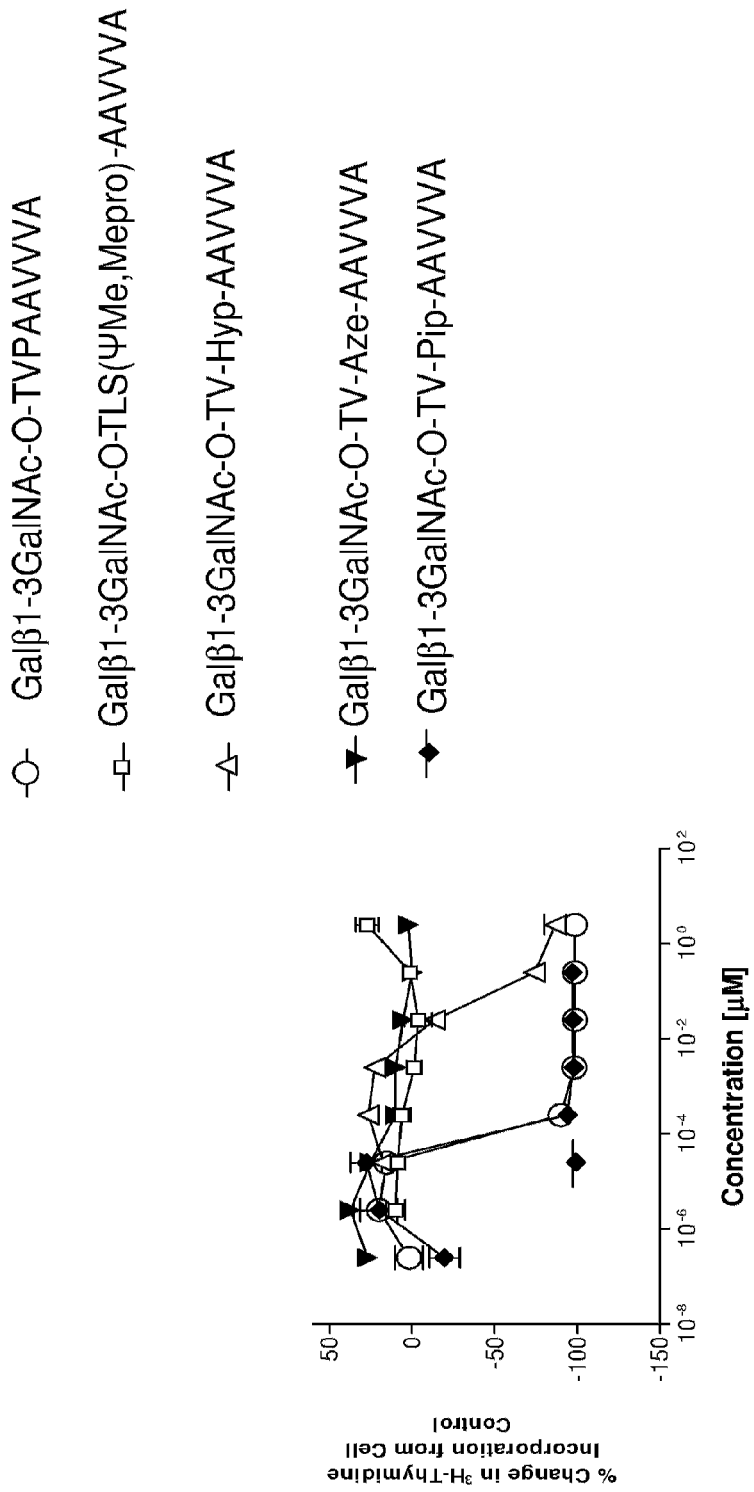
FIG. 4 provides antiproliferative activity of specific APF derivatives (modifications to Pro$^3$-Ala$^4$). Inhibition of tritiated thymidine incorporation by primary normal bladder epithelial cells was determined for each derivative at the concentrations indicated. Experiments were run in triplicate on two separate occasions. Data are expressed as the mean percent change in thymidine incorporation relative to a cell control treated with diluent (acetonitrile: $H_2O$ at 1:1) alone; bars indicate standard error of the mean for all six data points, wherein TVPAAVVVA is SEQ ID NO:1; TLS$^{(\Psi Mc, Mc}$pro)-AAVVVA is SEQ ID NO:22; TV-Hyp-AAVVVA is SEQ ID NO:23; TV-Aze-AAVVVA is SEQ ID NO:24, and TV-Pip-AAVVVA is SEQ ID NO:15.
Figure 5:
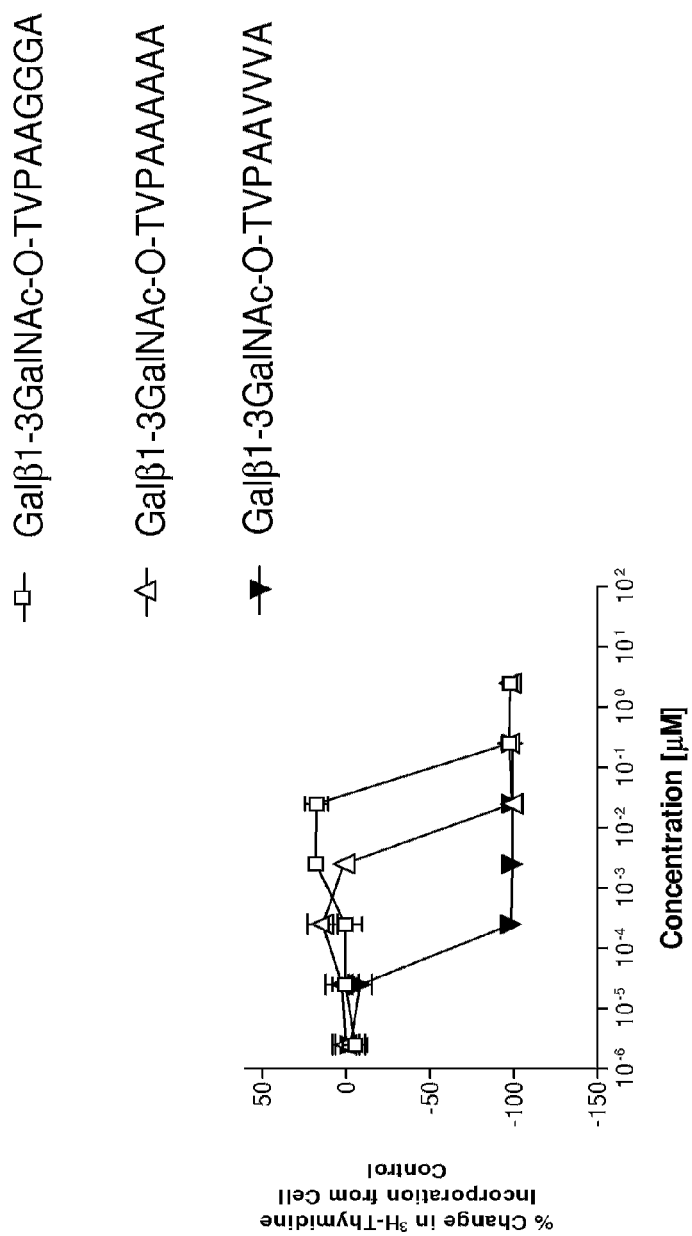
FIG. 5 demonstrates antiproliferative activity of specific APF derivatives (changes in amino acids 6-8 (VVV)). Inhibition of tritiated thymidine incorporation by primary normal bladder epithelial cells was determined for each derivative at the concentrations indicated. Experiments were run in triplicate on two separate occasions. Data are expressed as the mean percent change in thymidine incorporation relative to a cell control treated with diluent (acetonitrile: $H_2O$ at 1:1) alone; bars indicate standard error of the mean for all six data points wherein TVPAAVVVA is SEQ ID NO:1; TVPAAGGGA is SEQ ID NO:8; and TVPAAAAAA is SEQ ID NO:18.

Except for the N-terminal glycosylated threonine, the amino acid residues of as-APF are made up of only 3 different amino acids, one of these being proline. The cyclic nature of the proline sidechain is often a source of conformational adjustment in a peptide/protein sequence, being involved in turns and changes in directionality of the sequence following this residue. The proline in APF appears to be useful for its activity, as substitution of proline with all but one of the modified amino acids tested was detrimental to biological function (Table 2). For example, substitution of L-proline with D-proline (8), pseudoproline (Ser ($\psi^{Me,Me}$ pro), 9) (FIG. 4), or azetidine 2'-carboxylic acid (Aze) (10) (FIG. 4) completely abolished activity (Table 2). While certain other substitutions did not completely destroy activity, substitution of $Pro^3$ with Ala (11), trans-4-hydroxyproline (12) (FIG. 4), or O-t-butyryl-trans-4-hydroxyproline (13) resulted in 2-3 orders of magnitude decrease, and substitution of $Pro^3$ with N-methylalanine (14) resulted in 4 orders of magnitude decrease in biological activity. Only substitution of Pro3 with pipecolic acid, the six-membered ring analog of proline (15) resulted in complete retention of as-APF's biological activity (FIG. 4).

Substitution of AAVVVA (SEC, ID NO:7) with 12-aminododecanoic Acid

Because APF is a highly hydrophobic peptide with only the N-terminal glycosylated threonine offering any measure of hydrophilicity, in a specific embodiment the three N-terminal amino acids (TVP) is useful for specific interaction with the receptor while the following hydrophobic C-terminal amino acids may interact nonspecifically with (e.g., intercalate into) the lipid-containing cell membrane. It was therefore determined whether complete replacement of AAVVVA (SEQ ID NO:7) with the amino-substituted fatty acid 12-aminododecanoic acid (12-Ado) (16) affected biological activity. This derivative proved to be completely inactive, however (Table 3), indicating a utility for one or more additional specific structural characteristics of the carboxy-terminal peptide segment, in a particular aspect of the invention.

Modifications of Carboxy-Terminal Amino Acids 5-9 (AVVVA; SEQ ID NO:10)

To determine the length of the C-terminal tail that is useful for activity, as-APF containing only 5 of the 9 amino acids (i.e., truncated by 4 amino acids at the carboxy terminal end (17)) was tested, and it was determined that this derivative was completely inactive. Then, truncations of as-APF beginning at the carboxy terminal end were examined. as-APF containing all but the carboxy-terminal alanine (18) had full activity, but as-APF truncated by only one additional amino acid (19) proved to be completely inactive (Table 3). Taken together, these findings indicate that a minimum of the eight N-terminal amino acids is useful to maintain a structural element of as-APF, in certain embodiments.

It was noted that the 5 amino acid C-terminal "tail" of APF contains the AXXXA (SEQ ID NO:11) sequence, a common α-helical motif in proteins (Kleiger et al., 2002). In specific embodiments of the invention, the amino acid sequence of this segment of as-APF is also useful for interaction with its receptor because similar motifs have been shown to function in protein-protein dimerization (Dawson et al., 2002; Schneider et al., 2004; Gimpelev et al., 2004). To further characterize this, $Val^8$ and $Ala^9$ (20), or replaced either $Ala^9$ or $Ala^5$ with more branched but similarly charged amino acids (such as $Leu^9$, 21; or $Val^5$, 22) all of which changes resulted in loss of most or all biological activity (Table 4). While $Ala^9$ is not required for as-APF activity, these findings provide evidence that $Ala^5$ and $Ala^9$ are useful for optimal activity of APF containing 9 amino acids.

The phenomenon of protein-protein dimerization can also occur for GXXXG (SEQ ID NO:12) or SXXXS (SEQ ID NO:13) motifs, so as-APF derivatives containing GXXXG (SEQ ID NO:12) or SXXXS (SEQ ID NO:13) in place of AXXXA (SEQ ID NO:11) were next tested. Additional evidence for the importance of alanine in the 5th and 9th positions was provided by the partial inactivation resulting from replacement of both $Ala^5$ and $Ala^9$ with serine ($Ser^{5,9}$, "SXXXS" (SEQ ID NO:13), 23) and complete inactivation resulting from replacement with glycine ($Gly^{5,9}$, "GXXXG"; (SEQ ID NO:12), 24) (Table 4). However, substitution of $Val^{6-8}$ with alanine residues with retention of Ala5 (25) also resulted in decreased antiproliferative activity in primary normal bladder epithelial cells (although the extent to a substitution of $Val^{6-8}$ with alanine residues decreased activity relative to as-APF varied depending on the donor of the primar bladder epithelial cells, with cells from one of three donors having similar sensitivity to both derivatives). In comparison, substitution of $Val^{6-8}$ with glycine residues (26), substitution of Val$^7$ with D-valine (27), or substitution of Val$^6$ and Val$^8$ with isoleucines (28) resulted in complete inactivation of antiproliferative activity in normal bladder epithelial cells. Taken together, all of the above findings suggest that both the presence of alanine in the 5th position and the presence of valine in the 6th through 8th positions are important for optimal activity of as-APF in primary normal bladder epithelial cells from some donors.

Figure 6:
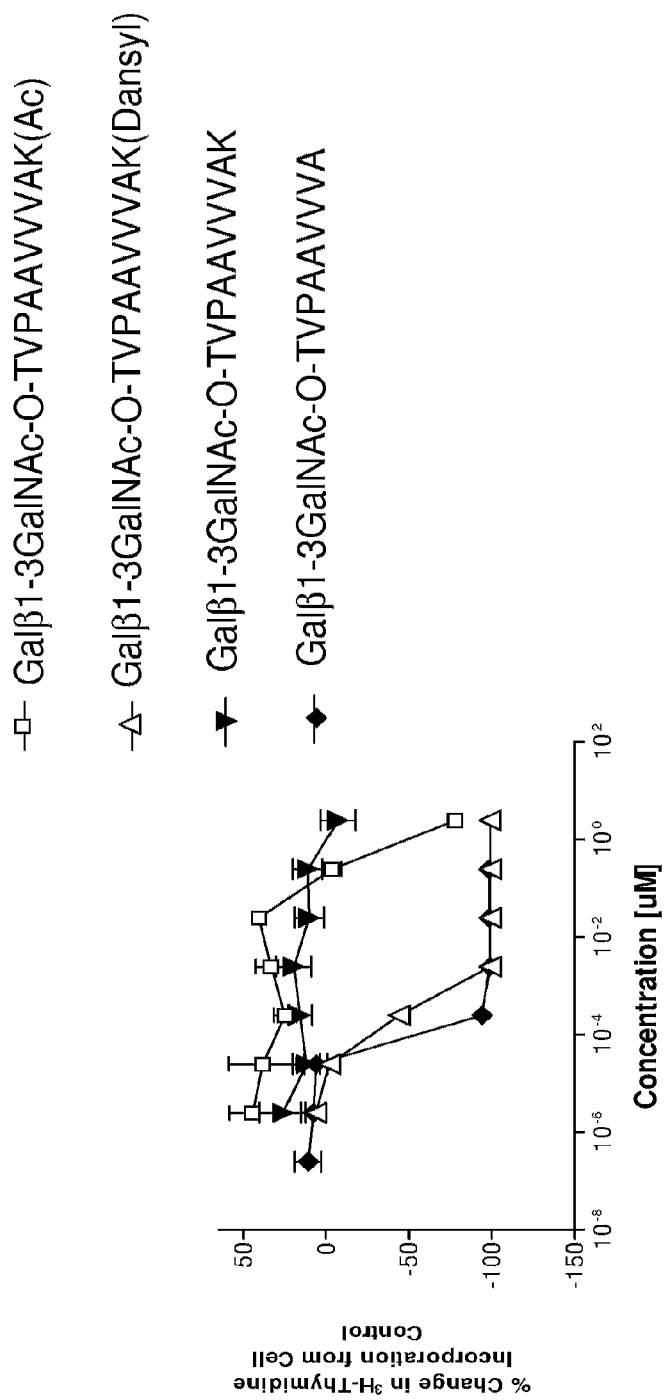
FIG. 6 shows antiproliferative activity of specific APF derivatives (modifications to carboxy-terminal alanine). Inhibition of tritiated thymidine incorporation by primary normal bladder epithelial cells was determined for each derivative at the concentrations indicated. Experiments were run in triplicate on two separate occasions. Data are expressed as the mean percent change in thymidine incorporation relative to a cell control treated with diluent (acetonitrile: $H_2O$ at 1:1) alone; bars indicate standard error of the mean for all six data points, wherein TVPAAVVVA is SEQ ID NO:1; TVPAAVVVAK is SEQ ID NO:9; TVPAAVVVAK(Ac) is SEQ ID NO:25; and TVPAAVVVAK(Dansyl) is SEQ ID NO:26.

Carboxyamidation of Ala9 in as-APF (29) also resulted in decreased activity (Table 5), indicating the possibility that a negative charge in the 9th position is useful for APF activity. Interestingly, the addition of cysteine to the carboxy terminus (30) resulted in a decrease in APF activity of two orders of magnitude while the addition of lysine with a much larger N$^ε$-attached dansyl group in the 10th position (31) resulted in no loss of activity (FIG. 6). In a specific embodiment, this latter finding indicates additional interaction between the dansyl group and the APF receptor. However, the addition of either Glu (32) or Lys (33) (FIG. 6) to the carboxy terminus in the 10th position (for possible subsequent cyclization, see below) resulted in the complete loss of activity, some of which was restored by neutralizing the charge on the Glu or Lys sidechains while maintaining the C-terminal carboxylate [(34) and (35) (FIG. 6)] (Table 5). These findings indicate that the presence of either a positively or negatively charged side chain in the 10th position is detrimental to APF activity.

Finally, an as-APF derivative was synthesized in which the entire peptide portion was cyclized from the amino group on the N-terminus to the carboxyl group on the C-terminus (36). Although the complete inactivity of head-to-tail cyclized APF peptide is evidence for the usefullness of both C- and N-terminal charges, in certain embodiments, in other embodiments this derivative's inactivity resulted from conformational changes occurring as a result of cyclization.

Significance of Certain Embodiments of the Invention

It was previously shown that glycosylation of APF with at least the first two sugars (Galβ1-3GalNAcα) is necessary for biological activity (Keay et al., 2004), and it is now determined that several structural aspects of the 9 amino acid peptide segment are useful for structural integrity of the active compound, in particular embodiments.

The data clearly show that the biological activity of APF is sensitive to changes in the N-terminus of the glycopeptide. The N-terminal two amino acids (Thr-Val) can be substituted with Ser-Leu with two orders of magnitude loss of activity, but sole substitution of Thr with Ser (3) resulted in even greater loss of potency, indicating that the number and positioning of the methyl groups in this location are useful for as-APF activity. A recent report showed that the ψ angle preferences are very different in simple GalNAc-containing glycoaminoacids depending on whether the amino acid is serine or threonine (Corzana et al., 2007). NMR studies can be performed to determine whether this is operational in the N-terminal-substituted APF derivatives. However, the lone substitution of Val$^2$ with Leu resulted in complete inactivation, indicating that an additional methyl group in this location prevents optimal interaction between as-APF and its receptor, in specific embodiments. In addition, the 100-fold decrease in activity caused by either extension of the N-terminus with tyrosine (the amino acid preceding threonine in the frizzled 8 protein sequence (Saitoh et al., 2001)) or acetylation of the N-terminal amino group, provides evidence for the functional importance of the very specific positioning of a positively charged N-terminal amino group relative to the sugar moieties for maintenance of as-APF activity.

Conformation of as-APF in the area of the proline residue is useful in certain embodiments, as substitution of L-proline with various other modified amino acids that can affect conformation also resulted in complete, or substantial, loss of activity. Ring size, functionality and polarity can affect the conformation and potencies of proline-substituted APF derivatives, as shown by the decreased activity following substitution with D-proline, pseudoproline, azetidine 2'-carboxylic acid, trans-4-hydroxyproline, O-t-butyryl-trans-4-hydroxyproline, alanine, and N-methylalanine. In the D-proline derivative, the internal backbone torsion angle φ effectively changes sign, which in turn changes the orientation of the peptide segments on either side of the Pro residue relative to native APF, resulting in complete inactivation. Inactivation of as-APF following substitution of proline with pseudoproline (the latter of which often results in a high percentage of cis amide bonds preceding this residue (Keller et al., 1998)) may indicate a requirement for a trans conformation, a finding compatible with NMR data showing that APF does not contain any cis peptide bonds. In comparison, substitution of L-proline with pipecolic acid had no apparent effect on activity, indicating this derivative maintains a similar conformation to as-APF, in certain embodiments of the invention.

The decreased activity of as-APF following replacement of the proline with alanine or N-methylalanine might be explained by the fact that these derivatives, while likely to be more flexible than the parent APF congener, can have a small number of the angles in that location topochemically identical with bioactive APF, allowing some activity. In addition, the relatively greater activities of 11, 12, 13, 14, or the parent congener as compared to 10 is most likely explained by the unfavorable restriction of conformation for the azetidine derivative, in particular embodiments.

The data also indicate that Ala$^5$ and Val$^{6-8}$ are useful for optimal biological activity, and that a minimum of 8 amino acids is required for biological activity, in specific embodiments. The decrease in activity resulting from replacement of Ala$^5$ or Ala$^9$ with amino acids containing larger side chains is compatible with the embodiment that both amino acids may form a flat surface on an α-helix that may be important for interaction with the APF receptor (Kleiger et al., 2002). However, the equal activity of 1 and 18 indicates that this interaction, if it occurs, may only be required for Ala$^5$. CD measurements have not revealed an ordered structure of the parent congener 1 in water solution, and comprehensive NMR studies of as-APF in water solution confirm the lack of ordered structure in water. However, there is some evidence for an ordered structure in higher concentrations (45%) of trifluoroethanol, making it reasonable to hypothesize that the carboxy terminal tail of as-APF may be able to adopt an α helical-like conformation either in a cellular milieu and/or upon interaction with its receptor. Extensive molecular dynamics studies based on the limited NMR restraints available clearly show that the C-terminal stretch of amino acids (AVVVA; SEQ ID NO:10)) in as-APF can adopt folded structures with concomitant adjustments in the rotamer distribution about the anomeric bond of the disaccharide after 1 ns. NMR studies of as-APF and several less potent analogues in the presence of its receptor in both aqueous and lipid environments are useful to determine the precise structural features associated with maximum activity of these glycopeptides.

In addition, a negatively charged species at the carboxyterminal end is useful for as-APF activity, in certain cases. Moreover, when a negative charge state is maintained in that location, additional steric bulk can be tolerated at this end of the peptide, allowing for the synthesis of active derivatives containing fluorescent labels on the C-terminus to follow temporal and spatial aspects of the APF-cellular receptor interaction.

Figure 7:
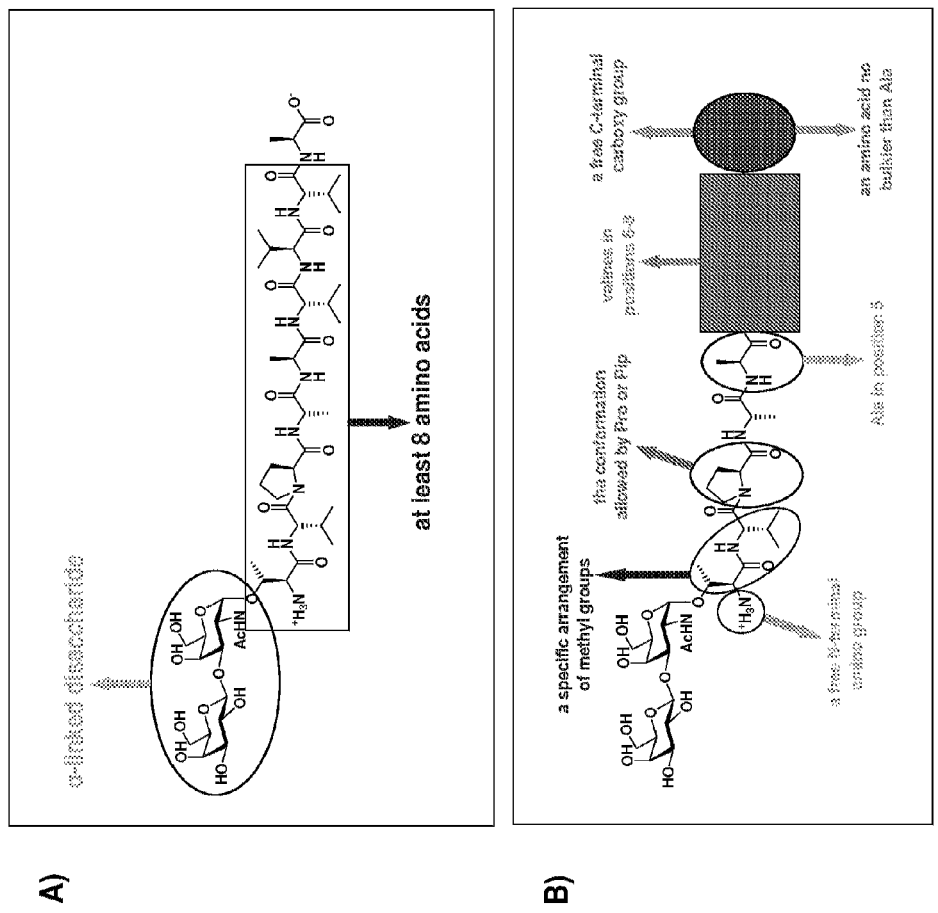
FIG. 7 provides a schematic diagram indicating (A) essential and (B) important structural elements for some embodiments of APF derivative activity, such as as-APF activity, for example FIGS. 8A-8AJ provide HPLC traces of exemplary as-APF analogues.
Figure 8A:
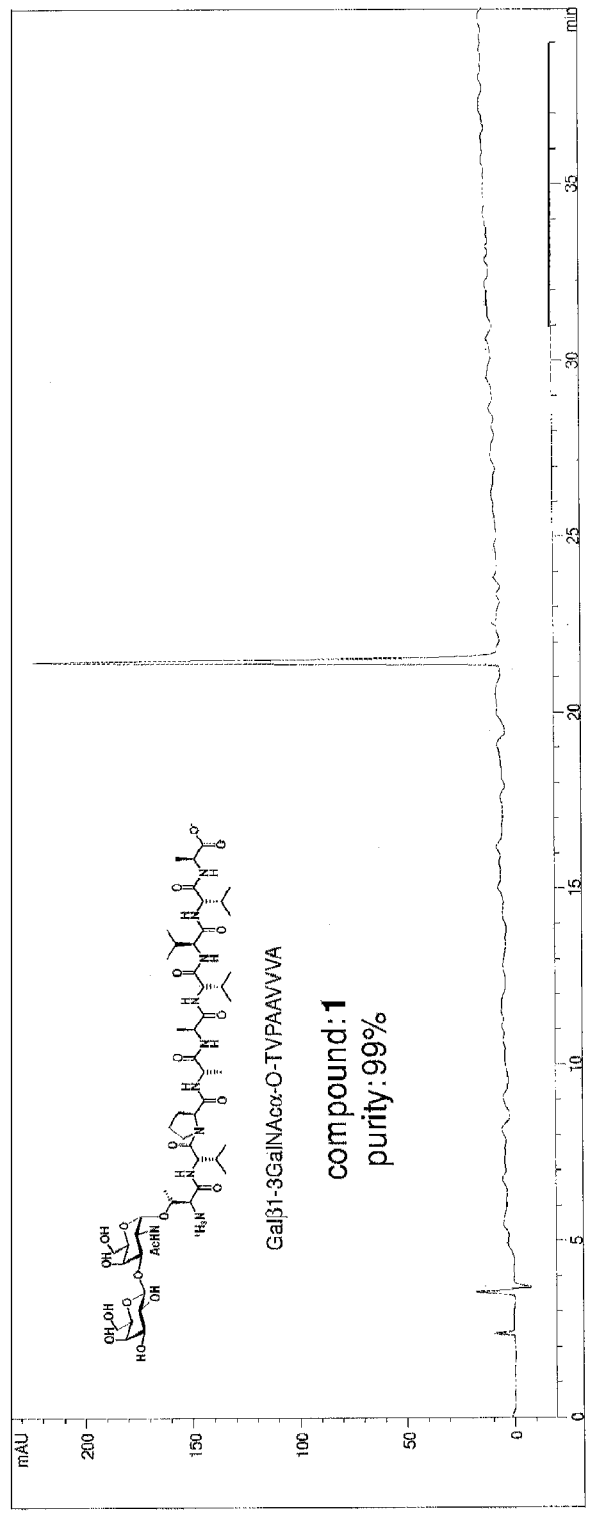
Figure 8B:
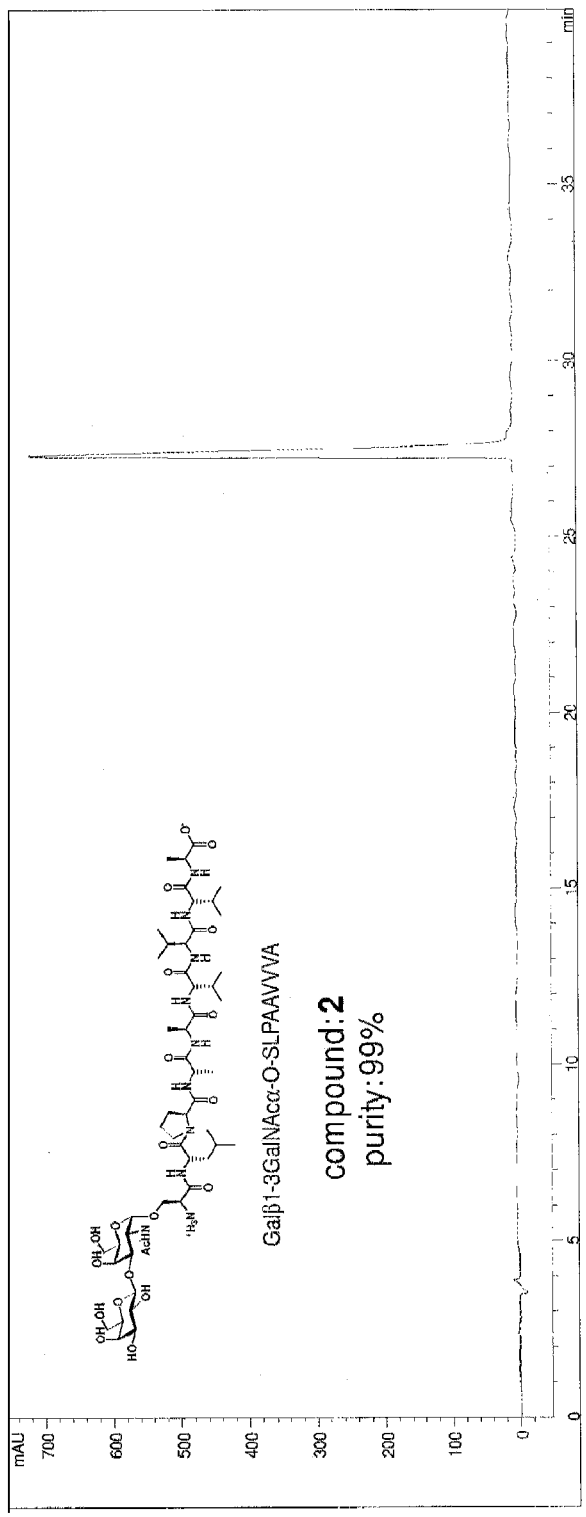
Figure 8C:
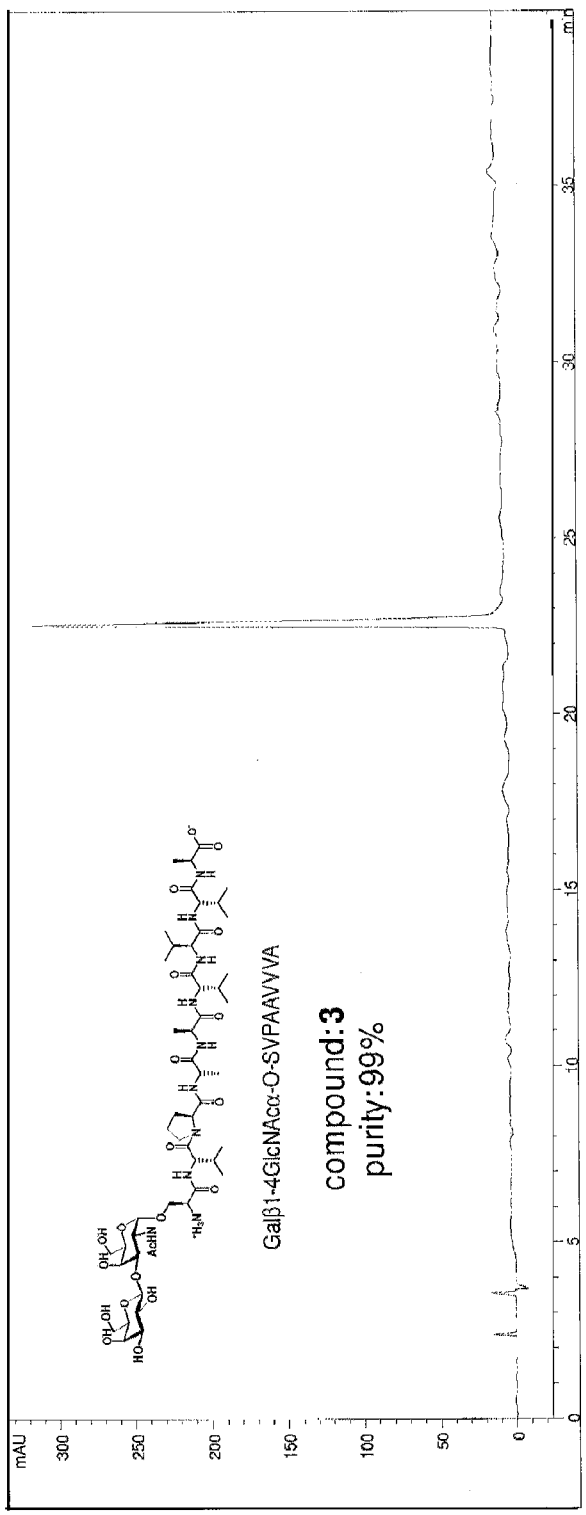
Figure 8D:
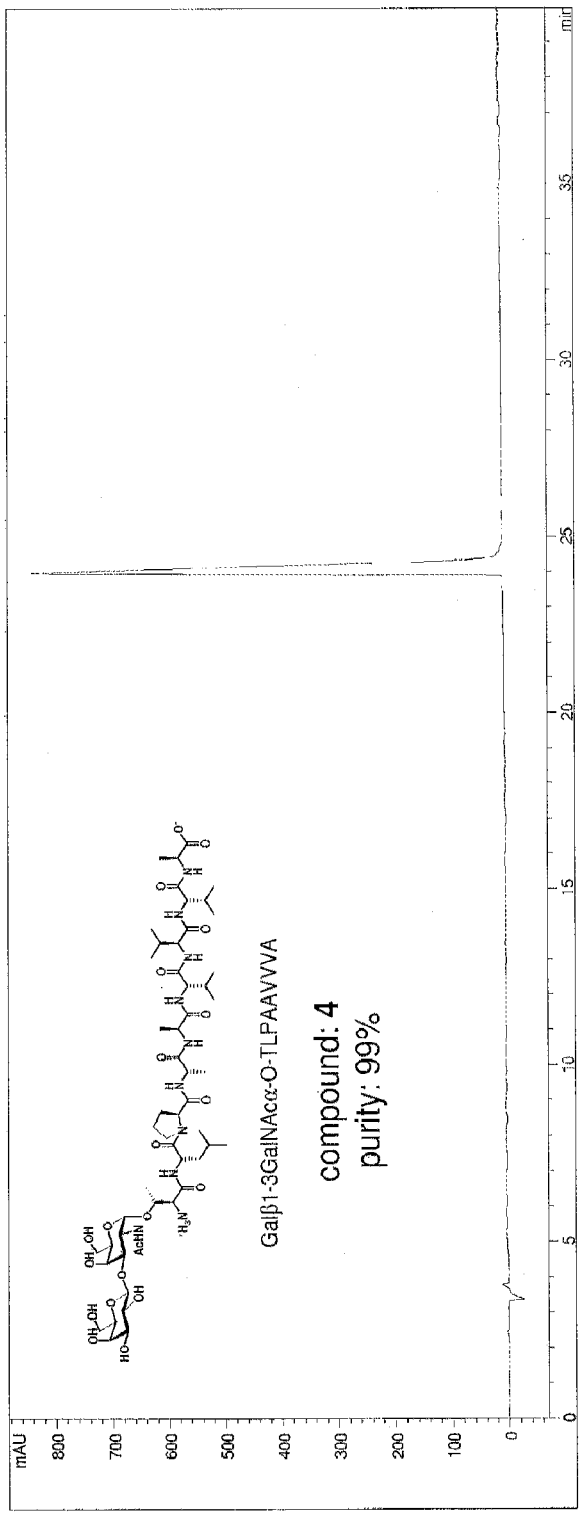
Figure 8E:
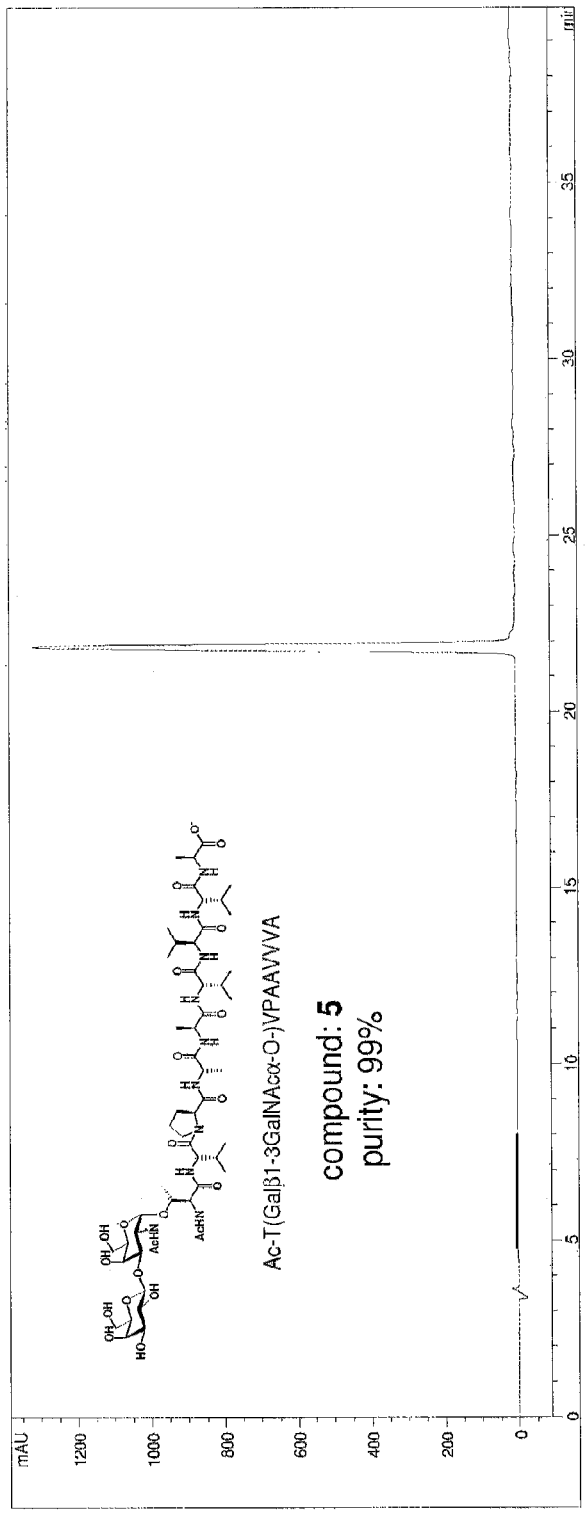
Figure 8F:
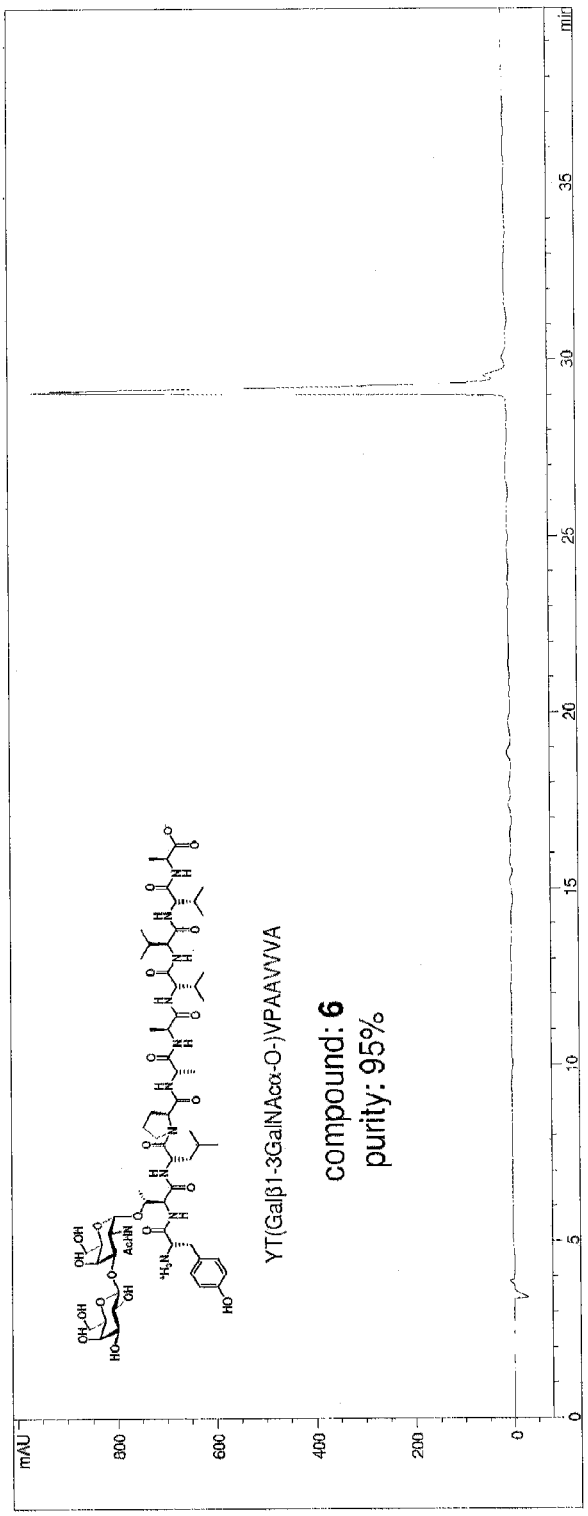
Figure 8G:
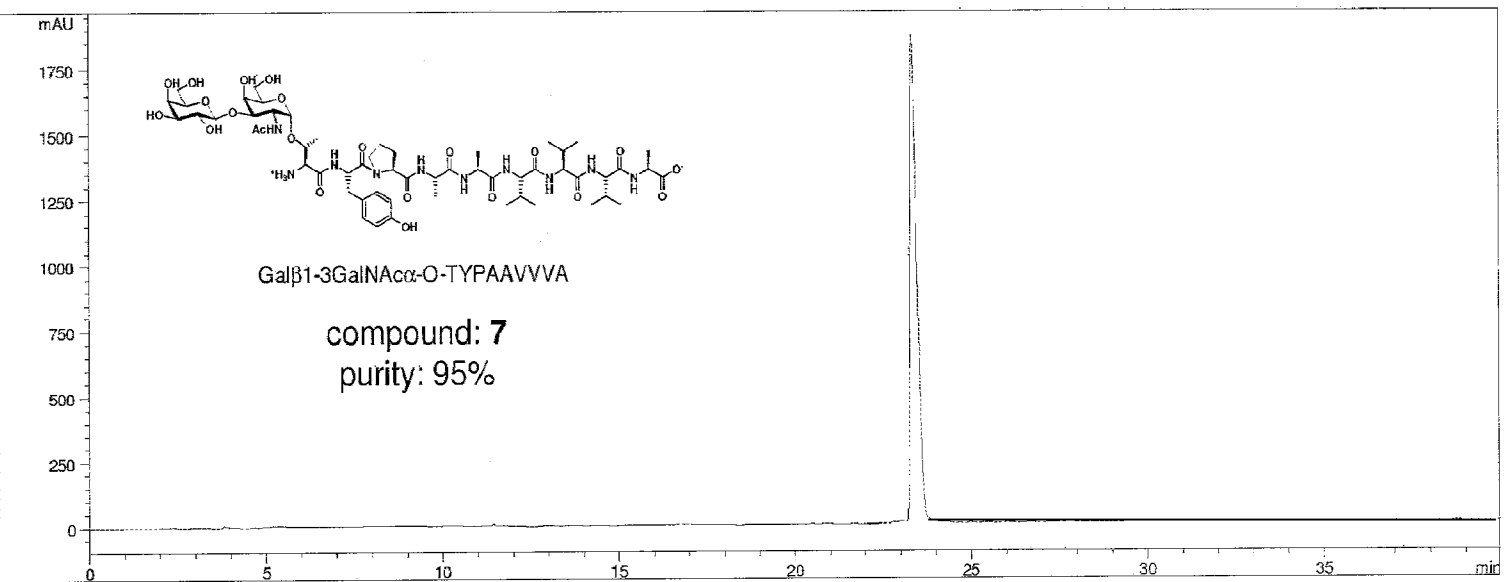
Figure 8H:
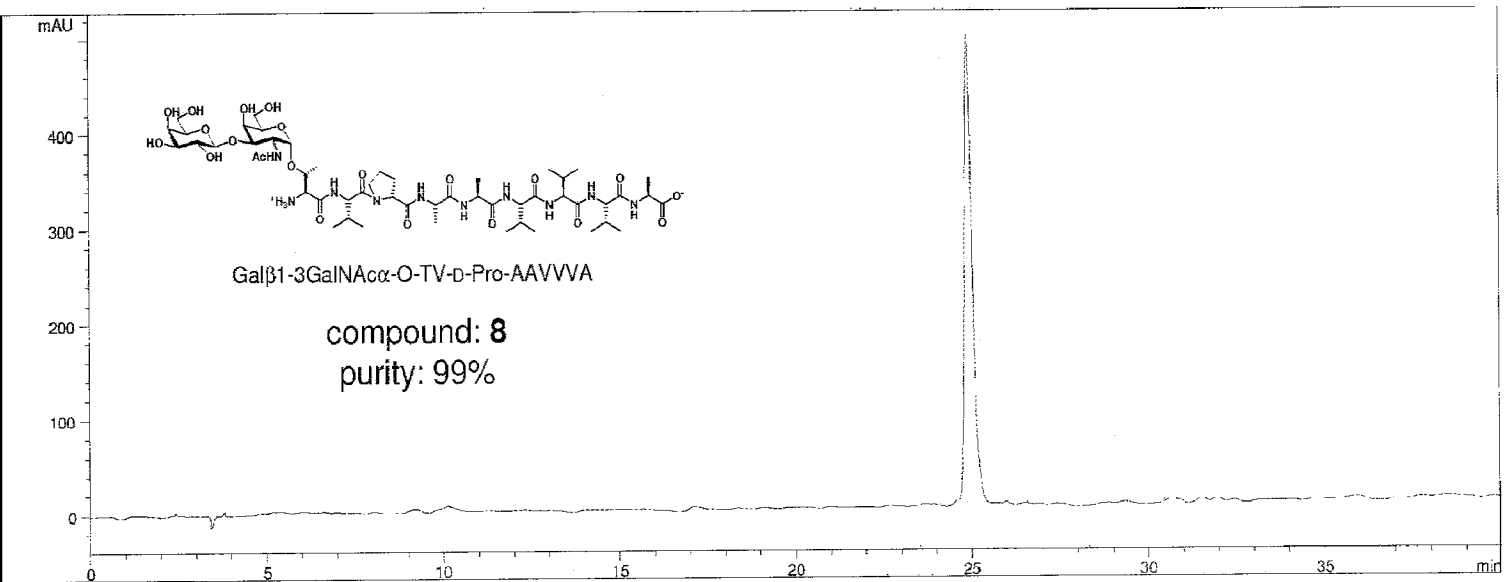
Figure 8I:
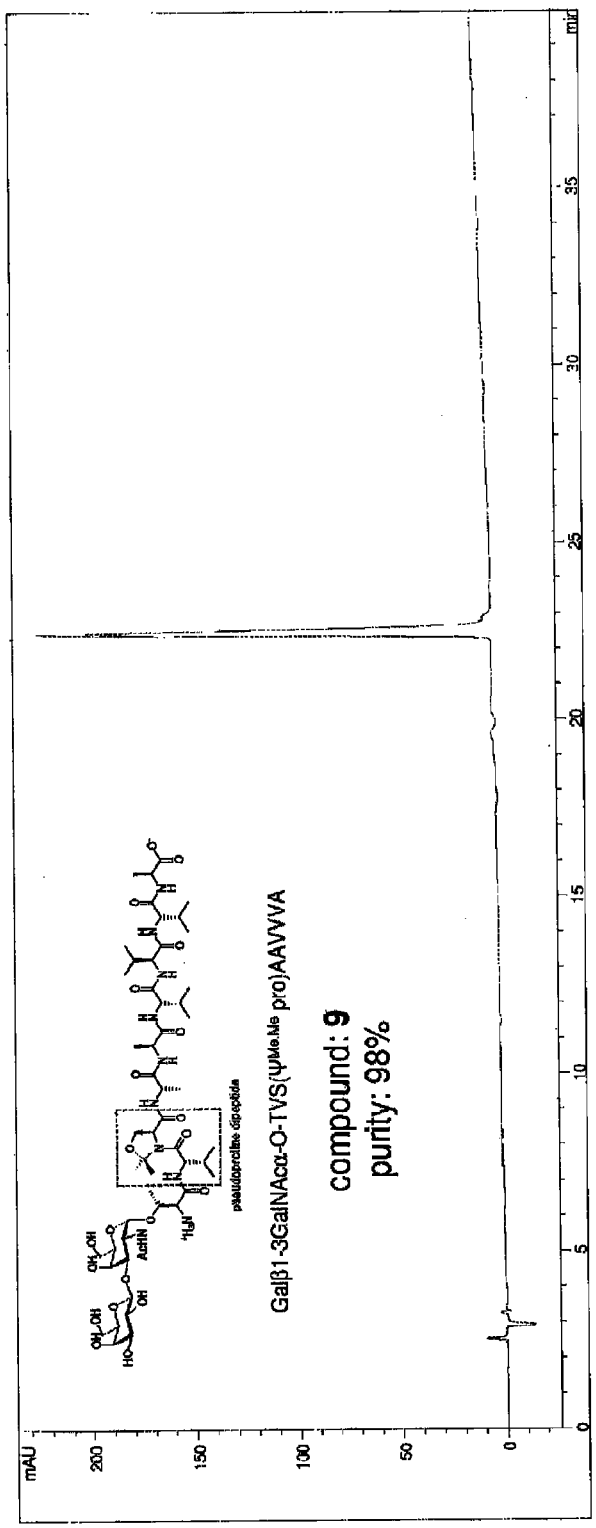
Figure 8J:
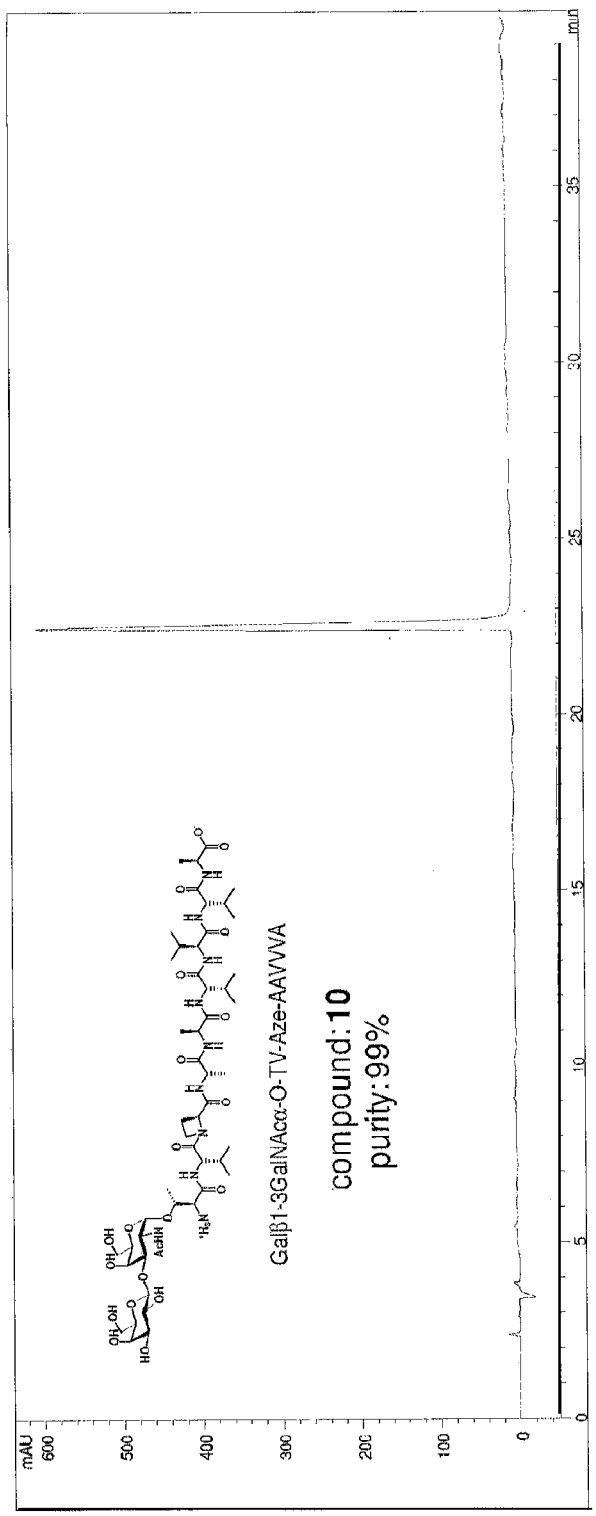
Figure 8K:
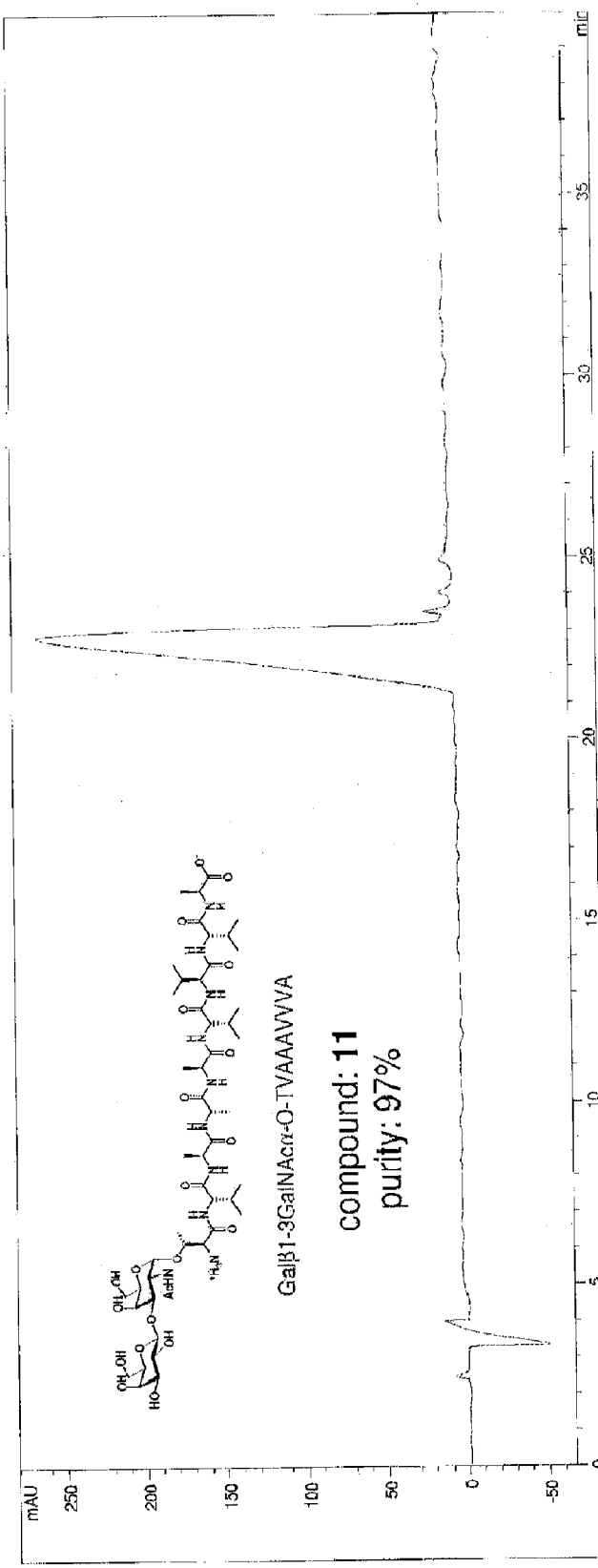
Figure 8L:
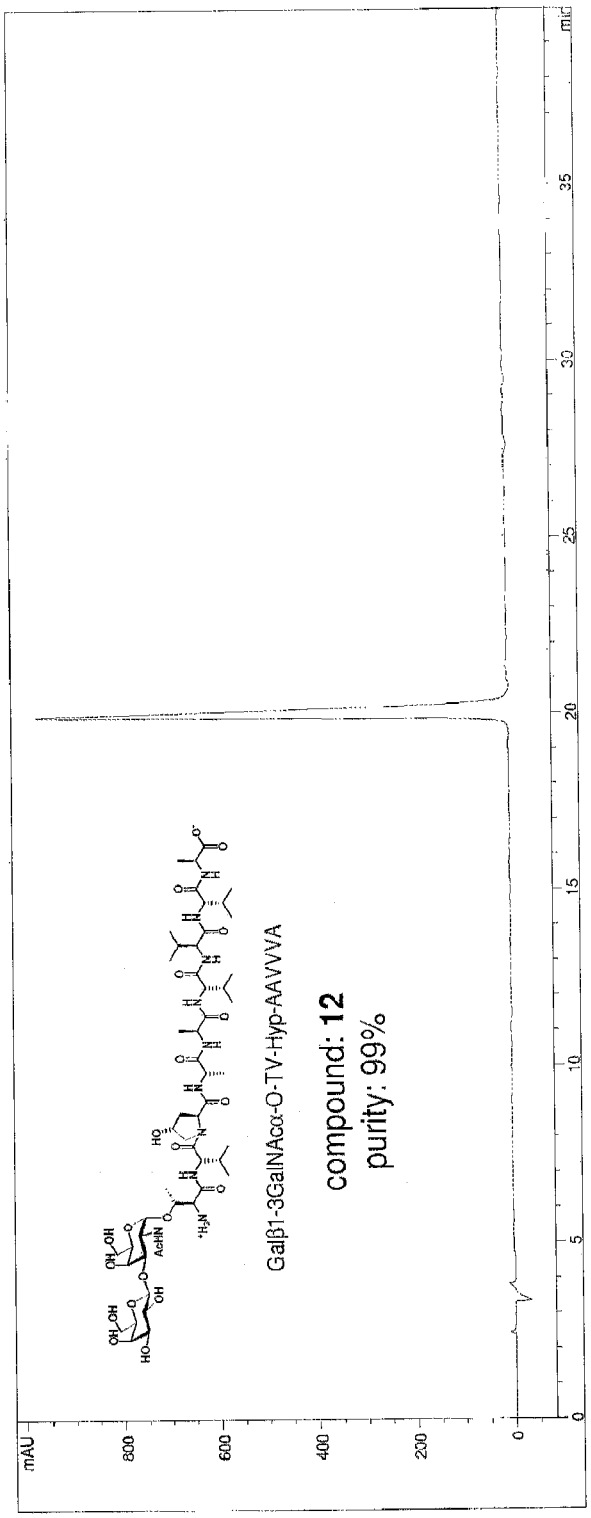
Figure 8M:
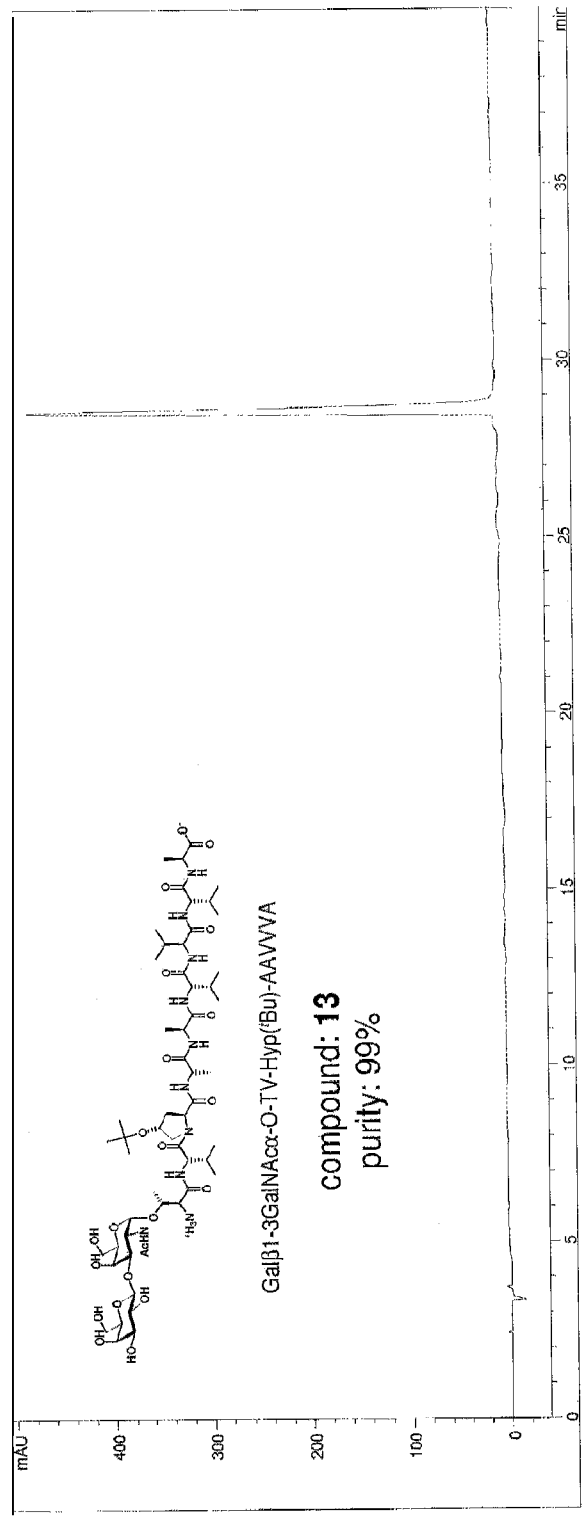
Figure 8N:
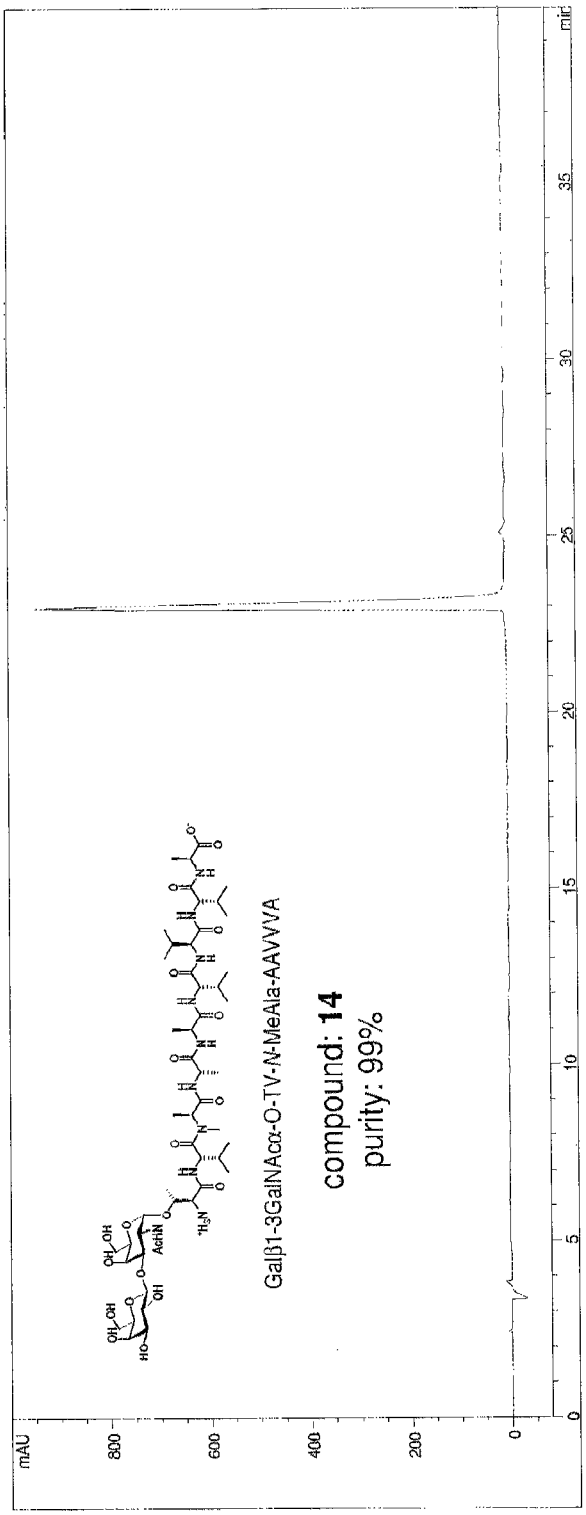
Figure 80:
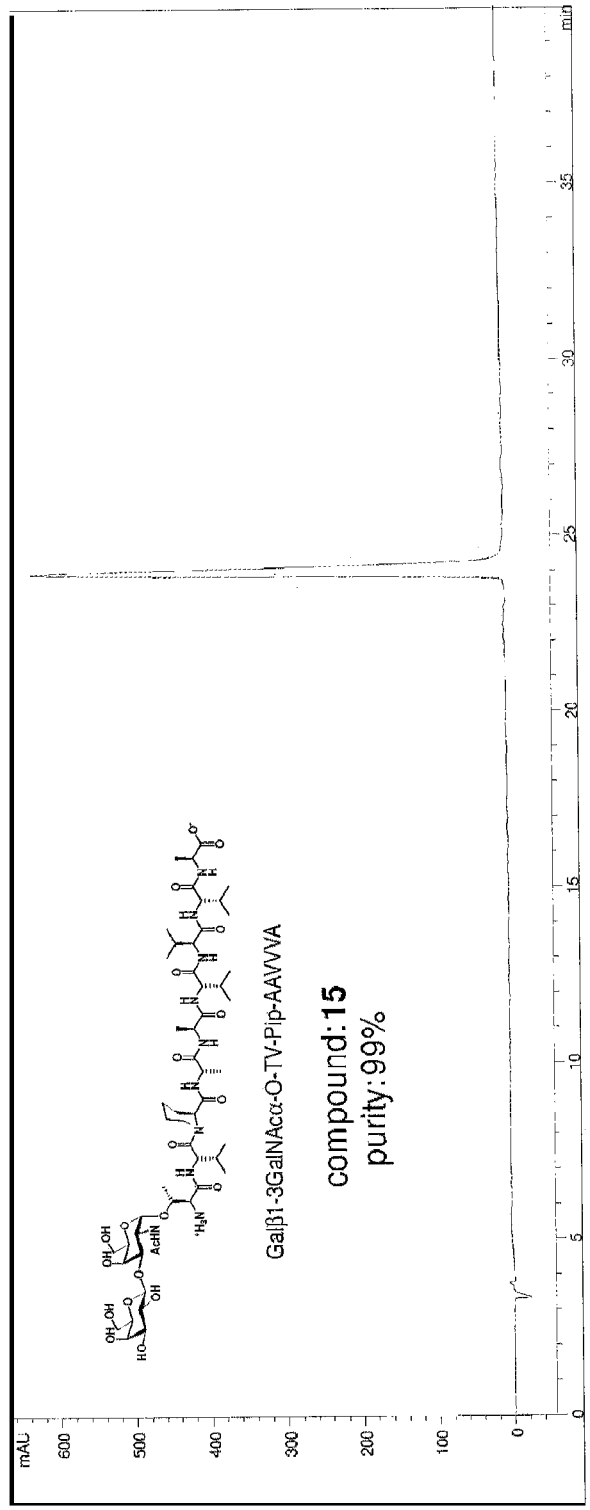
Figure 8P:
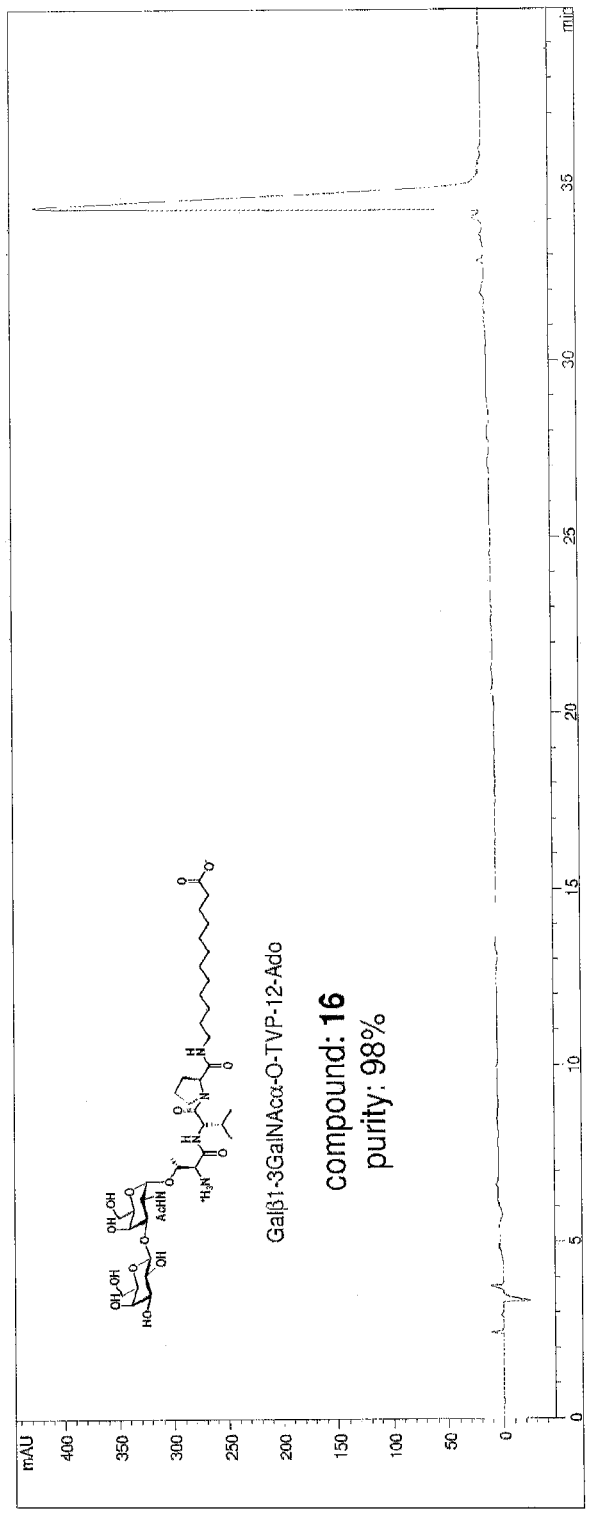
Figure 8Q:
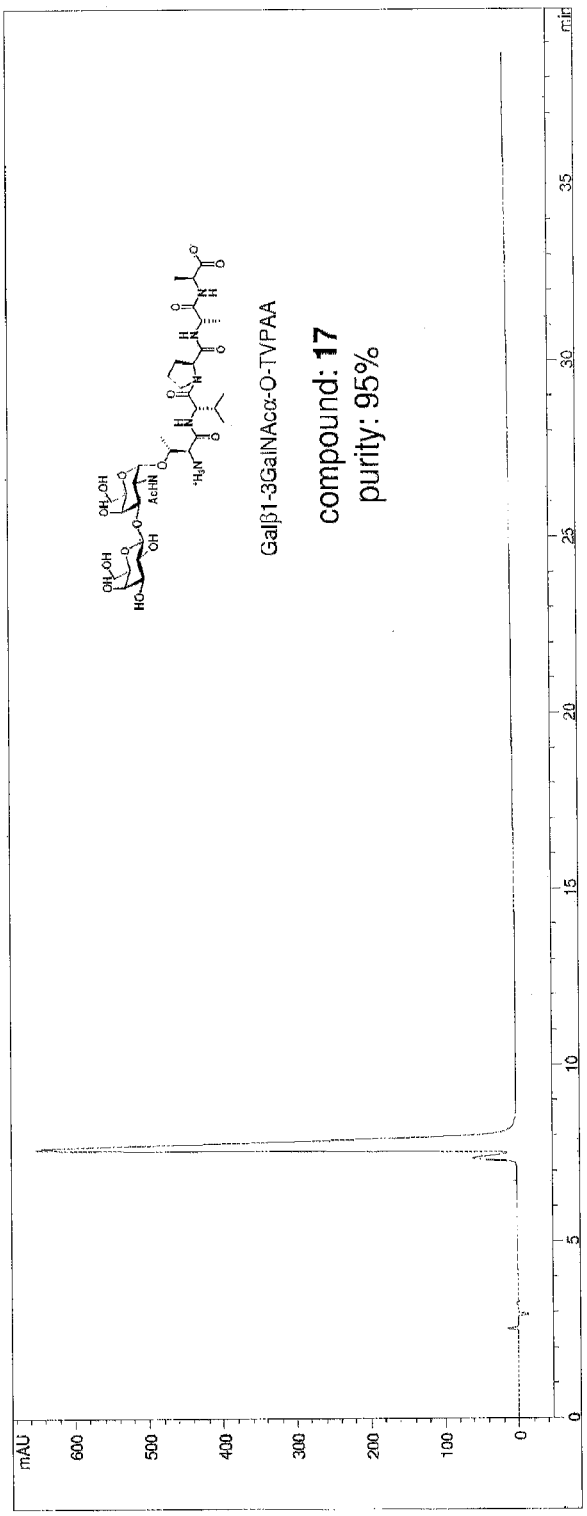
Figure 8R:
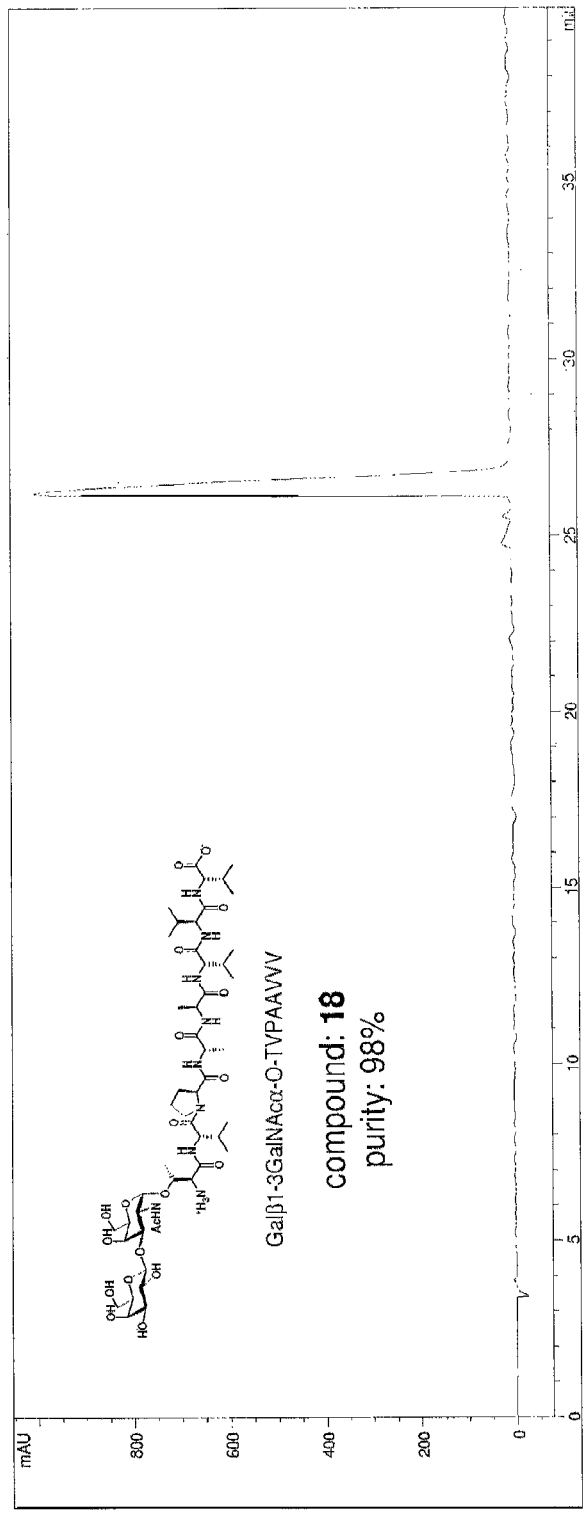
Figure 8S:
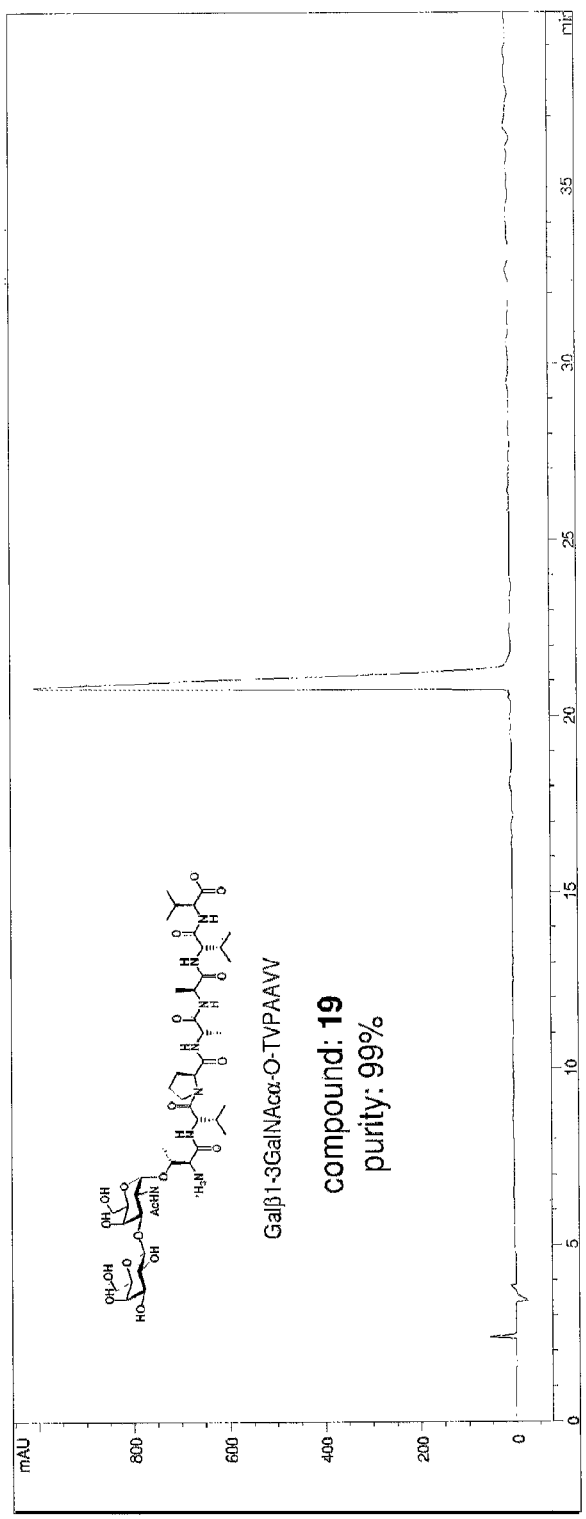
Figure 8T:
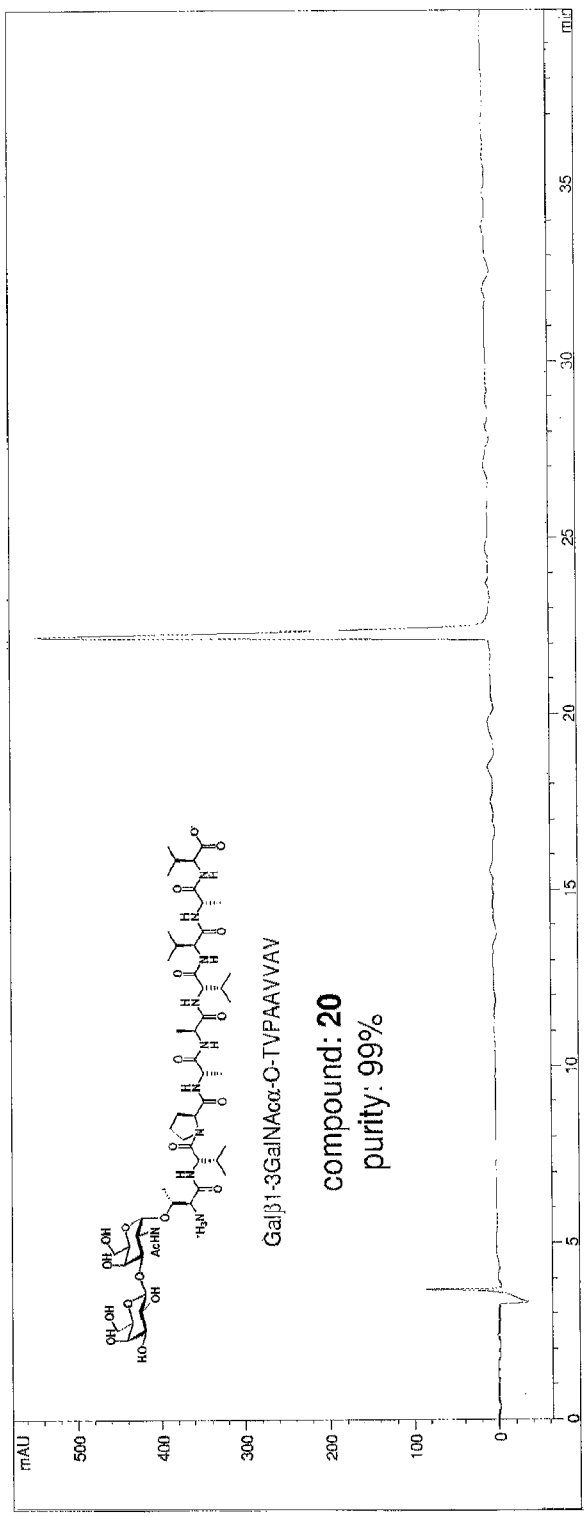
Figure 8U:
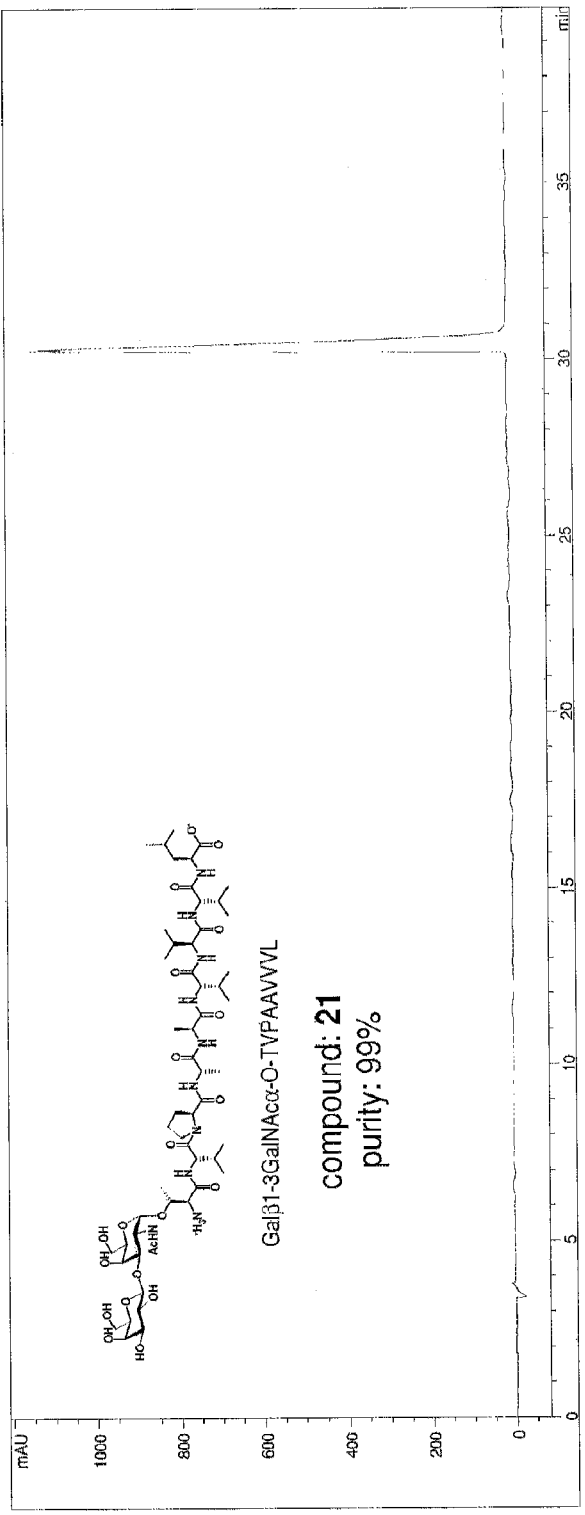
Figure 8V:
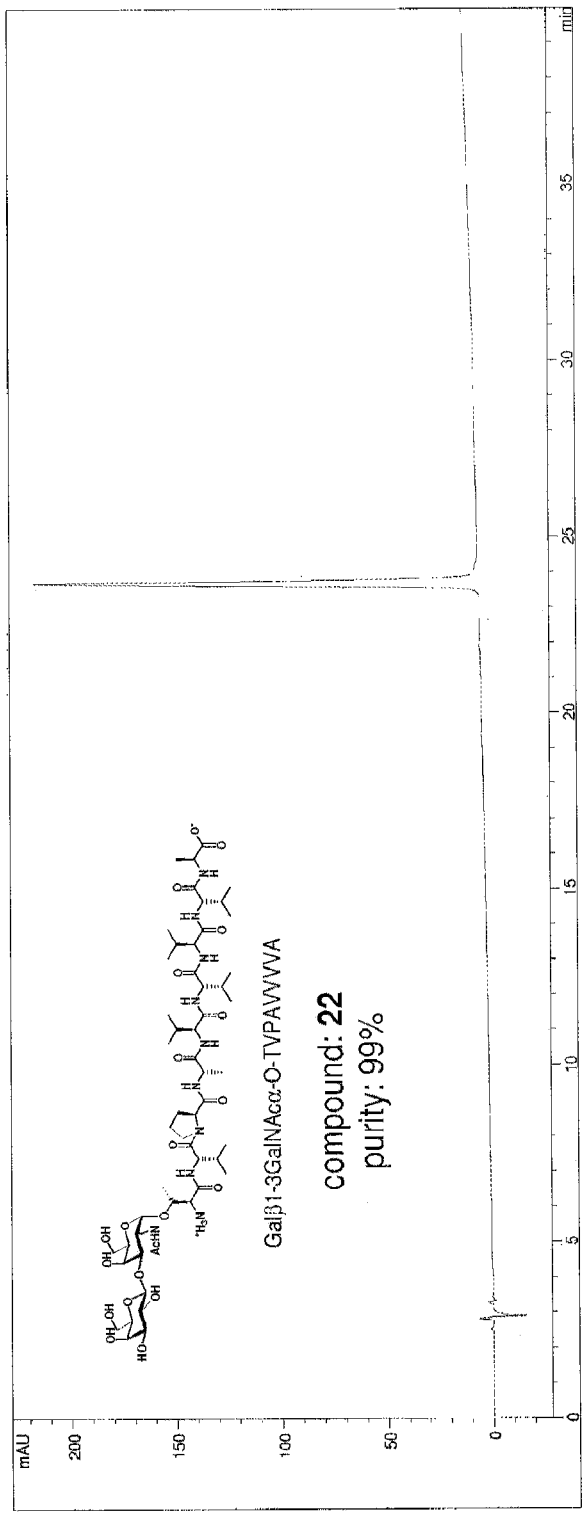
Figure 8W:
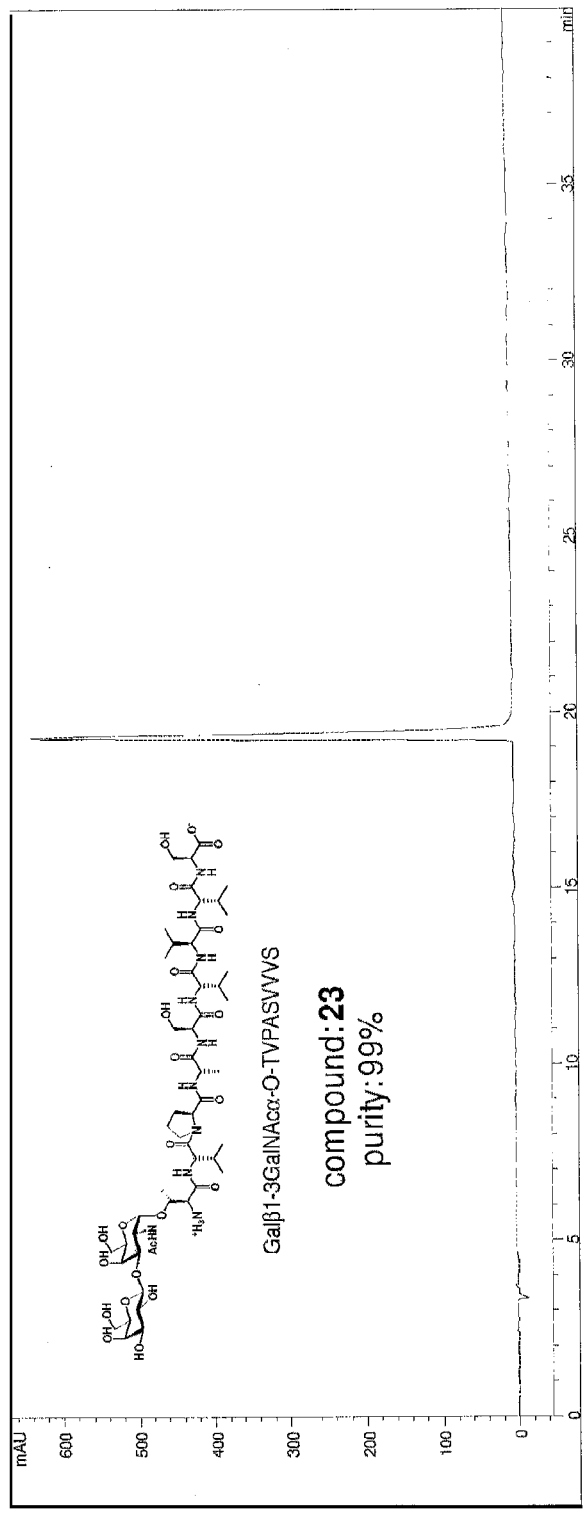
Figure 8X:
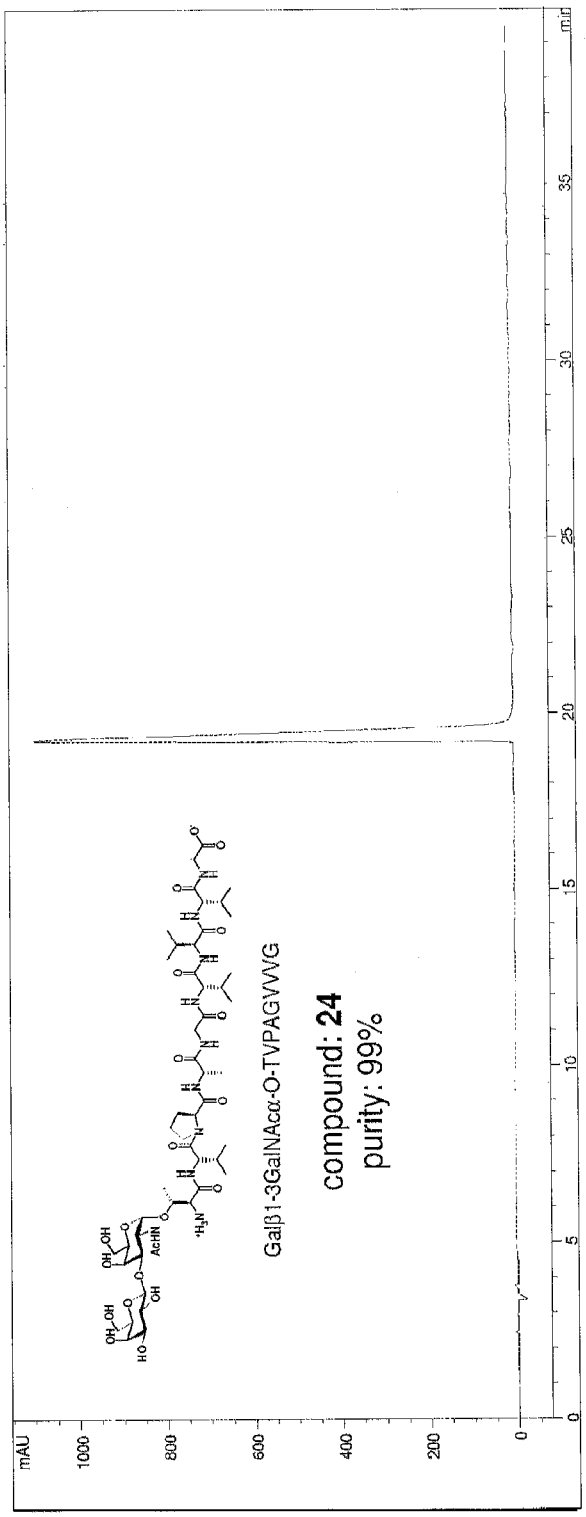
Figure 8Y:
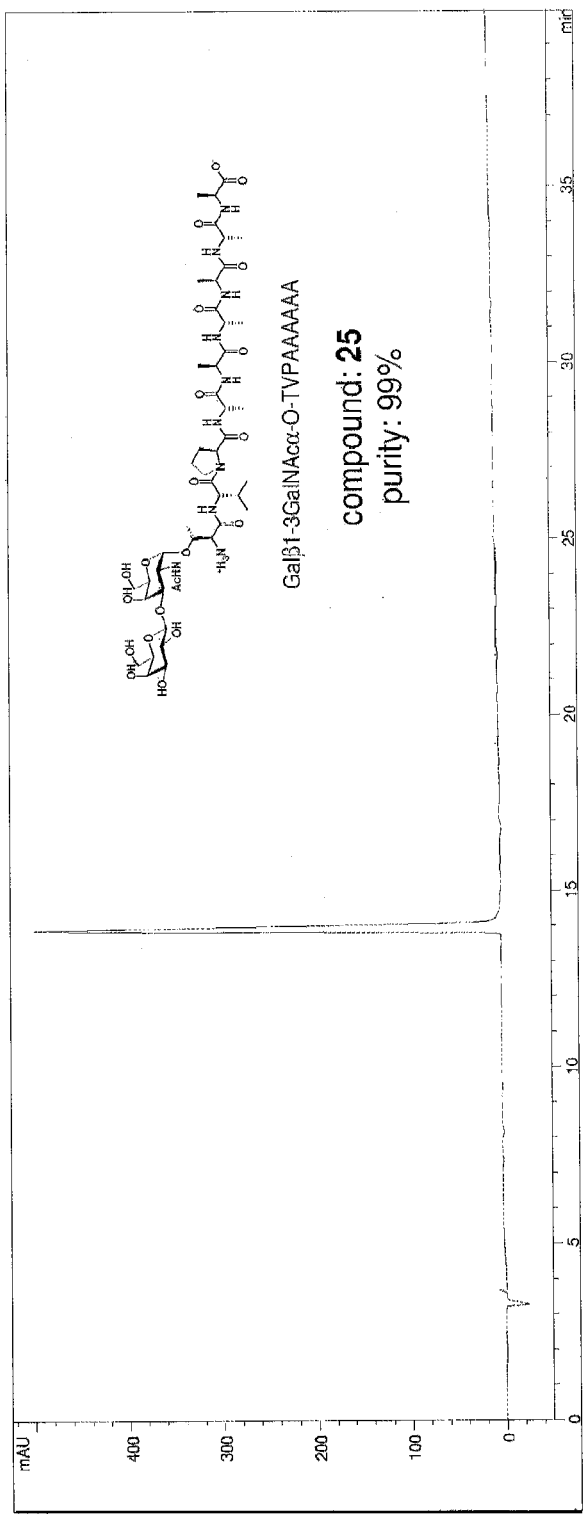
Figure 8Z:
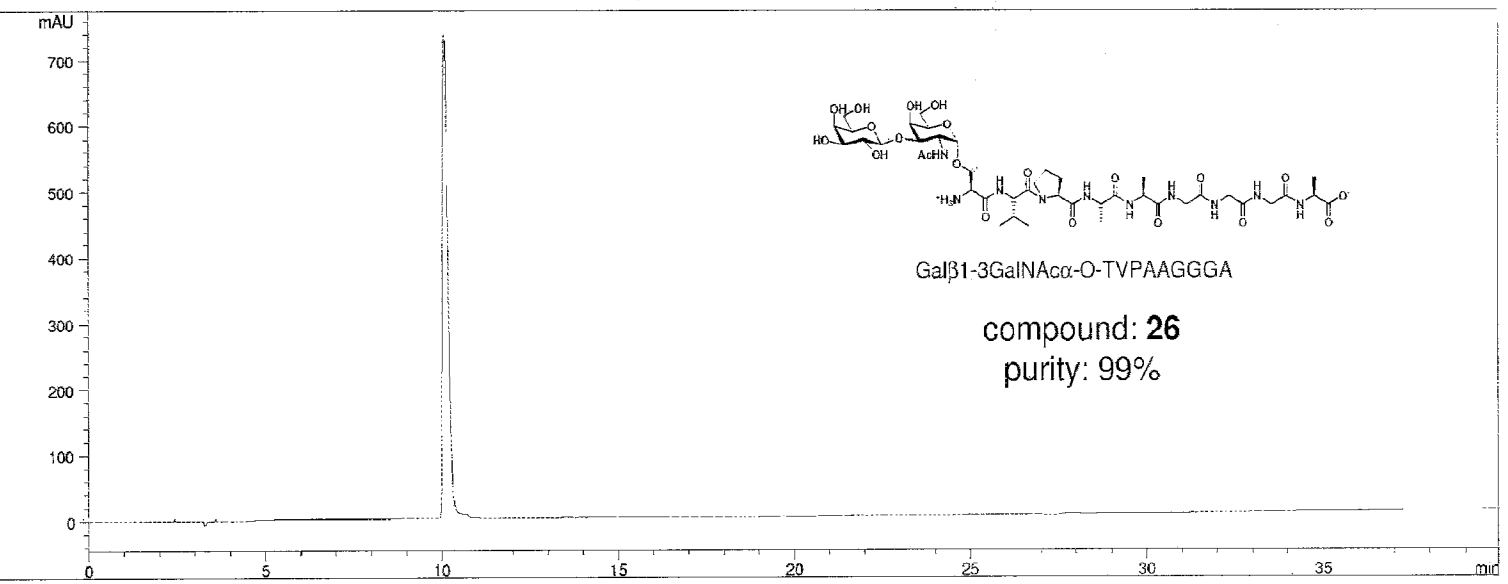
Figure 8A:
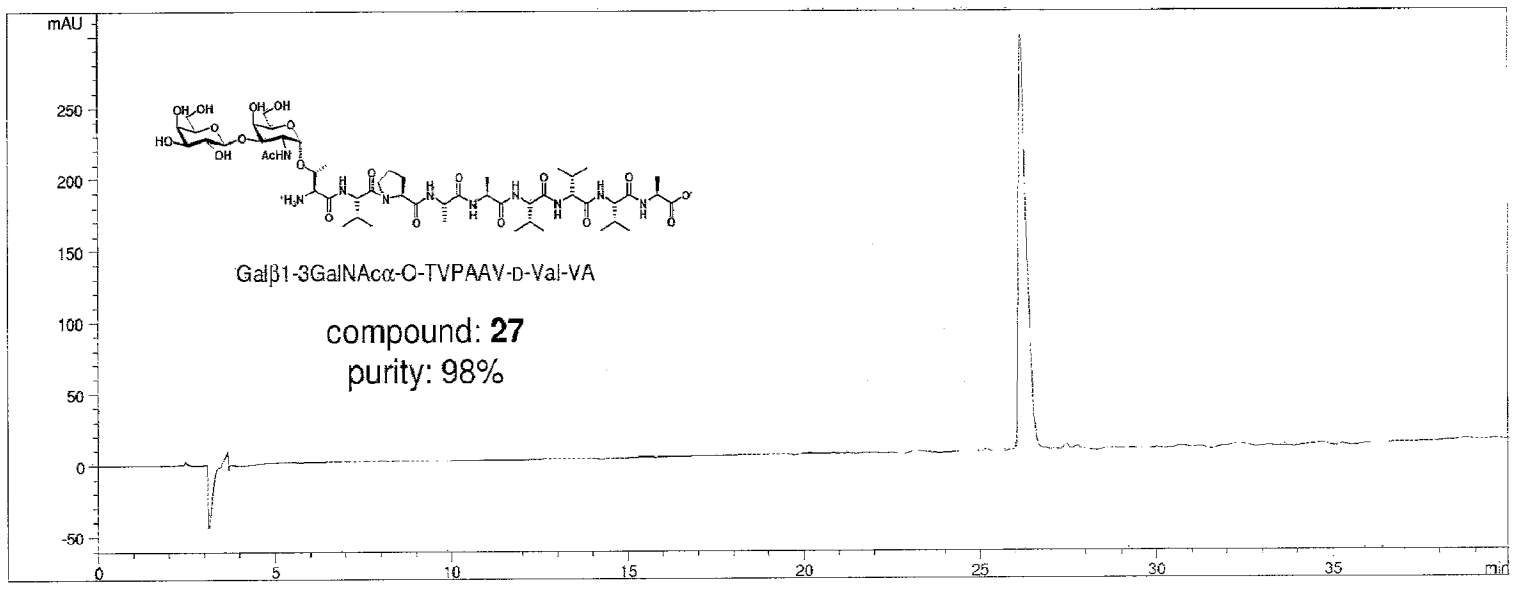
Figure 8A:
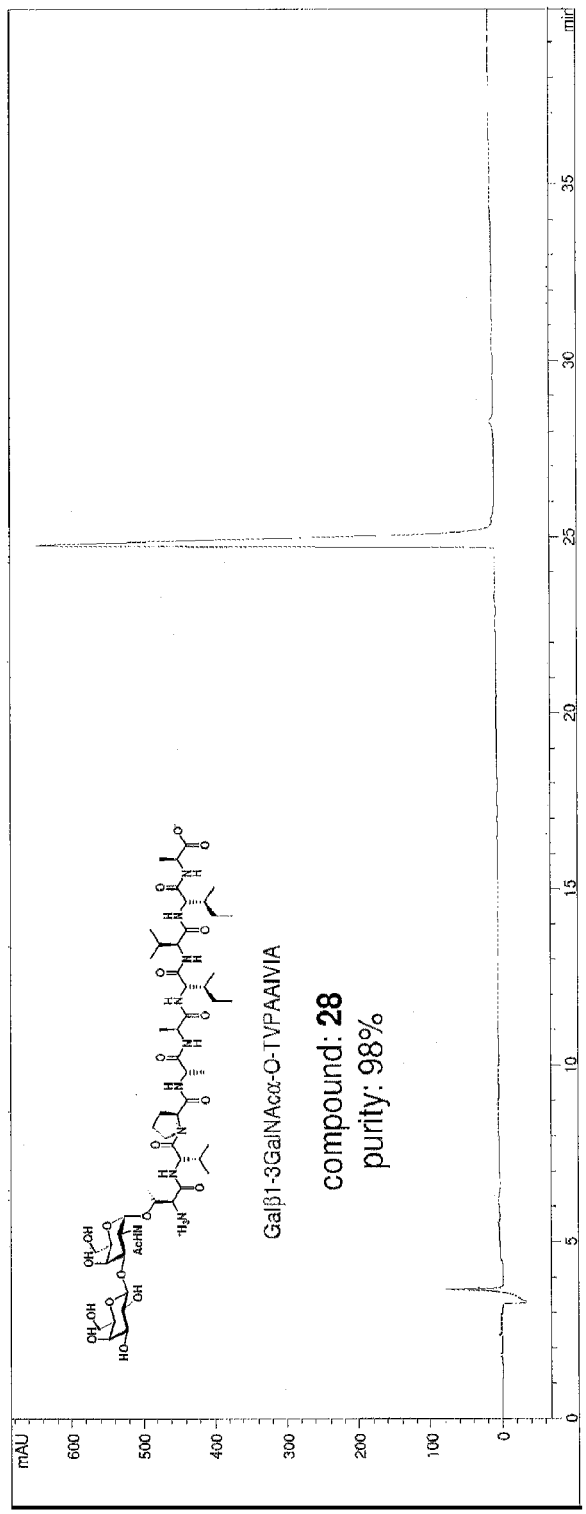
Figure 8A:
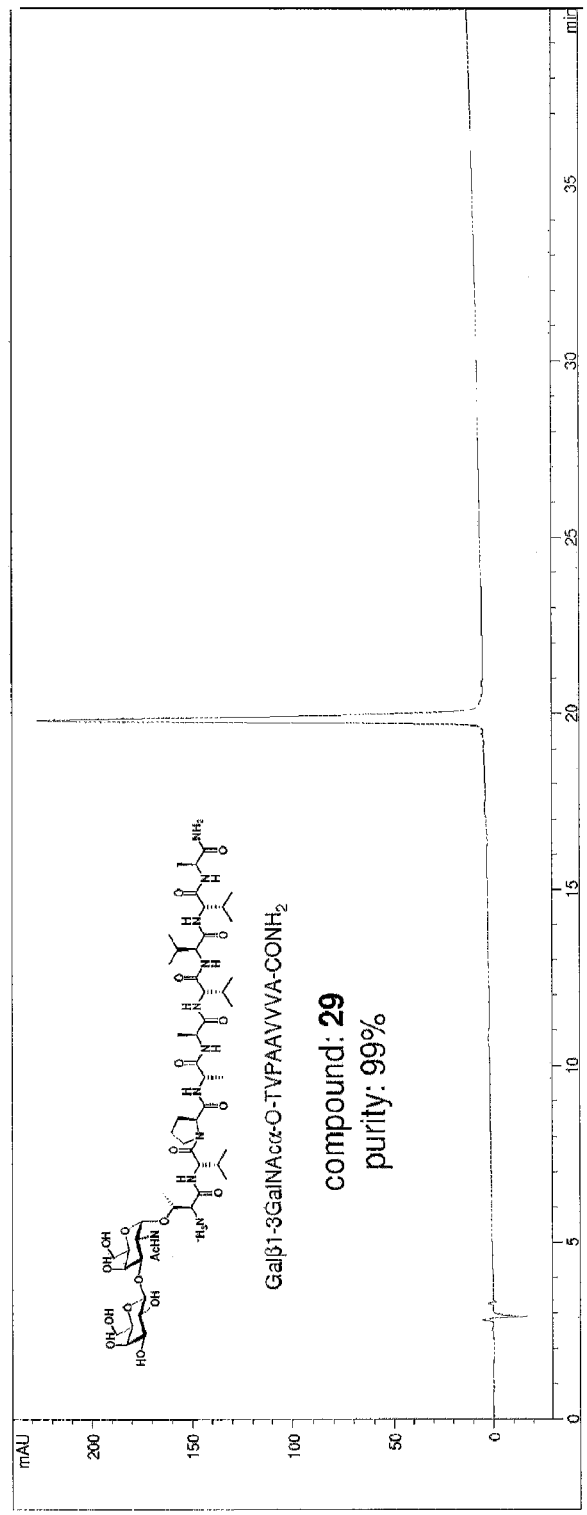
Figure 8A:
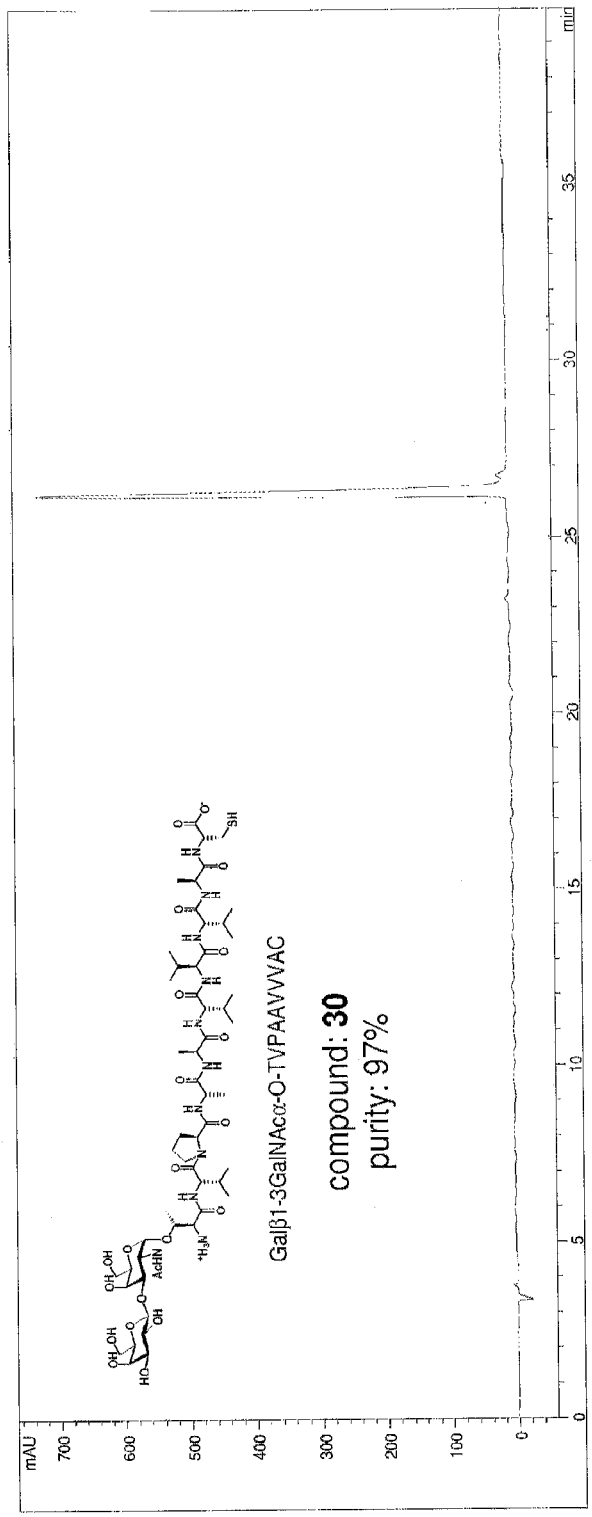
Figure 8A:
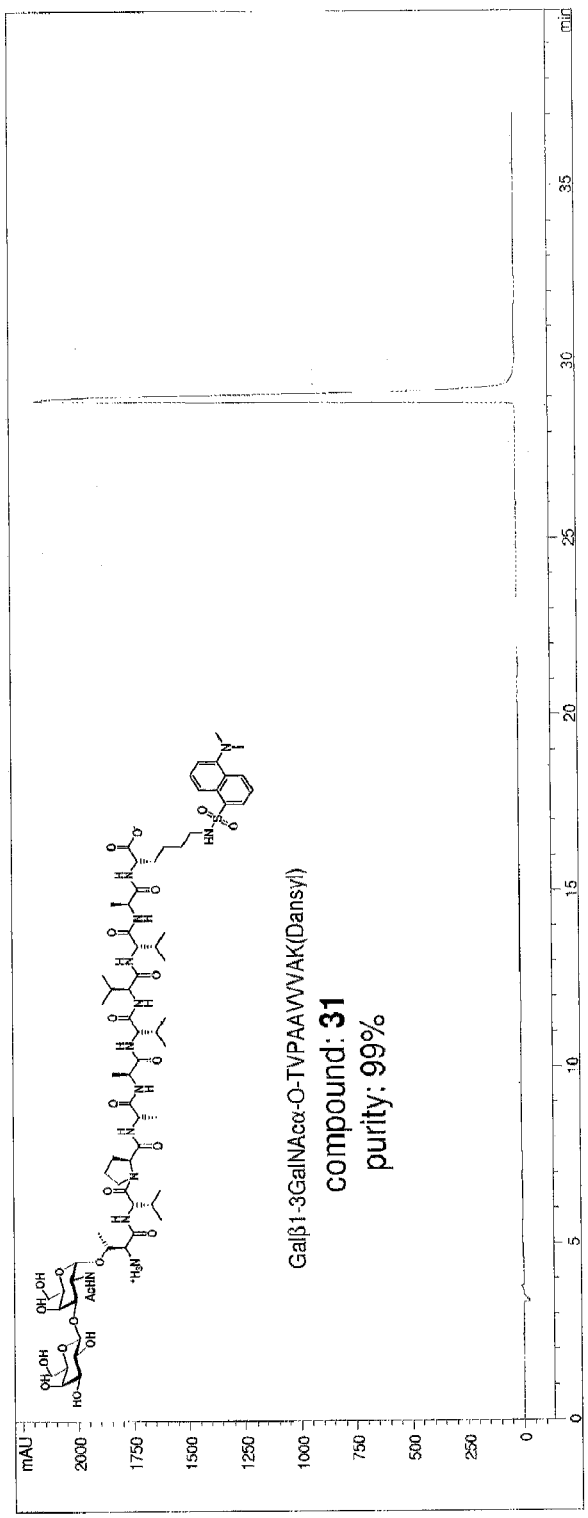
Figure 8A:
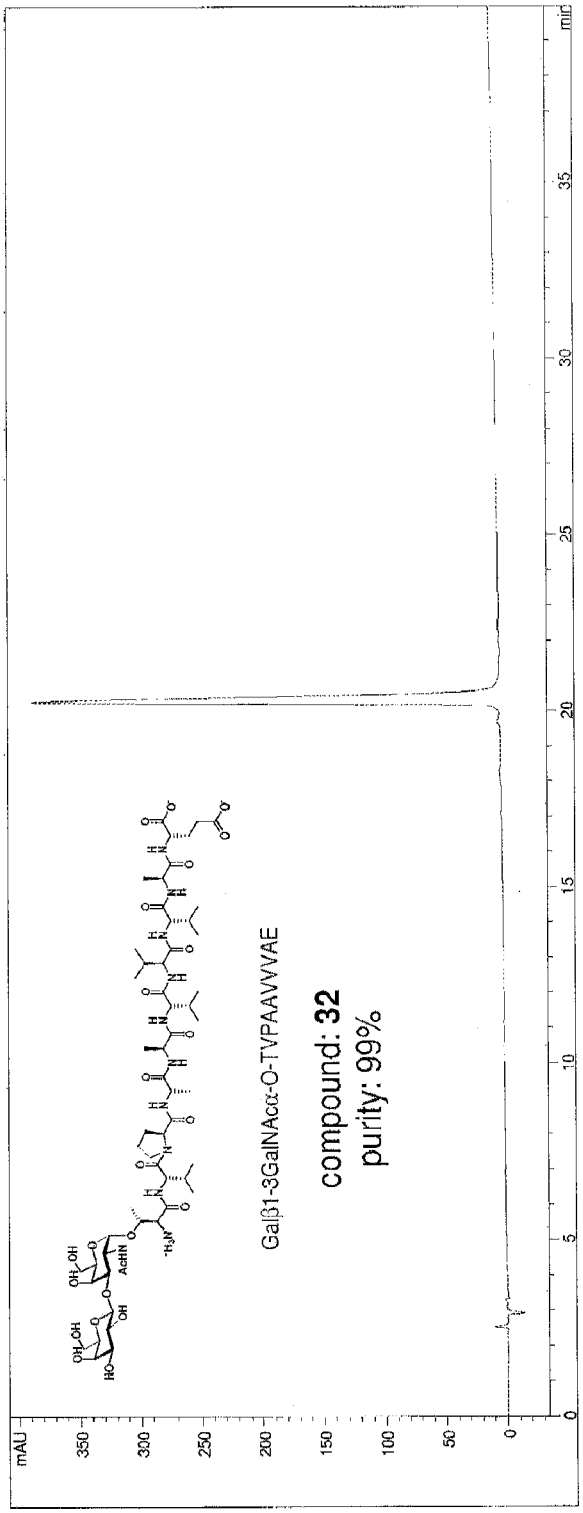
Figure 8A:
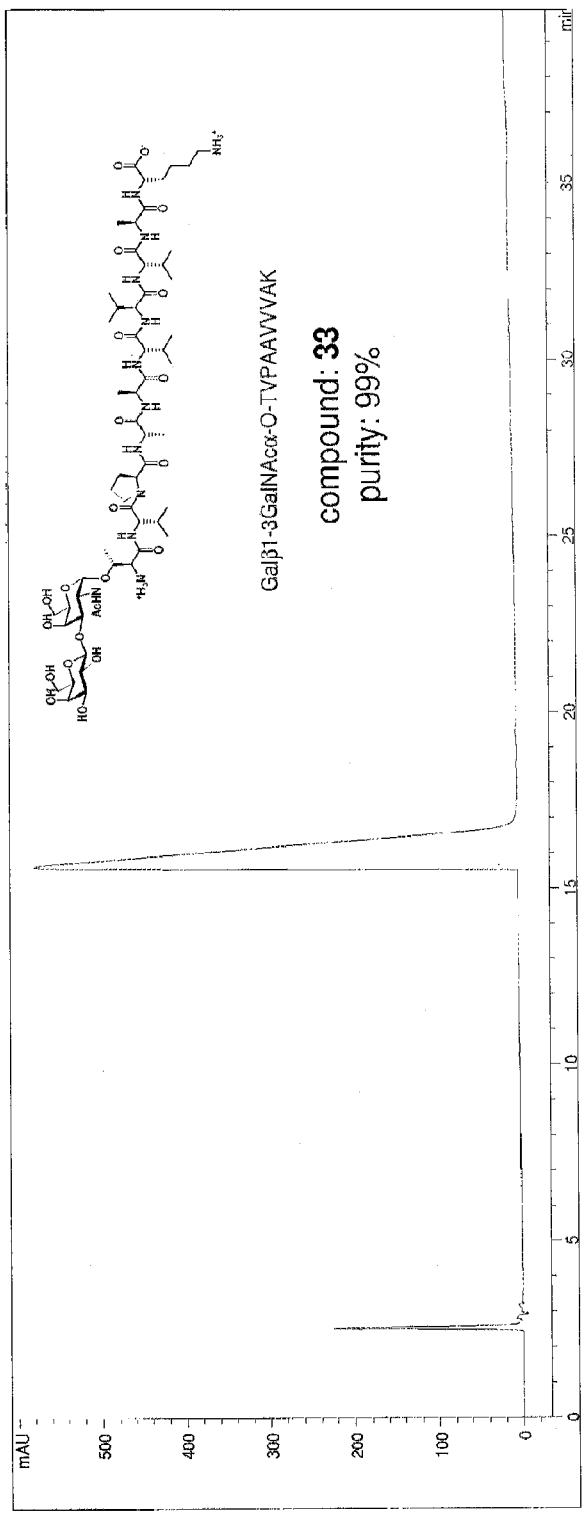
Figure 8A:
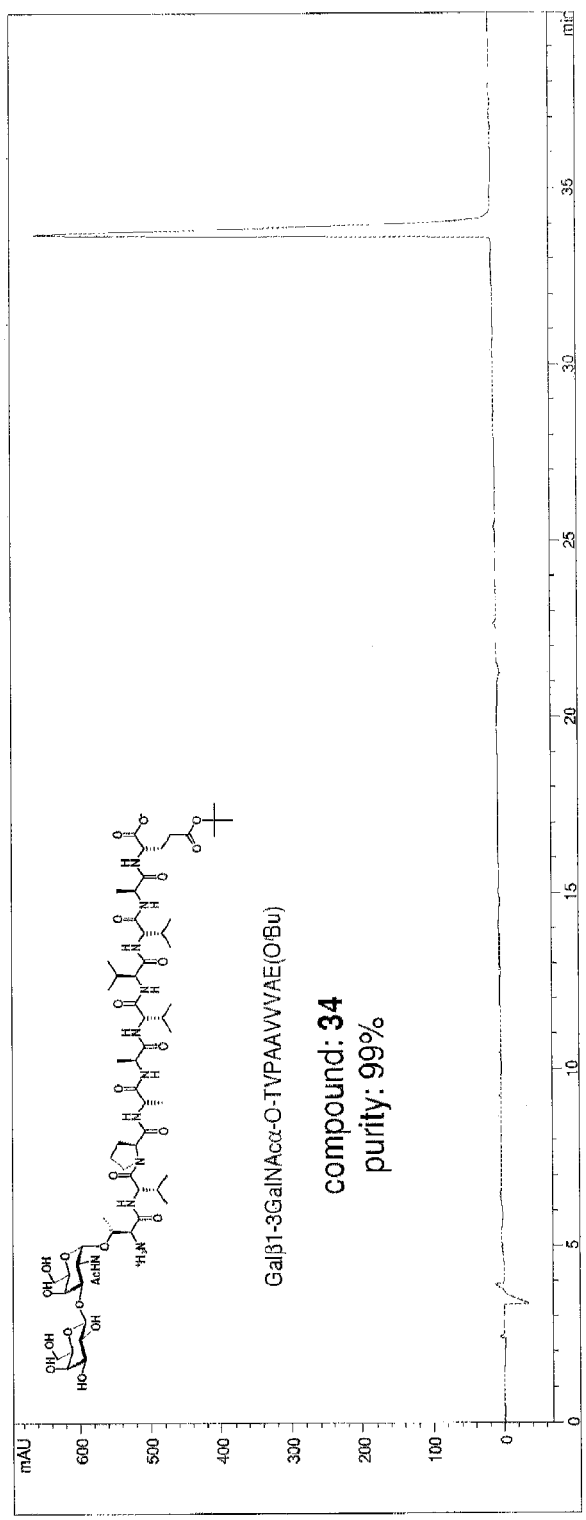
Figure 8A:
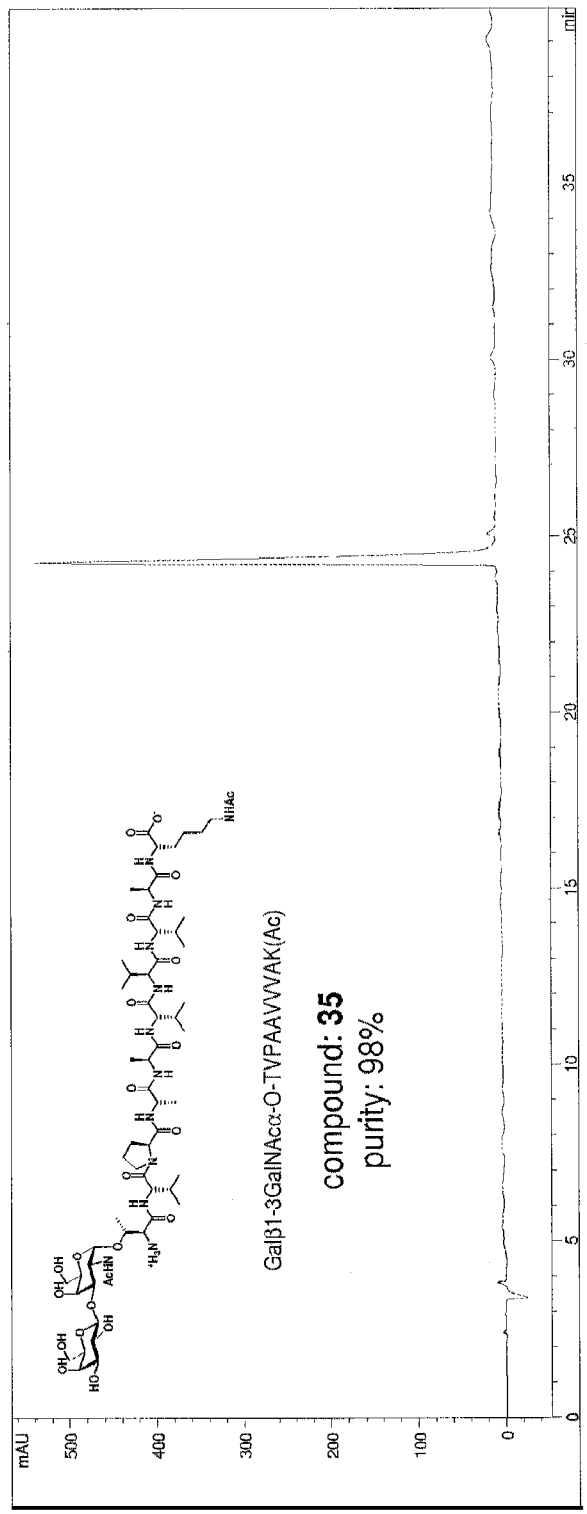
Figure 8A:
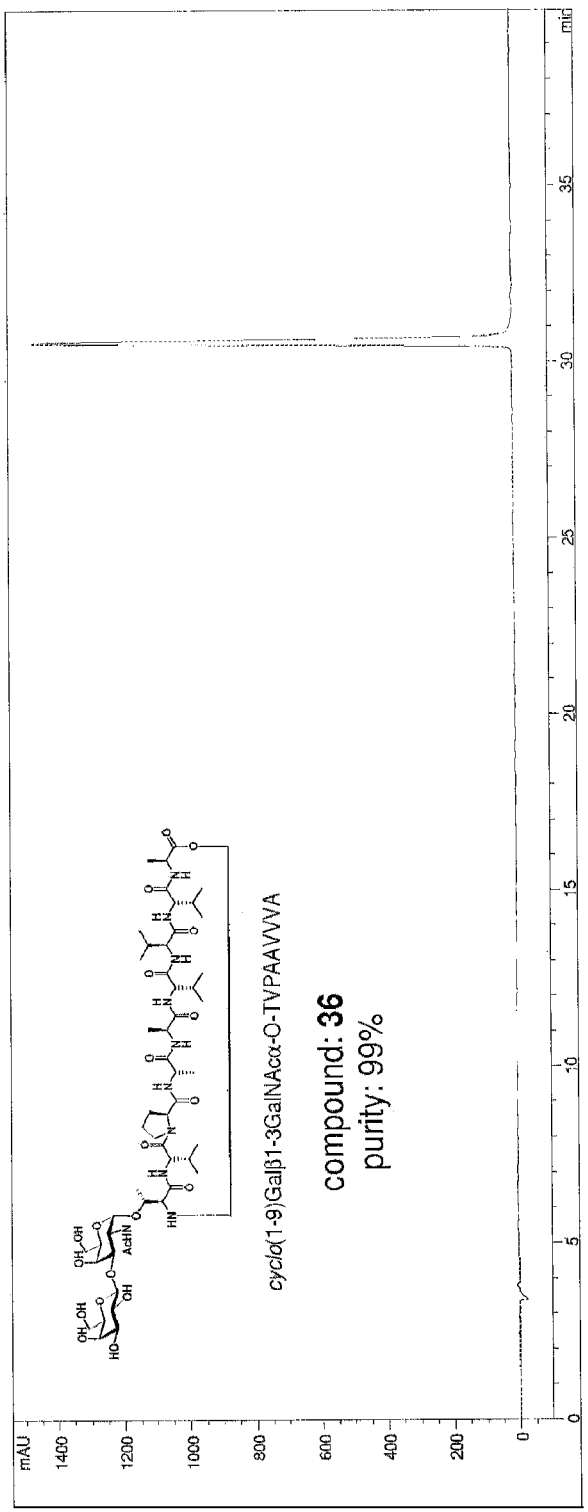

Based on these data, in some embodiments there are certain aspects of the peptide portion of as-APF for its antiproliferative activity in bladder epithelial cells. This disclosure demonstrates that the peptide portion of as-APF is useful to have at least 8 N-terminal amino acids. A summary of these requirements is illustrated in FIG. 7. The data also indicate another embodiment of the invention being a trans conformation for the Pro-Ala peptide bond. In addition, for optimal activity the peptide portion of as-APF comprises: 1) a specific amino acid sequence with alanine in position 5 and valines in positions 6-8; 2) the conformation allowed by proline or pipecolic acid in position 3; 3) a very specific arrangement of methyl groups on the two N-terminal amino acids; 4) an amino acid no bulkier than alanine in the 9th position; and/or 5) a free N-terminal amino group and a free C-terminal carboxy group. These exemplary features are highlighted in FIG. 7.

Materials and Methods

General. Amino acids and resins were purchased from AnaSpec, Inc. (San Jose, Calif.), or EMD Chemicals (San Diego, Calif.) PyAOP, AcOH and $Ac_2O$ from Sigma Aldrich (St. Louis, Mo.), HOAt and HATU from AK Scientific, Inc. (Mountain View, Calif.) and solvents from American Bioanalytical (Natick, Mass.). Peptide synthesis was performed on a Nautilus 2400 Parallel synthesizer (Argonaut, Technologies, Foster City, Calif.). Preparative HPLC was performed on a Waters 600 instrument with UV detection (Waters 2487) on reverse phase $C_{18}$ or $C_8$ silica (mobile phase: Solvent A, $H_2O$/0.1% TFA, Solvent B, $CH_3CN$ in 0.1% TFA). NMR analyses were performed on a Varian INOVA instrument operating at 500 MHz for proton from 15 to 40° C. in either $D_2O$ or $H_2O/D_2O$ 9:1. Water suppression was accomplished by standard WATERGATE or WET pulse sequences for observation of amide protons. CD measurements were performed on an AVIV 202 spectrometer in water (50 µM, pH=6.0) and neat TFE (50 µM).

Patients. Normal controls who were asymptomatic for urinary tract disease and undergoing cystoscopy following abdominal or pelvic surgery as standard of care were consented to provide biopsy for the generation of normal bladder epithelial cell explants. These participants were all at least 18 years old and enrolled in accordance with guidelines of the Institutional Review Board of the University of Maryland School of Medicine.

The synthesis of APF derivatives is described elsewhere herein.

Cell Culture. Cystoscopy was performed under general anesthesia, and 4-mm² pieces of transitional epithelium with submucosal bladder tissue were obtained for the growth of primary bladder epithelial cells, as previously described (Keay et al., 1996; 2004). Primary normal bladder epithelial cells were propagated in DMEM-F12 (Media-Tech, Herndon Va.) with 10% heat-inactivated fetal bovine serum (FBS), 1% antibiotic/antimycotic solution, 1% L-glutamine, 0.25 units/mL insulin (all from Sigma, St. Louis, Mo.), and 5 ng/mL hEGF (R&D Systems, Minneapolis, Minn.) at 37° C. in a 5% $CO_2$ atmosphere and characterized by binding of AE-1/AE-3 pancytokeratin antibodies (Signet, Dedham, Mass.).

Ovarian carcinoma (Caov-3), prostate carcinoma (LNCaP), melanoma (Hs839.T), pancreatic carcinoma (PANC-1), bladder carcinoma (T24, RT4 and TCCSuP), kidney carcinoma (ACHN), cervical carcinoma (HeLa), lung carcinoma (A549), colon carcinoma (WiDr), and breast carcinoma (Bt-474) cells were all purchased from the American Type Culture Collection (ATCC). Caov-3, HS839.T, PANC-1, and BT-474 cells were grown in DMEM medium (with 4 mM L-glutamine—Gibco BRL) containing 10% heat-inactivated fetal calf serum, 4.5 g/L glucose, 1.5 g/L sodium bicarbonate and 1% antibiotic/antimycotic solution (all supplements from Sigma except sodium bicarbonate which is from Gibco BRL). LNCaP cells were grown in RPMI medium (with 2 mM L-glutamine—Gibco BRL) containing 10% heat-incativated fetal calf serum, 10 mM HEPES buffer, 1 mM sodium pyruvate, 4.5 g/L glucose, 1.5 g/L sodium bicarbonate, and 1% antibiotic/antimycotic solution (all supplements from Sigma except sodium bicarbonate which is from Gibco BRL). T24 and RT4 cells were grown in McCoy's 5A medium (Gibco BRL) containing 10% heat-inactivated fetal calf serum, 1% L-glutamine, 2.2 g/L sodium bicarbonate, and 1% antibiotic/antimycotic solution (all supplements from Sigma except sodium bicarbonate which is from Gibco BRL). TCCSuP, HeLa, and WiDr cells were grown in MEM (Gibco BRL) containing 10% heat-inactivated fetal calf serum, 1% L-glutamine, 1 mM sodium pyruvate, and 1% antibiotic/antimycotic solution (all supplements from Sigma). ACHN cells were grown in the same medium as TCCSuP and HeLa cells with the exception that it also contained 1.5 g/L sodium bicarbonate (Gibco BRL). A549 cells were grown in F12 medium (Gibco BRL) containing 10% heat-inactivated fetal calf serum, 1% L-glutamine, and 1% antibiotic/antimycotic solution (all supplements from Sigma).

$^3$H-Thymidine Incorporation. Cell proliferation was measured by $^3$H-thymidine incorporation into explanted normal human bladder epithelial cells, plating $1.5 \times 10^4$ cells/well onto a 96 well cell culture plate (VWR 29442-054), in 150 ul/well MEM containing 10% heat inactivated FBS, 1% antibiotic/antimycotic solution, and 1% L-glutamine (all from Sigma), resulting in a doubling time of 48-72 hours, as previously described (Keay et al., 1996; 2004). Each purified lyophilized synthetic APF congener was resuspended in acetonitrile/distilled water (1:1), and applied to the cells in serum-free MEM (containing only L-glutamine and antibiotics/antimycotics); cell controls received acetonitrile/distilled water diluted in serum-free MEM alone. Cells were then incubated at 37° C. in a 5% $CO_2$ atmosphere for 48 hours. The cell contents harvested and methanol-fixed onto glass fiber filter paper, and the amount of radioactivity incorporated determined. Significant inhibition of $^3$H-thymidine incorporation was defined as a mean decrease in counts per minute of greater than 2 standard deviations from the mean of control cells for each plate. Inhibition of cell proliferation was determined from a semi-log plot of dose-response for each APF derivative; $IC_{50}$ was determined as the concentration of each derivative that caused a mean 50% inhibition of thymidine incorporation as compared to the mean of untreated cell controls.

Cancer (carcinoma or melanoma) cell proliferation was measured by $^3$H-thymidine incorporation into each type of cancer cell, plating $3.0 \times 10^3$ cells/well (A549 cells) or $1.5 \times 10^3$ cells/well (all other cancer cells) onto a 96 well cell culture plate (VWR 29442-054), in 150 ul/well of the respective normal growth medium for each cell type (see above). All APF congeners were resuspended as described for normal bladder epithelial cells, except using the specific serum-free medium appropriate for each cell type, and the remainder of the assay was performed as described for normal bladder cells, above.

Statistical Analysis. The thymidine incorporation (APF biological activity) assay was performed in triplicate on at least two separate runs, with 1 run simultaneously in triplicate on the same plate. The significance of the difference between mean values for each congener vs. mean values for compound 1 was determined by an analysis of variance.

Example 3

Structure-Activity Relationship Studies for the Peptide Portion of APF

Table 6 shows analytical data for exemplary as-APF analogs. FIG. 8 provides HPLC traces of as-APF analogs. HPLC traces. HPLC system: Agilent 1100 with UV detection (227 nm). Column: Varian Microsorb-MV 100-5 $C_8$ 250×4.6. Gradient: 5% B→50% B over 40 min; A—water (0.1% TFA); B—acetonitrile (0.1% TFA). Flow rate: 1 mL/min.

Figure 9:
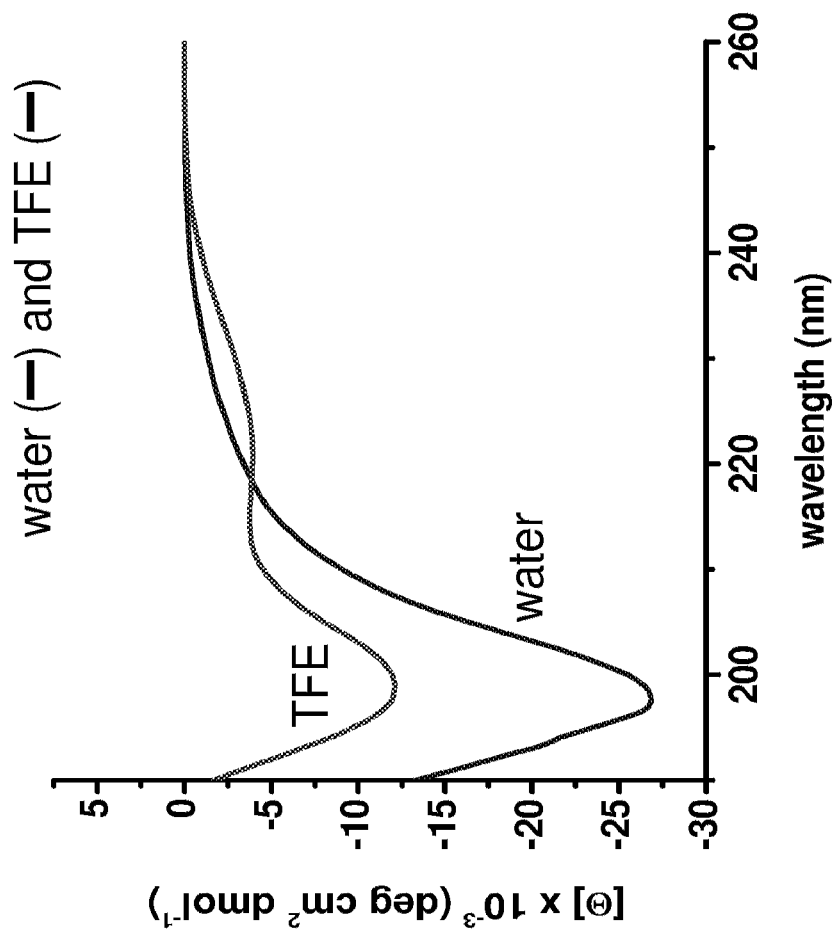
FIG. 9 demonstrates CD spectrum of as-APF in water and TFE.
Figure 10A:
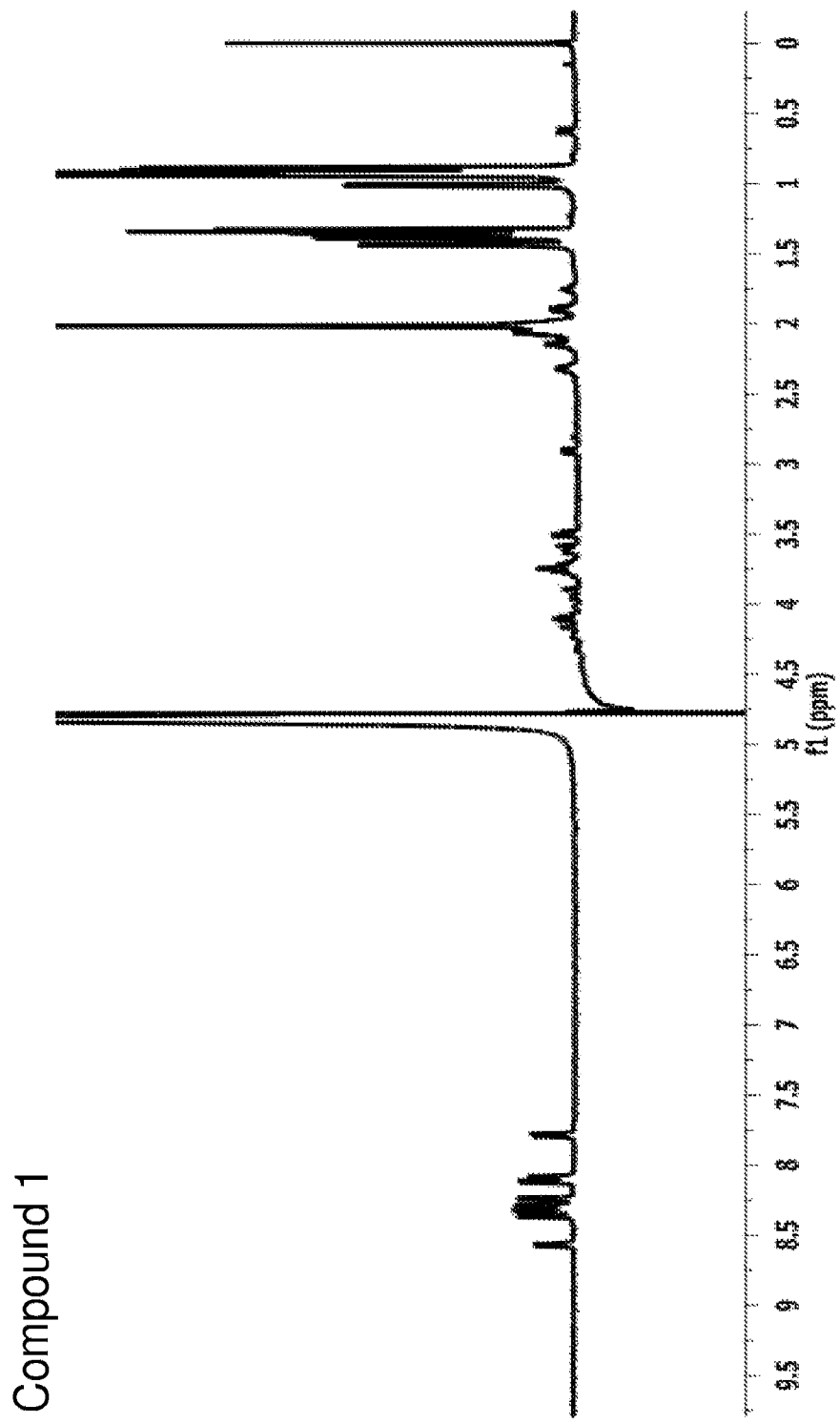
FIGS. 10A-10AJ show proton NMR spectra of exemplary as-APF analogues.
Figure 10B:
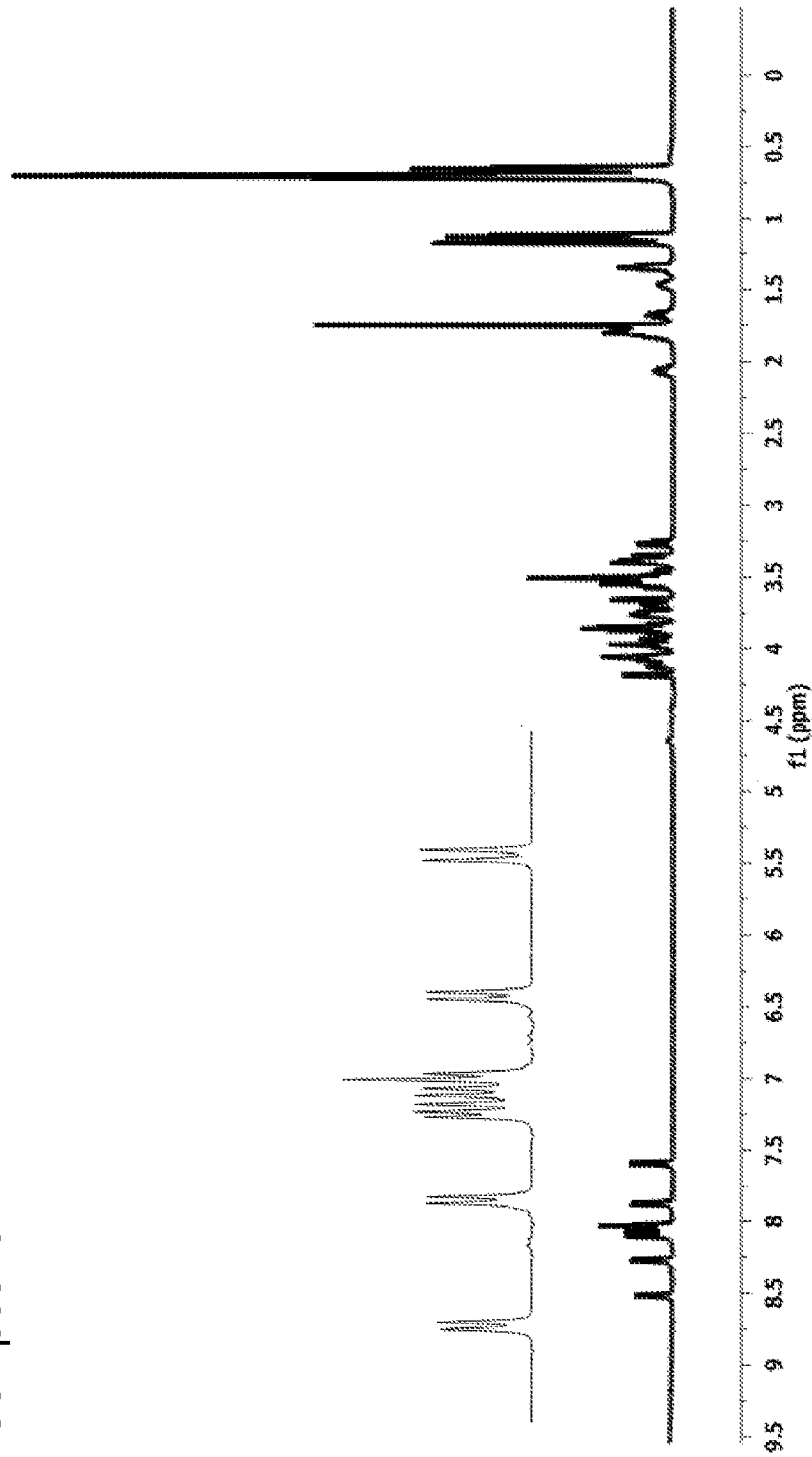
Figure 10C:
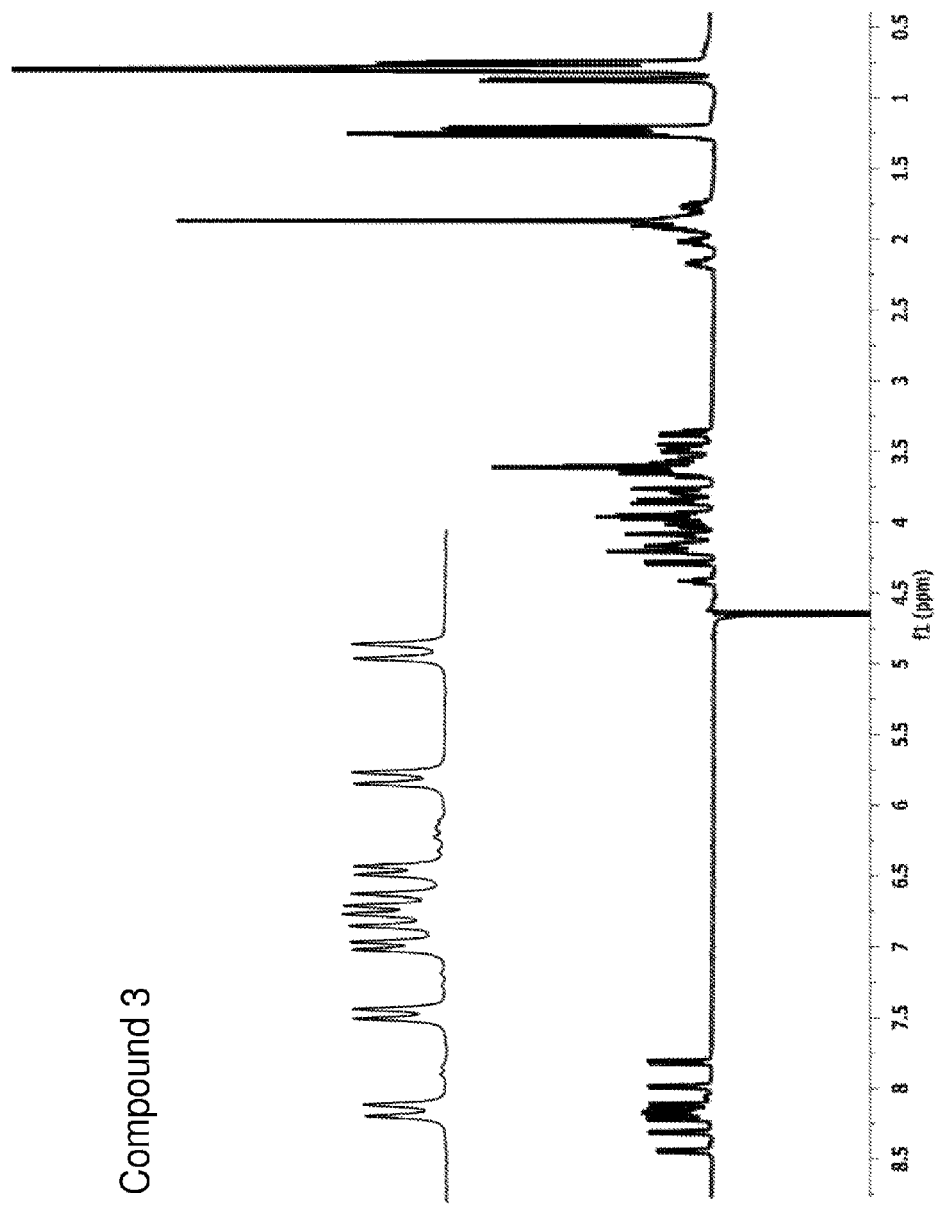
Figure 10D:
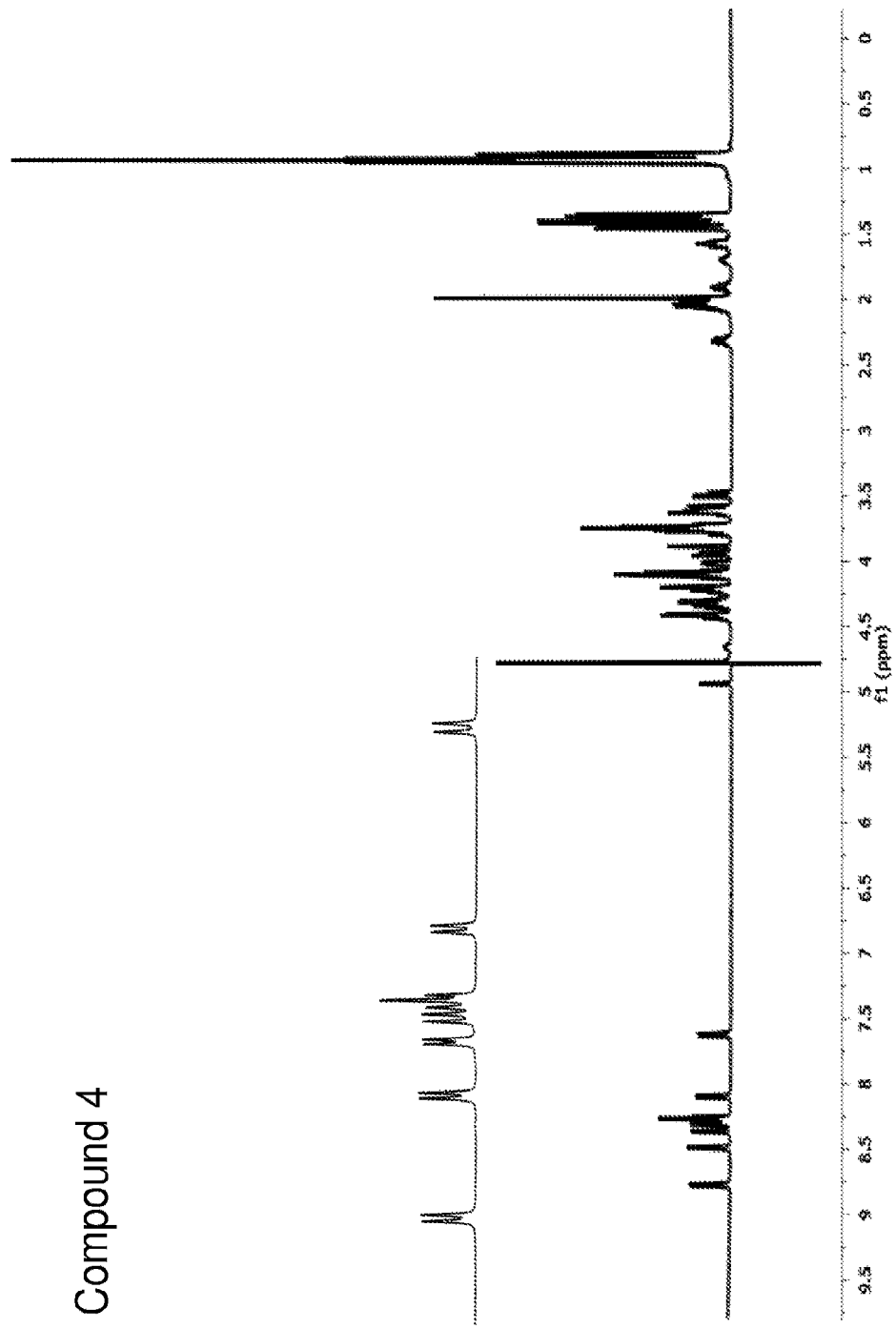
Figure 10E:
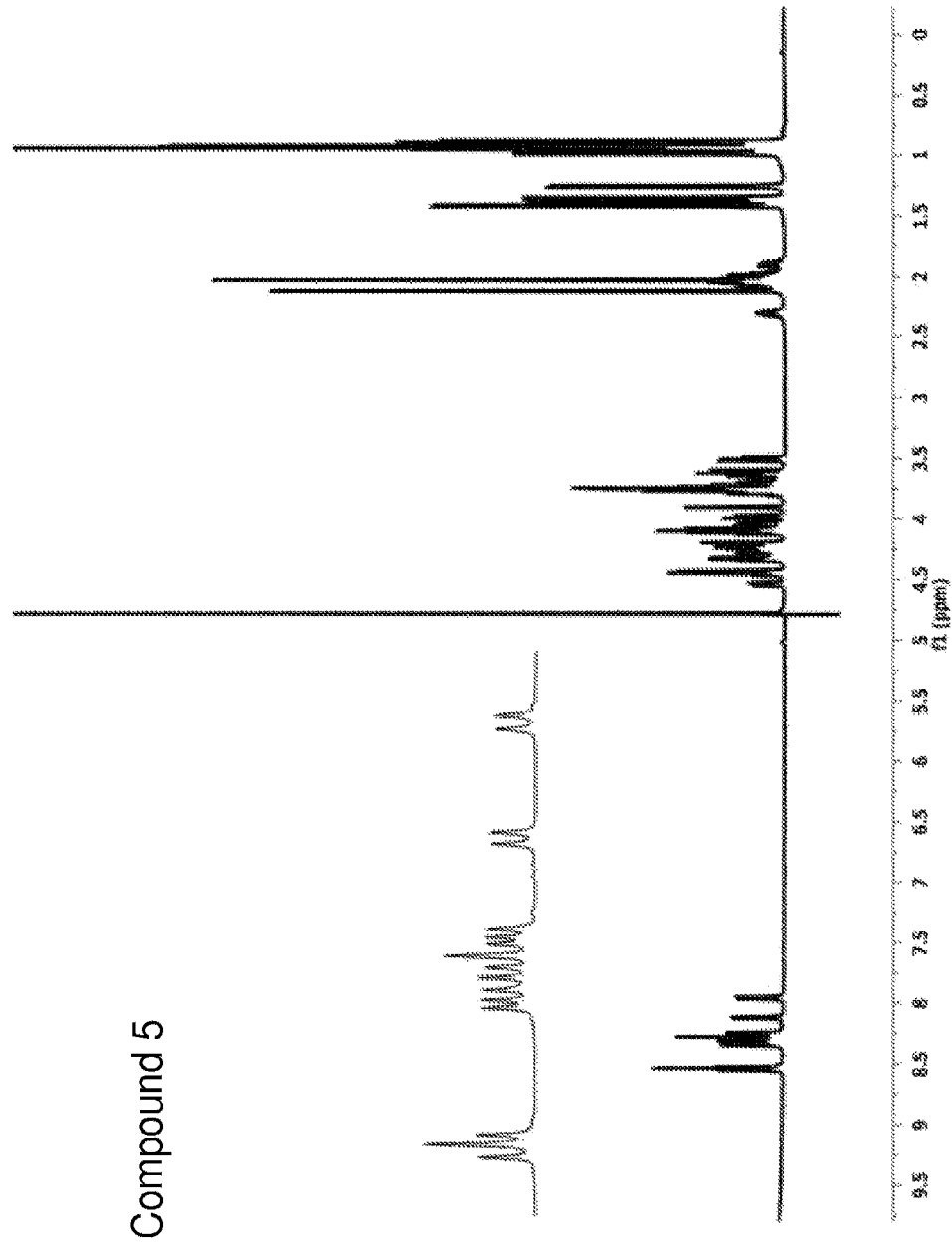
Figure 10F:
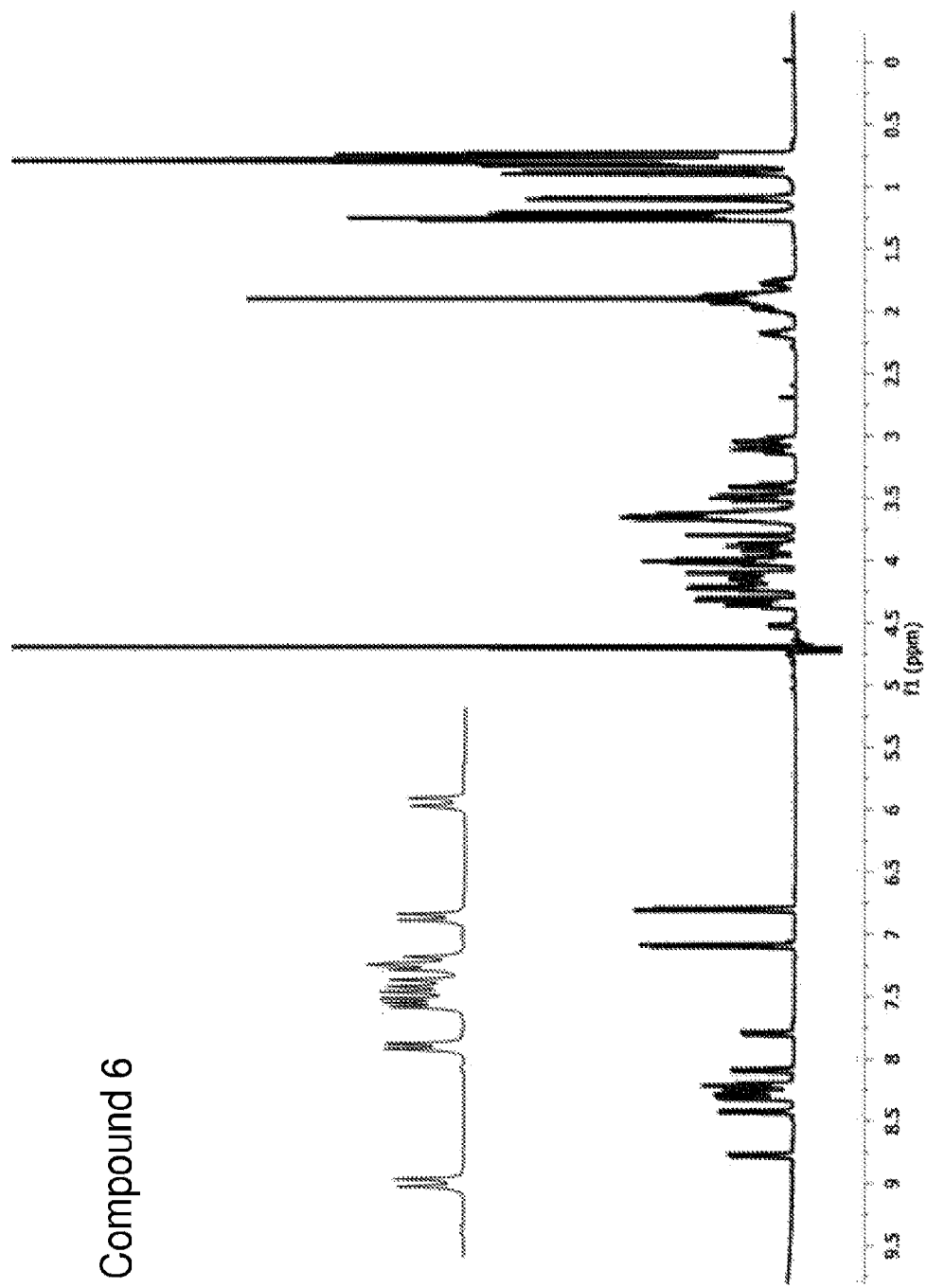
Figure 10G:
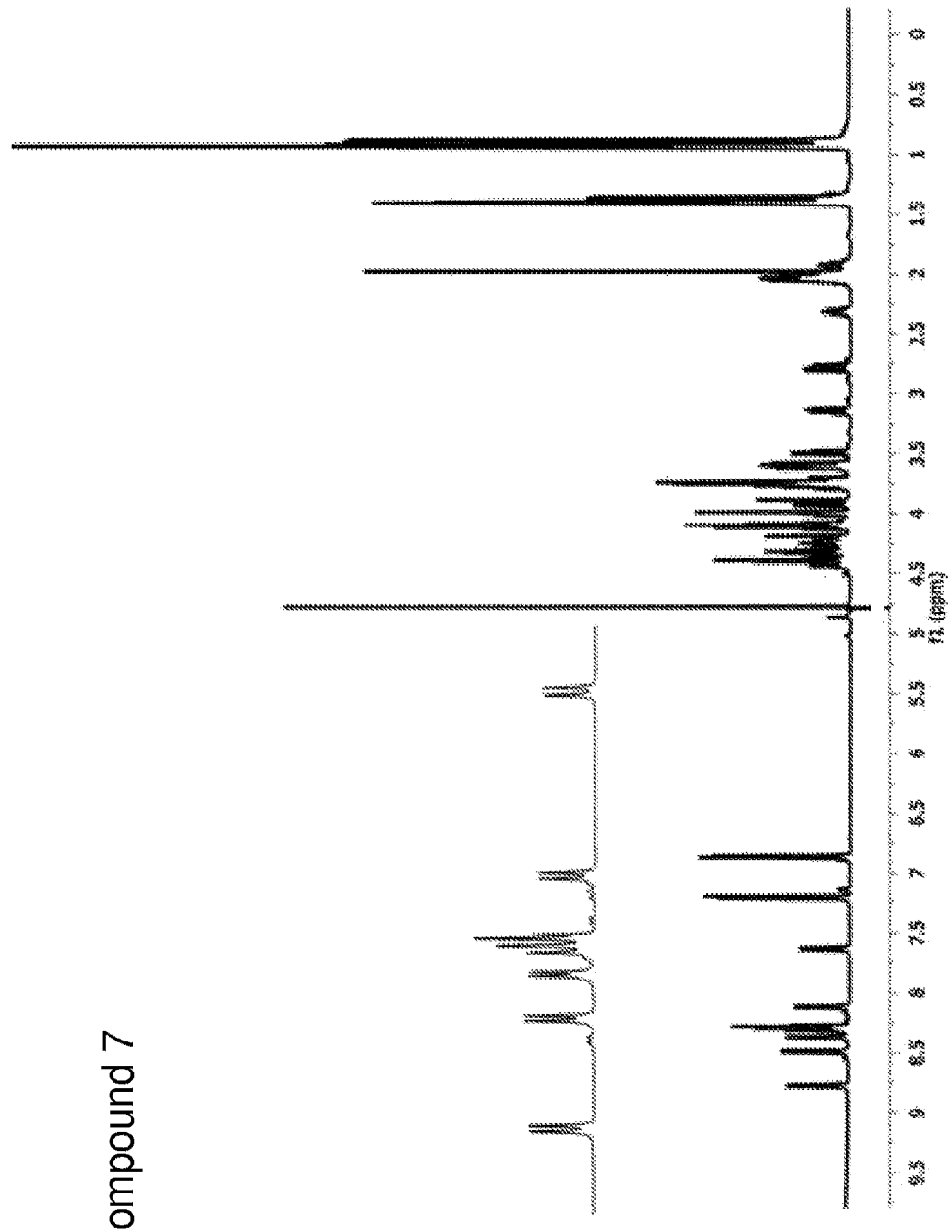
Figure 10H:
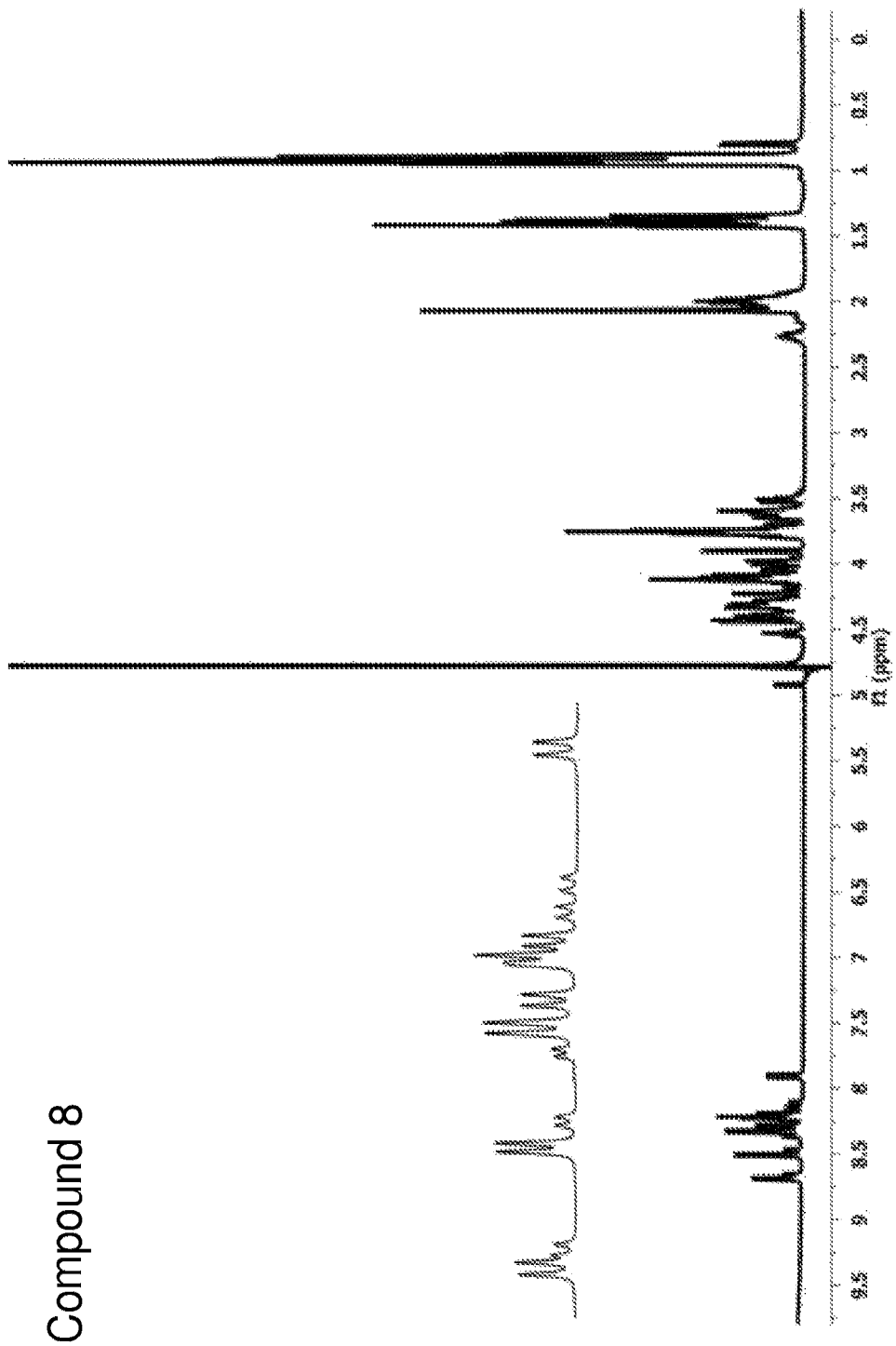
Figure 10I:
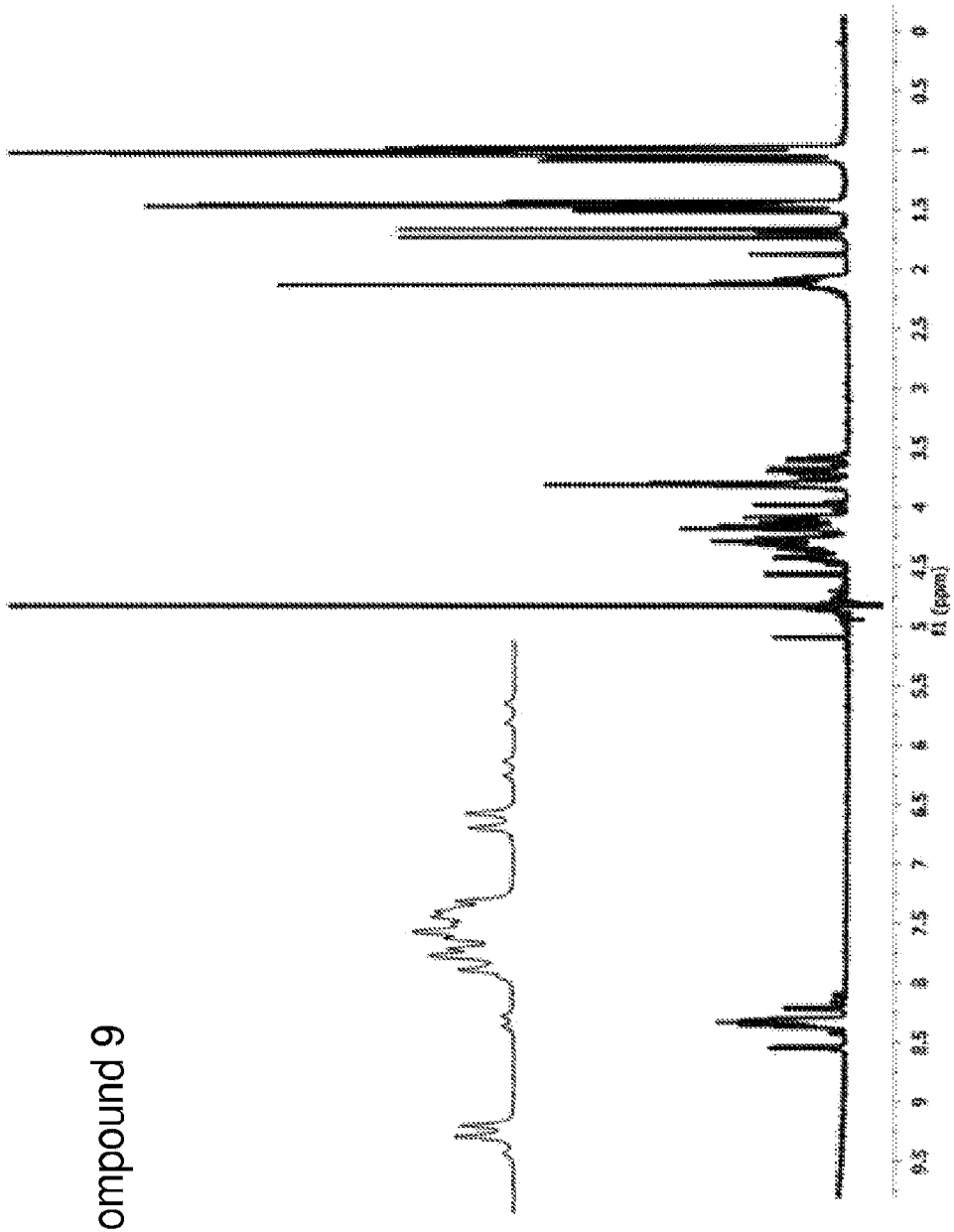
Figure 10J:
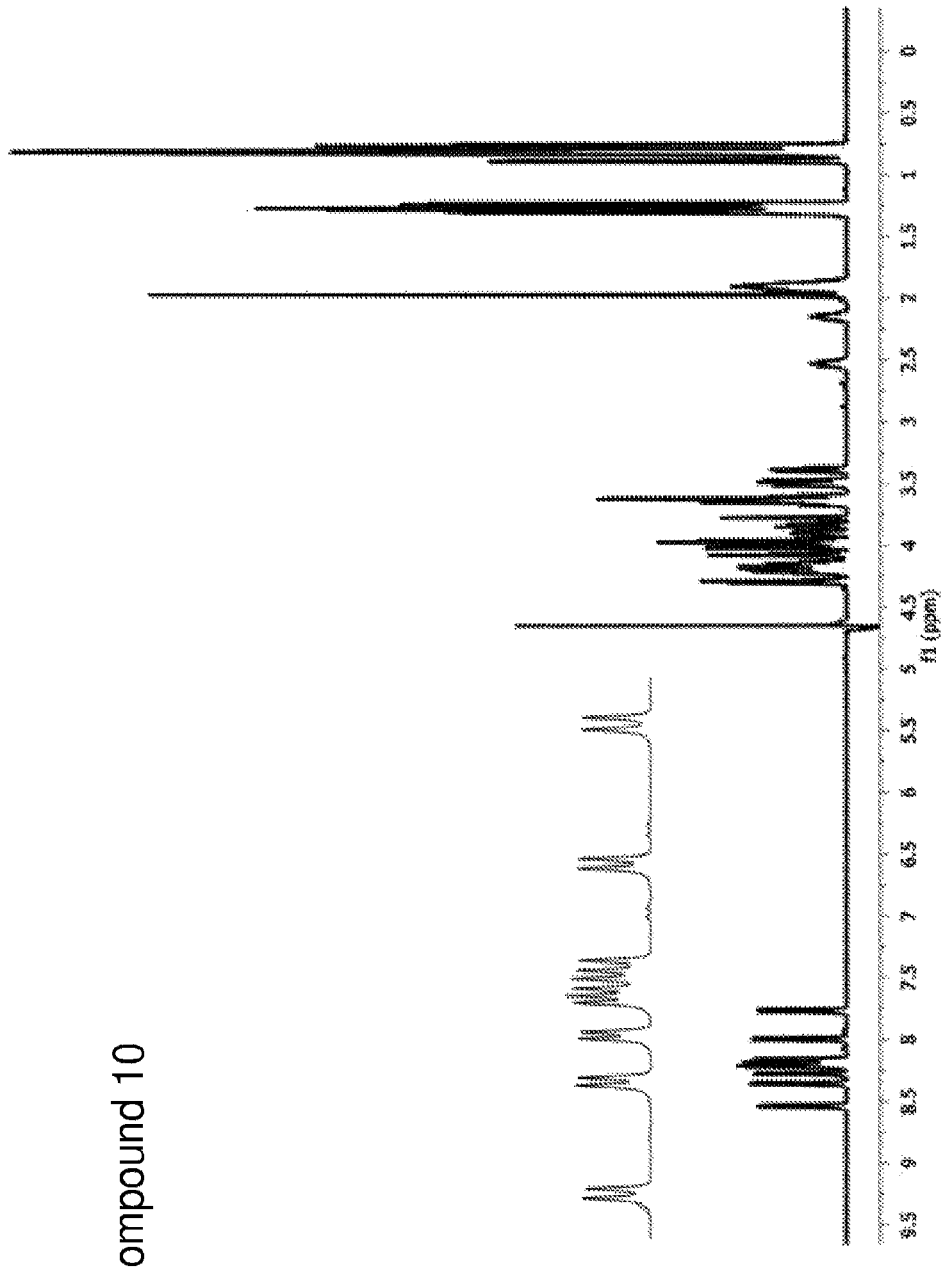
Figure 10K:
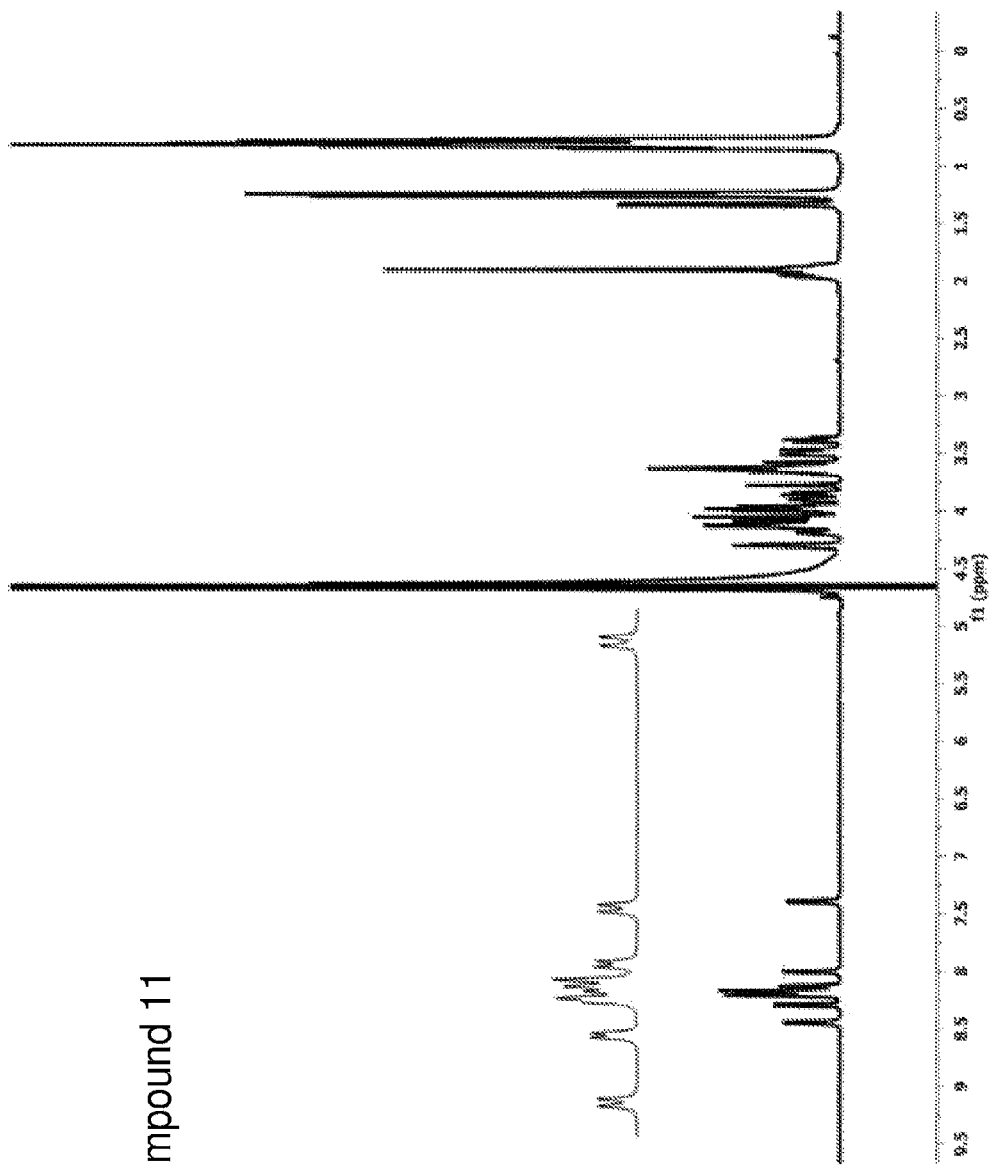
Figure 10L:
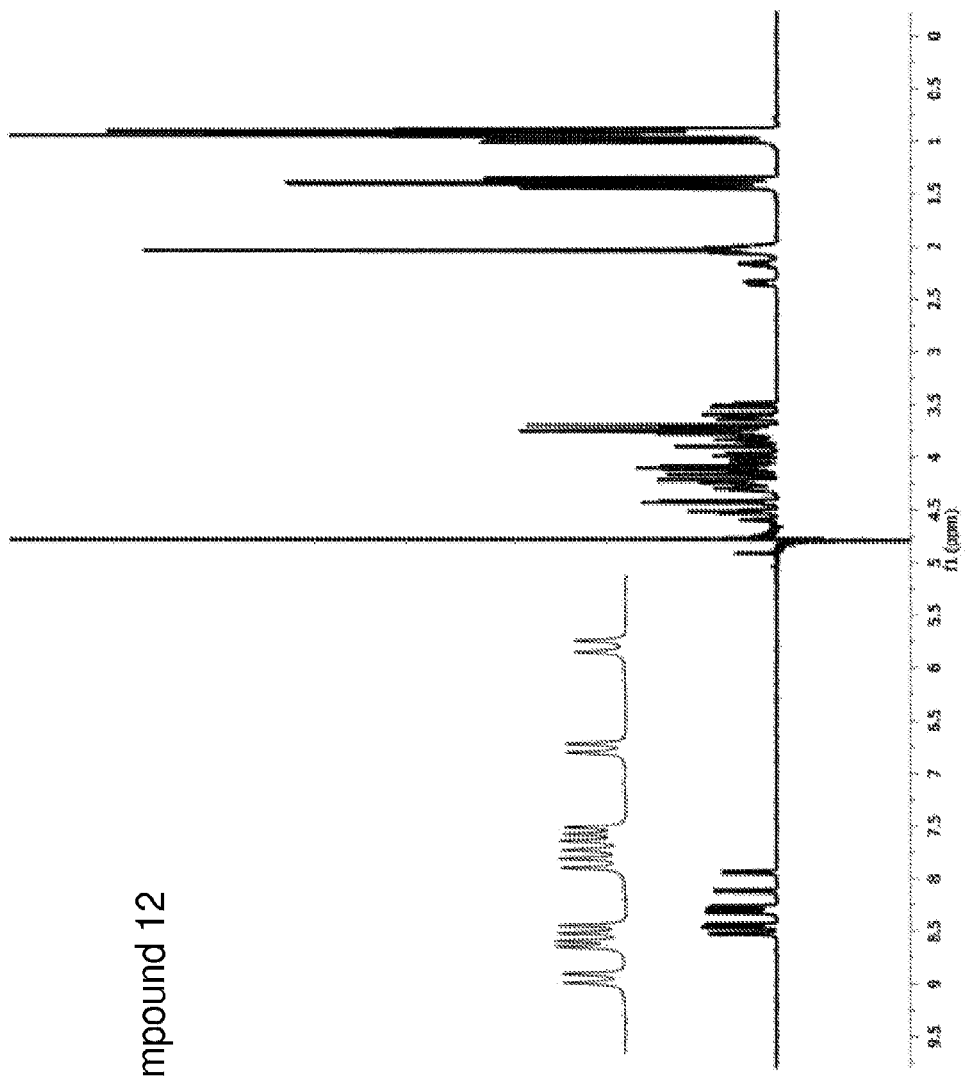
Figure 10N:
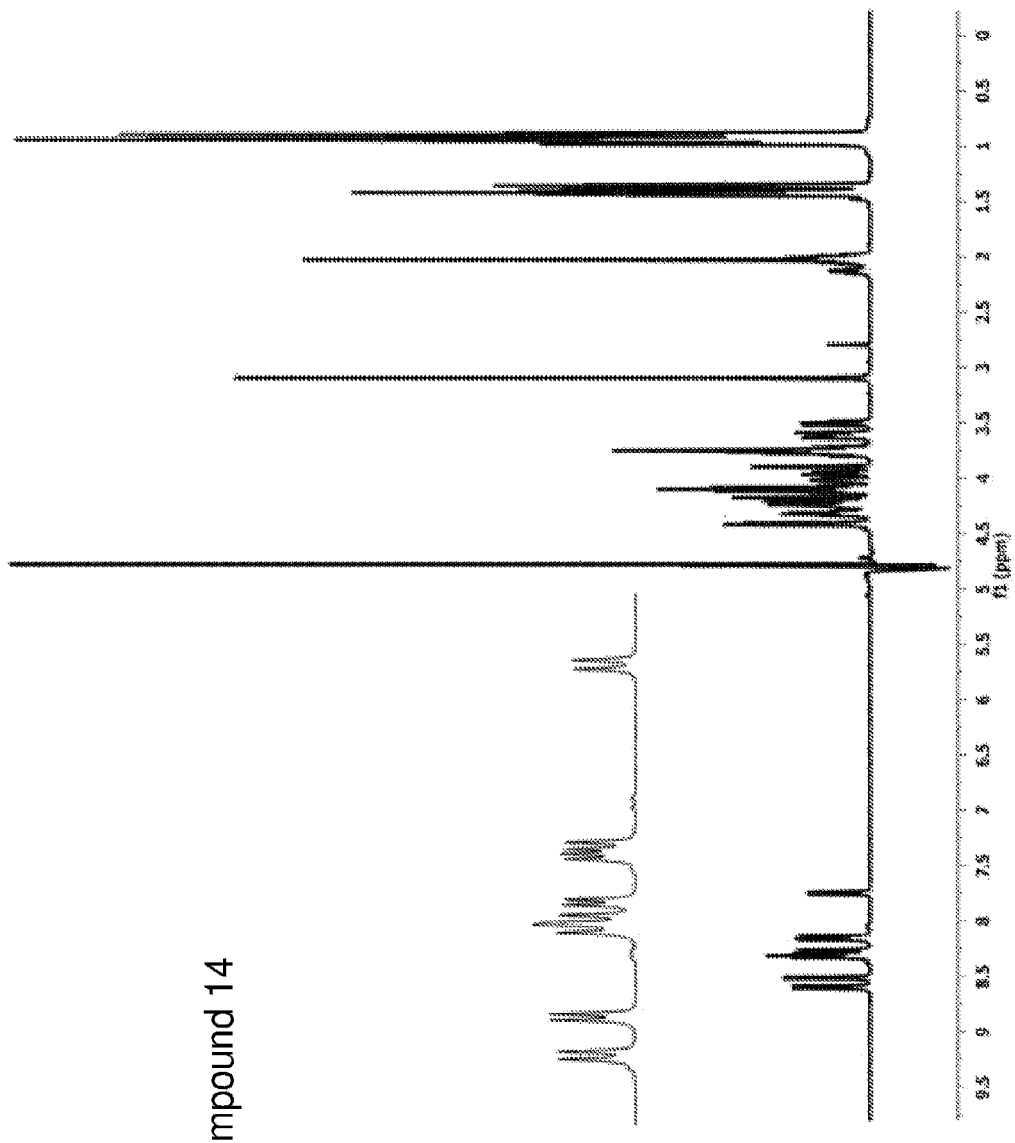
Figure 10O:
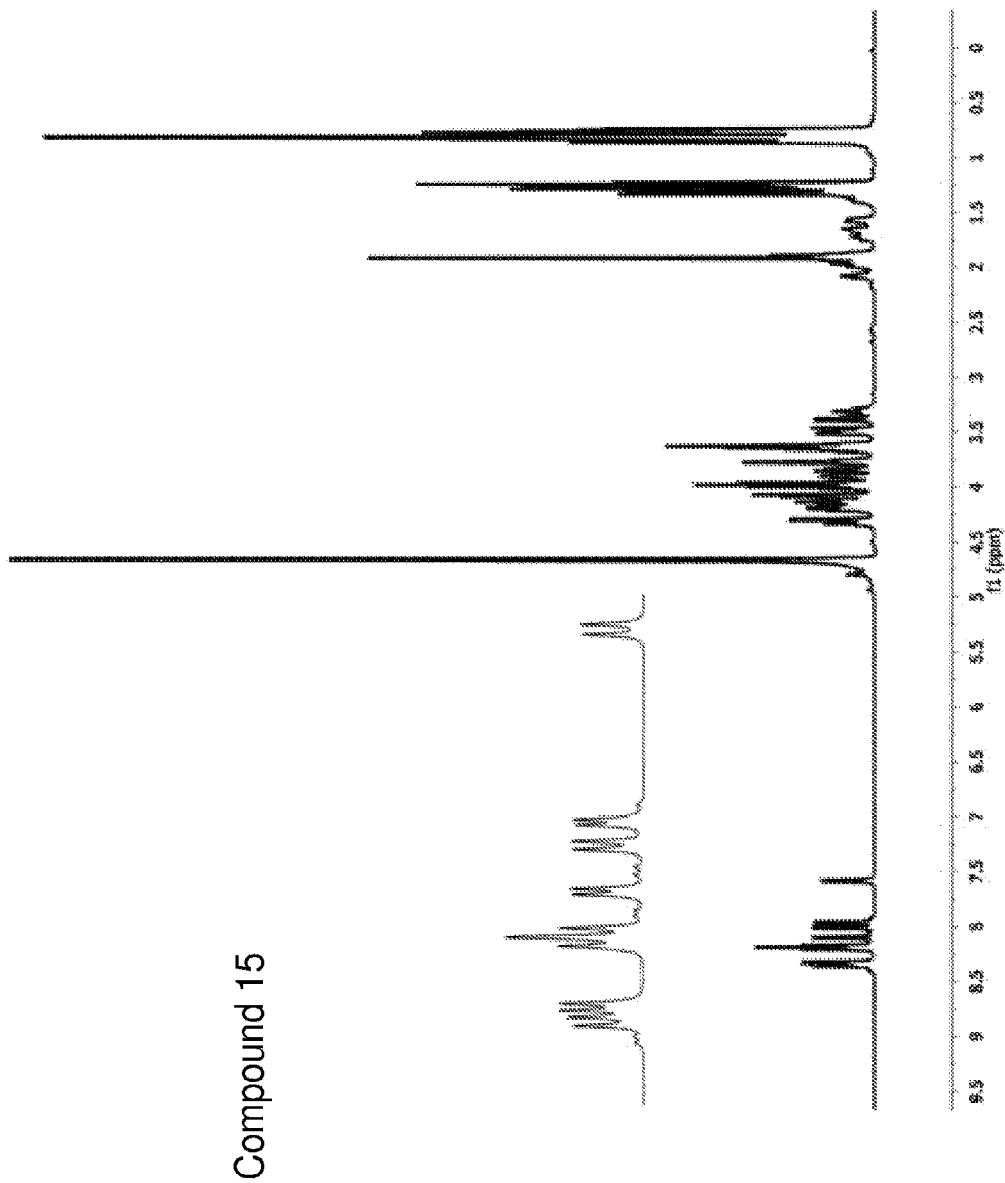
Figure 10P:
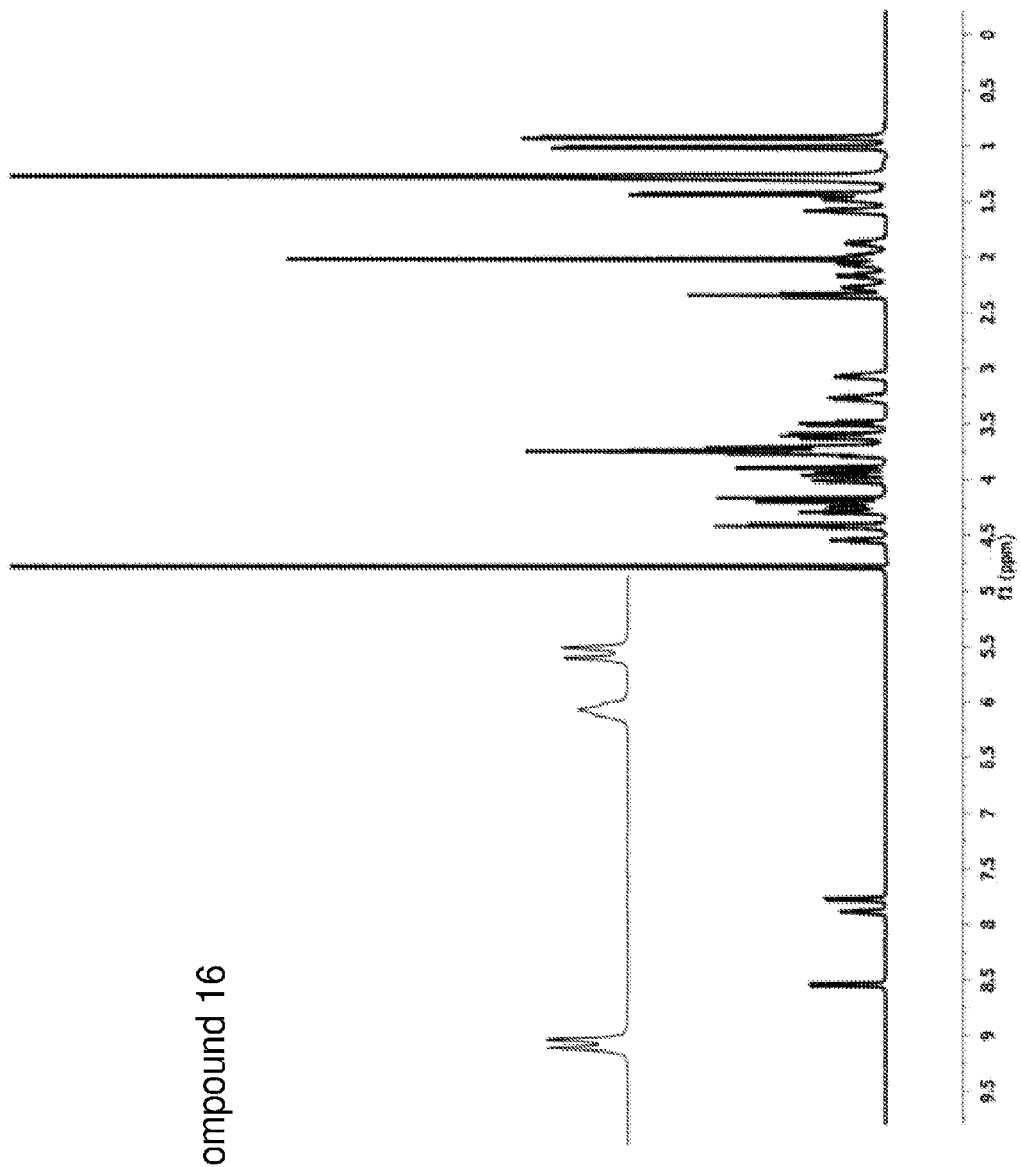
Figure 10Q:
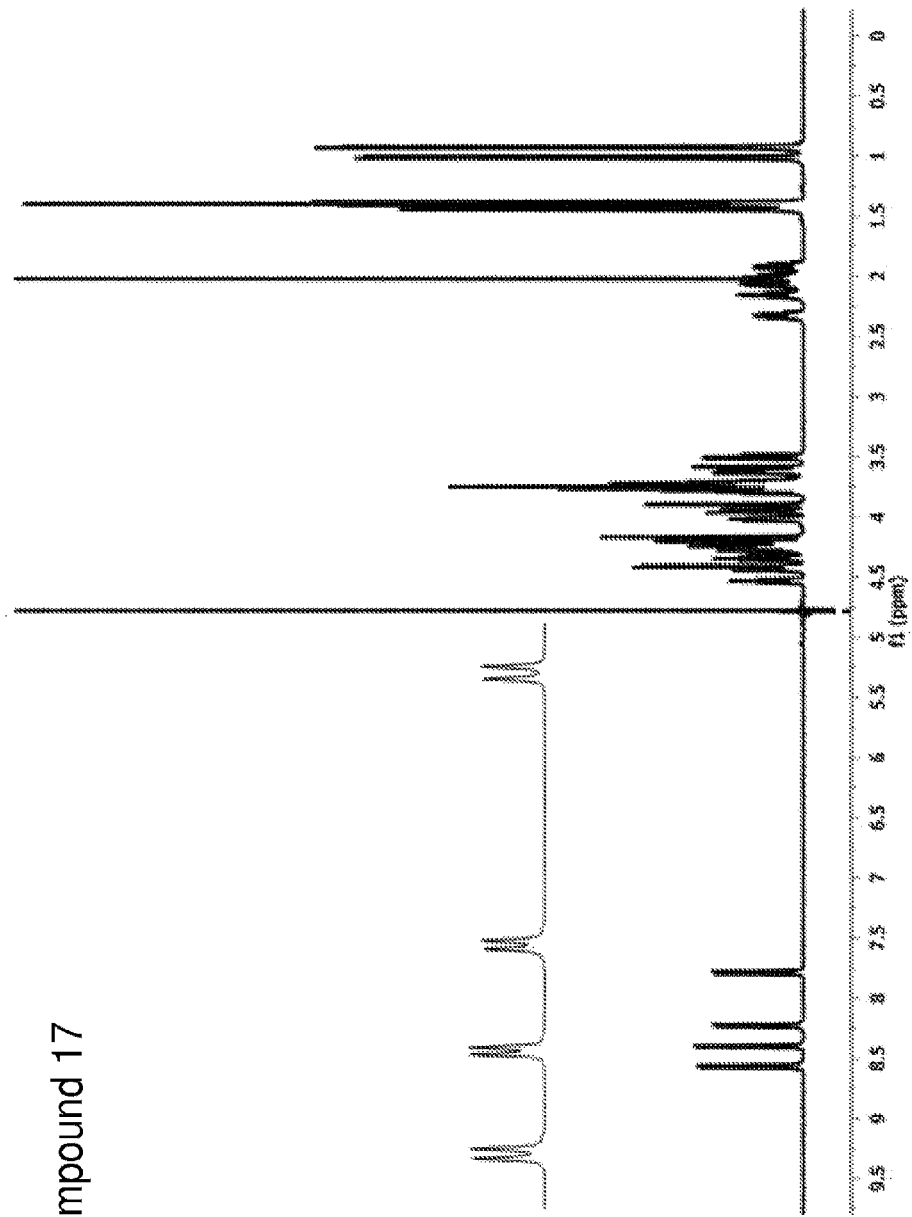
Figure 10S:
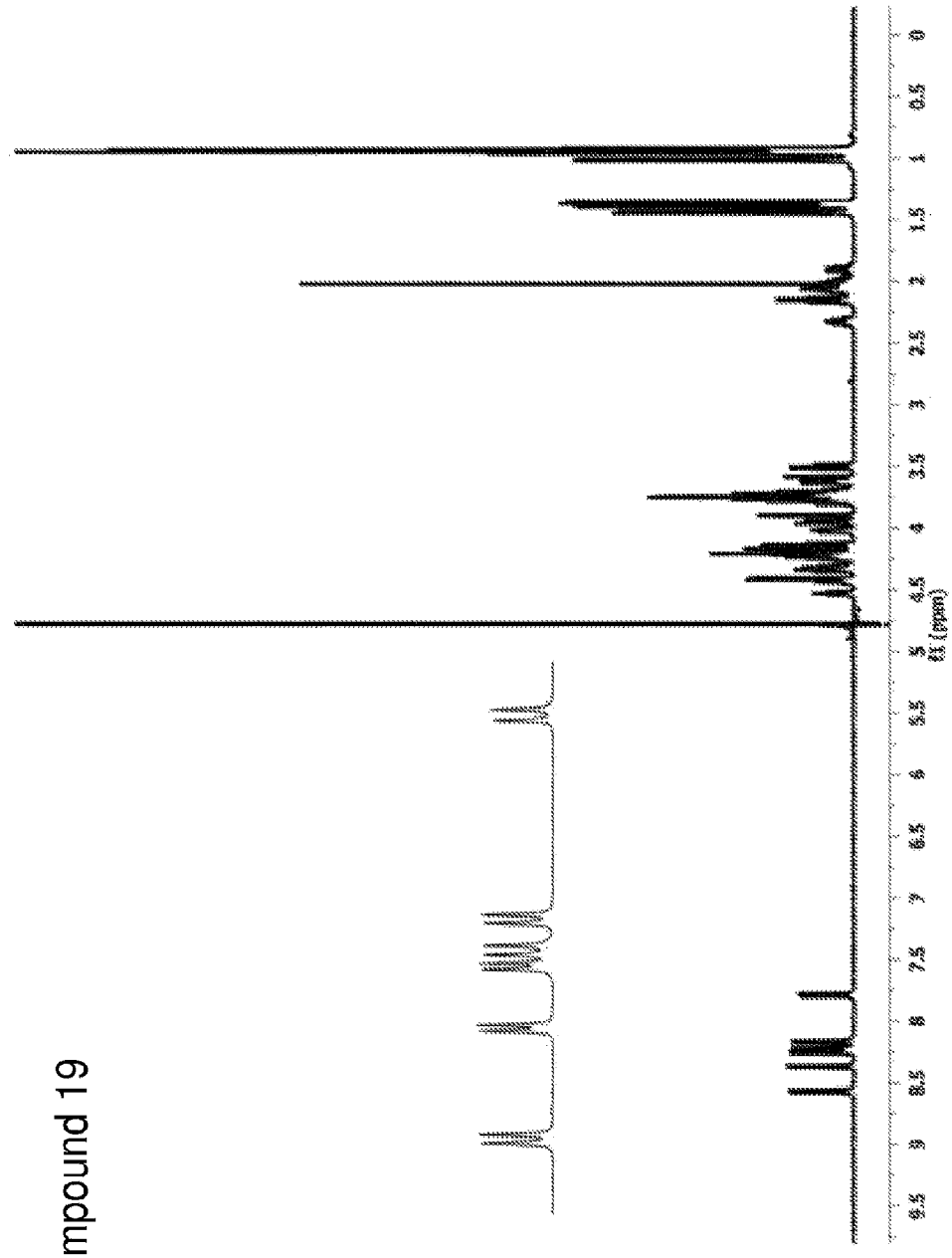
Figure 10T:
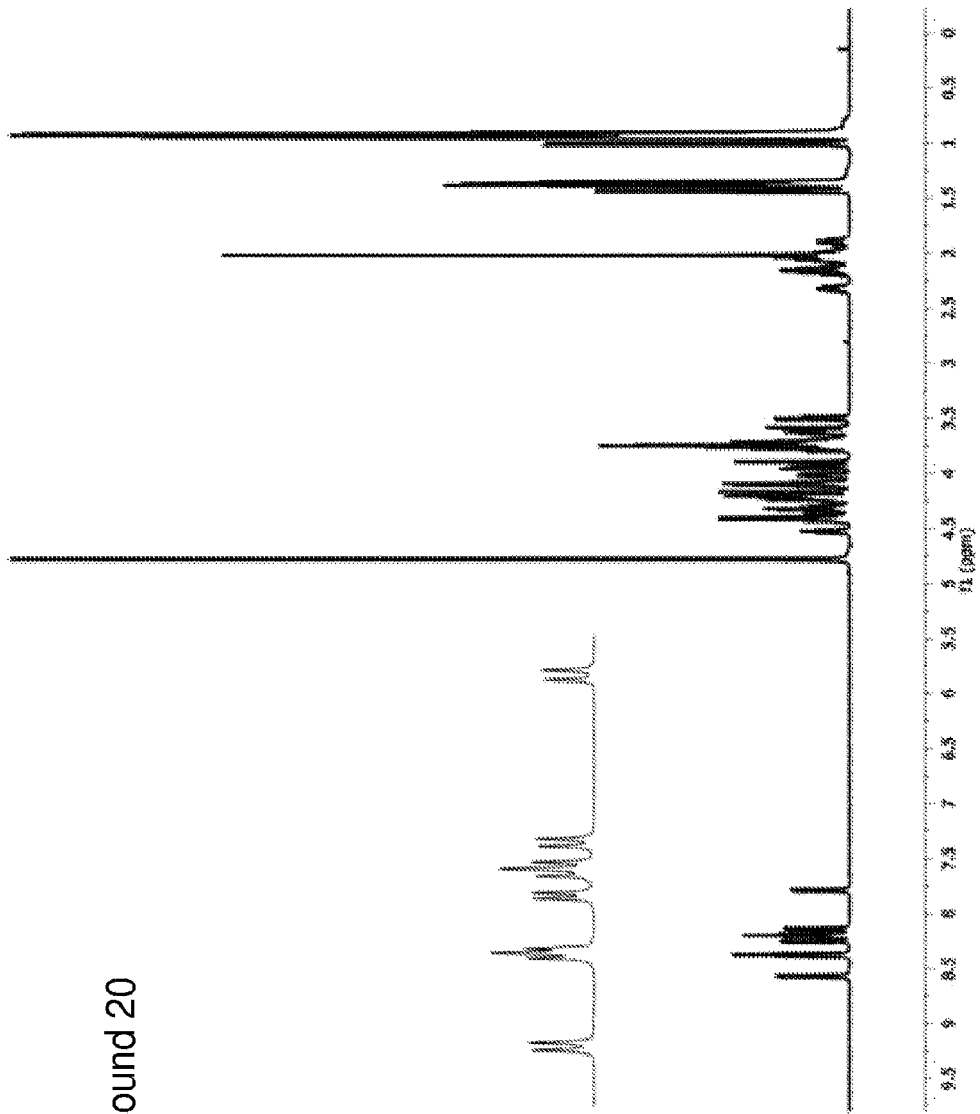
Figure 10U:
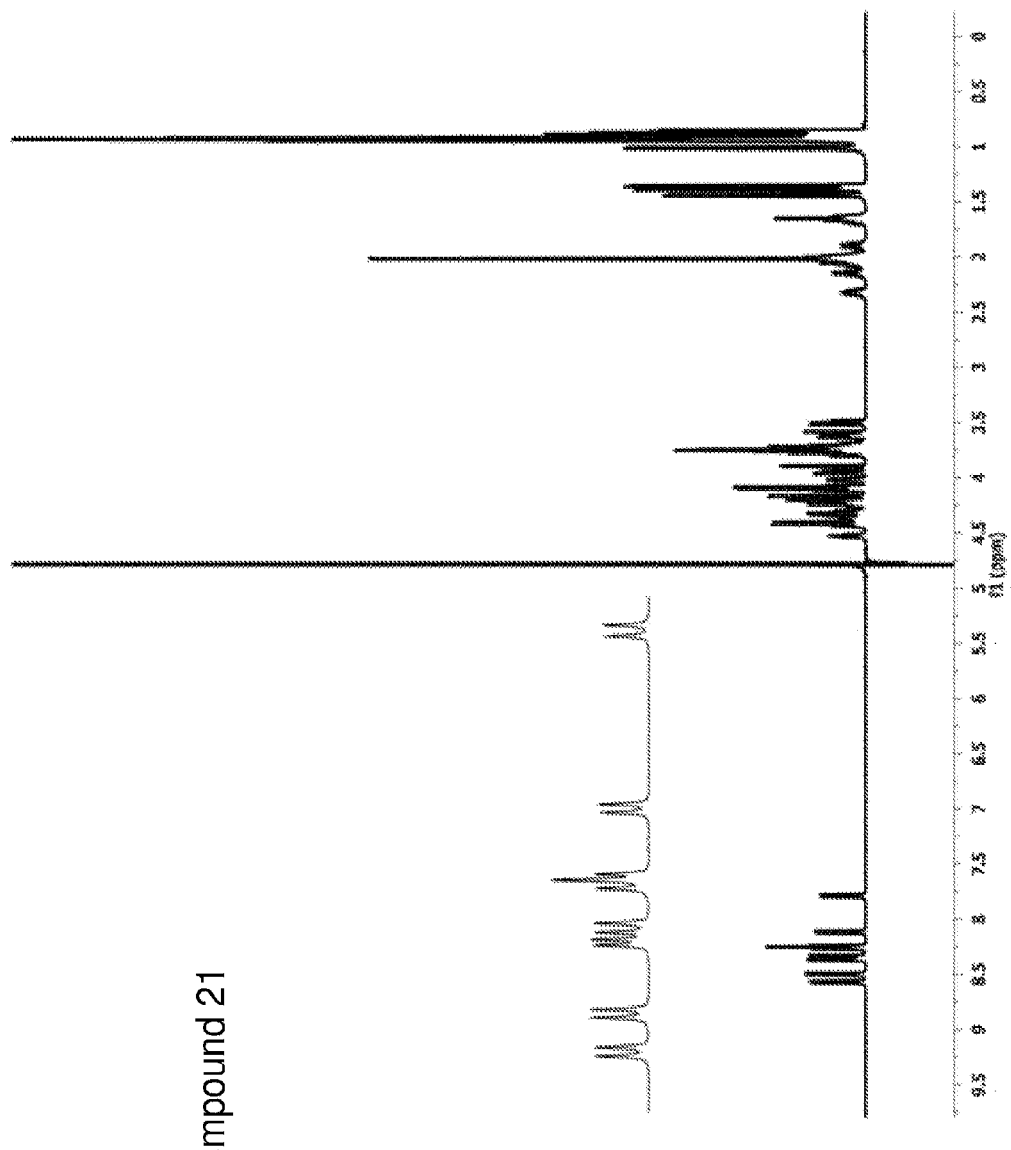
Figure 10V:
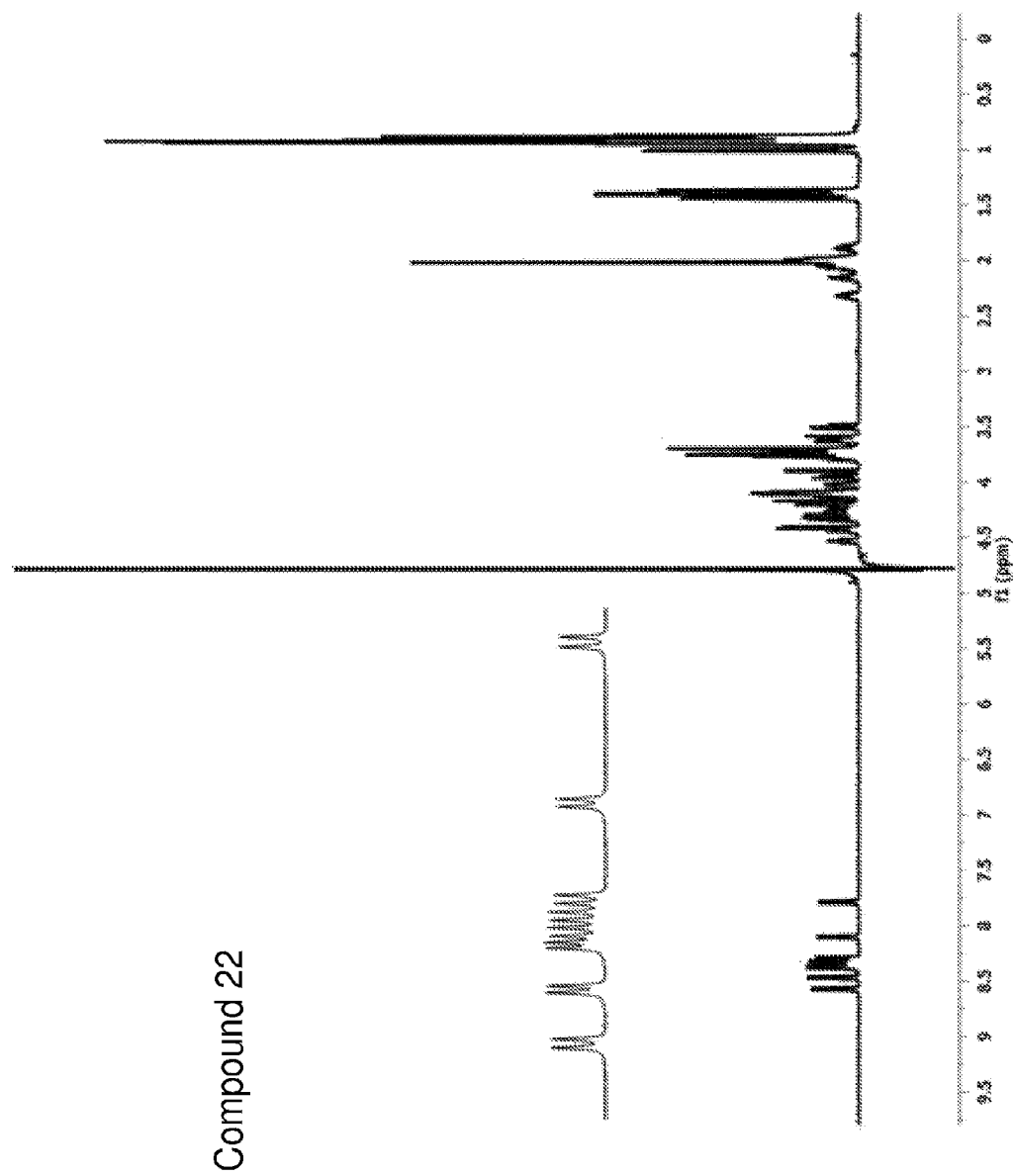
Figure 10W:
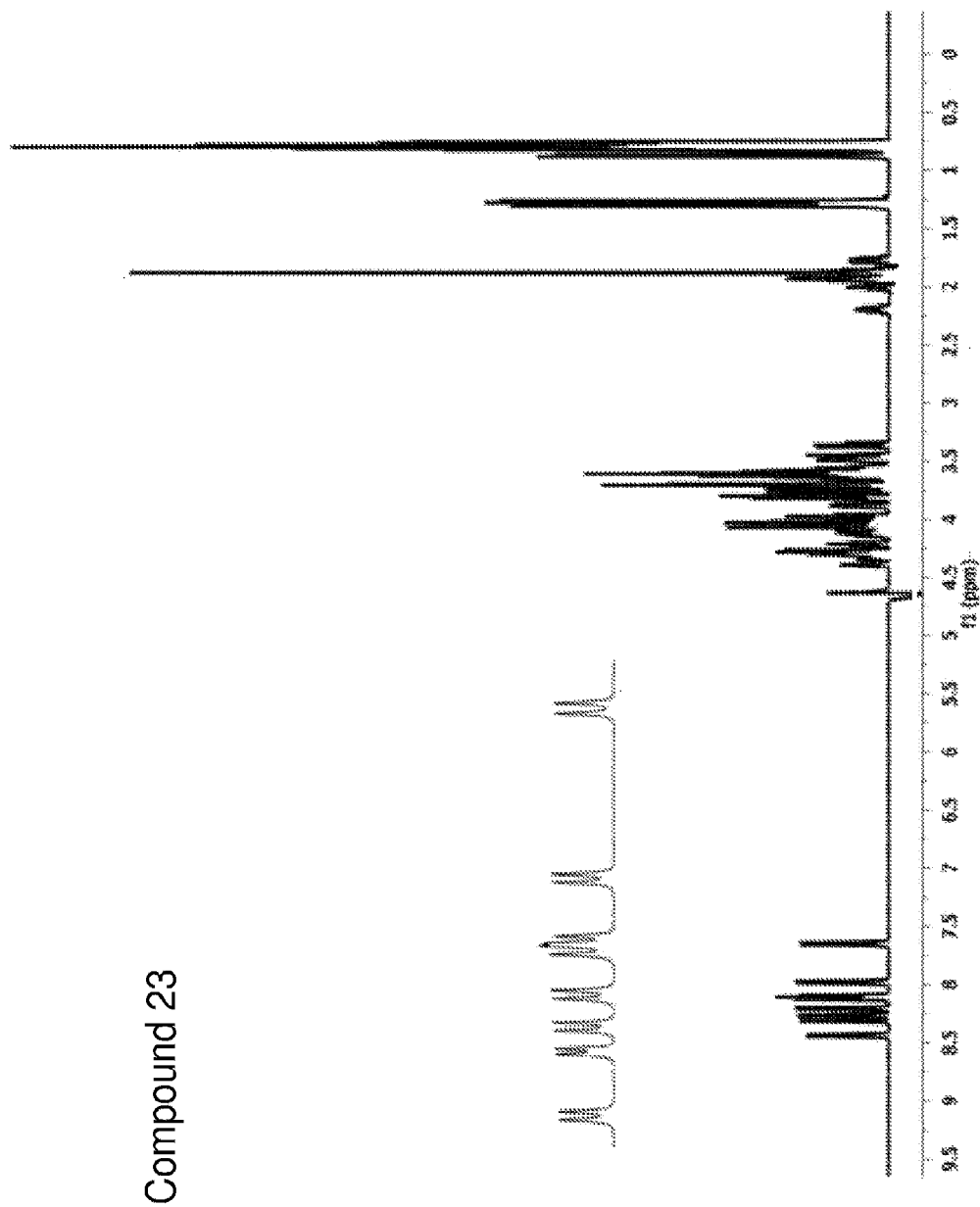
Figure 10X:
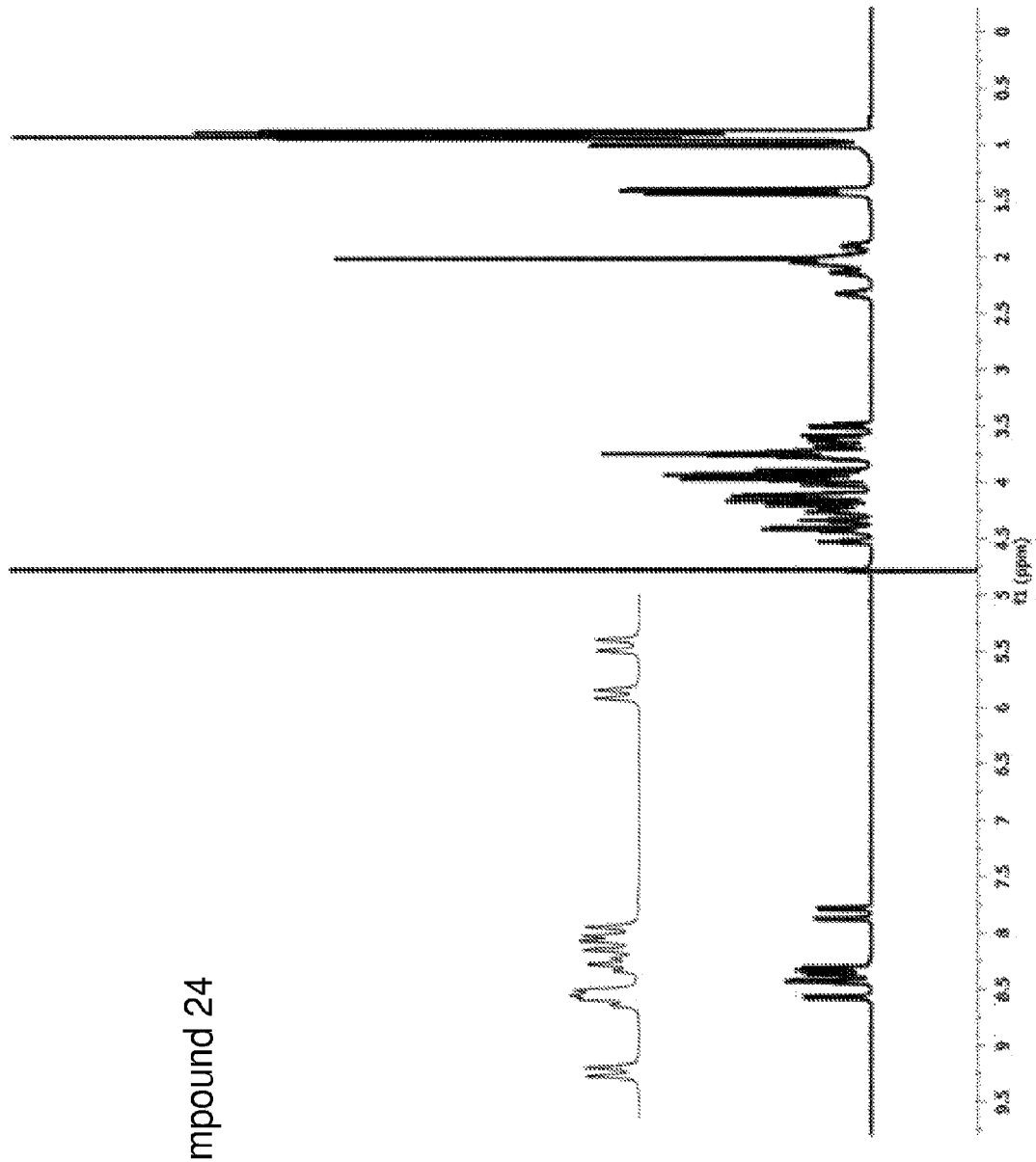
Figure 10Y:
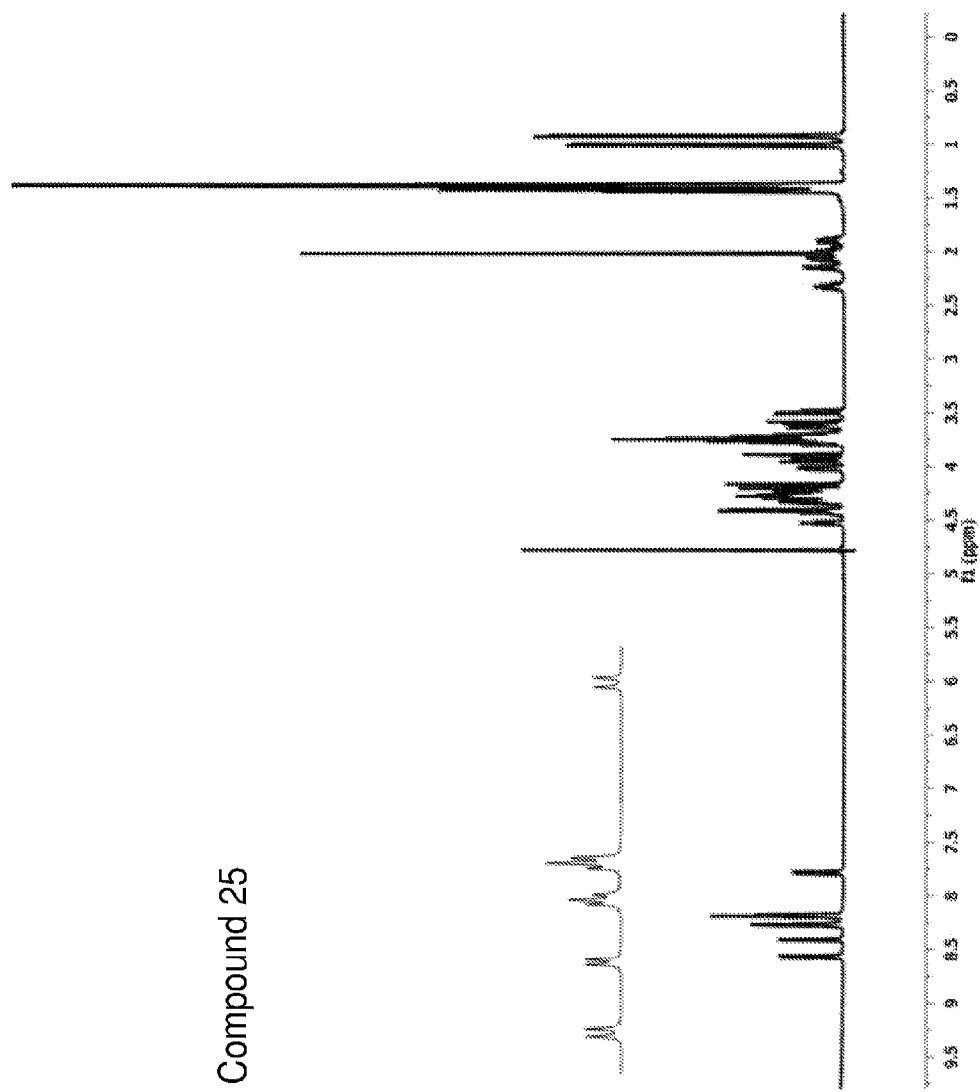
Figure 10Z:
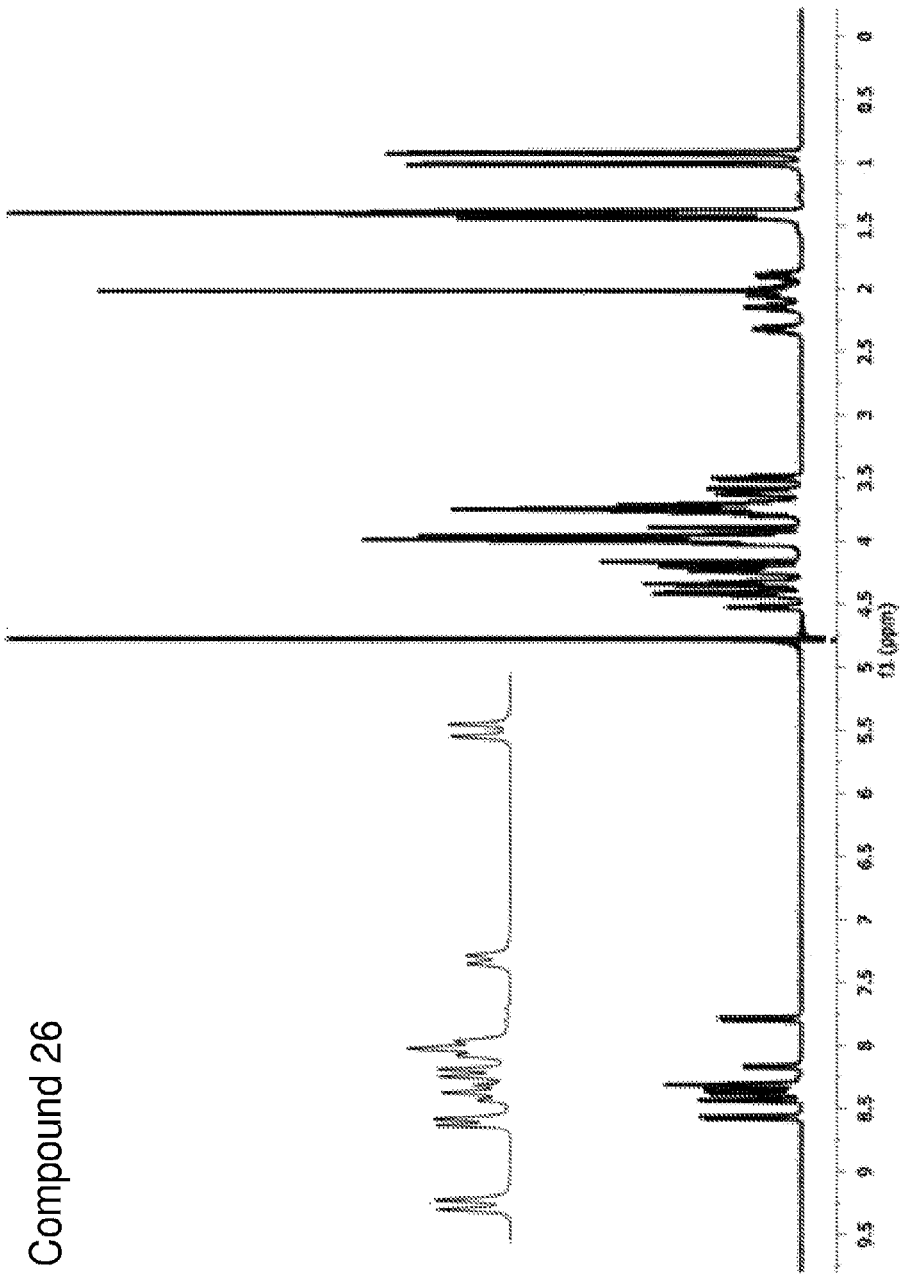
Figure 10A:
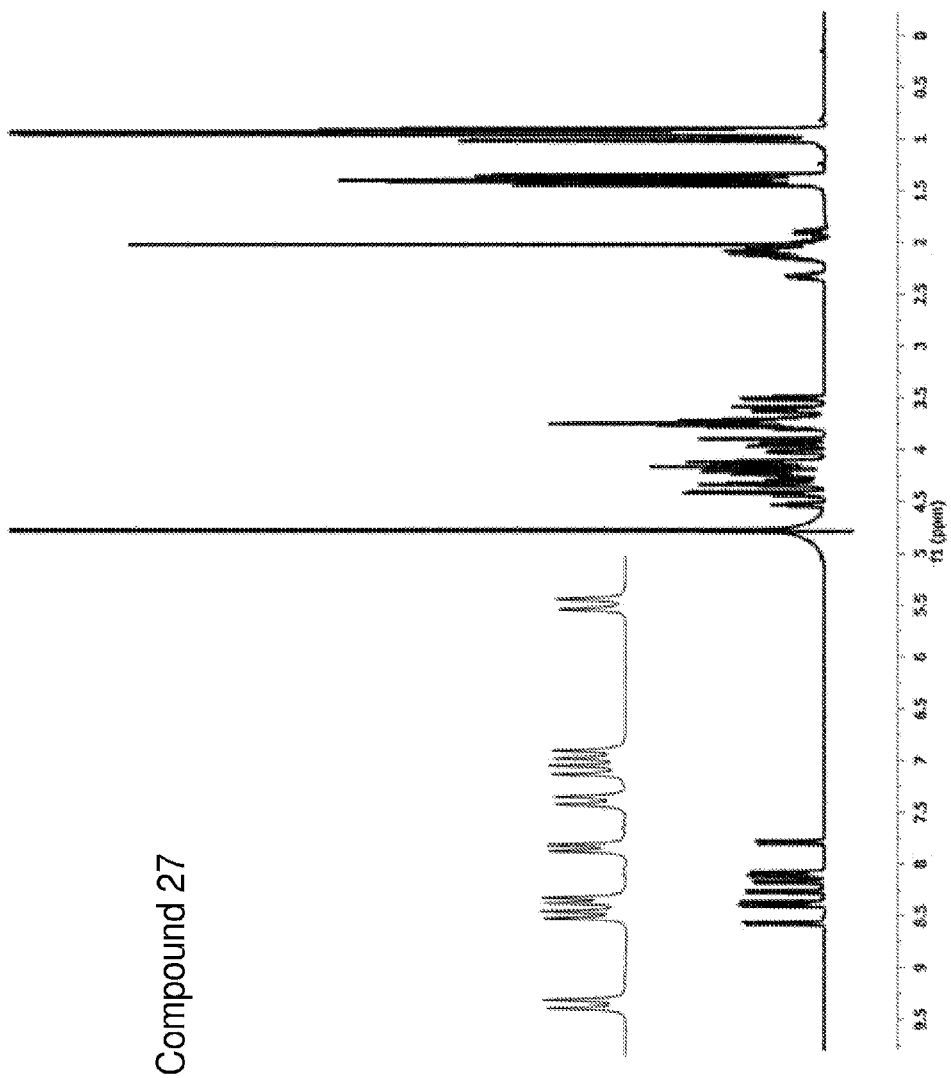
Figure 10A:
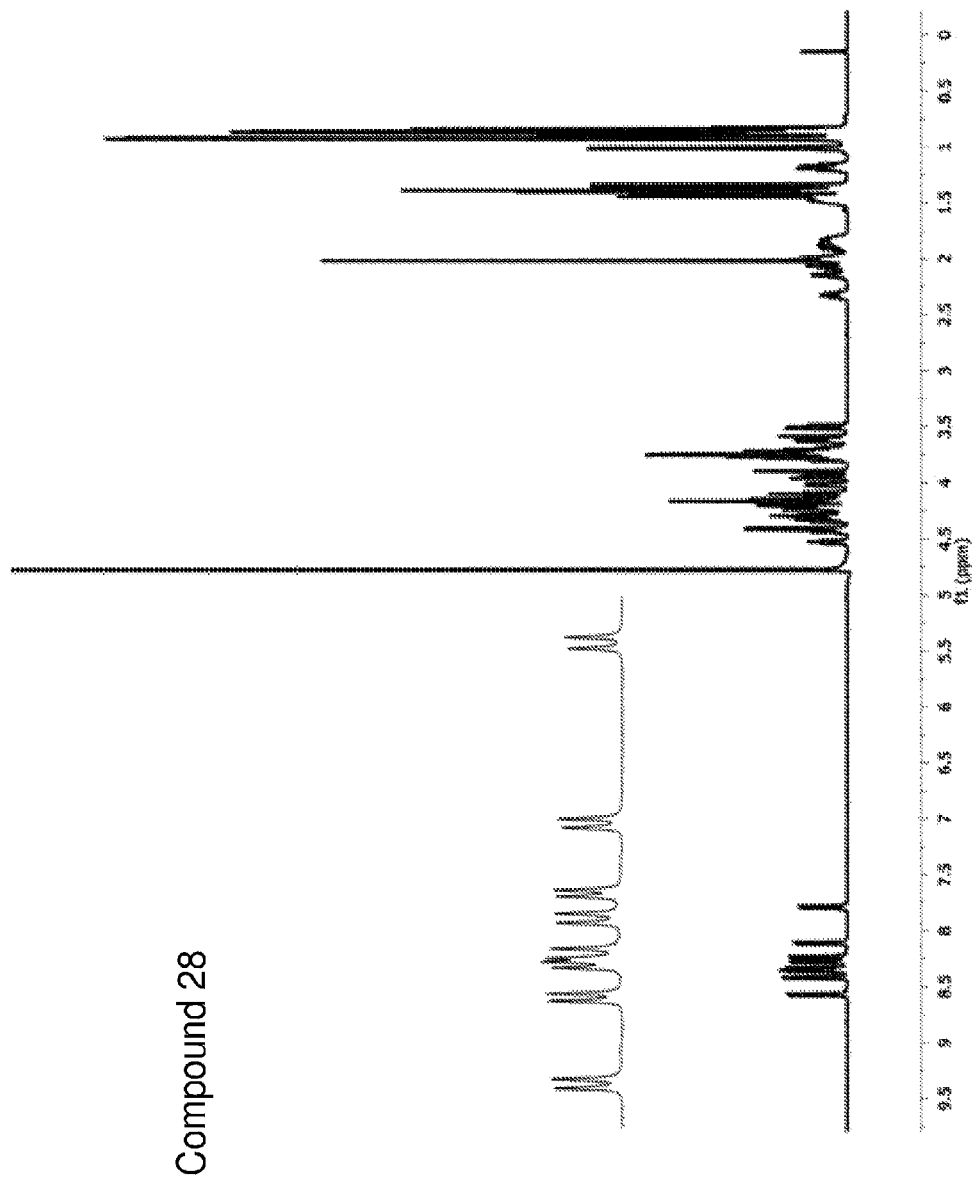
Figure 10A:
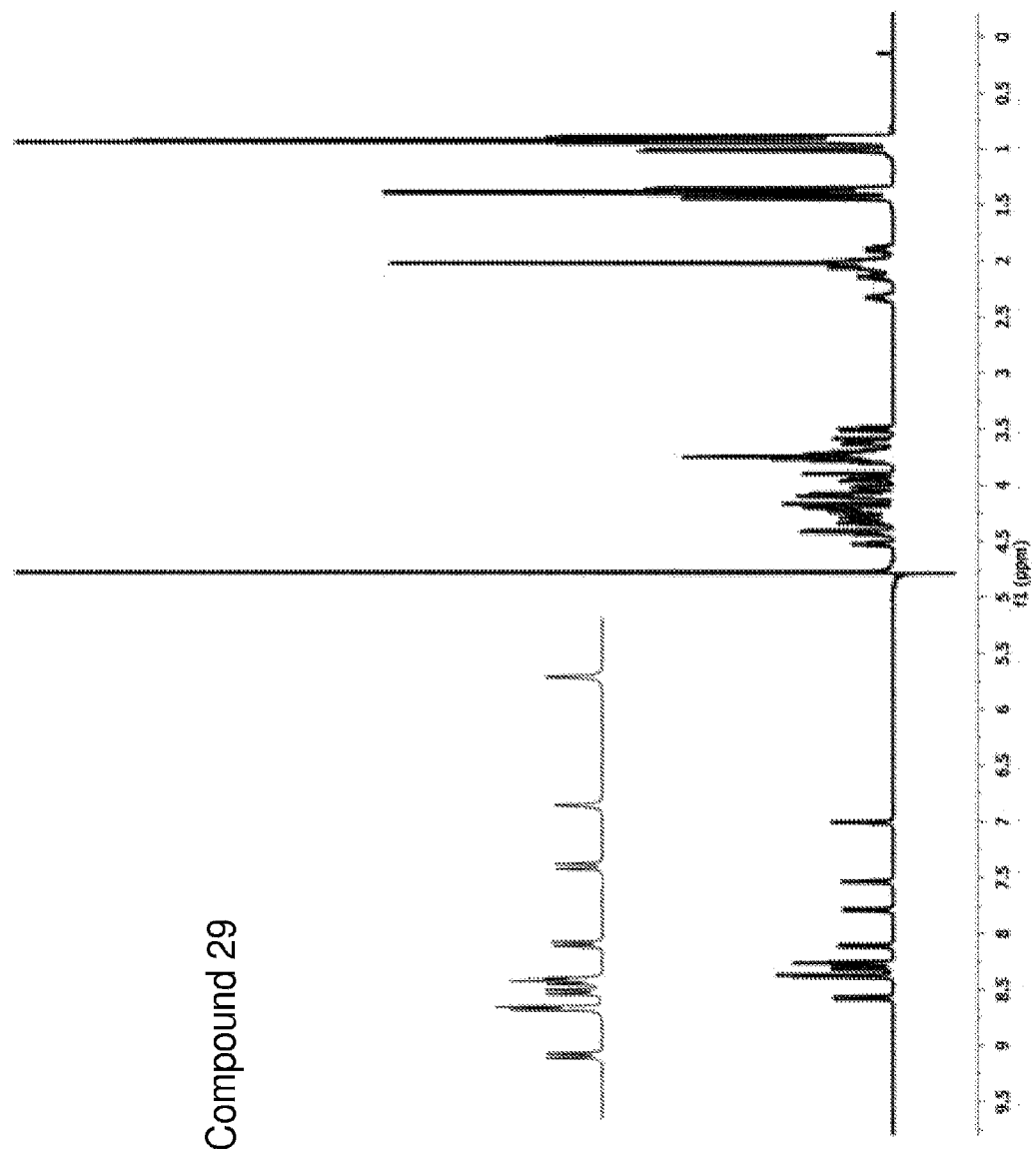
Figure 10A:
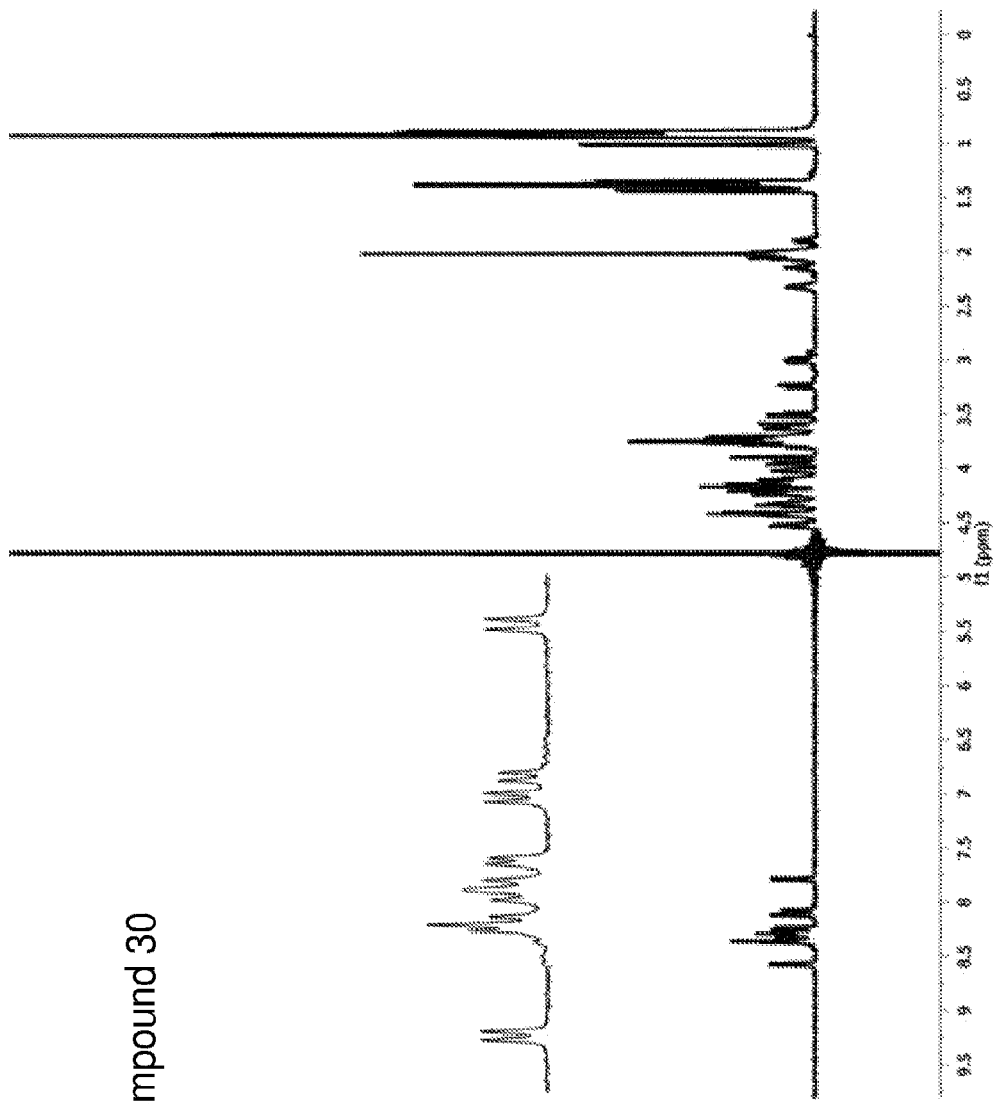
Figure 10A:
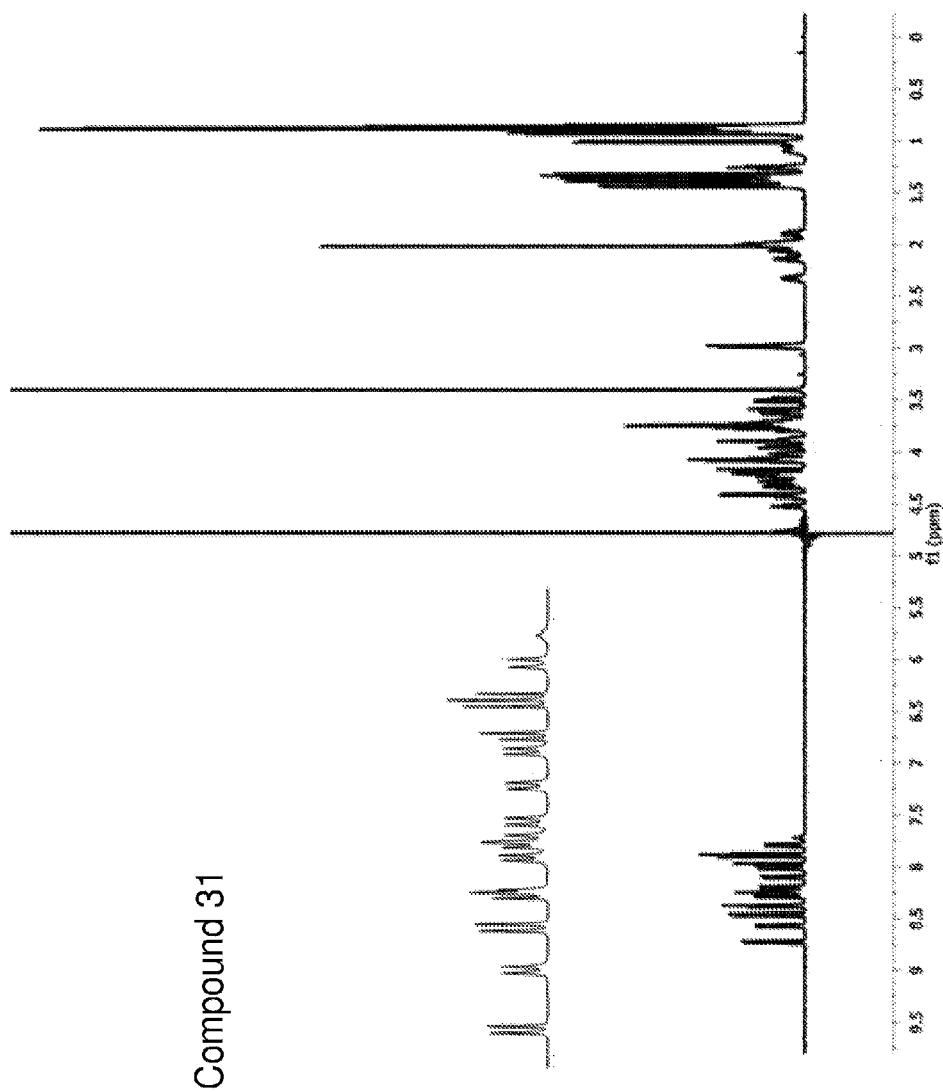
Figure 10A:
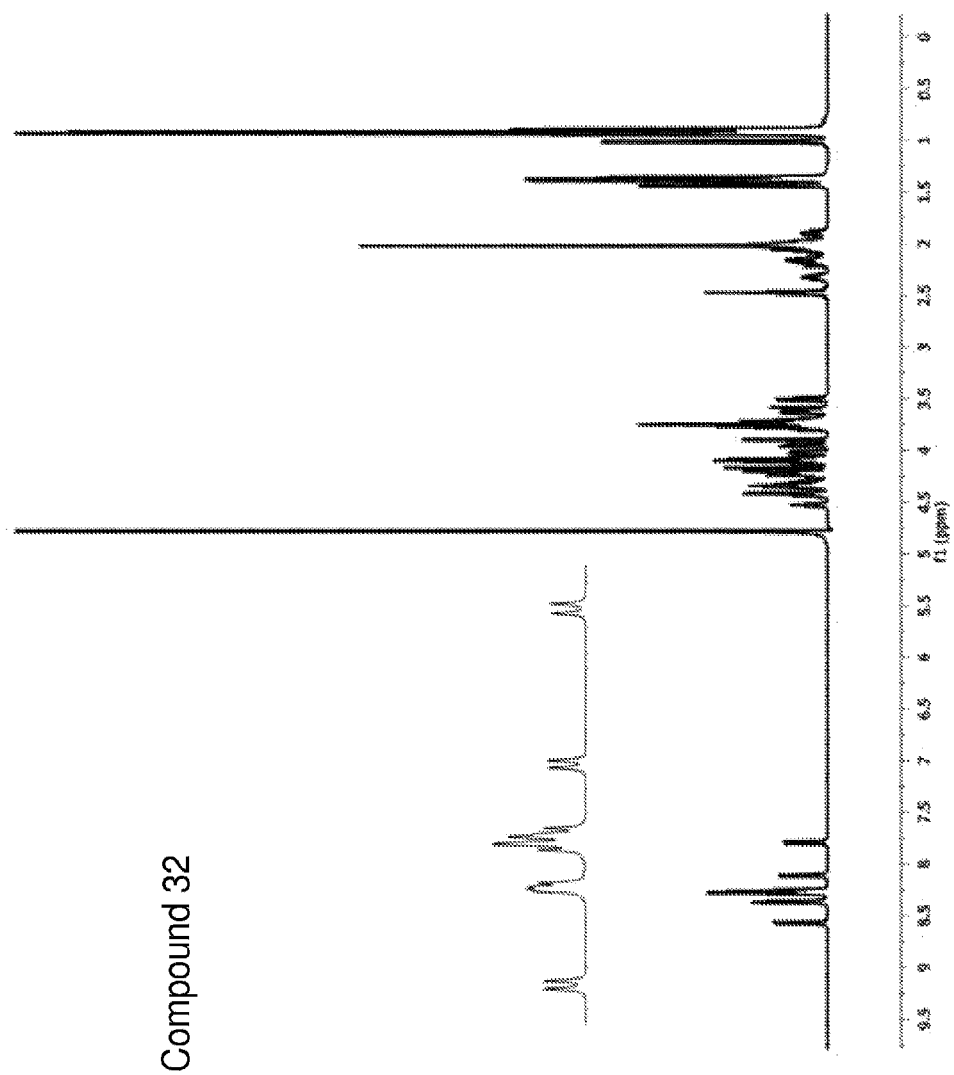
Figure 10A:
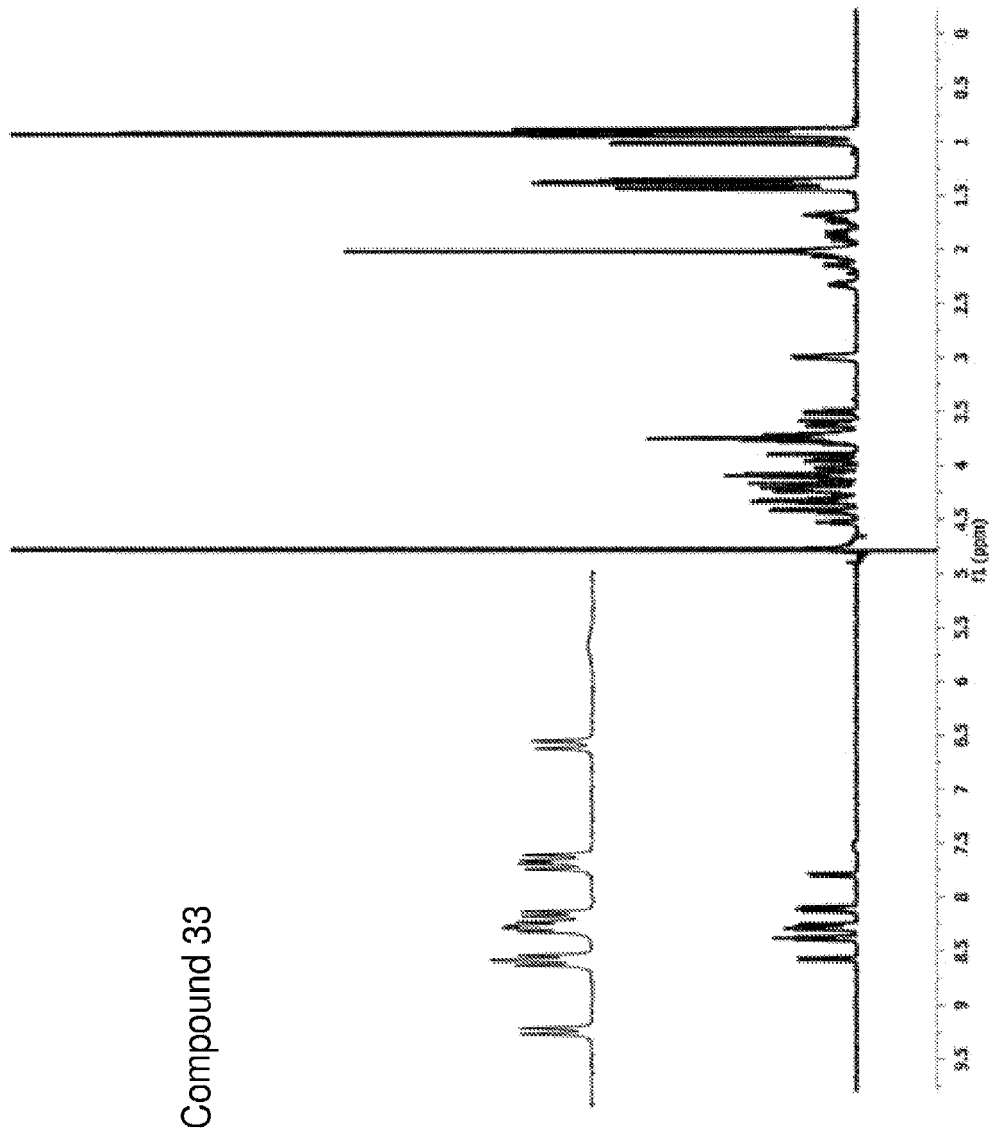
Figure 10A:
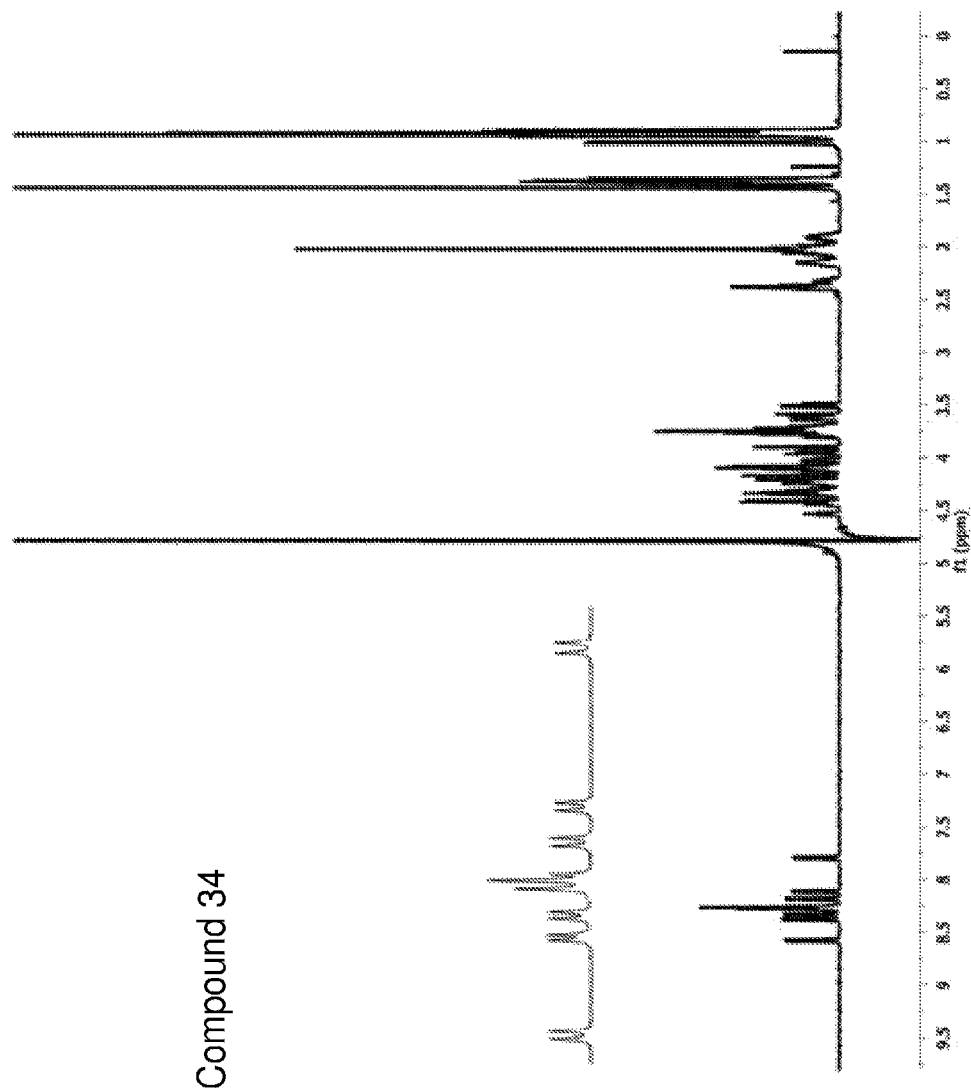
Figure 10A:
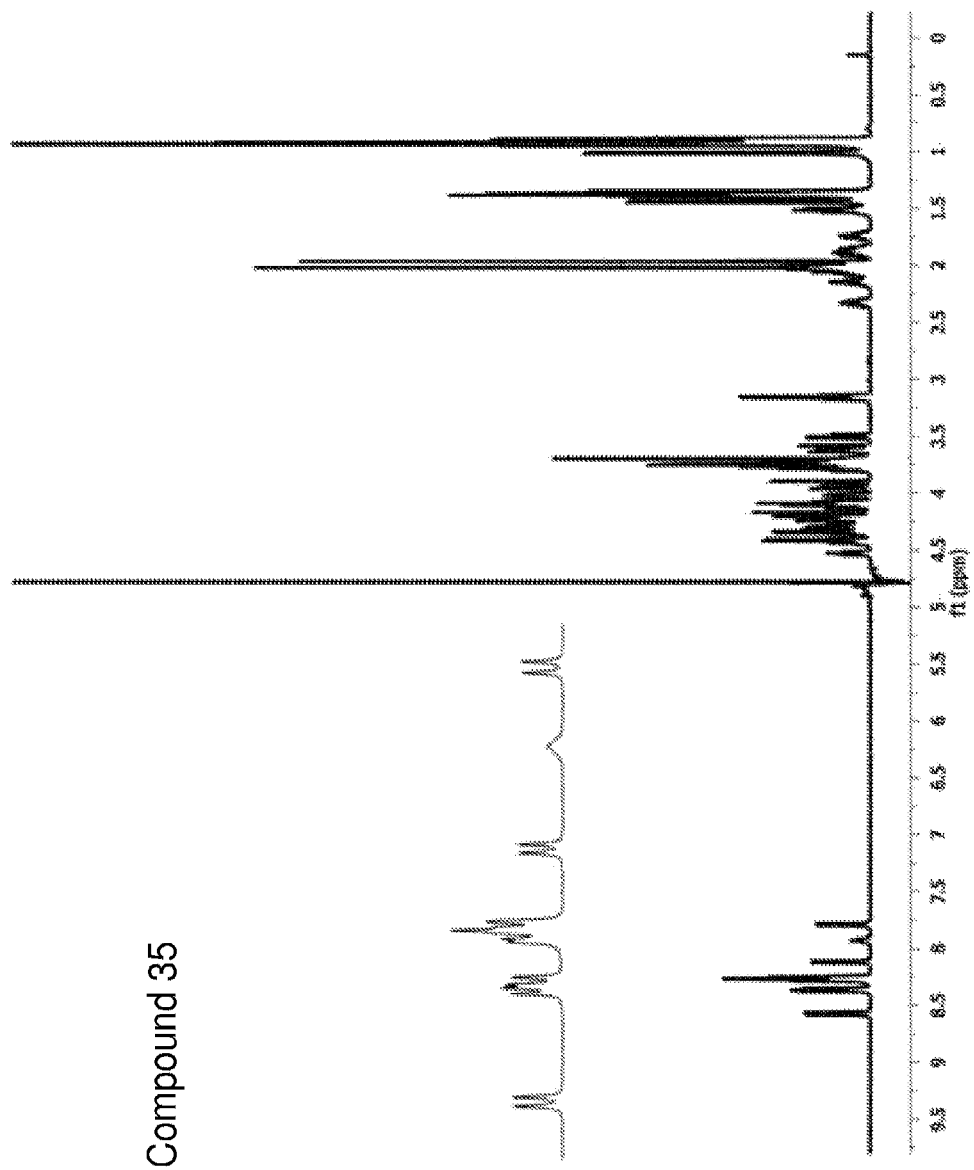
Figure 10A:
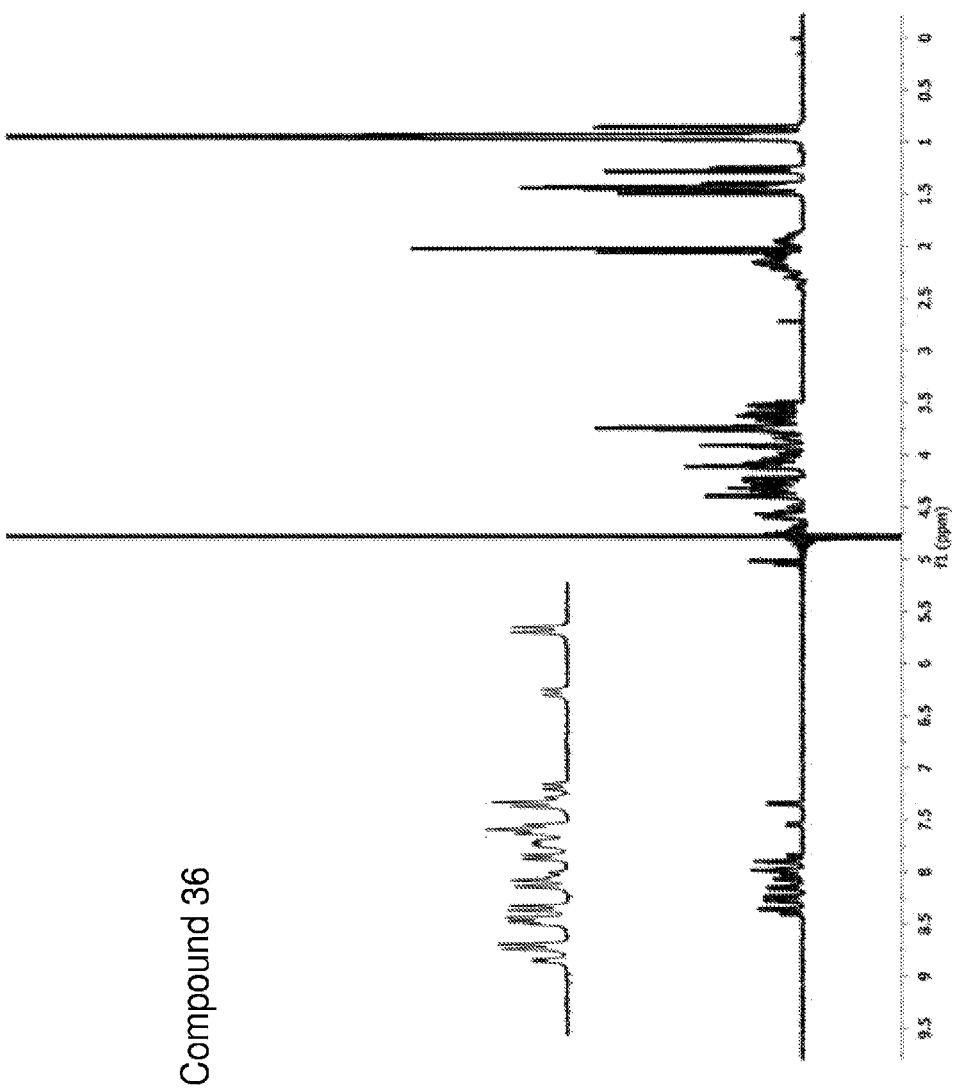
Figure 11:
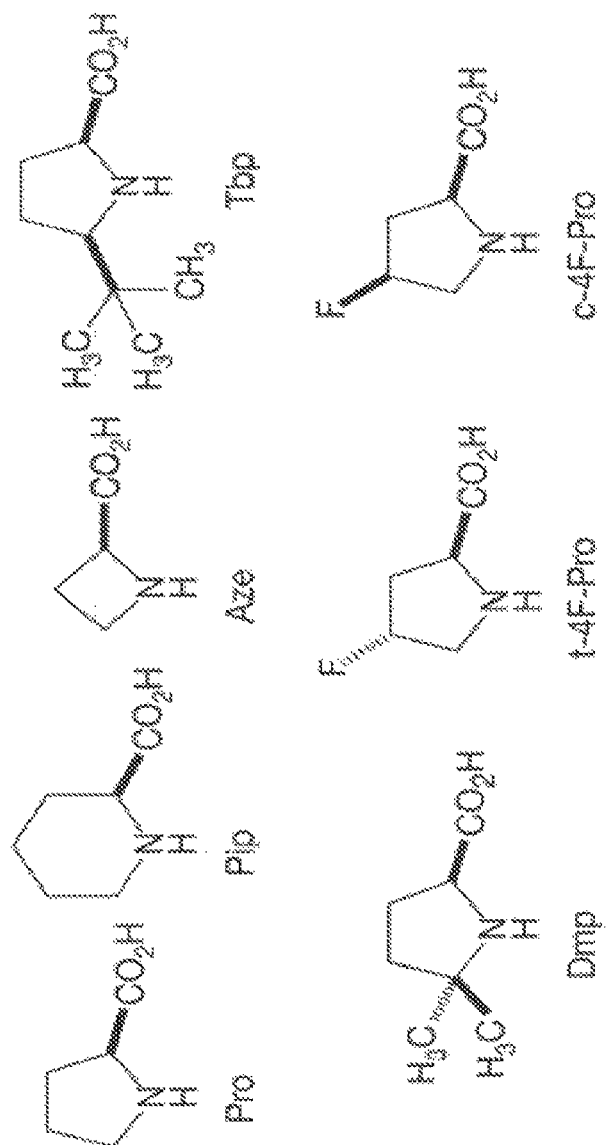
FIG. 11 shows exemplary proline derivatives.
Figure 12:
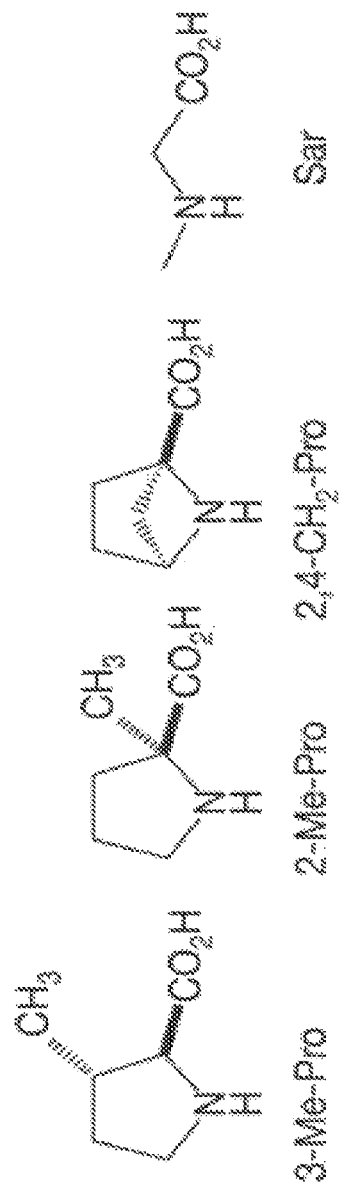
FIG. 12 shows additional exemplary proline derivatives.
Figure 13:
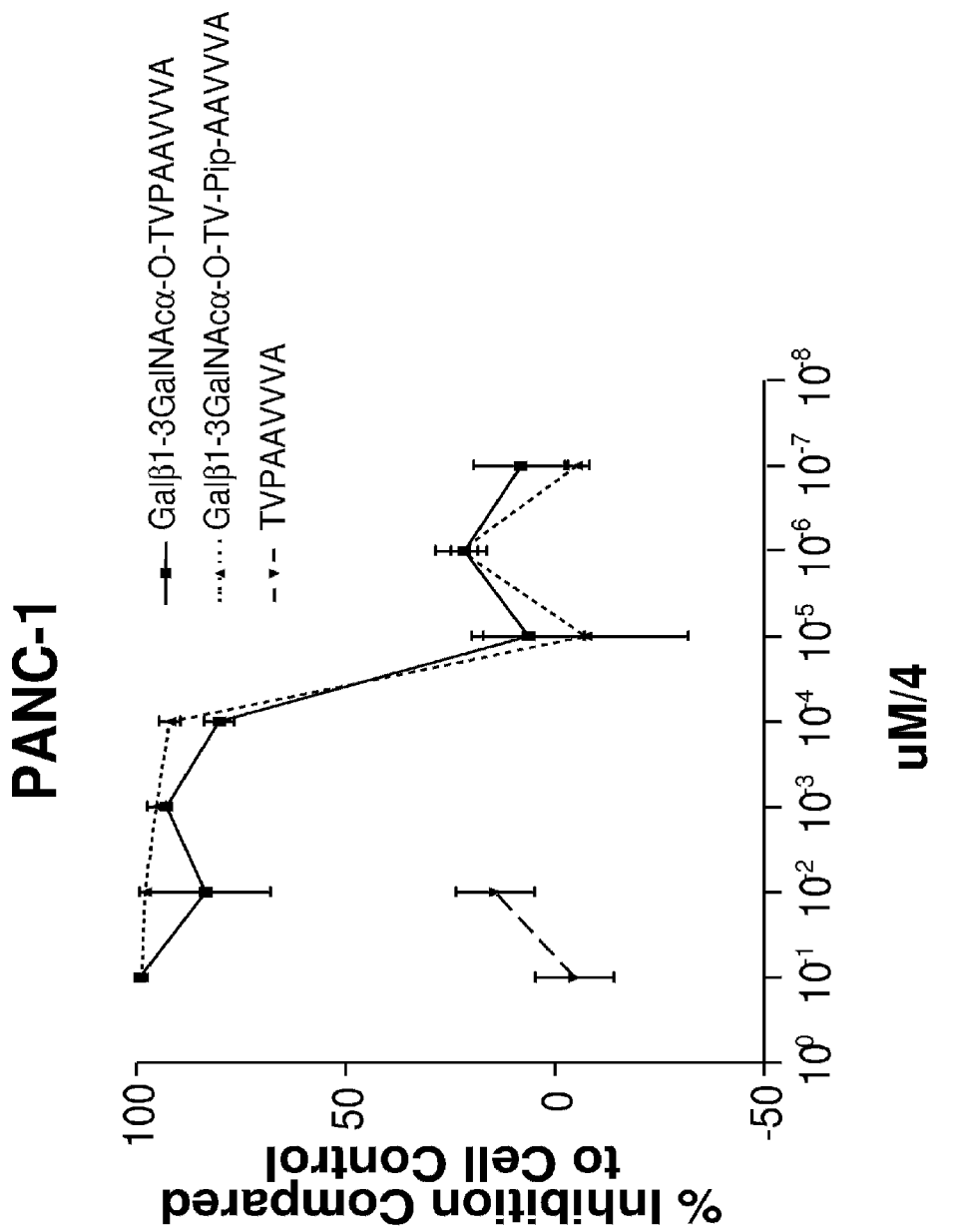
FIG. 13 illustrates antiproliferative activity of particular APF derivatives in PANC-1 pancreatic cancer cells.
Figure 14:
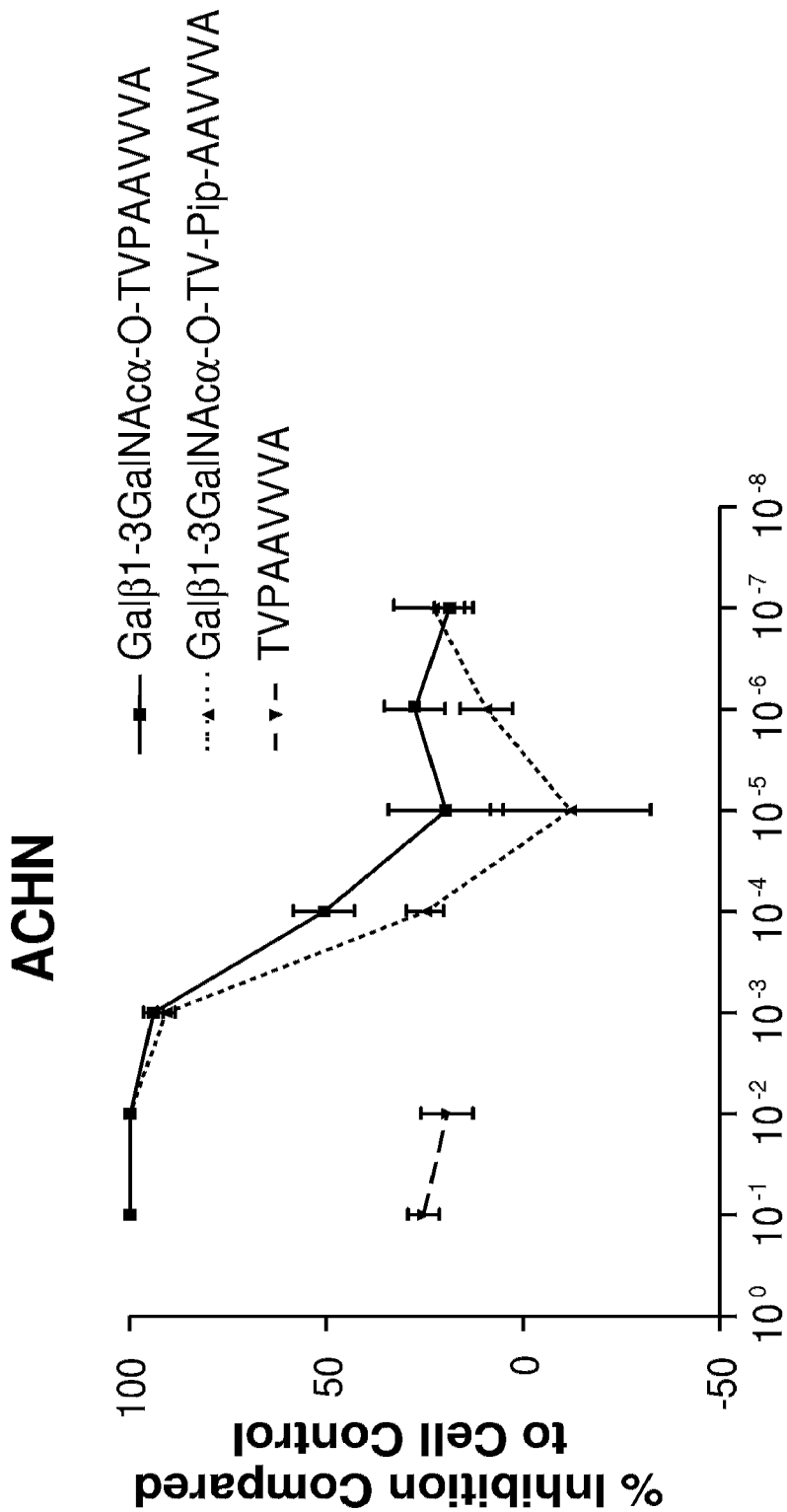
FIG. 14 demonstrates antiproliferative activity of particular APF derivatives in ACHN kidney cancer cells.
Figure 15:
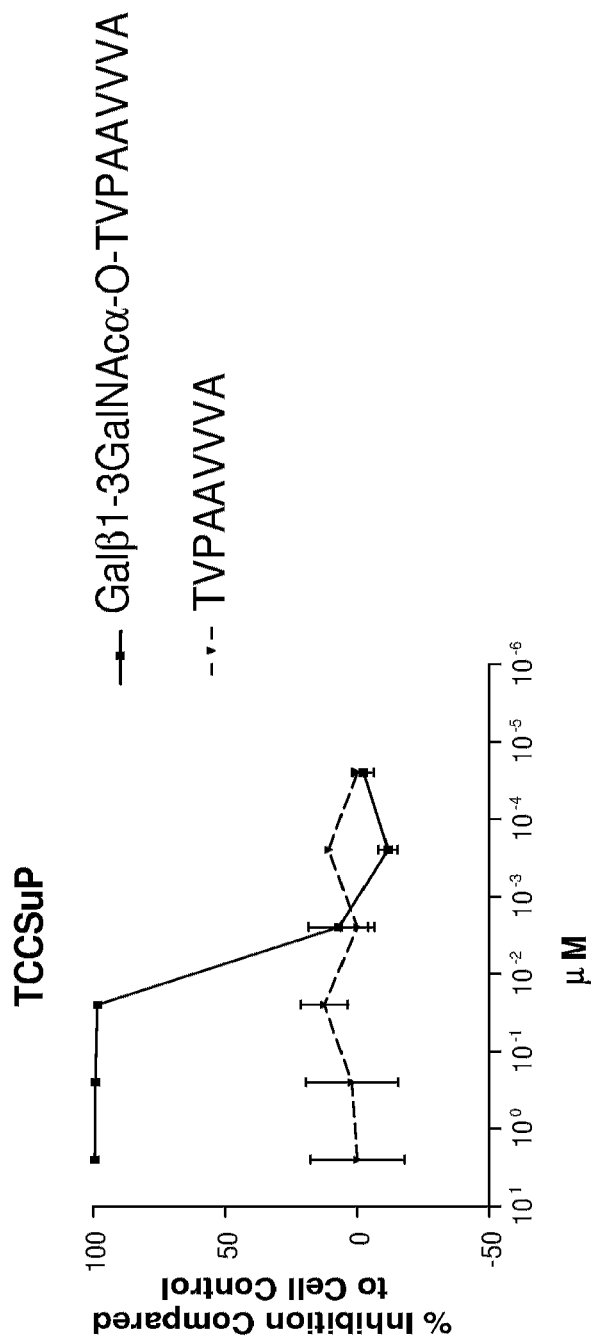
FIG. 15 demonstrates antiproliferative activity of a particular APF derivative in TCCSuP bladder cancer cells.
Figure 16:
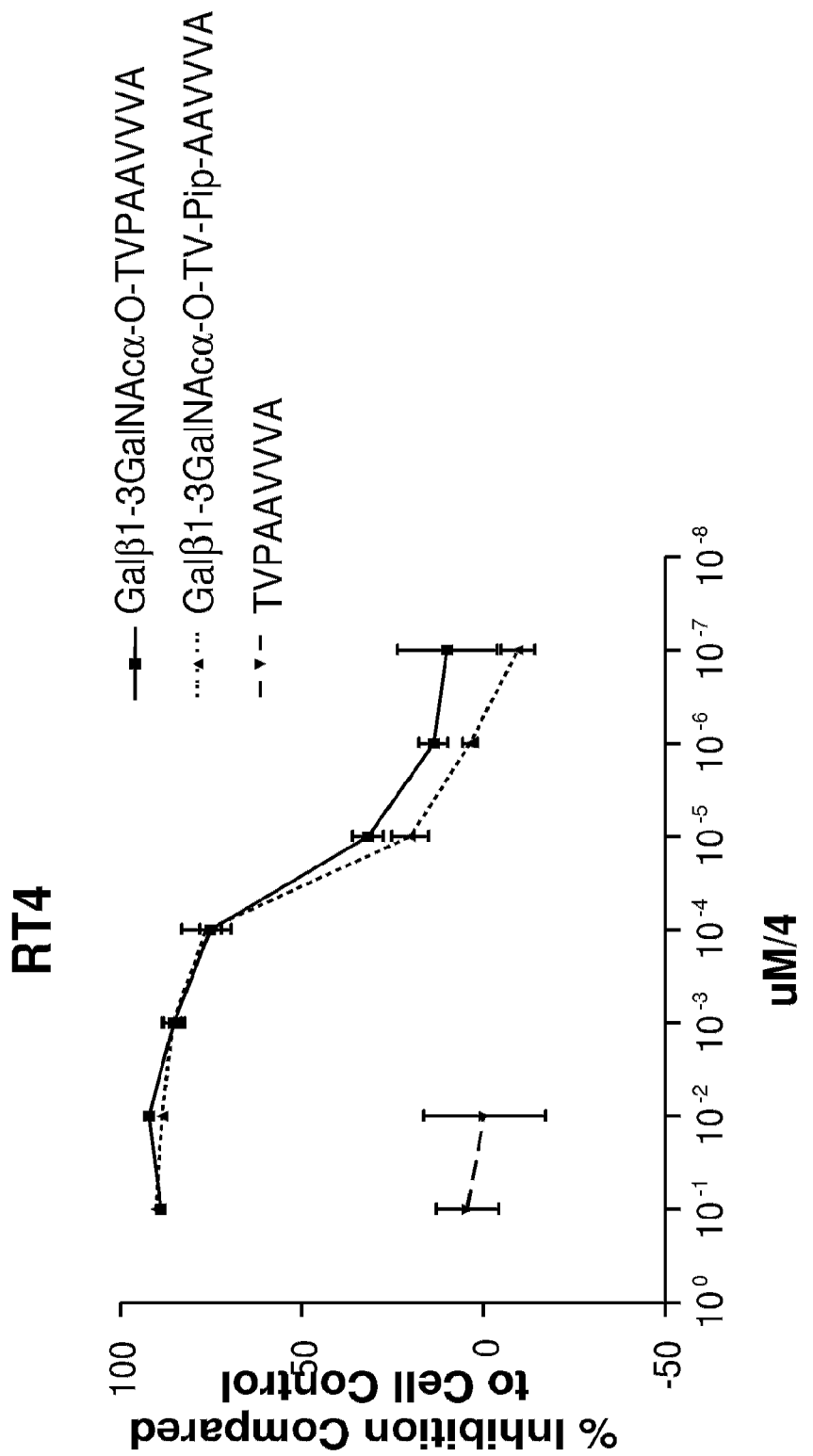
FIG. 16 demonstrates antiproliferative activity of particular APF derivatives in RT4 bladder cancer cells.
Figure 17:
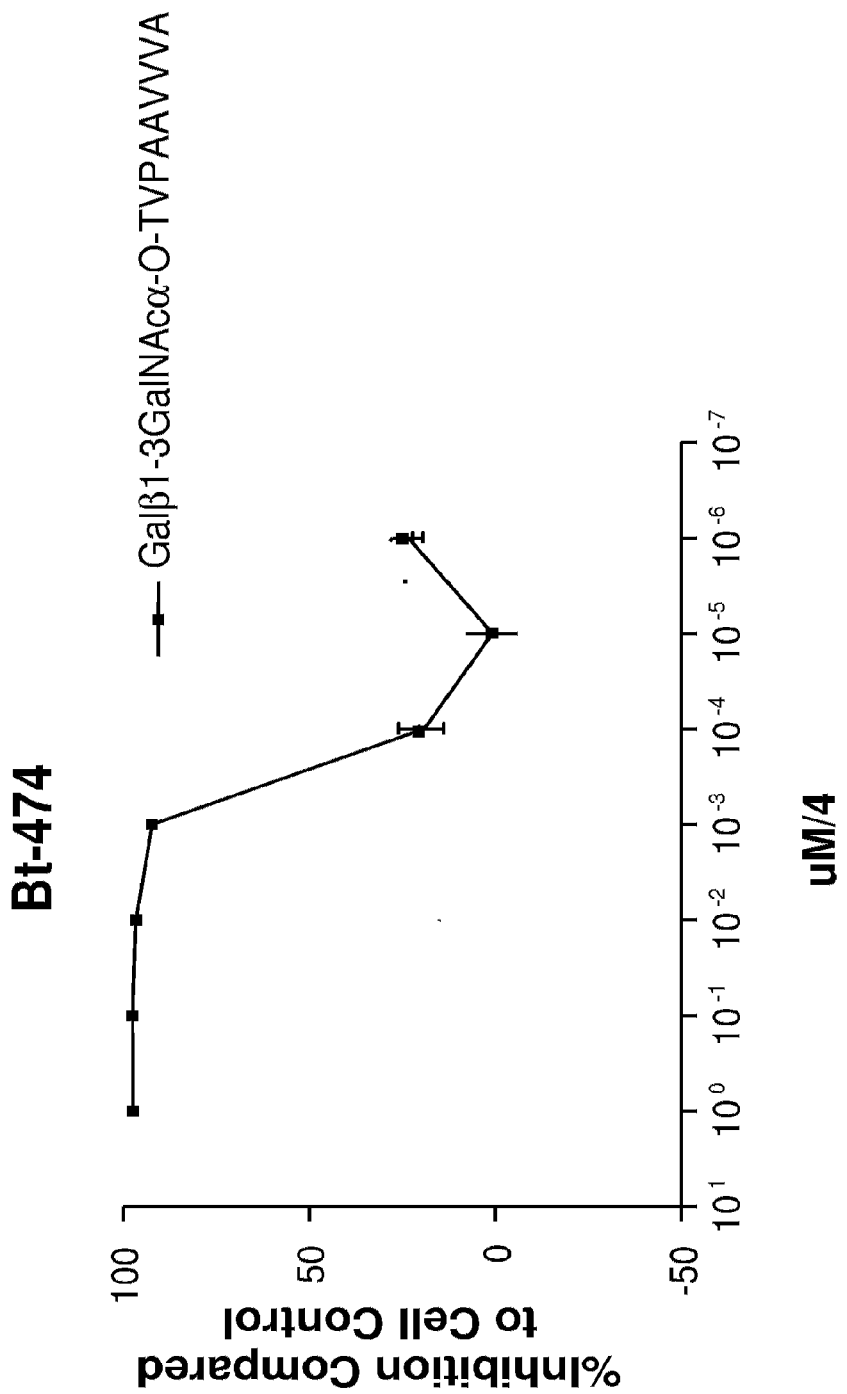
FIG. 17 shows antiproliferative activity of particular APF derivatives in BT-474 breast cancer cells.
Figure 18:
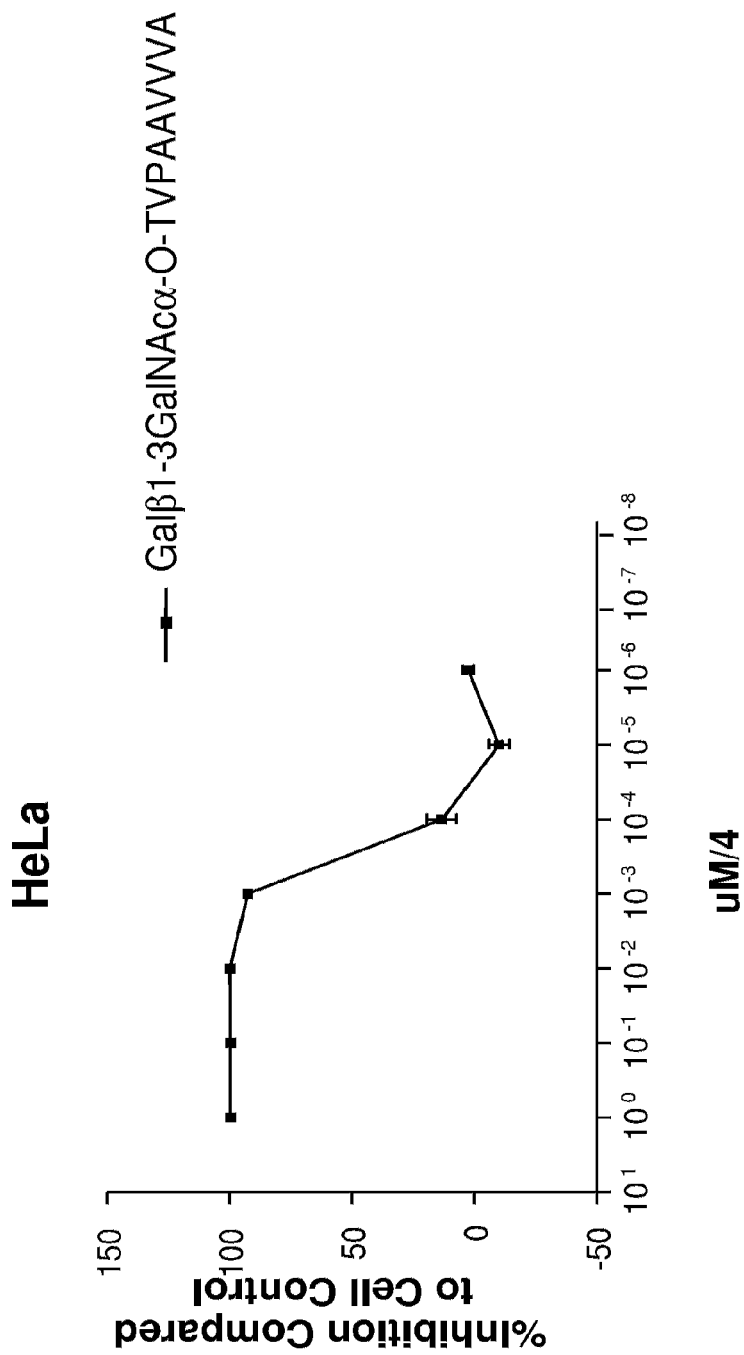
FIG. 18 demonstrates antiproliferative activity of particular APF derivatives in HeLa cervical cancer cells.
Figure 19:
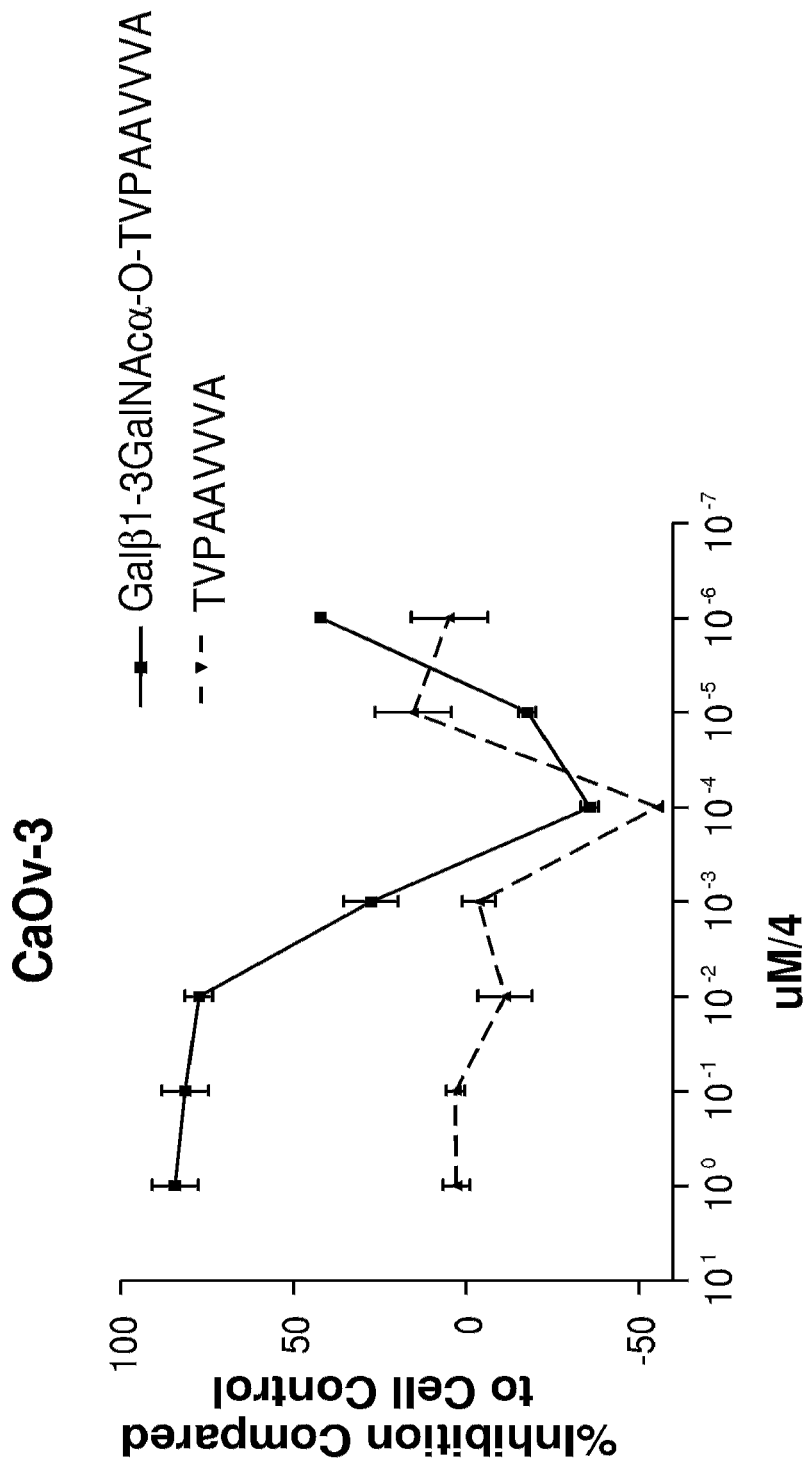
FIG. 19 shows antiproliferative activity of a particular APF derivative in Caov-3 ovarian cancer cells.
Figure 20:
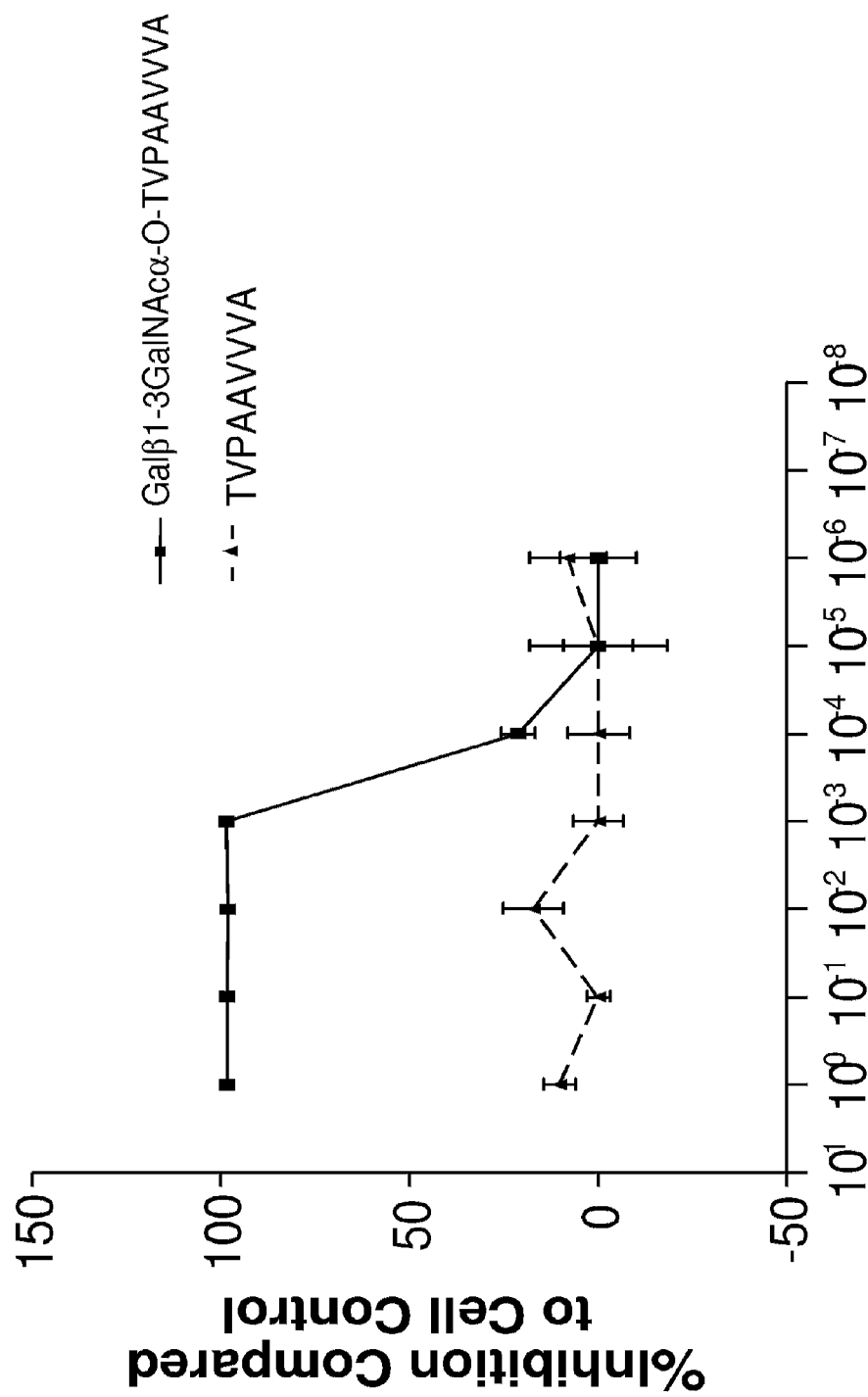
FIG. 20 shows activity of particular APF derivatives in A549 lung cancer cells.
Figure 21:
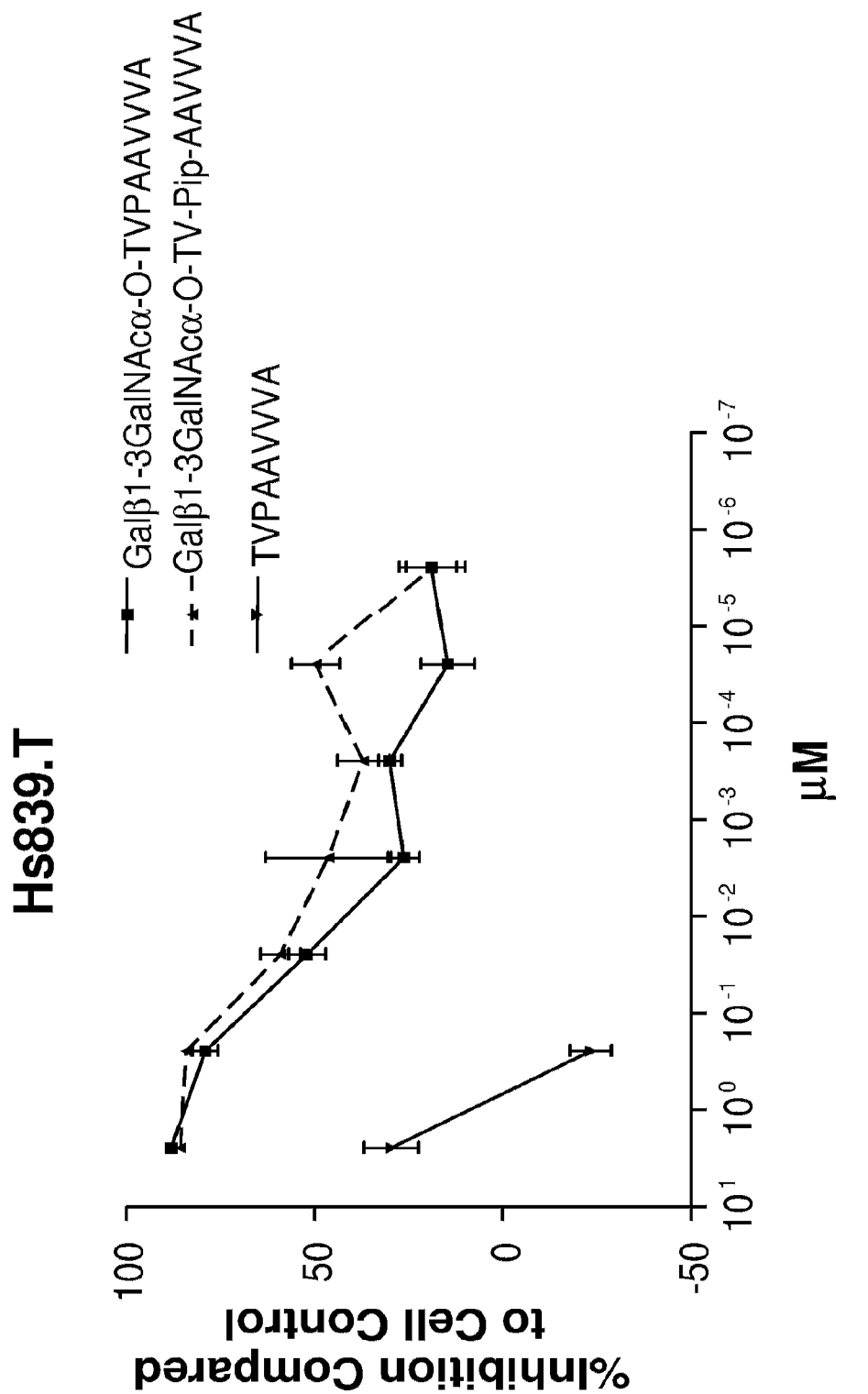
FIG. 21 demonstrates activity of particular APF derivatives in and Hs839.T melanoma cells.

FIG. 9 demonstrates CD spectrum of exemplary as-APF in water and TFE. CD spectrum of 1 in water (the line beginning at about −13) and TFE (the line beginning at about −2.5).

FIG. 10 shows proton NMR spectra of all exemplary as-APF analogues. $^1H$ NMR spectra of APF analogues at 25° C. in 9:1 $H_2O/D_2O$. The full spectrum is on top and an expansion of the amide region is shown in the inset to the low field of the water peak.

FIGS. 13 through 21 illustrate activity of particular APF derivatives in a variety of cancer cells.

TABLE 6
Analytical data for as-APF analogues.
| No | SEQ ID NO: of peptide Derivative | Derivative | MW obs | MW calc | $r_t$ [min] | purity |
|---|---|---|---|---|---|---|
| 1 | 1 | 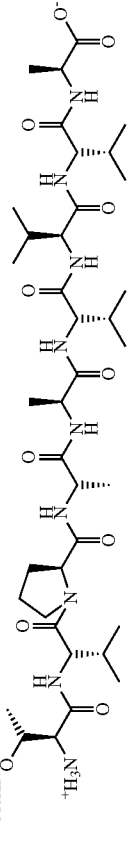 Galβ1-3GalNAcα-O-TVPAAVVVA | 1190.66 | 1190.63 | 21.436 | >99% |
| 2 | 5 | 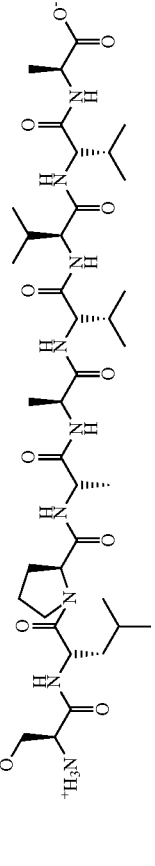 Galβ1-3GalNAcα-O-SLPAAVVVA | 1190.59 | 1190.63 | 27.303 | >99% |

TABLE 6-continued

Analytical data for as-APF analogues.

| No | SEQ ID NO: of peptide of Derivative | Derivative | MW obs | MW calc | r_t [min] | purity |
|---|---|---|---|---|---|---|
| 3 | 3 | Galβ1-3GalNAcα-O-SVPAAVVVA | 1176.50 | 1176.61 | 22.539 | >99% |
| 4 | 6 | Galβ1-3GalNAcα-O-TLPAAVVVA | 1204.55 | 1204.64 | 23.966 | >99% |

TABLE 6-continued

Analytical data for as-APF analogues.

| No | SEQ ID NO: of peptide of Derivative | Derivative | MW obs | MW calc | r_t [min] | purity |
|---|---|---|---|---|---|---|
| 5 | 28 | Ac-T(Galβ1-3GalNAcα-O-)VPAAVVVA | 1232.63 | 1232.64 | 21.838 | >99% |
| 6 | 29 | YT(Galβ1-3GalNAcα-O-)VPAAVVVA | 1353.62 | 1353.69 | 29.094 | >95% |

TABLE 6-continued

Analytical data for as-APF analogues.

| No | SEQ ID NO: of peptide of Derivative | Derivative | MW obs | MW calc | $r_t$ [min] | purity |
|---|---|---|---|---|---|---|
| 7 | 30 | Galβ1-3GalNAcα-O-TYPAAVVVA | 1254.50 | 1254.62 | 23.314 | >99% |
| 8 | 27 | Galβ1-3GalNAcα-O-TV-D-Pro-AAVVVA | 1190.57 | 1190.63 | 24.895 | >99% |

TABLE 6-continued

Analytical data for as-APF analogues.

| No | SEQ ID NO: of peptide of Derivative | Derivative | MW obs | MW calc | $r_t$ [min] | purity |
|---|---|---|---|---|---|---|
| 9 | 32 | Galβ1-3GalNAcα-O-TVS(ψ$^{Me,Me}$pro)AAVVVA | 1220.58 | 1220.64 | 22.423 | 98% |
| 10 | 24 | Galβ1-3GalNAcα-O-TV-Aze-AAVVVA | 1176.59 | 1176.61 | 22.460 | >99% |

TABLE 6-continued

Analytical data for as-APF analogues.

| No | SEQ ID NO: of peptide of Derivative | Derivative | MW obs | MW calc | r$_t$ [min] | purity |
|---|---|---|---|---|---|---|
| 11 | 33 | Galβ1-3GalNAcα-O-TVAAAVVVA | 1164.57 | 1164.61 | 22.843 | >97% |
| 12 | 23 | Galβ1-3GalNAcα-O-TV-Hyp-AAVVVA | 1206.53 | 1206.62 | 19.906 | >99% |

TABLE 6-continued

Analytical data for as-APF analogues.

| No | SEQ ID NO: of peptide of Derivative | Derivative | MW obs | MW calc | $r_t$ [min] | purity |
|---|---|---|---|---|---|---|
| 13 | 34 | Galβ1-3GalNAcα-O-TV-Hyp(tBu)-AAVVVA | 1262.73 | 1262.69 | 28.520 | >99% |
| 14 | 35 | Galβ1-3GalNAcα-O-TV-N-MeAla-AAVVVA | 1178.55 | 1178.63 | 22.953 | >99% |

TABLE 6-continued

Analytical data for as-APF analogues.

| No | SEQ ID NO: of peptide of Derivative | Derivative | MW obs | MW calc | $r_t$ [min] | purity |
|---|---|---|---|---|---|---|
| 15 | 15 | Galβ1-3GalNAcα-O-TV-Pip-AAVVVA | 1204.55 | 1204.64 | 23.923 | >99% |
| 16 | 36 | Galβ1-3GalNAcα-O-TVP-12-Ado | 877.43 | 877.49 | 34.351 | >98% |

TABLE 6-continued
Analytical data for as-APF analogues.
| No | SEQ ID NO: of peptide of Derivative | Derivative | MW obs | MW calc | $r_t$ [min] | purity |
|---|---|---|---|---|---|---|
| 17 | 37 | Galβ1-3GalNAcα-O-TVPAA | 822.33 | 822.39 | 7.617 | >95% |
| 18 | 19 | Galβ1-3GalNAcα-O-TVPAAVVV | 1119.58 | 1119.59 | 26.196 | >98% |
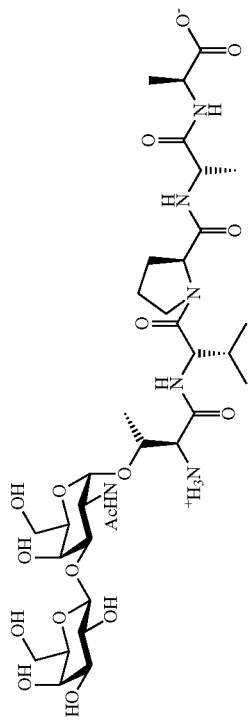
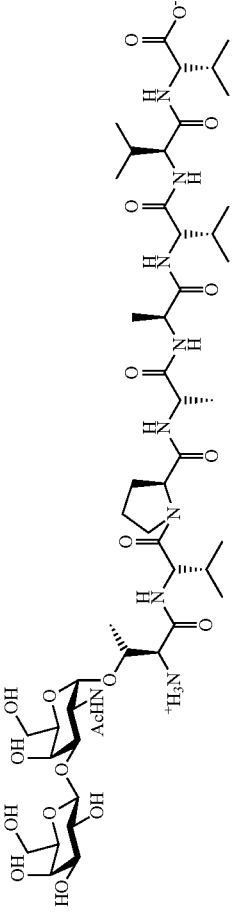

TABLE 6-continued

Analytical data for as-APF analogues.

| No | SEQ ID NO: of peptide of Derivative | Derivative | MW obs | MW calc | r_t [min] | purity |
|----|---|---|---|---|---|---|
| 19 | 20 | Galβ1-3GalNAcα-O-TVPAAVV | 1020.50 | 1020.52 | 20.805 | >99% |
| 20 | 38 | Galβ1-3GalNAcα-O-TVPAAVVAV | 1190.60 | 1190.63 | 22.182 | >99% |

TABLE 6-continued

Analytical data for as-APF analogues.

| No | SEQ ID NO: of peptide of Derivative | Derivative | MW obs | MW calc | $r_t$ [min] | purity |
|---|---|---|---|---|---|---|
| 21 | 39 | Galβ1-3GalNAcα-O-TVPAAVVVL | 1232.61 | 1232.68 | 30.274 | >99% |
| 22 | 40 | Galβ1-3GalNAcα-O-TVPAVVVVA | 1218.51 | 1218.66 | 23.667 | >99% |

TABLE 6-continued

Analytical data for as-APF analogues.

| No | SEQ ID NO: of peptide of Derivative | Derivative | MW obs | MW calc | r$_t$ [min] | purity |
|---|---|---|---|---|---|---|
| 23 | 41 | Galβ1-3GalNAcα-O-TVPASVVVS | 1222.50 | 1222.62 | 19.268 | 99% |
| 24 | 42 | Galβ1-3GalNAcα-O-TVPAGVVVG | 1162.49 | 1162.60 | 19.241 | 99% |

TABLE 6-continued

Analytical data for as-APF analogues.

| No | SEQ ID NO: of peptide of Derivative | Derivative | MW obs | MW calc | r_t [min] | purity |
|---|---|---|---|---|---|---|
| 25 | 18 | Galβ1-3GalNAcα-O-TVPAAAAAA | 1106.41 | 1106.53 | 13.879 | 99% |
| 26 | 8 | Galβ1-3GalNAcα-O-TVPAAGGGA | 1064.40 | 1064.49 | 10.063 | 99% |

TABLE 6-continued

Analytical data for as-APF analogues.

| No | SEQ ID NO: of peptide of Derivative | Derivative | MW obs | MW calc | r_t [min] | purity |
|---|---|---|---|---|---|---|
| 27 | 43 | Galβ1-3GalNAcα-O-TVPAAV-D-Val-VA | 1190.56 | 1190.63 | 26.156 | 98% |
| 28 | 44 | Galβ1-3GalNAcα-O-TVPAAIVIA | 1218.63 | 1218.66 | 24.775 | 98% |

TABLE 6-continued
Analytical data for as-APF analogues.
| No | SEQ ID NO: of peptide of Derivative | Derivative | MW obs | MW calc | $r_t$ [min] | purity |
|---|---|---|---|---|---|---|
| 29 | 45 | Galβ1-3GalNAcα-O-TVPAAVVVA-CONH₂ | 1189.52 | 1189.64 | 19.798 | 99% |
| 30 | 46 | Galβ1-3GalNAcα-O-TVPAAVVVAC | 1293.51 | 1293.64 | 26.192 | 97% |
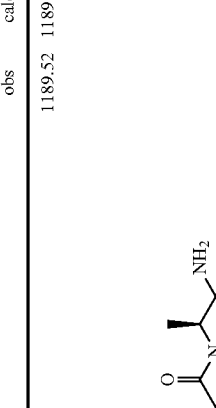
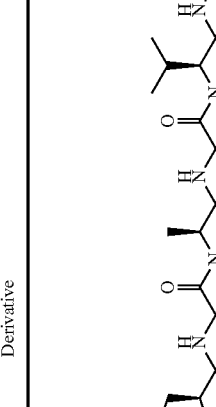

TABLE 6-continued

Analytical data for as-APF analogues.

| No | SEQ ID NO: of peptide of Derivative | Derivative | MW obs | MW calc | r_t [min] | purity |
|---|---|---|---|---|---|---|
| 31 | 26 | Galβ1-3GalNAcα-O-TVPAAVVVAK(Dansyl) | 1551.80 | 1551.77 | 28.939 | 99% |
| 32 | 47 | Galβ1-3GalNAcα-O-TVPAAVVVAE | 1319.65 | 1319.67 | 20.254 | 99% |

TABLE 6-continued

Analytical data for as-APF analogues.

| No | SEQ ID NO: of peptide of Derivative | Derivative | MW obs | MW calc | $r_t$ [min] | purity |
|---|---|---|---|---|---|---|
| 33 | 48 | Galβ1-3GalNAcα-O-TVPAAVVVAK | 1318.99 | 1318.72 | 15.615 | 99% |
| 34 | 49 | Galβ1-3GalNAcα-O-TVPAAVVVAE(O$^t$Bu) | 1375.67 | 1375.73 | 33.680 | >99% |

TABLE 6-continued

Analytical data for as-APF analogues.

| No | SEQ ID NO: of peptide of Derivative | Derivative | MW obs | MW calc | r_t [min] | purity |
|---|---|---|---|---|---|---|
| 35 | 25 | Galβ1-3GalNAcα-O-TVPAAVVAK(Ac) | 1360.71 | 1360.73 | 24.240 | >98% |
| 36 | 1 | cyclo(1-9)Galβ1-3GalNAcα-O-TVPAAVVVA | 1172.55 | 1172.62 | 30.537 | >99% |

Example 4

D-Pipecolic Acid APF and Normal Bladder Cells

D-pipecolic acid APF (GAlGalNAc-TV-D pip-AAVVVA; SEQ ID NO:14) inhibits APF activity in normal bladder cells. Explanted cells grown from the biopsies of normal controls were plated on Day 0 at $1.5 \times 10^4$ cells/well onto a 96-well cell culture plate (VWR 29442-054), in 150 µL/well MEM containing 10% heat-inactivated FBS, 1% antibiotic/antimycotic solution, and 1% L-glutamine (all from Sigma), serum starved on Day 1, and treated with varying concentrations of D-pipecolic acid diluted in phosphate buffered saline (PBS) for 2 hours at 37° C. in a 5% $CO_2$ atmosphere. Varying concentrations of synthetic GalGalNAc-TVPAAVVVA (SEQ ID NO:1) as-APF (0.25 or 0.025 µM) were then added to each well, and the cells were incubated for an additional 48 hours at 37° C. in a 5% $CO_2$ atmosphere prior to labeling with 1 µCi $^3$H-thymidine per well. Cells incubated with medium plus PBS or medium plus D-pipecolic acid APF served as negative controls for APF activity; cells incubated with as-APF alone served as positive controls for APF activity. The cell contents were then harvested and methanol-fixed onto glass fiber filter paper, and the amount of radioactivity incorporated was determined. Significance of the difference in mean values between groups was determined by an analysis of variance.

The data indicate that both the D-proline APF and the D-pipecolic acid APF derivatives inhibit the effect of as-APF on normal bladder epithelial cell proliferation, and that their potencies are similar (indicating that they are useful as a treatment at least for IC).

Example 5

Figure 22:
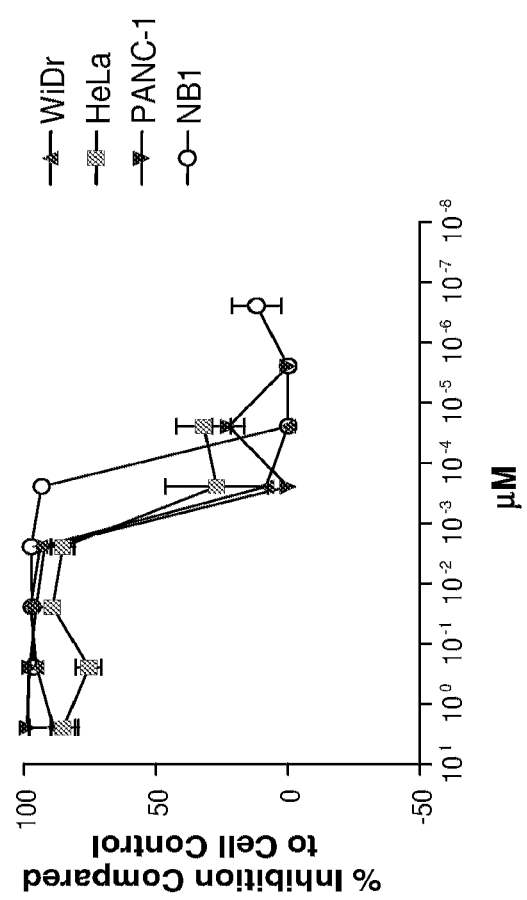
FIG. 22 provides exemplary cell line antiproliferative activity data for an APF derivative comprising pipecolic acid (Galβ1-3GalNAcα-O-TV-Pip-AAVVVA; SEQ ID NO:15) in a variety of cell lines including WiDr colon cancer cells, for example.
Figure 23:
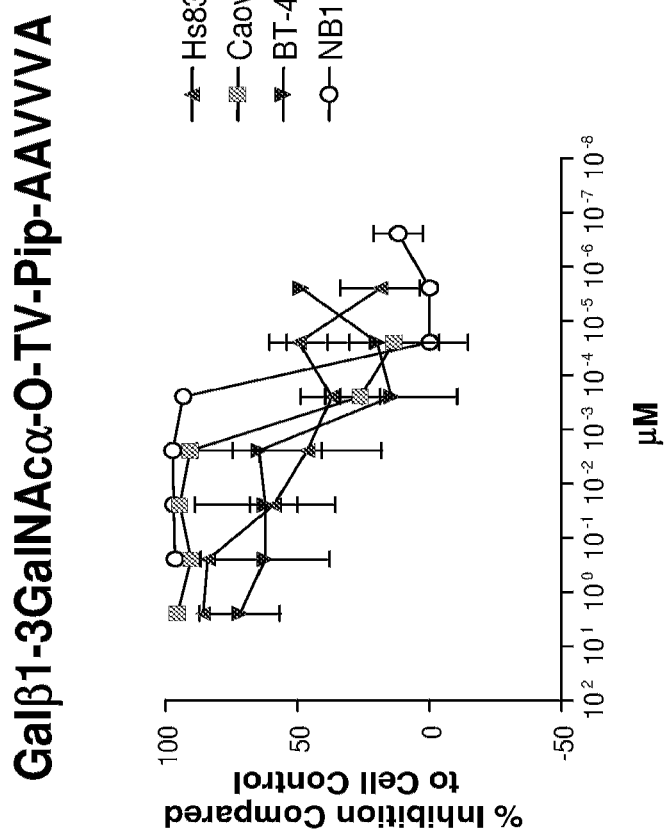
FIG. 23 provides exemplary cell line antiproliferative activity data for an APF derivative comprising pipecolic acid (Galβ1-3GalNAcα-O-TV-Pip-AAVVVA; SEQ ID NO:15) in a variety of cell lines.
Figure 24:
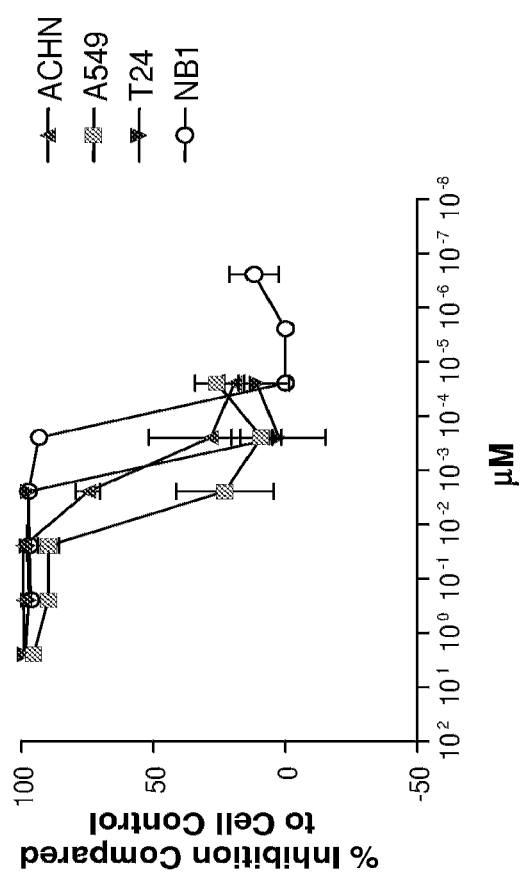
FIG. 24 provides exemplary cell line data for an APF derivative comprising pipecolic acid (Galβ1-3GalNAcα-O-TV-Pip-AAVVVA; SEQ ID NO:15) in a variety of cell lines.
Figure 25:
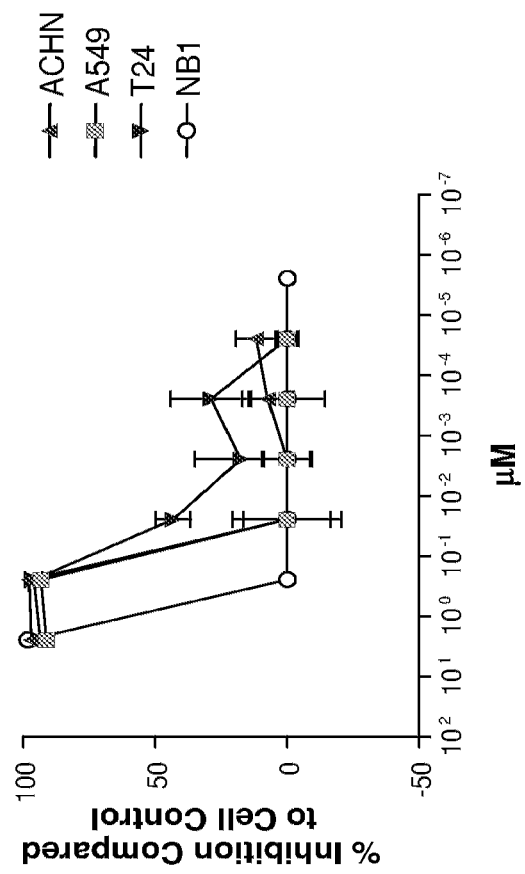
FIG. 25 provides exemplary cell line antiproliferative activity data for derivative #14.
Figure 26:
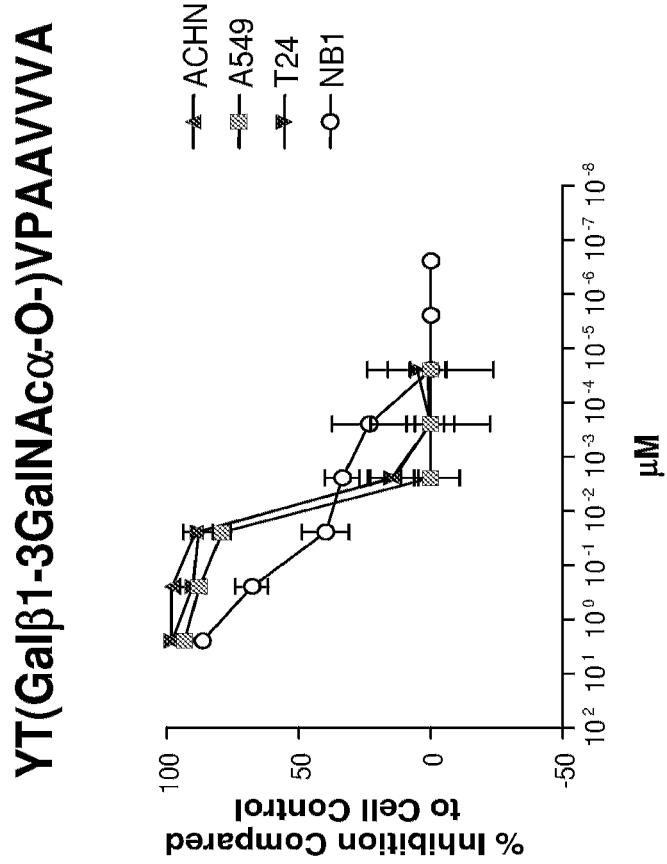
FIG. 26 provides exemplary cell line antiproliferative activity data for derivative #6.
Figure 27:
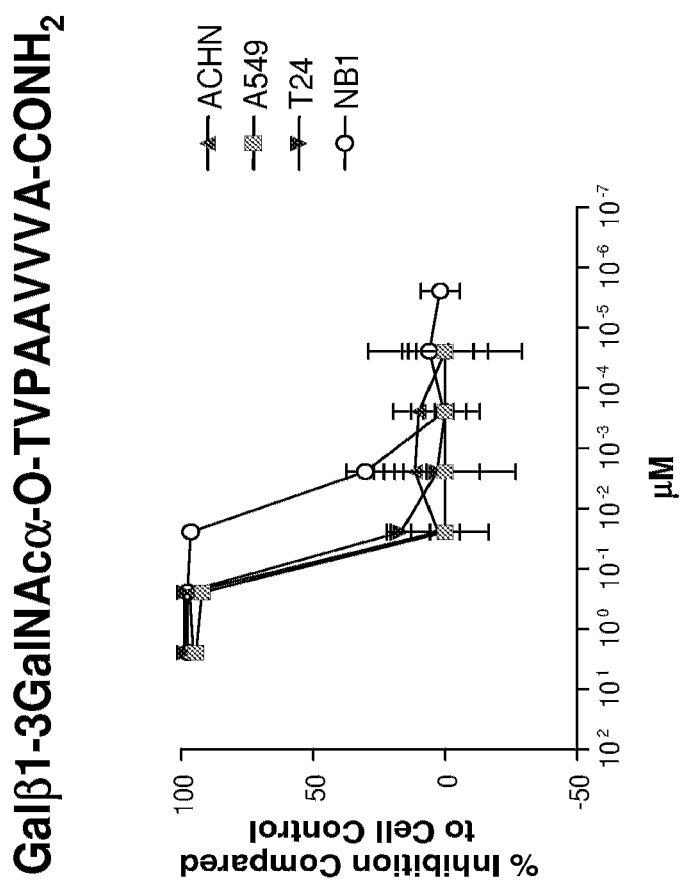
FIG. 27 provides exemplary cell line antiproliferative activity data for derivative #29.
Figure 28:
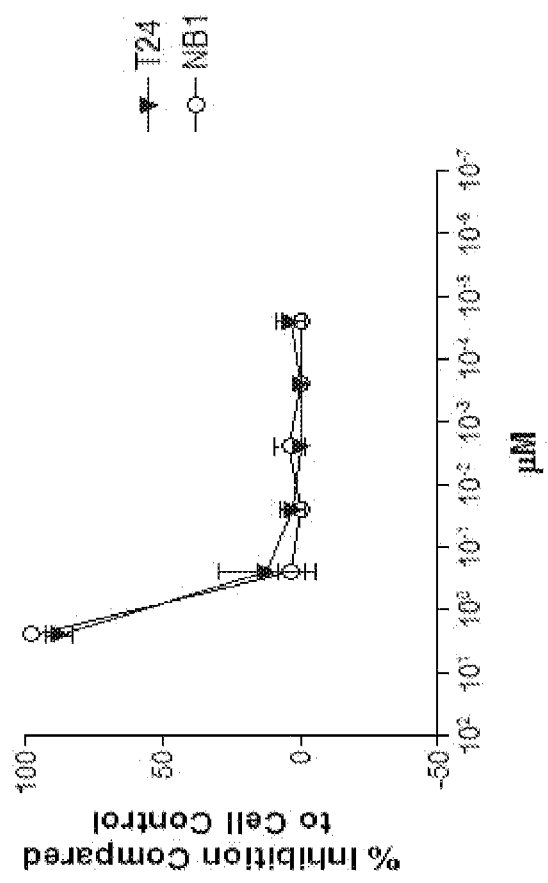
FIG. 28 provides exemplary cell line antiproliferative activity data for derivative #3.
Figure 29:
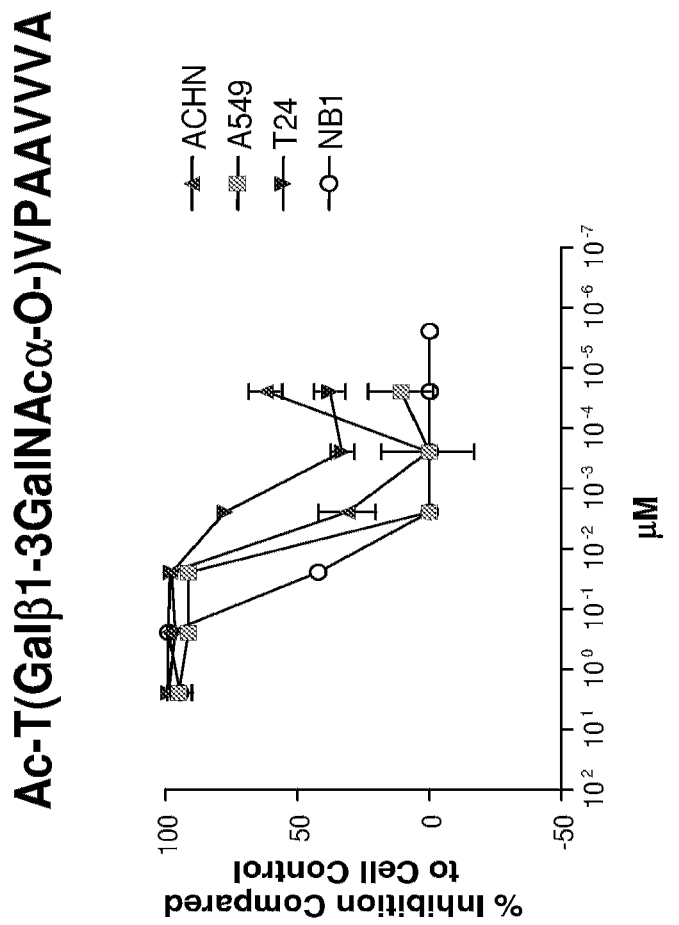
FIG. 29 provides exemplary cell line antiproliferative activity data for derivative #5.
Figure 30:
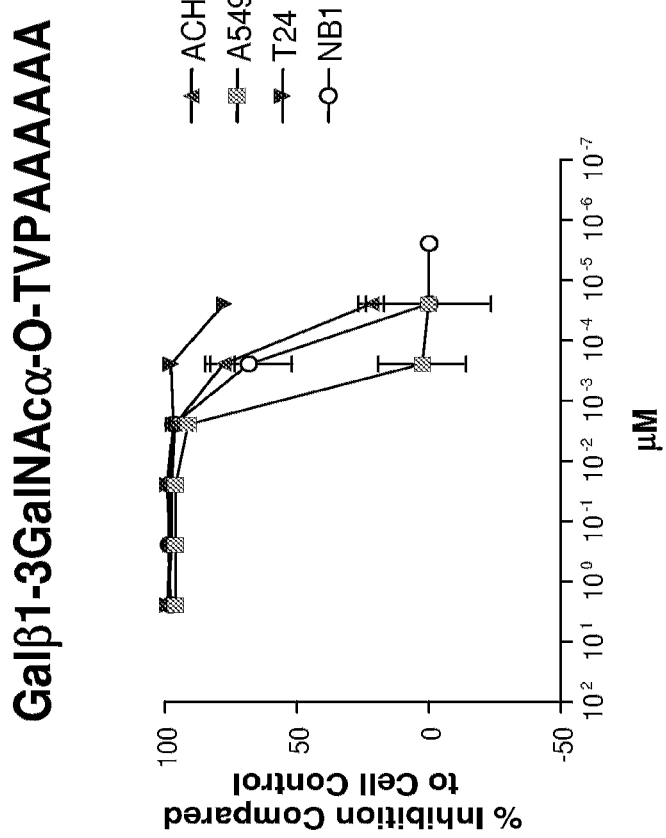
FIG. 30 provides exemplary cell line antiproliferative activity data for derivative #25.
Figure 31:
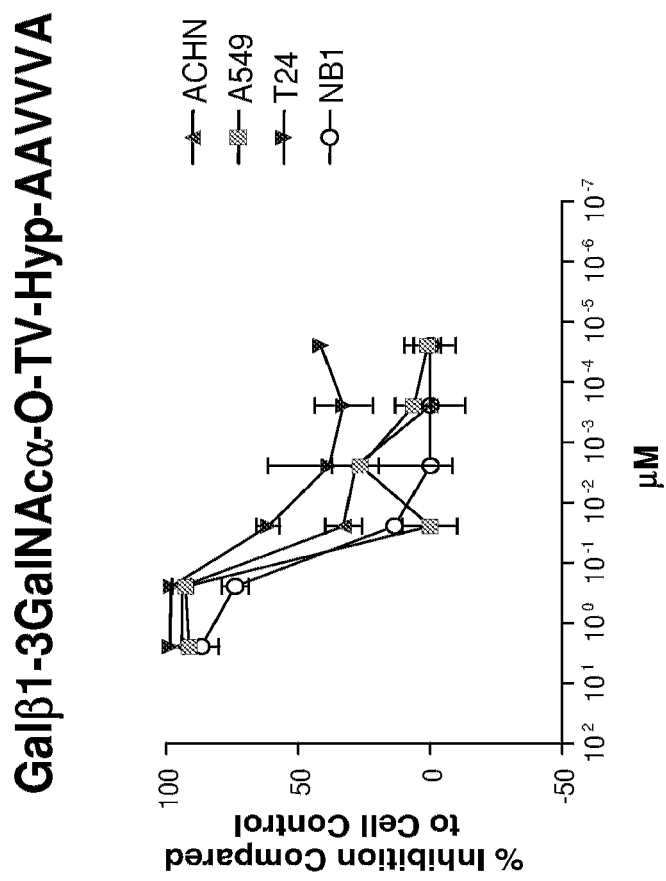
FIG. 31 provides exemplary cell line antiproliferative activity data for derivative #12.
Figure 32:
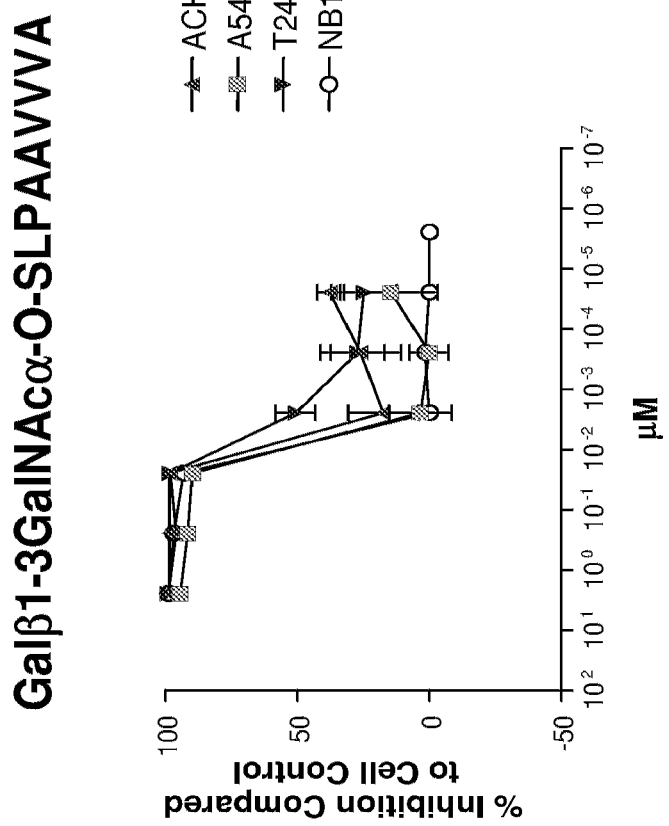
FIG. 32 provides exemplary cell line antiproliferative activity data for derivative #2.
Figure 33:
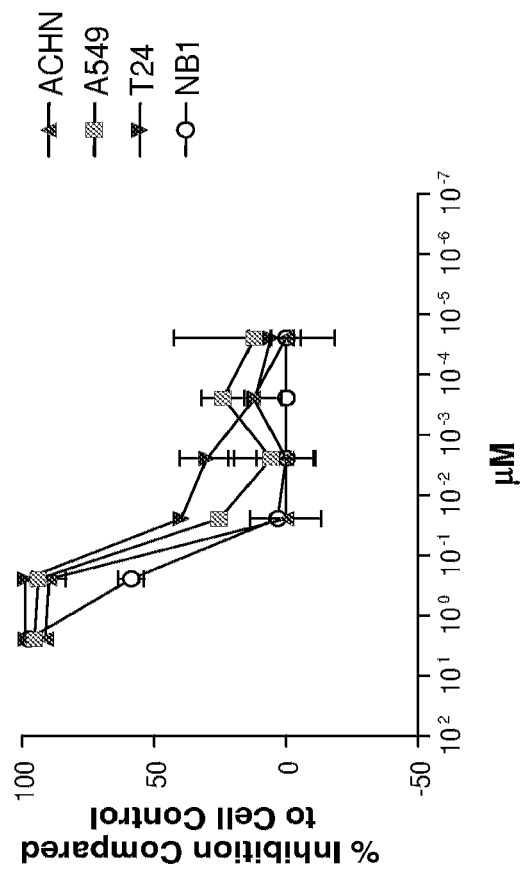
FIG. 33 provides exemplary cell line antiproliferative activity data for derivative #13.
Figure 34:
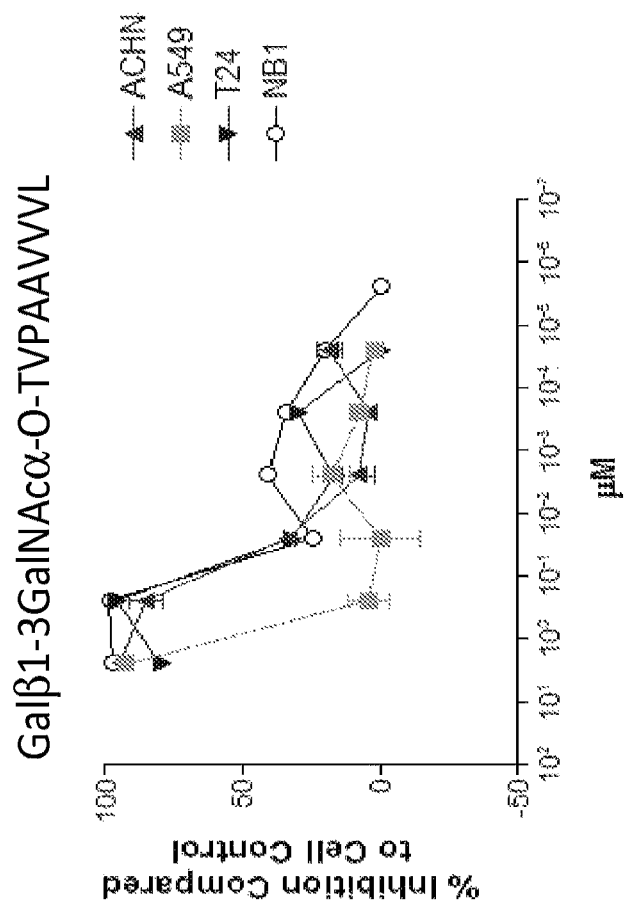
FIG. 34 provides exemplary cell line antiproliferative activity data for derivative #21.
Figure 35:
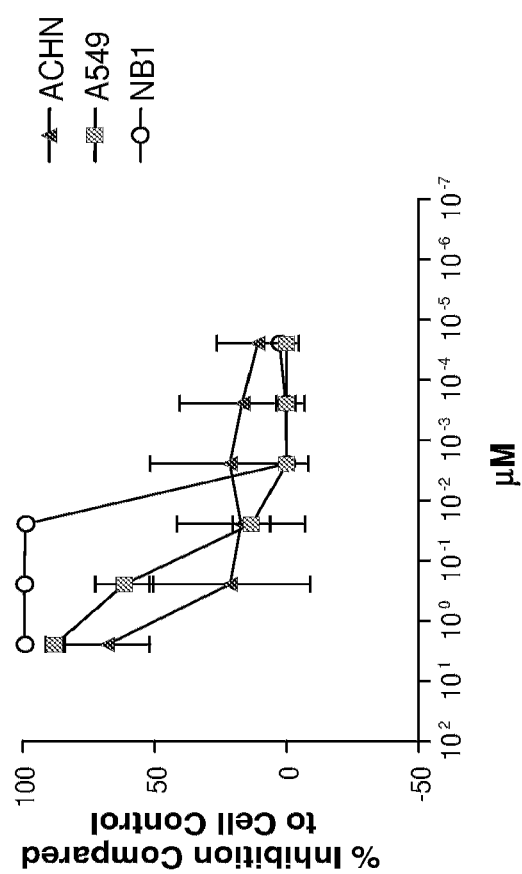
FIG. 35 provides exemplary cell line antiproliferative activity data for derivative #30.
Figure 36:
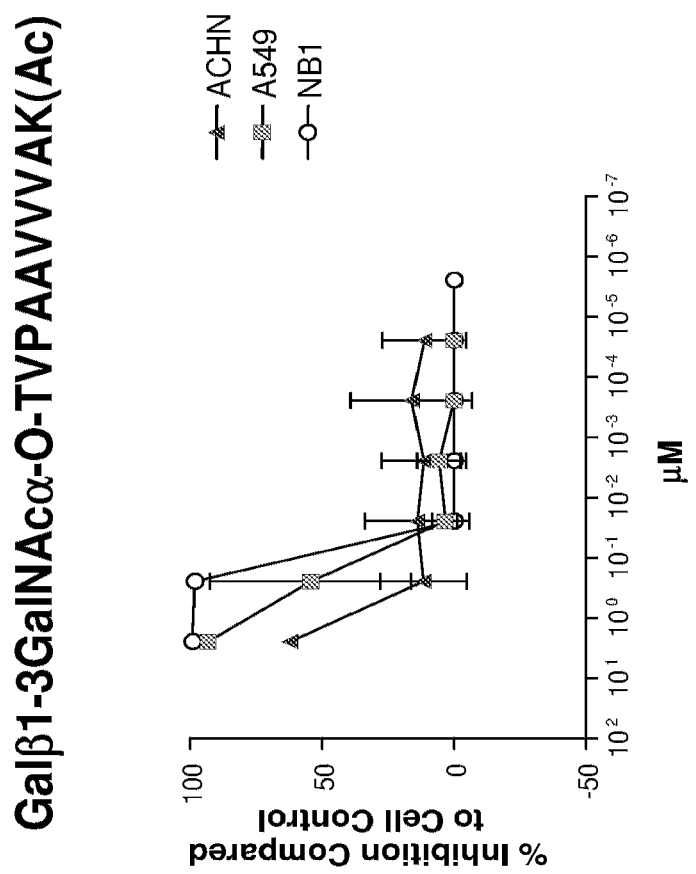
FIG. 36 provides exemplary cell line antiproliferative activity data for derivative #35.
Figure 37:
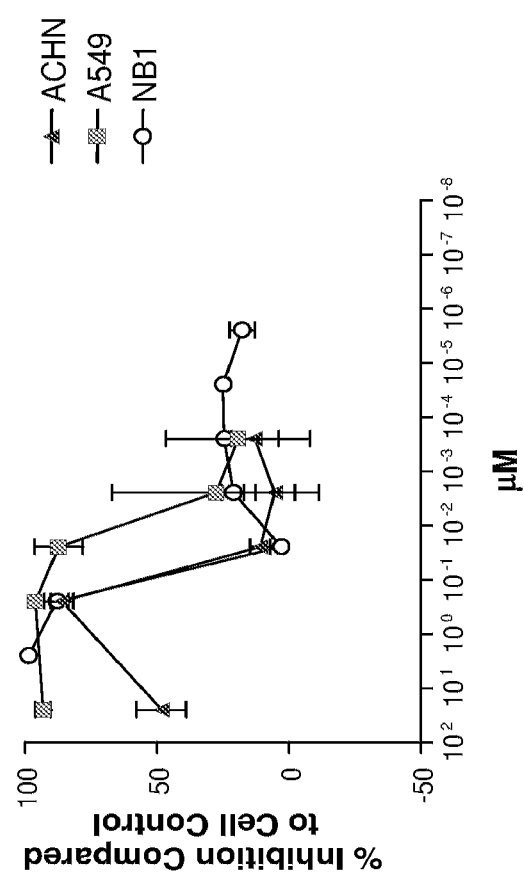
FIG. 37 provides exemplary cell line antiproliferative activity data for derivative #26.

Sensitivity of Several Different Exemplary Cancer Cell Lines to APF Derivatives FIGS. 22-24 provide data concerning sensitivity of several representative cancer cell lines to an exemplary derivative comprising L-pipecolic acid. The exemplary cell lines include the following: WiDr (colon cancer), HeLa (cervical cancer), PANC-1 (pancreatic cancer), Hs838T (melanoma), CaOv3 (ovarian cancer), BT474 (breast cancer), ACHN (kidney cancer), T24 (bladder cancer) and A549 (lung cancer). The term "NB1 cells" in each figure is data from normal bladder epithelial cells. FIGS. 25-37 provide data concerning sensitivity of certain cell lines to particular APF derivatives. In particular, FIG. 25 provides data for derivative #14; FIG. 26 provides data for derivative #6; FIG. 27 provides data for derivative #29; FIG. 28 provides data for derivative #3; FIG. 29 provides data for derivative #5; FIG. 30 provides data for derivative #25; FIG. 31 provides data for derivative #12; FIG. 32 provides data for derivative #2; FIG. 33 provides data for derivative #13; FIG. 34 provides data for #21; FIG. 35 provides data for derivative #30; FIG. 36 provides data for derivative #35; FIG. 37 provides data for derivative #26.

For each study, the various exemplary carcinoma and melanoma cells lines were obtained from the ATCC and grown under conditions suggested by the supplier (WiDr and HeLa cells—MEM with 10% FBS, 1% L-glutamine, 1 mM sodium pyruvate, and 1% antibiotic/antimycotic solution; PANC-1, HS838T and CaOv3 cells—DMEM with 4 mM L-glutamine, 10% FBS, 4.5 g/L glucose, 1.5 g/L sodium bicarbonate, and 1% antibiotic/antimycotic solution; ACHN cells—MEM with 10% FBS, 1% L-glutamine, 1 mM sodium pyruvate, 1.5 g/L sodium bicarbonate, and 1% antibiotic/antimycotic solution; T24 cells—McCoy's 5A medium with 10% FBS, 1% L/glutamine, 2.2 g/L sodium bicarbonate and 1% antibiotic/antimycotic solution; and A549 cells—DMEM/F12 medium with 10% FBS and 1% antibiotic/antimycotic solution). Cells were incubated in triplicate with varying concentrations of synthetic as-APF (Galβ1-3GalNAcα-O-TVPAAVVVA; SEQ ID NO:1), L-pipecolic acid APF, or the inactive unglycosylated control peptide for 48 hrs prior to determination of cell growth by $^3$H-thymidine incorporation, as described above. Synthetic as-APF-treated normal bladder cells served as a positive control for the assay; cells incubated with medium alone or inactive peptide served as negative controls for APF activity. Significance of the difference in mean values between groups was determined by an analysis of variance.

Synthetic as-APF and L-pipecolic acid APF both significantly inhibited proliferation of each carcinoma cell line and the melanoma cell line compared to cell medium alone (p<0.00001), with maximum $IC_{50}$'s in the low nanomolar range; in comparison, the negative control peptide had no effect in those cells treated with this control (WiDr, T24, PANC-1, HS838T, CaOv3, ACHN, and A549 cells). Although the $IC_{50}$ for both inhibitors was similar in epithelial and melanoma cells, the slope of the dose response curve was lower and the inhibitor concentration at which significant inhibition occurred was 1-2 orders of magnitude higher in melanoma cells than in the carcinoma cells tested for both synthetic factors. However, the different dose-response curves for the melanoma cells (as compared to all normal epithelial or carcinoma cells tested to date) indicates that in specific embodiments there is a different receptor or signaling pathway inhibition in cells of neuroectodermal vs. epithelial origin.

Example 6

Inhibitoin of Antiproliferative Factor (APF) Activity in Bladder Epithelial Cells by Two Synthetic APF Derivatives Interstitial cystitis/painful bladder syndrome (IC/PBS) is a chronic disorder with bladder epithelial thinning or ulceration, pain, urinary frequency and urgency. Bladder epithelial cells from IC/PBS patients make a small glycopeptide antiproliferative factor or "APF" (GalGalNAc-TVPAAVVVA; SEQ ID NO:1) that inhibits cell growth, decreases tight junctions, and increases paracellular permeability. Inactive synthetic APF derivatives were screened for their ability to inhibit APF in normal bladder cells, and the ability of two inhibitory derivatives to normalize tight junction protein gene expression, paracellular permeability, and/or proliferation of IC/PBS cells was determined.

Normal bladder cells were pretreated with inactive APF derivatives [see J Med Chem. 2008; 51:5974-83], then incubated with active synthetic APF. IC/PBS cells were incubated with varying concentrations of two derivatives shown to inhibit APF activity in normal bladder cells—GalGalNAc-TV(D-pipecolic acid) AAVVVA (SEQ ID NO:14) and GalGalNAc-TV (D-proline)AAVVVA (SEQ ID NO:27). Cell proliferation was determined by $^3$H-thymidine incorporation; gene expression by quantitative RT-PCR; specific protein expression by Western blot analysis; tight junction formation by confocal immunofluorescence microscopy; and paracellular permeability by $^{14}$C-mannitol and $^3$H-inulin flux between confluent cells on Transwell plates. Significance of the difference in mean values between groups was determined by an analysis of variance for each assay.

Only two of 30 screened inactive APF derivatives [GalGalNAc-TV(D-pipecolic acid)AAVVVA (SEQ ID NO:14) and GalGalNAc-TV(D-proline)AAVVVA (SEQ ID NO:27)] blocked APF activity in IC/PBS and/or normal bladder cells (p<0.05 for each agent). GalGalNAc-TV(D-proline)AAVVVA (SEQ ID NO:27) was also shown to significantly increase zonula occludens-1 and claudin 1, 4 and 8 expression, and decrease permeability of IC/PBS cells (p<0.01 for each parameter).

GalGalNAc-TV(D-pipecolic acid) AAVVVA (SEQ ID NO:14) and GalGalNAc-TV(D-proline)AAVVVA (SEQ ID NO:27) can inhibit APF activity in bladder epithelial cells in vitro. Additional studies to determine the effect of GalGalNAc-TV(D-pipecolic acid)AAVVVA (SEQ ID NO:14) on tight junction protein expression and permeability of IC/PBS cells are performed along with pharmacokinetic/toxicology studies for both agents, to characterize their use as an IC/PBS therapy.

Example 7

Inhibition of Antiproliferative Factor (APF) Activity by Anti-APF Antibodies and Small Interfering RNA (SIRNA)

The ability of 3 polyclonal anti-APF antibodies and 2 forms of siRNA to inhibit the in vitro biological effects of APF, a small antiproliferative glycopeptide made by bladder epithelial cells from IC/PBS patients, was determined.

Rabbit antibodies raised against 3 APF derivatives (GalGalNAc-TVPAAVVVA; SEQ ID NO:1, GalNAc-TVPAAVVVA (SEQ ID NO:1), and TVPAAVVVA (SEQ ID NO:1)) were tested for their ability to inhibit the biological effects of APF using explanted cells from 6 IC/PBS patients as well as APF-treated normal explanted cells from 6 matched controls. Single- and double-stranded siRNAs against APF (based on nucleic acid sequence of the corresponding human frizzled 8 segment) were tested for their ability to inhibit the effects of APF in IC/PBS cells. Cell proliferation was determined by $^3$H-thymidine incorporation; gene expression by quantitative RT-PCR; specific protein expression by Western blot analysis; tight junction formation by confocal immunofluorescence microscopy; and paracellular permeability by $^{14}$C-mannitol and $^3$H-inulin flux between confluent cells on Transwell plates. Significance of the difference in mean values between groups was determined by an analysis of variance for each assay.

Anti-APF antibodies raised against all 3 APF derivatives blocked APF's inhibition of cell growth (p<0.05); however, only antibodies raised against GalGalNAc-TVPAAVVVA (SEQ ID NO:1) were effective in also significantly blocking the other measured effects of APF (growth factor production, tight junction protein production, and paracellular permeability). These same anti-GalGalNAc-TVPAAVVVA (SEQ ID NO:1) antibodies were also the only anti-APF antibodies that significantly normalized all of these parameters in cells from IC/PBS patients (p<0.02) while having no effect on cells from normal donors, indicating their specificity for IC/PBS cells. Treatment of IC/PBS cells with either single- or double-stranded APF siRNA also significantly improved cell growth, growth factor production, tight junction production, and paracellular permeability in IC/PBS cells as compared to negative control scrambled siRNA (p<0.05), but the double-stranded APF siRNA had an equal or greater effect than the single-stranded agent in each assay.

Based on their ability to inhibit APF activity and normalize several parameters in vitro, anti-GalGalNAc-TVPAAVVVA (SEQ ID NO:1) antibodies and double-stranded siRNA against APF are useful as IC/PBS therapies.

Example 8

CKAP4/P63 Mediates Antiproliferative Factor (APF) Inhibition of AKT/GSK3 Signaling in T24 Bladder Carcinoma Cells Antiproliferative factor (APF) is a potent frizzled 8 protein-related sialoglycopeptide inhibitor of epithelial cell proliferation made by bladder epithelial cells from patients with interstitial cystitis/painful bladder syndrome (IC/PBS). APF mediates its antiproliferative activity in bladder epithelial cells from IC/PBS patients and normal controls by binding to cytoskeletal associated protein 4 (CKAP4/p63). Synthetic asialo-APF inhibits both normal bladder epithelial as well as bladder cancer (T24) cell proliferation in vitro at low nanomolar concentrations. It was determined whether synthetic asialo-APF regulates the activation of enzymes involved in Wnt/frizzled signaling (AKT/GSK3/beta catenin) in T24 cells, and whether such regulation is mediated by the CKAP4/p63 receptor.

Figure 38:
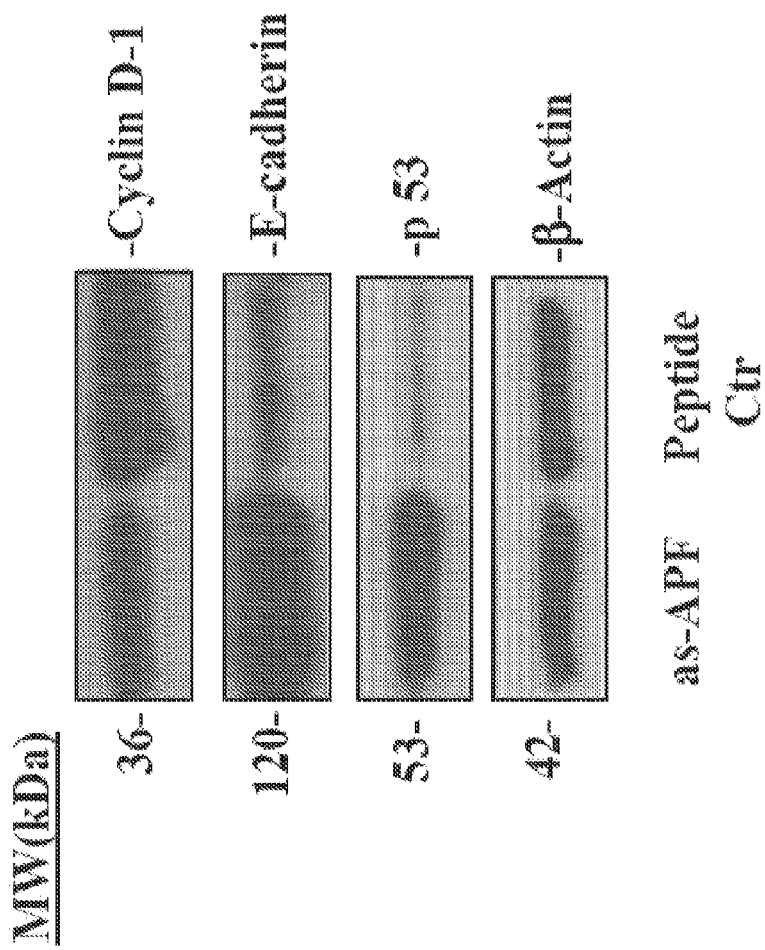
FIG. 38 shows Western blot data in T24 cells for a variety of proteins in the presence of as-APF or a control.
Figure 39:
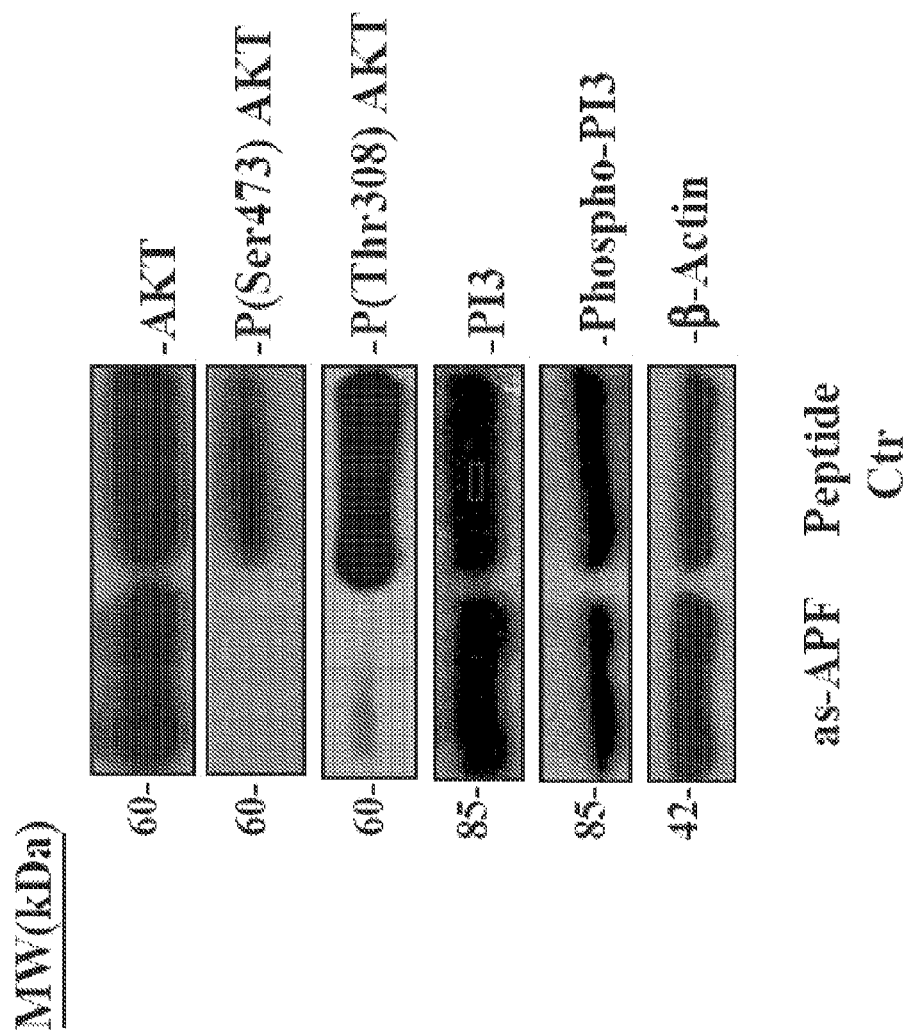
FIG. 39 shows Western blot data in T24 cells for a variety of proteins in the presence of as-APF or a control.
Figure 40:
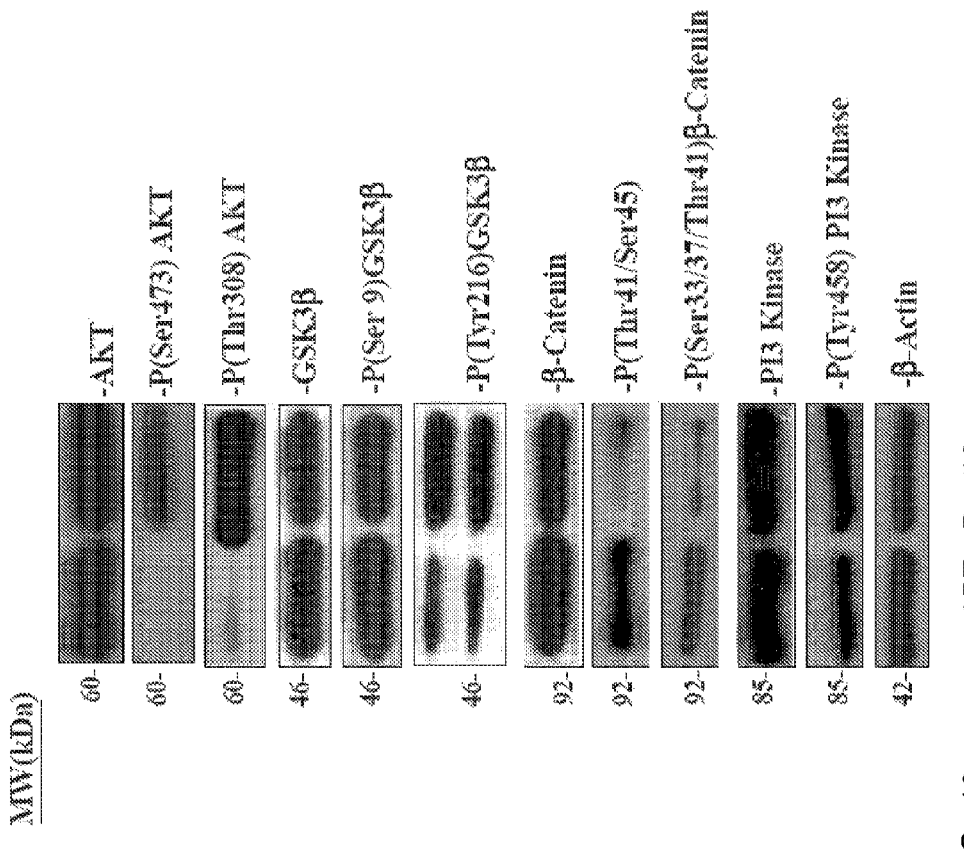
FIG. 40 shows Western blot data in T24 cells for a variety of proteins in the presence of as-APF or a control.

T24 bladder carcinoma cells (obtained from ATCC) were transfected by electroporation with double-stranded siRNAs against CKAP4/p63 and treated with 50 nM synthetic asialo-APF (or its inactive control nonglycosylated peptide). Cells that did not undergo electroporation, and cells transfected with scrambled double-stranded siRNA, both served as negative controls for CKAP4/p63 knockdown. Gene expression was determined by quantitative RT-PCR, and specific protein expression or phosphorylation was determined by Western blot. p53 mRNA and protein expression served as positive controls for APF activity. Beta actin expression served as a standard control for Western blot analyses (see FIGS. 38-40).

Akt phosphorylation (serine 473 and threonine 308), GSK3beta phosphorylation (tyrosine 216), and beta catenin phosphorylation (serine 45) were all significantly decreased, and beta catenin phosphorylation (serine 33/37 and threonine 41) was significantly increased following APF treatment of nonelectroporated T24 control cells (p<0.05); in comparison, neither mRNA nor protein expression of total Akt, GSK3beta, or beta catenin changed significantly in response to synthetic asialo-APF (p>0.05). Further, the changes in Akt, GSK3beta, and beta catenin protein phosphorylation in response to synthetic asialo-APF treatment were all specifically abrogated following CKAP4/p63 siRNA knockdown.

Synthetic asialo-APF inhibits Akt/GSK3/beta catenin signaling in T24 bladder carcinoma cells via the CKAP4/p63 receptor. Enzyme activity assays and experiments with specific kinase activity modifiers are performed to characterize the role of this signaling pathway in mediating APF inhibition of T24 carcinoma cell proliferation.

Example 9

Inhibition of Carcinoma and Melanoma Cell Proliferation in Vitro by a Novel Frizzled 8 Protein-Related Antiproliferative Factor (APF)

Antiproliferative factor (APF) is a potent frizzled protein 8-related sialoglycopeptide inhibitor of bladder epithelial cell proliferation that mediates its activity in normal bladder cells by binding to cytoskeletal associated protein 4 in the cell membrane. A synthetic nonsialylated APF (Galβ1-3GalNAcα-O-TVPAAVVVA; SEQ ID NO:1) inhibits both normal bladder epithelial as well as bladder cancer (T24) cell proliferation in vitro at low nanomolar concentrations (PNAS 2004; 101:11803-11808), and a pipecolic acid derivative (Galβ1-3GalNAcα-O-TV-pipecolic acid-AAVVVA; SEQ ID NO:15) was previously shown to inhibit normal bladder cell proliferation (J Med Chem 2008; 51:5974-83). The inventors therefore determined the sensitivity of T24 cells to the pipecolic acid derivative, as well as compared the activity of both synthetic growth inhibitors in T24 cells to their activity in several exemplary nonurologic carcinoma and melanoma cell lines.

CaOv3 (ovarian), A549 (lung), PANC-1 (pancreatic), and HeLa (cervical) carcinoma cells, plus melanoma (Hs839.T) cells, were incubated in triplicate with varying concentrations of synthetic asialo-APF, pipecolic acid APF, or the inactive unglycosylated control peptide for 48 hrs prior to determination of cell growth by $^3$H-thymidine incorporation. Synthetic asialo (as)-APF-treated T24 cells served as a positive control for the assay; cells incubated with medium alone or inactive peptide served as negative controls for APF activity. Significance of the difference in mean values between groups was determined by an analysis of variance.

Synthetic asialo-APF and pipecolic acid APF both significantly inhibited proliferation of each of the four carcinoma cell lines and the melanoma cells compared to cell medium alone ($p<0.00001$), with maximum $IC_{50}$'s in the low nanomolar range, while none of these cell lines was inhibited by the negative control peptide. Although the $IC_{50}$ for both inhibitors was similar in epithelial and melanoma cells, the slope of the dose response curve was lower, and the inhibitor concentration at which significant inhibition occurred was 2 orders of magnitude higher, in melanoma cells than in the carcinoma cell lines for both synthetic factors.

Synthetic asialo-APF and its pipecolic acid derivative are potent inhibitors of nonurologic carcinoma as well as urologic carcinoma and melanoma cells. However, the markedly different dose-response curves for the melanoma cells (as compared to all normal epithelial or carcinoma cells tested to date) indicates the possibility of a different receptor or signaling pathway inhibition in cells of neuroectodermal vs. epithelial origin, in specific embodiments.

Example 10

APF Pathway Embodiments

In specific embodiments of the invention, APF does not inhibit transcription of the genes for Akt, GSK3 or beta catenin. In particular embodiments of the invention, APF regulates the activity of these enzymes (which in turn is regulated in each case by phosphorylation of specific sites). In additional specific embodiments, CKAP4/p63 is involved in mediating the effects of APF on Akt pathway activation, in that the changes in phosphorylation of Akt, GSK3 and beta catenin in response to APF activity are blocked significantly by CKAP4/p63 knockdown (by siRNA).

Example 11

Exemplary APF Proline and Pipecolic Acid Derivatives Studies

Figure 41:
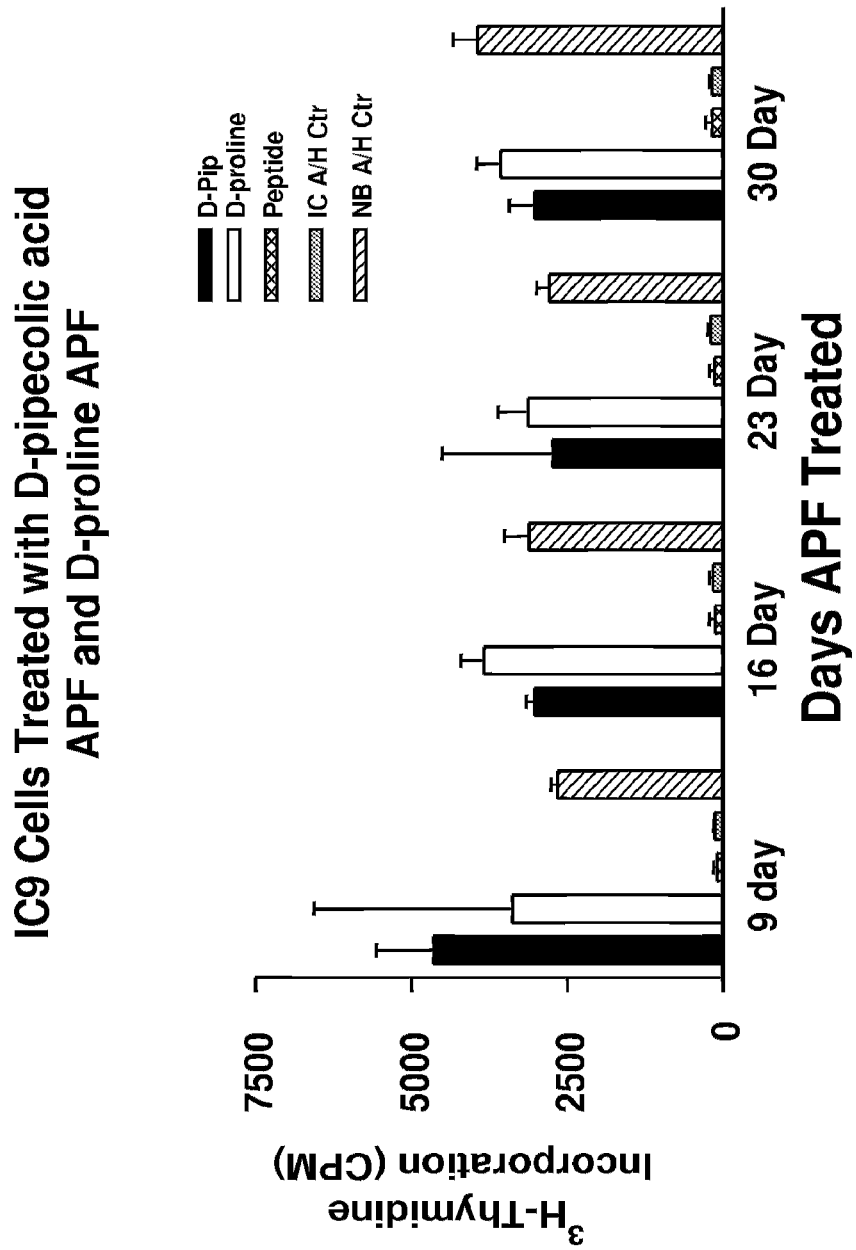
FIG. 41 shows a comparison of the effect of both APF proline and APF pipecolic acid agents on IC cell proliferation (as measured by thymidine incorporation) following 9, 16, 23, and 30 day treatment with 0.25 uM of each agent.

FIG. 41 shows a comparison of the effect of both APF proline and APF pipecolic acid agents on IC cell proliferation (as measured by thymidine incorporation) following 9, 16, 23, and 30 day treatment with 0.25 µM of each agent. Optimal stimulation of IC cell proliferation was observed up to the level of normal bladder cell proliferation achieved following only 9 days treatment in vitro.

Figure 42:
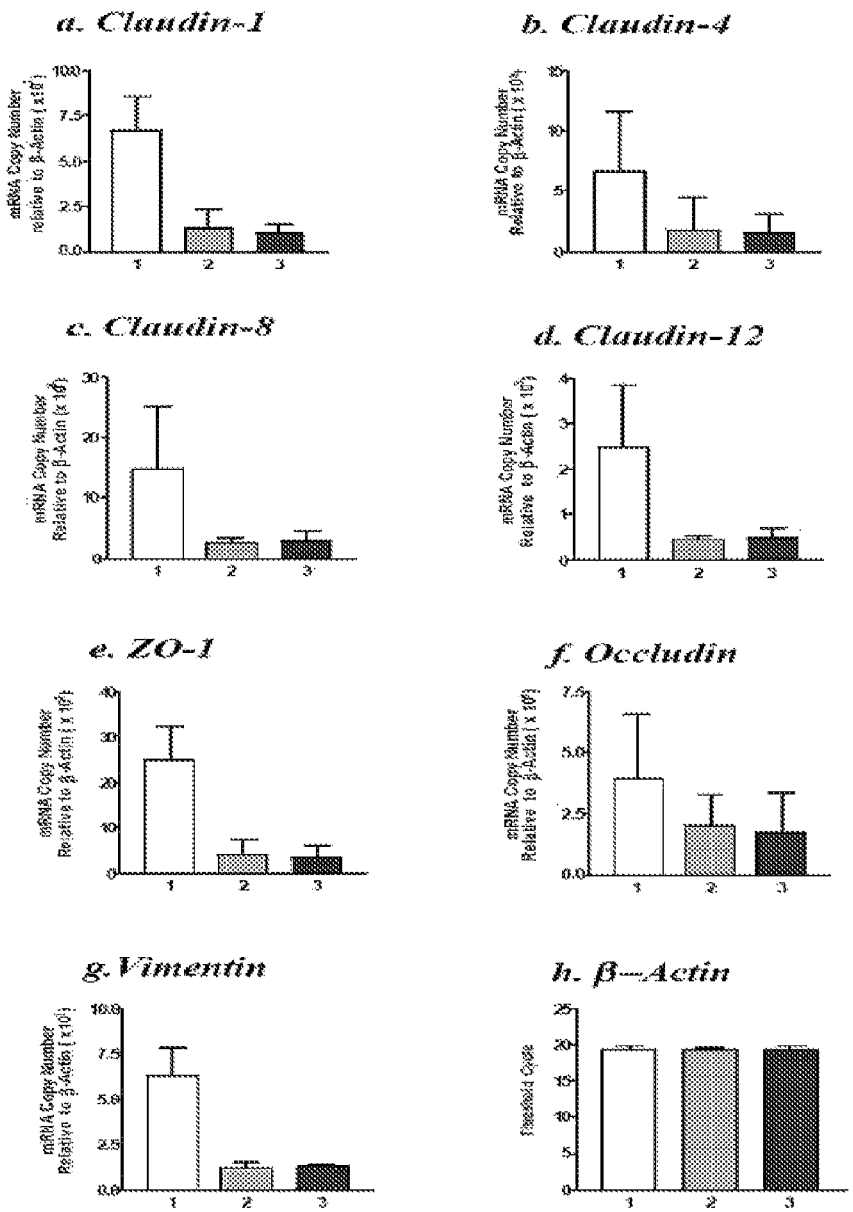
FIG. 42 shows the effect of 16 day treatment on mRNA expression for various cell proteins (claudins, occludin, and ZO-1 are tight junction proteins), where the white bar (1) is the D-proline treated sample, the gray bar (2) is a peptide-control-treated sample, and the black bar (3) is an untreated cell control sample.
Figure 44:
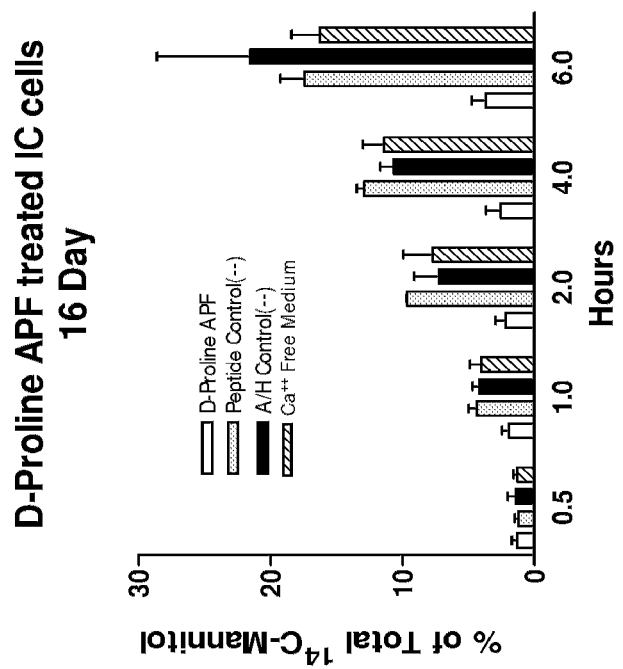
FIG. 44 shows the effects of D-proline APF on paracellular permeability of a radioactive tracer molecule ($^{14}C$-mannitol) following 16 day treatment.
Figure 45:
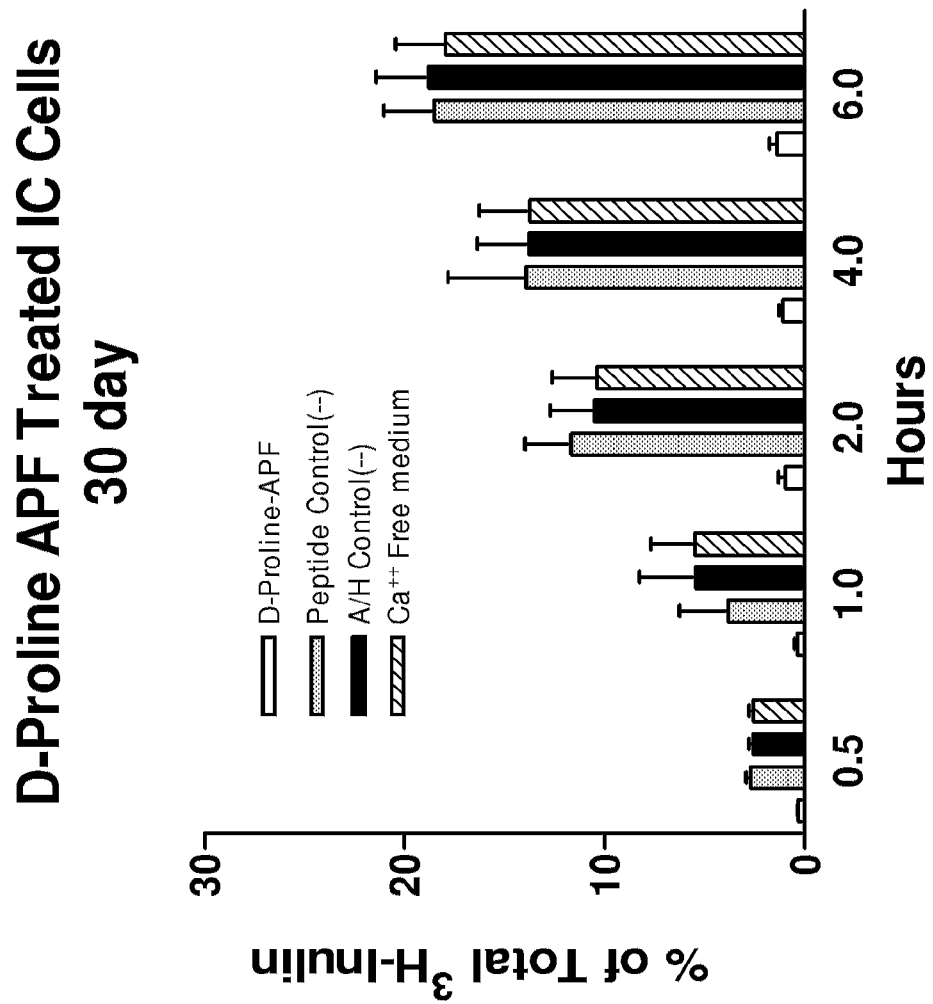
FIG. 45 shows the effects of D-proline APF on paracellular permeability of a radioactive tracer molecule ($^{3}H$-inulin) following 30 day treatment.
Figure 46:
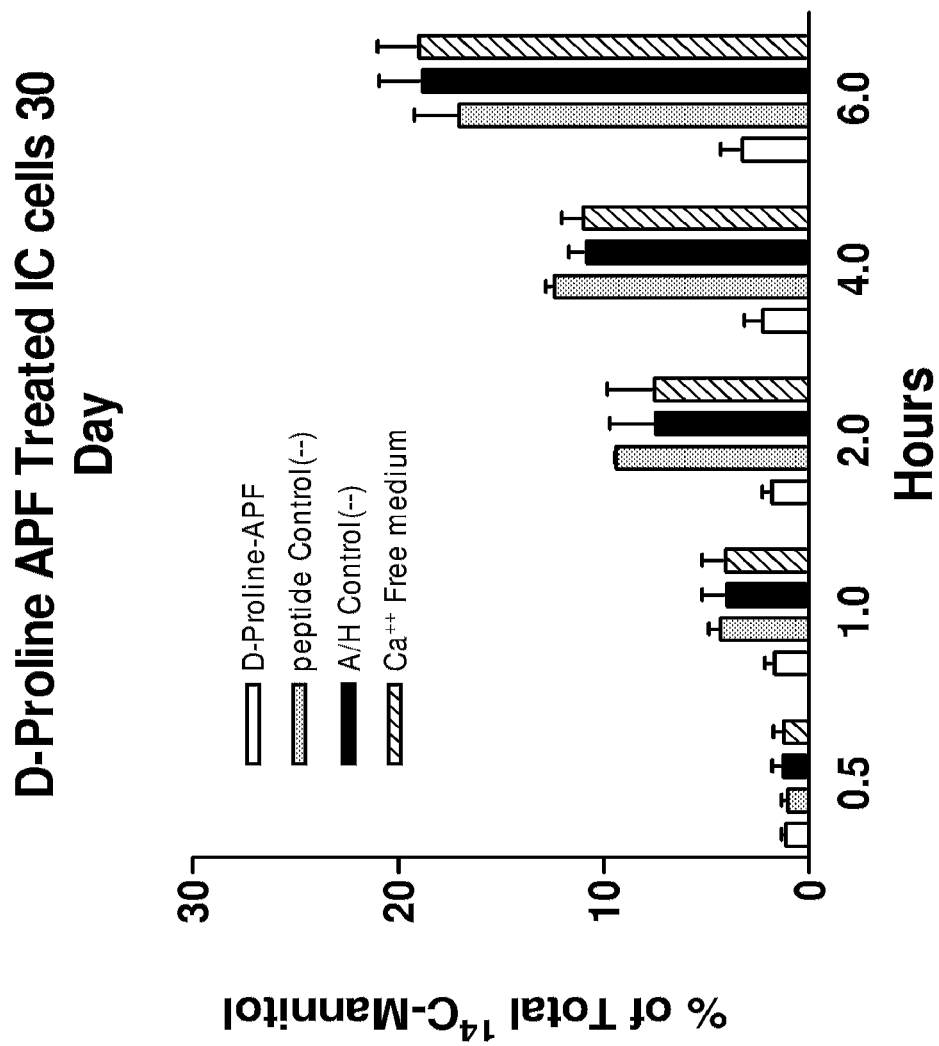
FIG. 46 shows the effects of D-proline APF on paracellular permeability of a radioactive tracer molecule ($^{14}C$-mannitol) following 30 day treatment.
Figure 47:
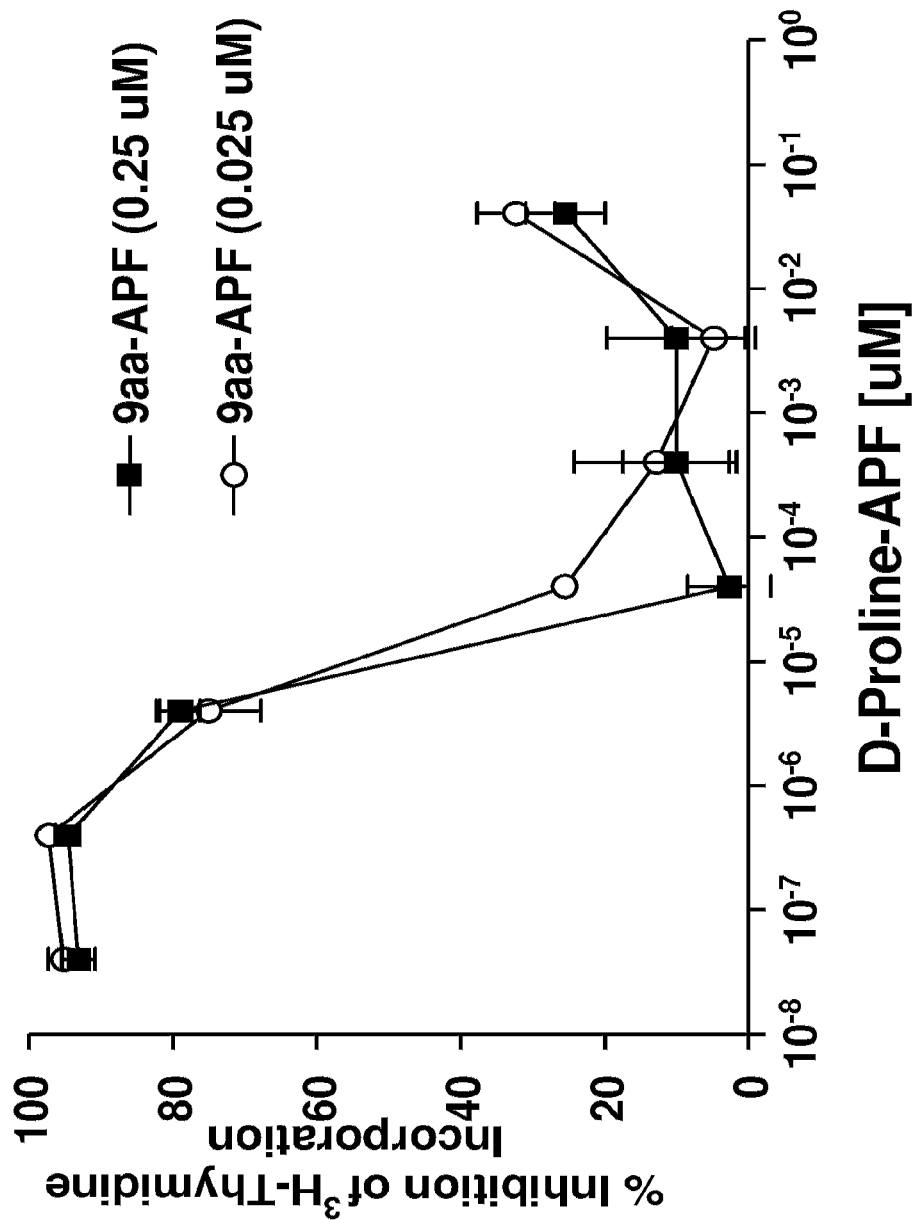
FIG. 47 shows the dose response of D-proline APF on the proliferation of APF-treated normal bladder cells (as measured by thymidine incorporation). Cells were treated with two different concentrations of APF (0.25 and 0.025 μM).
Figure 48:
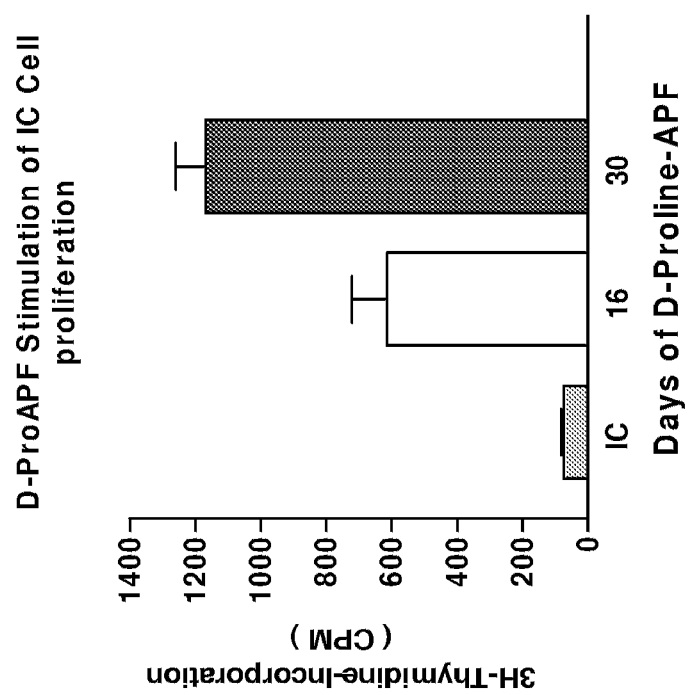
FIG. 48 shows the effect on IC cell proliferation following 16 and 30 days of treatment as compared to untreated controls.

FIGS. 42-48 provide a series of figures showing the effect of D-proline APF on IC cell proliferation, paracellular permeability and tight junction protein expression. FIGS. 42-43 show the effect of 16 and 30 day treatment (respectively) on mRNA expression for various cell proteins (claudins, occludin, and ZO-1 are tight junction proteins), where the white bar (1) is the D-proline treated sample, the gray bar (2) is a peptide-control-treated sample, and the black bar (3) is an untreated cell control sample. Beta actin is an exemplary housekeeping (control) cell protein; D-proline treatment resulted in stimulation of tight junction protein expression, which is significantly decreased in IC cells as compared to normal bladder cells. FIGS. 44-46 show the effects of D-proline APF on paracellular permeability of two radioactive tracer molecules ($^{14}$C-mannitol and $^3$H-inulin) following either 16 or 30 days treatment; paracellular permeability, which is abnormally high in IC cells as compared to normal bladder cells is normalized following 16 or 30 days treatment with D-proline APF. FIG. 47 shows the dose response of D-proline APF on the proliferation of APF-treated normal bladder cells (as measured by thymidine incorporation)—cells were treated with two different concentrations of APF (0.25 and 0.025 uM). In FIG. 48, there is shown the effect on IC cell proliferation following 16 and 30 days of treatment; IC cell proliferation was significantly stimulated at both time points by D-proline APF (as compared to untreated controls).

Example 12

Structure-Activity Relationship Studes and Modification of APF

Figure 49:
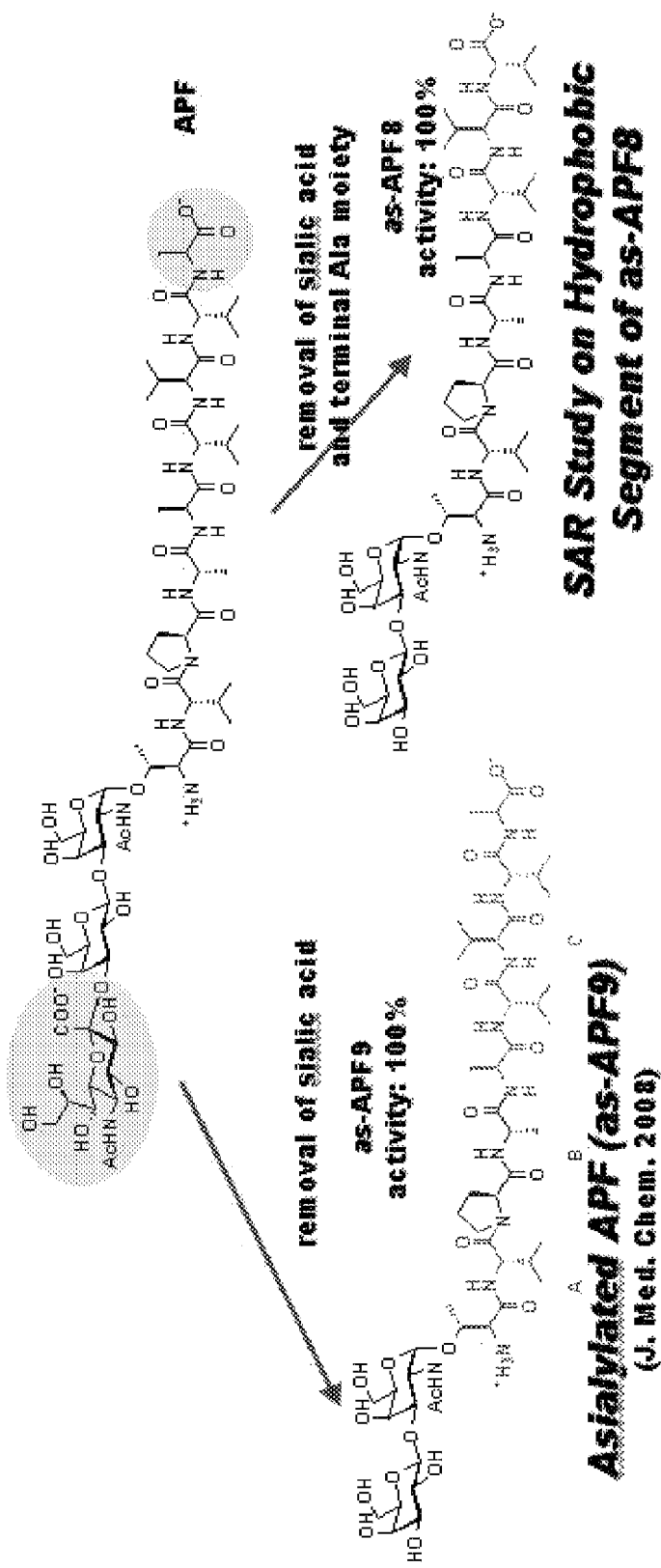
FIG. 49 shows different structures of exemplary APF derivatives.

Modifications of the APF structures (Asialylated APF (as-APF9) and the hydrophobic segment of as-APF8) in FIG. 49 were done to study the structure-activity of APF. Further studies showed that either extension of the APF sequence with Tyr or acetylation of the N-terminal amino group significantly suppressed the activity. Thus, in an embodiment of the invention, modified APF structures may maintain a positively charged N-terminus for optimal activity. Additionally, the number and positioning of the methyl groups on APF were also found in certain embodiments to affect activity.

Activity, in certain embodiments, was influenced by the amino acid at position 3. For example, specifically constrained amino acid structures such as proline or pipecolic acid showed significant activity. However, the pseudoproline derivative of was found to be inactive, indicating a trans conformation of the peptide bond may influence activity, in certain embodiments.

In one example, AVVVA (SEQ ID NO:10) could not be replaced with 12-aminododecanoic acid, indicating that there may be a requirement for a specific structural characteristics at the C-terminus. The presence of helix-disrupting amino acids in AVVVA (SEQ ID NO:10), in certain embodiments of the invention, may decrease the activity. Further studies also indicate that APF generally requires at least 8 amino acids to be active, however, the 9$^{th}$ amino acid is not necessary for activity. Both carboxyamidation of the C-terminus and extension of APF with neutral amino acids resulted in a loss of activity. Additionally, in one embodiment of the invention, position 9 positively influences activity when it contains a negatively charged carboxylic group. Extension of APF with amino acid containing charged (either positive or negative) side chains was not well tolerated, in one example. In a further embodiment of the invention, small amino acid side chains are found in the 5th and 9th amino acid position.

TABLE 7

Exemplary modifications of the hydrophobic segment of as-APF8
Galβ1-3GalNAcα-O-TVPAA-R-R-R (SEQ ID NO: 21)

| Structure | R | activity | LogP |
|---|---|---|---|
| (Leu side chain) | Leu | 10% | −3.35 |
| (Val side chain) | Val | 100% | −4.42 |
| (Abu side chain) | Abu | inactive | −5.73 |
| (Ala side chain) | Ala | 100% | −7.31 |
| (Gly side chain) | Gly | inactive | −8.51 |
| (βAla side chain) | βAla | 0.1% | −8.81 |
| (β³hALA side chain) | β³hALA | inactive | −7.51 |

Figure 50:
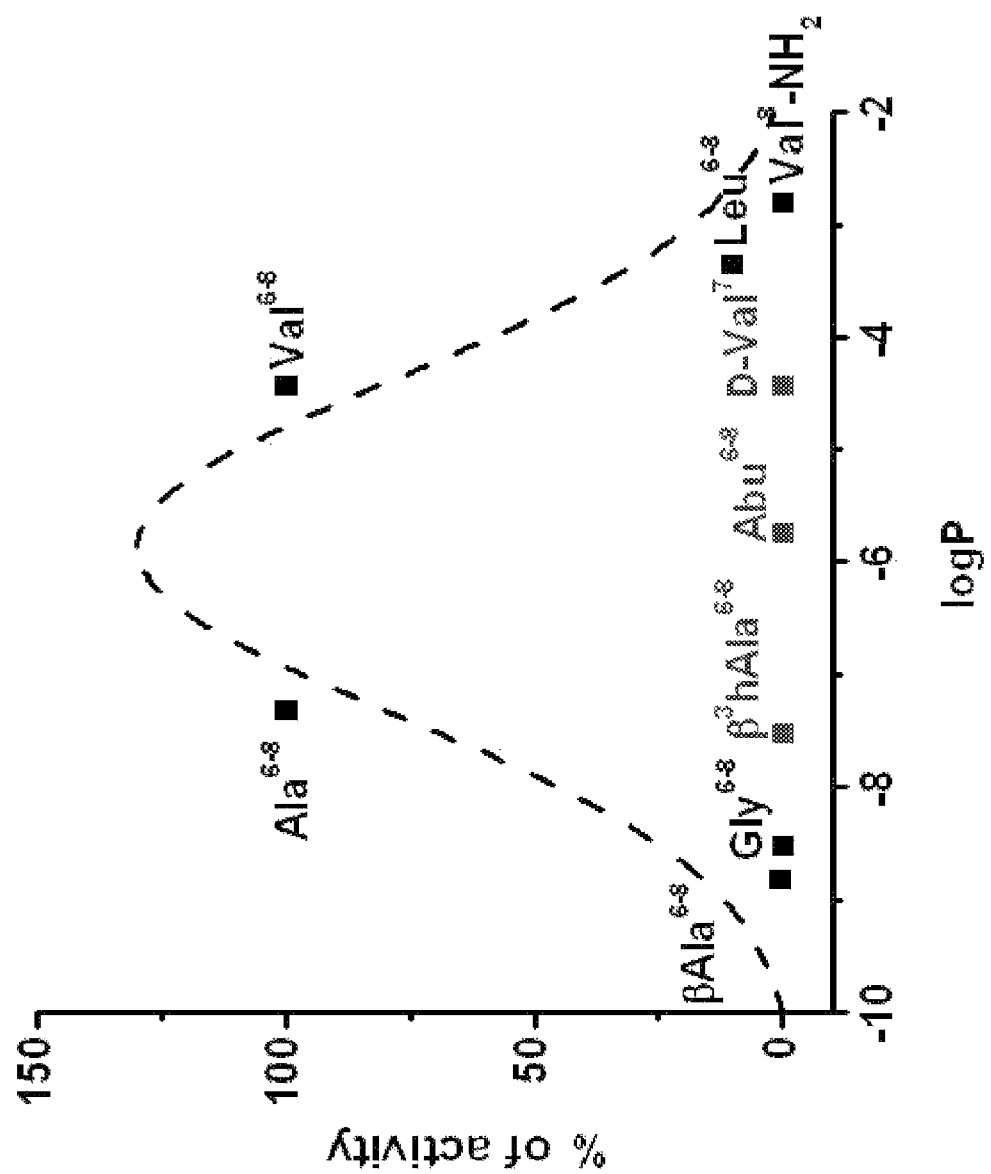
FIG. 50 illustrates activity correlation to hydrophobicity of as-APF8.
Figure 51:
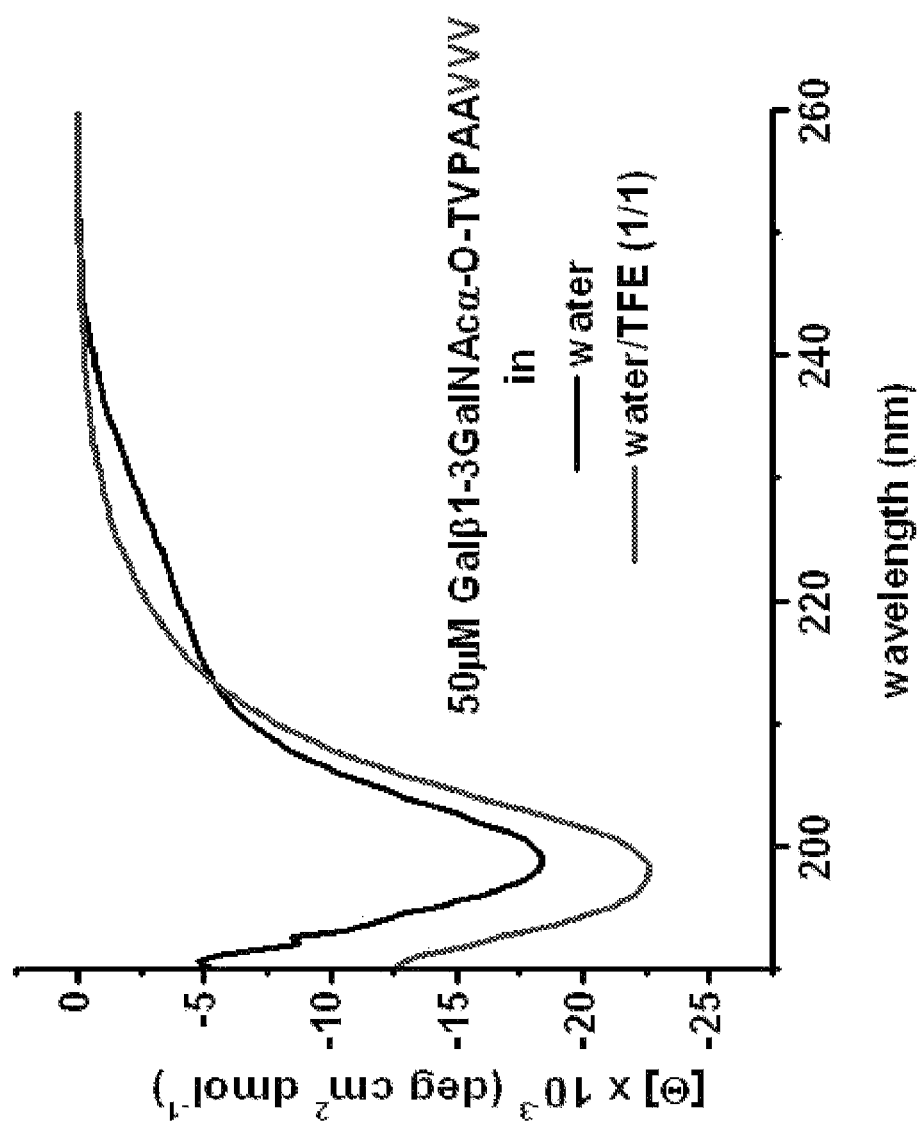
FIG. 51 is the circular dichroism (CD) spectra of as-APF8 in water and in water plus TFE. TVPAAVVV is SEQ ID NO:19.
Figure 52:
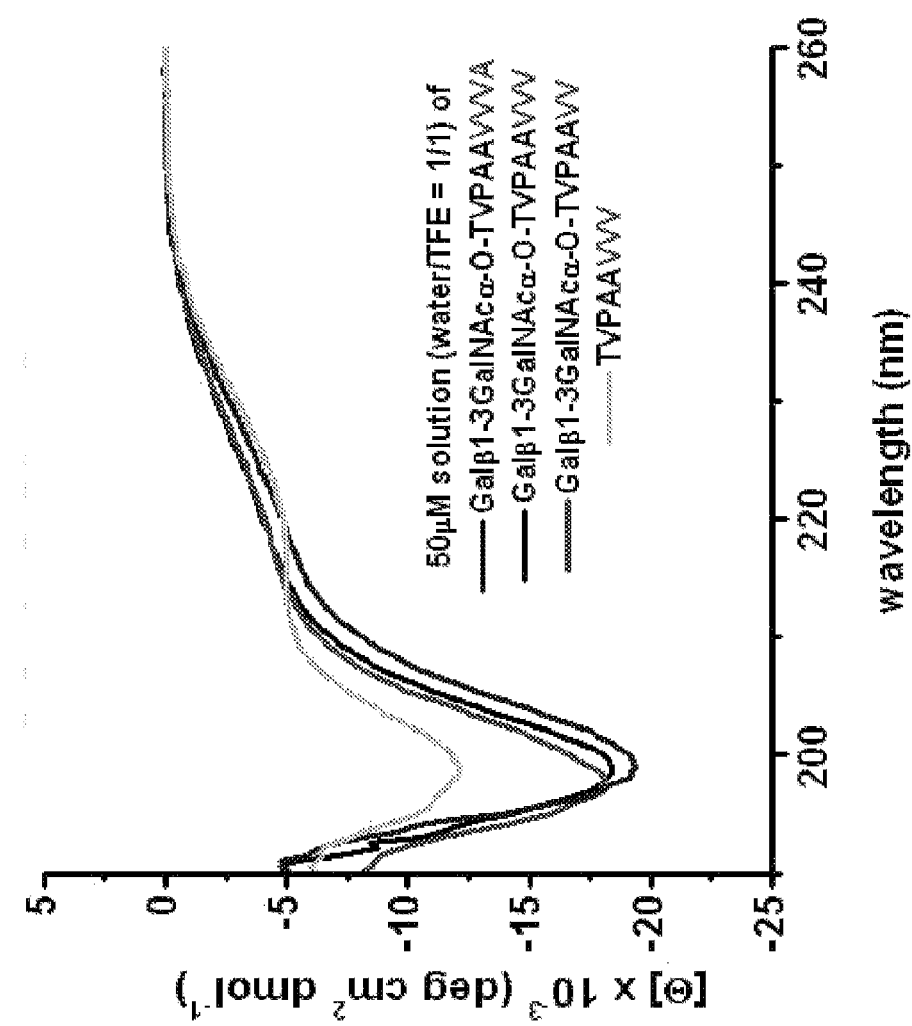
FIG. 52 is the CD spectra of a 50 μM solution (water/TFE=1/1) of Galβ1-3GalNAcα-O-TVPAAVVVA (SEQ ID NO:1; lowest line), Galβ1-3GalNAcα-O-TVPAAVVV (SEQ ID NO:19)(second to lowest line), Galβ1-3GalNAcα-O-TVPAAVV (SEQ ID NO:20) (second to highest line), and TVPAAVVV (SEQ ID NO:19) (highest line).

The hydrophobic tail of Galβ1-3GalNAcα-O-TVPAA-R-R-R (the R-R-R) (SEQ ID NO:21) was modified and activities are shown in FIG. 50 to demonstrate how the activity correlates with hydrophobicity. FIG. 51 illustrates that as-APF8 does not have a secondary structure in water. However, there is some secondary structure that is induced by TFE. FIG. 52 demonstrates the relation of length/glycosylation to secondary structure.

The studies in this example showed that some embodiments of the 8-amino acid derivatives are as active as APF. Carboxyamidation of the C-terminus leads to substantial inactivity, in some examples. Differences in the activity of similar analogs of 8- and 9-mer APF derivatives were observed. Secondary structure is seen in water plus TFE. The CD spectrum of as-APF8 changes with concentration indicating aggregation. No correlation was found between activity and structure in water plus TFE. Introduction of some unnatural amino acids (D-Val, Abu or β³hALA) in some embodiments shown in Table 7 lead to substantially inactive compound.

Example 13

Normalization of Proliferation and Paracellular Permeability of Bladder Epithelial Cells from IC Patients by a Synthetic Inhibitor of Antiproliferative Factor General Overview Inactive synthetic APF derivatives were screened for their ability to inhibit APF in normal bladder cells, and then the ability of two exemplary inhibitory derivatives to normalize tight junction protein gene expression, paracellular permeability, and/or proliferation of IC/PBS cells was determined. In particular embodiments, some derivatives of the present invention are useful as APF inhibitors for the treatment of IC/PBS.

Overview of Methods

Normal bladder cells were pretreated with inactive APF derivatives, then incubated with active synthetic APF. IC/PBS cells were incubated with varying concentrations of two derivatives shown to inhibit APF activity in normal bladder cells -GalGalNAc-TV-(D-pipecolic acid)-AAVVVA (SEQ ID NO:7) and GalGalNAc-TV-(D-proline)-AAVVVA (SEQ ID NO:27). Cell proliferation was determined by $^3$H-thymidine incorporation; gene expression by quantitative RT-PCR; tight junction formation by confocal immunofluorescence microscopy; and paracellular permeability by $^{14}$C-mannitol and $^3$H-inulin flux between confluent cells on Transwell plates. Significance of the difference in mean values between groups was determined by an analysis of variance for each assay.

Overview of Results

Only two of 30 screened inactive APF derivatives [GalGalNAc-TV-(D-pipecolic acid)-AAVVVA (SEQ ID NO:14) and GalGalNAc-TV-(D-proline)-AAVVVA (SEQ ID NO:27)] blocked APF antiproliferative activity in IC/PBS and/or normal bladder cells ($p<0.05$ for each agent), and both agents also significantly increased ZO-1, occludin, and claudin 1, 4, 8, and 12 expression in IC/PBS cells. GalGalNAc-TV-(D-Proline)-AAVVVA (SEQ ID NO:27) was also shown to significantly decrease permeability of IC/PBS cells ($p<0.01$ for each parameter).

GalGalNAc-TV-(D-pipecolic acid)-AAVVVA (SEQ ID NO:14) and GalGalNAc-TV-(D-proline)-AAVVVA (SEQ ID NO:27) can inhibit APF activity in bladder epithelial cells in vitro.

Figure 53:
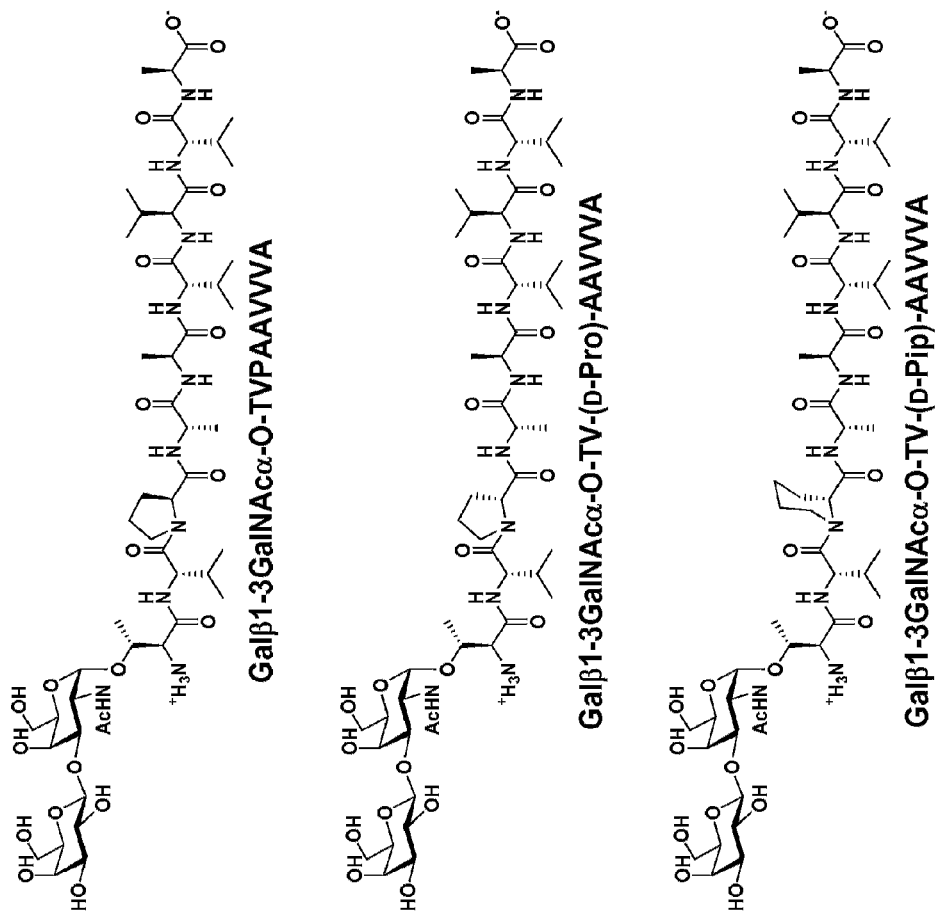
FIG. 53 shows the structure of APF, D-Proline APF, and D-Pipecolic Acid APF, wherein the respective peptide moities comprise SEQ ID NO:1, SEQ ID NO:27, and SEQ ID NO:14.
Figure 54:
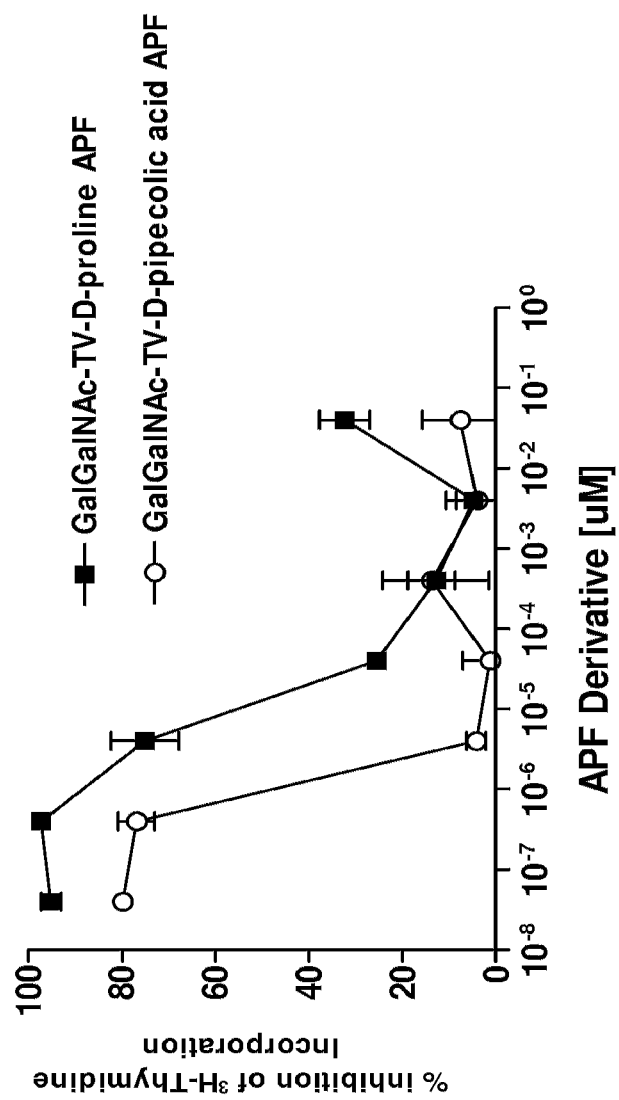
FIG. 54 shows the inhibition of APF activity by D-proline APF and D-pipecolic acid APF in normal bladder epithelial cells pretreated with 25 nM as-APF.

Inhibition of APF Antiproliferative Activity in Normal Bladder Epithelial Cells by APF Derivatives Over 40 synthetic APF derivatives were tested for their ability to inhibit normal bladder epithelial cell proliferation; 30 of these were found to be completely inactive in the inventors' cell proliferation assay. Therefore normal bladder cells were preincubated with each of the 30 inactive synthetic APF derivatives prior to incubation with active synthetic APF, to determine their ability to block APF activity. Only two of these derivatives (D-proline APF and D-pipecolic acid APF, structures shown with the active asialylated derivative "as-APF" in FIG. 53) were able to inhibit APF antiproliferative activity in as-APF-treated normal bladder epithelial cells, and they inhibited this activity in nanomolar concentrations in a dose-dependent manner (FIG. 54). Neither D-proline APF nor D-pipecolic acid APF had any intrinsic antiproliferative activity in primary normal bladder epithelial cells.

Normalization of IC/PBS Cell Proliferation by APF Derivatives

Figure 55:
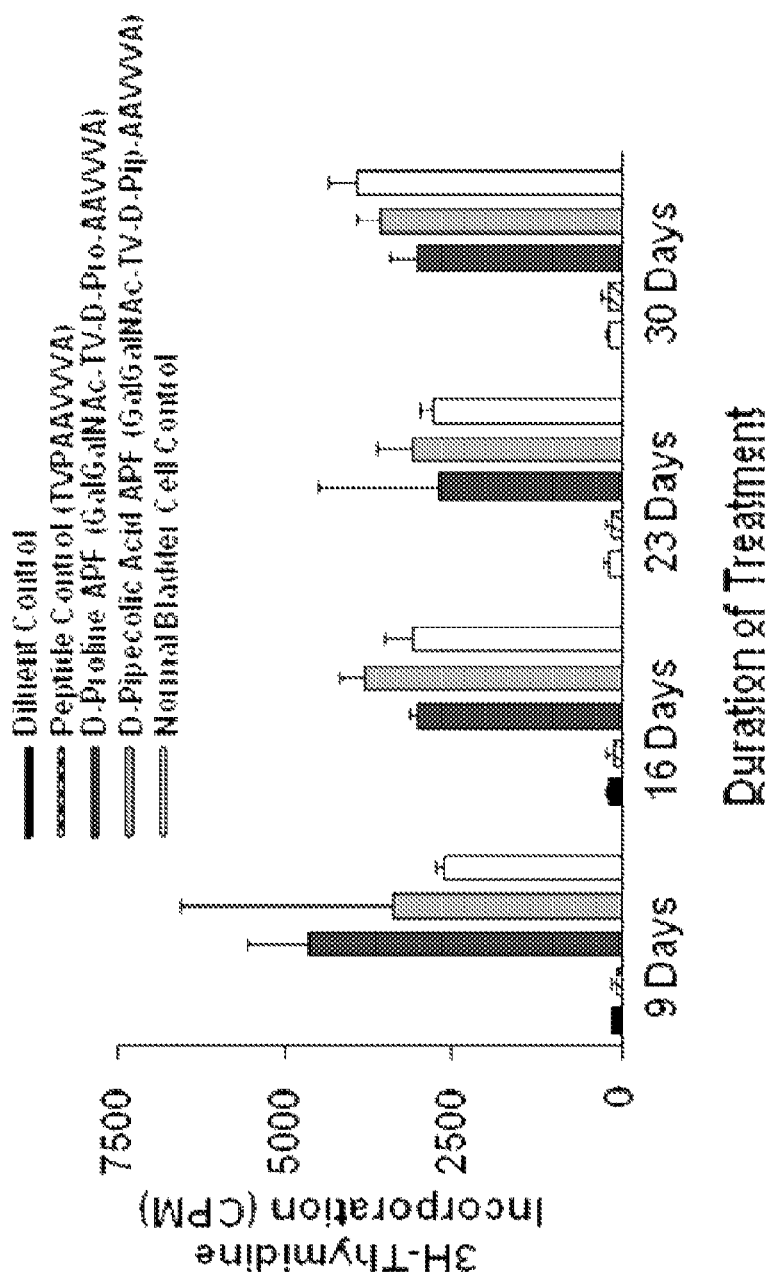
FIG. 55 shows stimulation of IC/PBS cell proliferation by D-Proline APF and D-Pipecolic acid APF.

IC/PBS cells produce APF and as a result have a profound decrease in cell proliferation. It was next determined whether these APF derivatives could also inhibit APF activity in bladder epithelial cells from IC/PBS patients (i.e., whether they could stimulate, or normalize, the proliferation of IC/PBS cells in vitro). Cells were treated with 1 nM D-proline or D-pipecolic acid APF twice weekly, and thymidine incorporation was determined at 9, 16, 23 and 30 days. As shown in FIG. 55, both of these APF derivatives significantly ($p<0.05$) stimulated IC/PBS cell proliferation by Day 16, resulting in proliferation similar to normal bladder epithelial cells.

Increased IC/PBS Cell Tight Junction Protein Gene Expression by APF Derivatives

Figure 56:
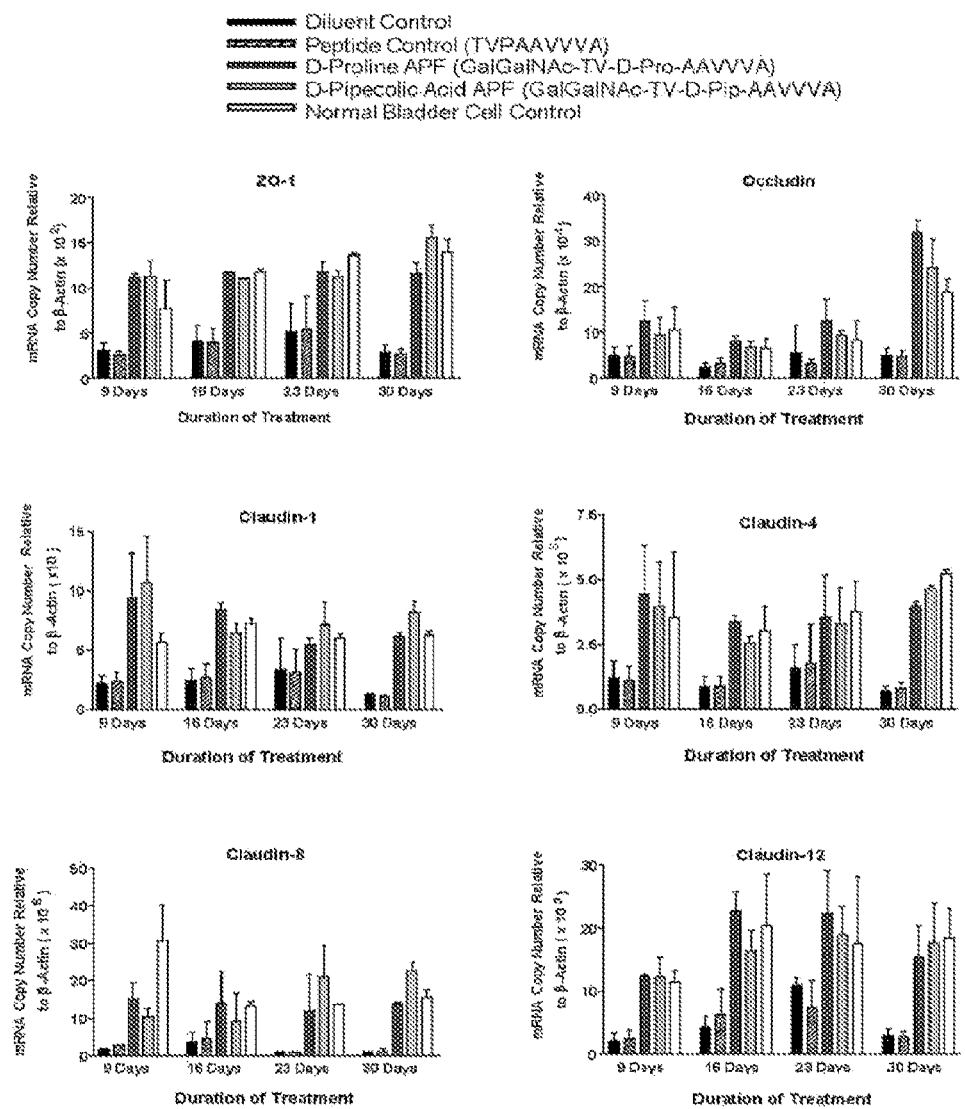
FIG. 56 shows RT-PCR analysis of tight junction protein mRNA expression in IC/PBS cells following treatment with D-proline APF for 16 days. (Data shown from study with the same IC/PBS cell donor and both D-pipecolic acid APF and D-proline APF; D-proline APF was tested on cells from a total of 4 IC/PBS donors, with similar results).

In addition to thinning and denudation, increased permeability of the IC/PBS bladder epithelium is thought to possibly contribute to the pain associated with this IC/PBS. Therefore, to understand whether D-proline and/or D-pipecolic acid APF might be useful for treatment of IC/PBS it was needed to be known whether they could also inhibit the effects of APF on tight junction protein gene expression. As shown in FIG. 56, by day 16 both APF derivatives were also able to significantly ($p<0.05$) stimulate mRNA expression for ZO-1, occludin, and specific claudin (1, 4, 8, and 12) in IC/PBS cells in vitro resulting in mRNA levels similar to those seen in normal bladder cells. In addition, immunofluorescence confocal microscopy showed that expression of the proteins corresponding to these mRNA's also increased in IC/PBS cells following treatment with D-proline or D-pipecolic acid APF, and that the expressed proteins were localilzed in the tight junctions between cells. In particular, immunofluorescence confocal microscopy of IC/PBS cell explants treated with D-pipecolic acid APF, D-proline APF, or vehicle (PBS) alone for 9 days. (Data was generated from study with one IC/PBS cell donor; both APF derivatives have been tested on cells from 3 IC/PBS donors to date, with similar results).

Decreased IC/PBS Monolayer Paracellular Permeability by APF Derivatives

Figure 57:
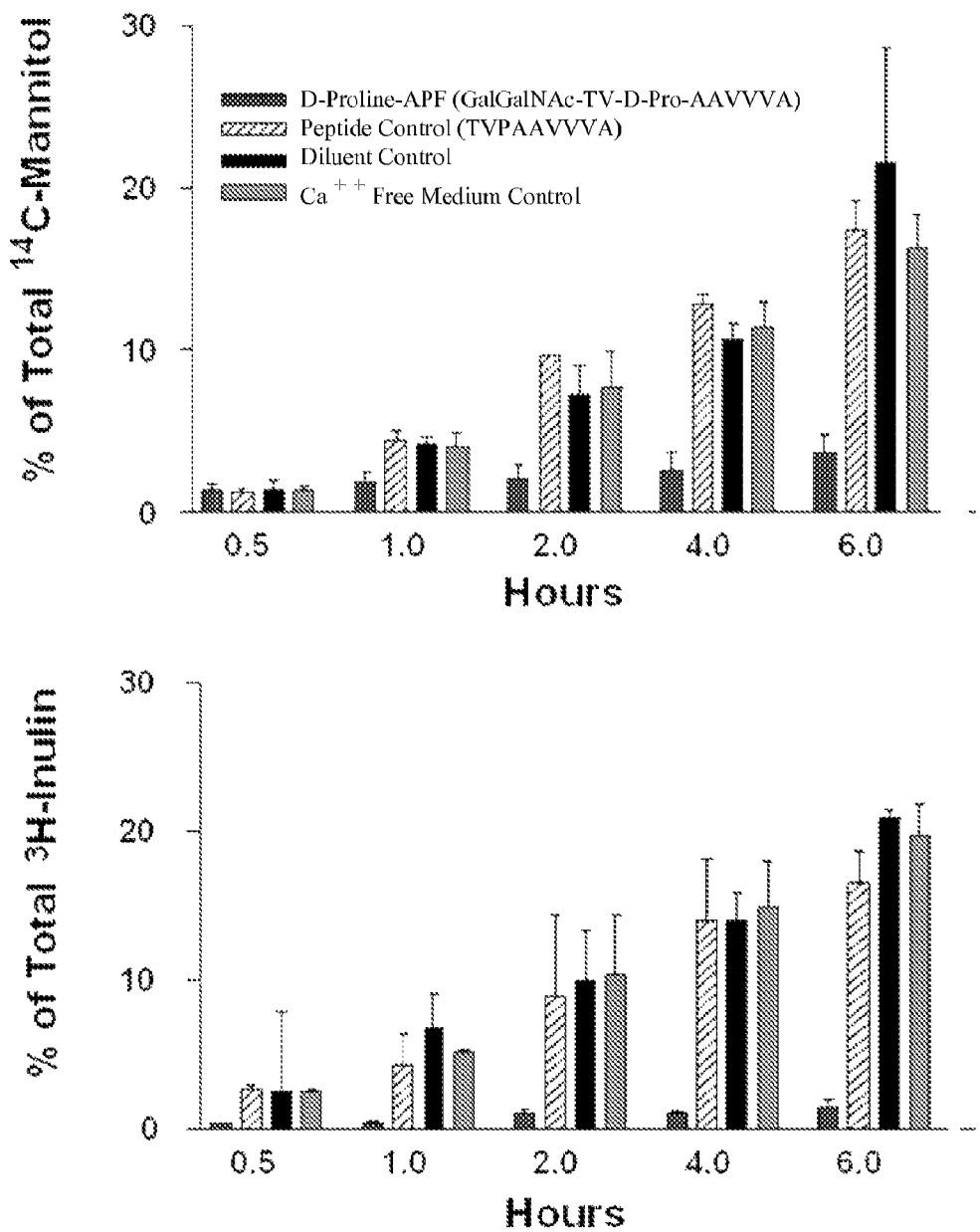
FIG. 57 shows decreased paracellular permeability of IC/PBS cells by D-Proline APF. Data shown from 4 studies using cells from 4 different IC/PBS donors.
Figure 58:
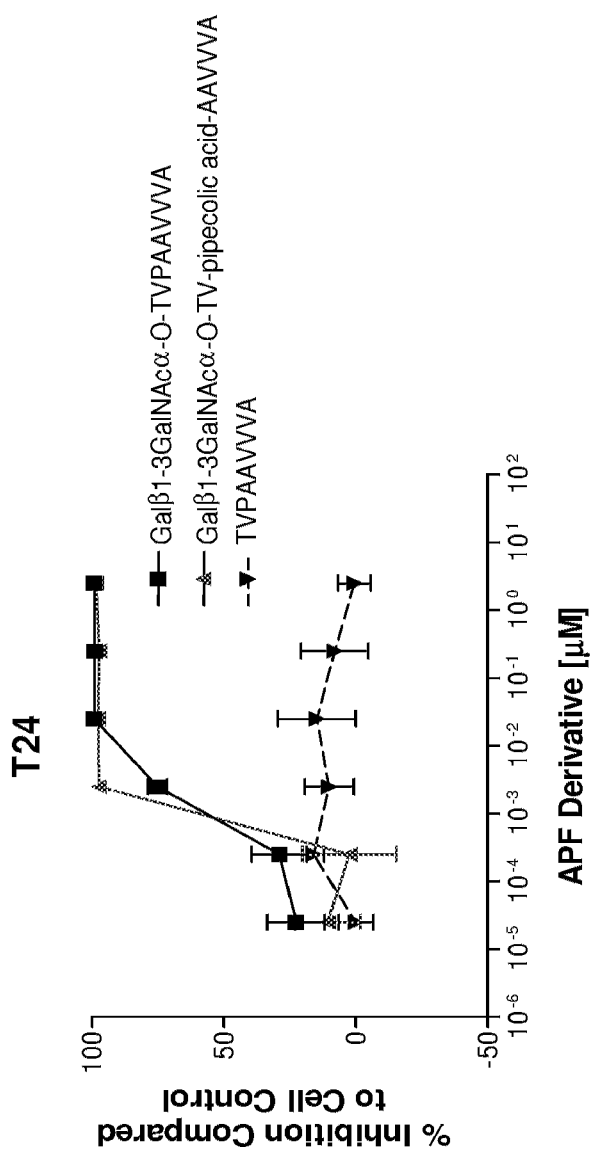
FIG. 58 illustrates inhibition of T24 cell proliferation with L-pipecolic acid APF derivative.
Figure 59:
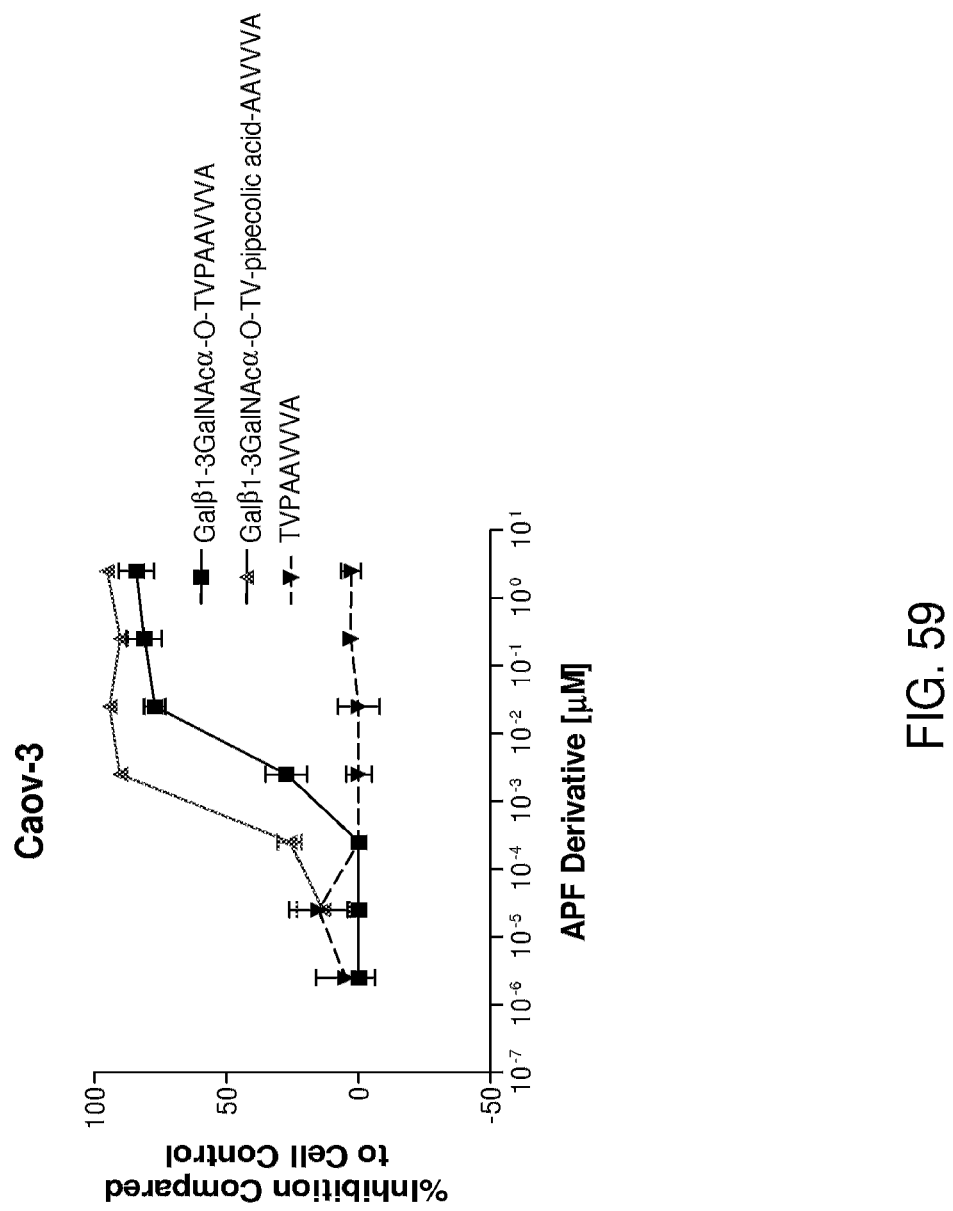
FIG. 59 illustrates inhibition of Caov-3 cell proliferation with L-pipecolic acid APF derivative.
Figure 60:
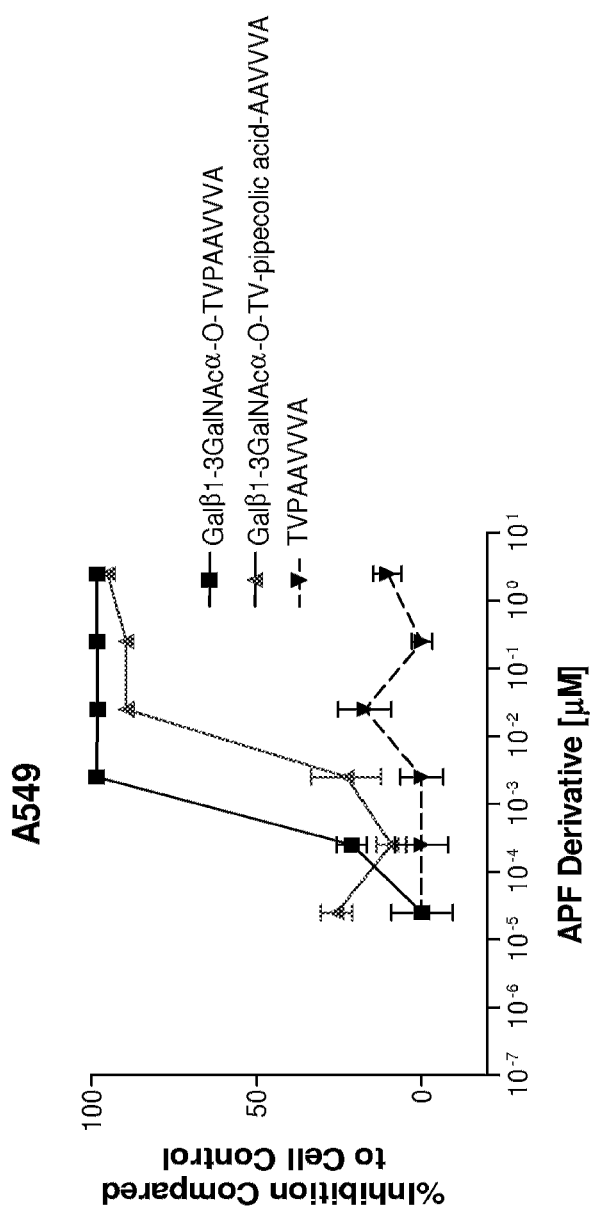
FIG. 60 illustrates inhibition of A549 cell proliferation with L-pipecolic acid APF derivative.
Figure 61:
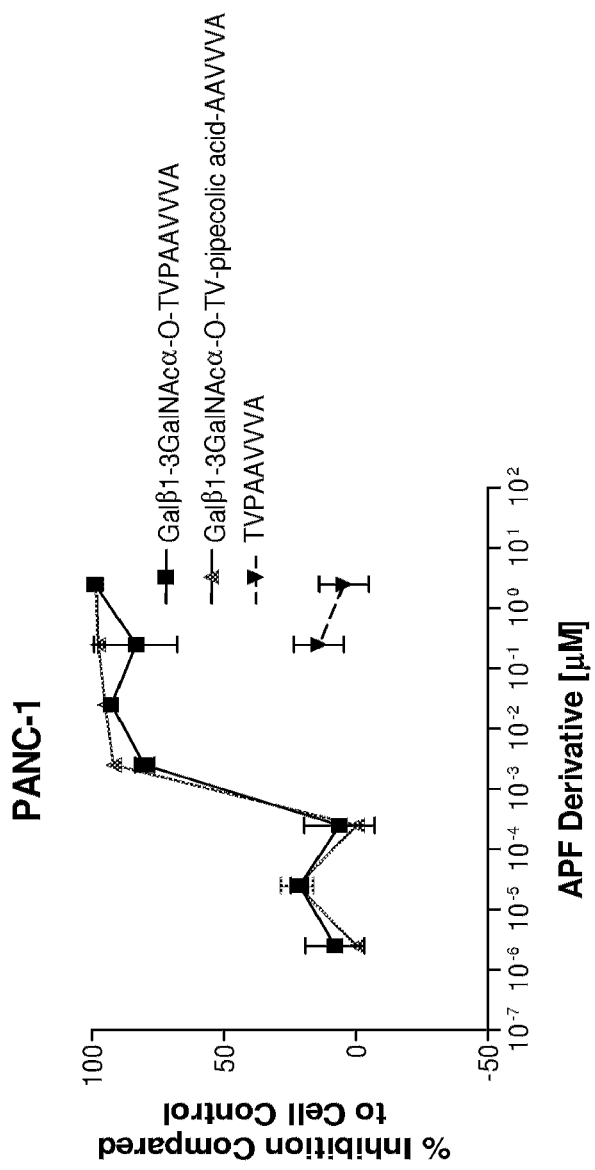
FIG. 61 illustrates inhibition of PANC-1 cell proliferation with L-pipecolic acid APF derivative.
Figure 62:
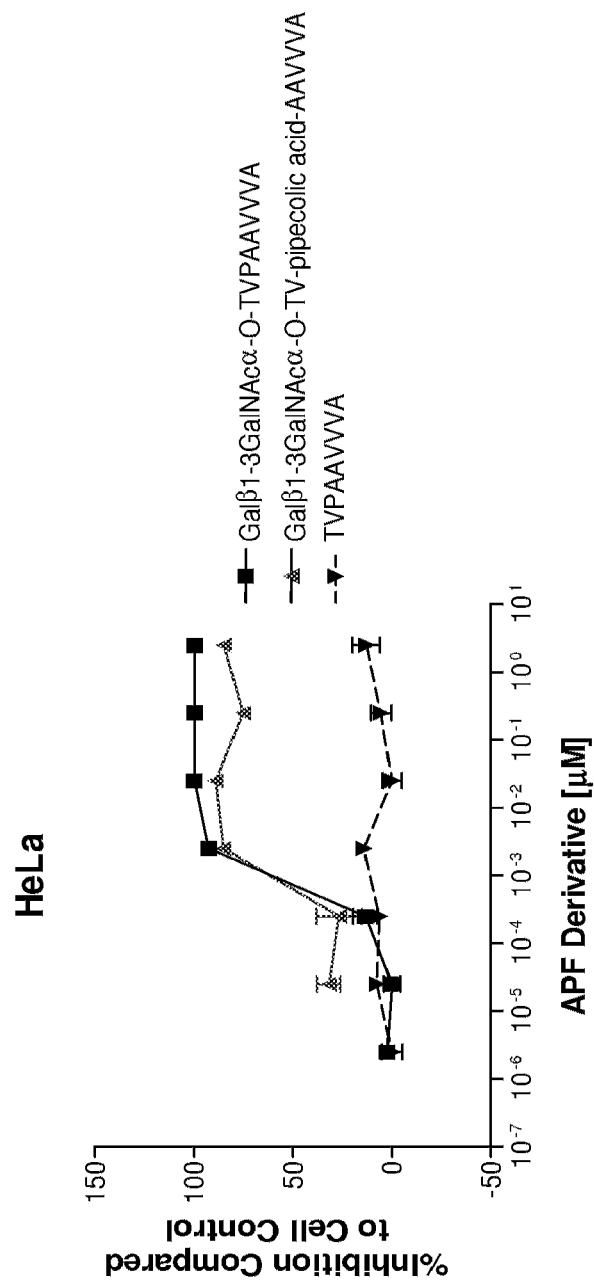
FIG. 62 illustrates inhibition of HeLa cell proliferation with L-pipecolic acid APF derivative.
Figure 63:
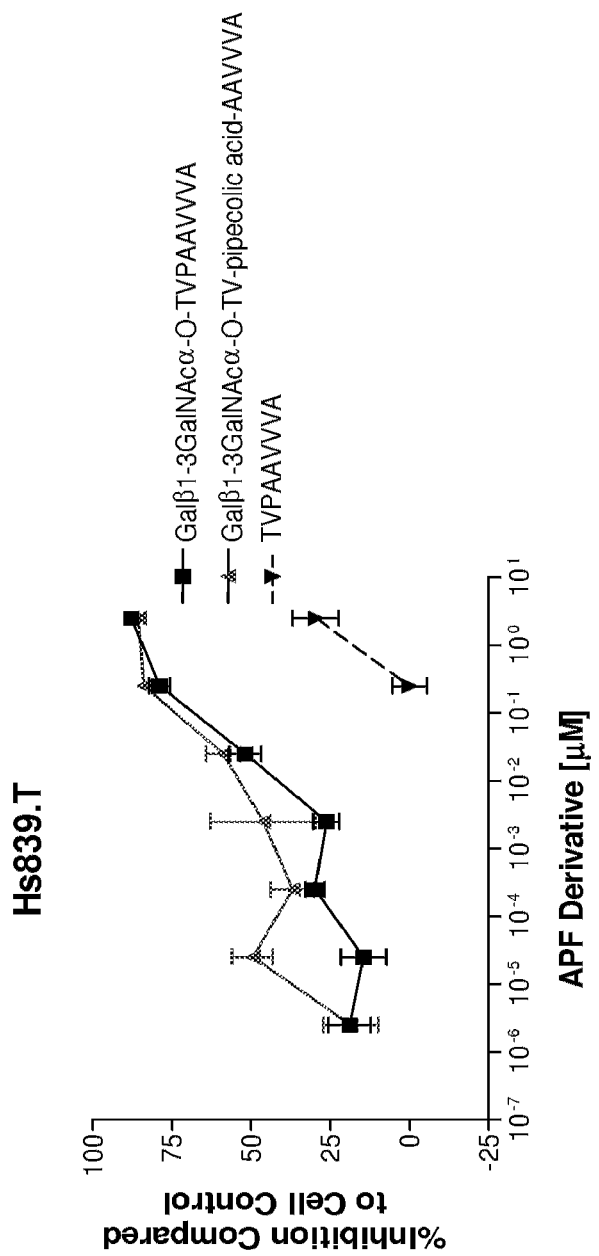
FIG. 63 illustrates inhibition of Hs839.T cell proliferation with L-pipecolic acid APF derivative.
Figure 64:
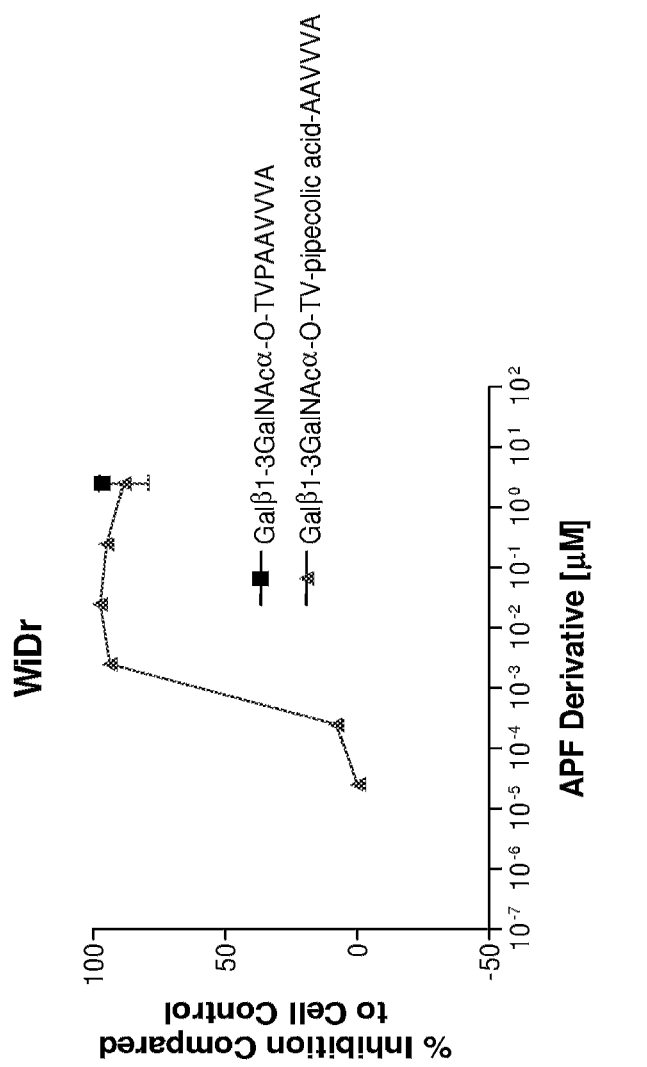
FIG. 64 illustrates inhibition of WiDr cell proliferation with L-pipecolic acid APF derivative.
Figure 65:
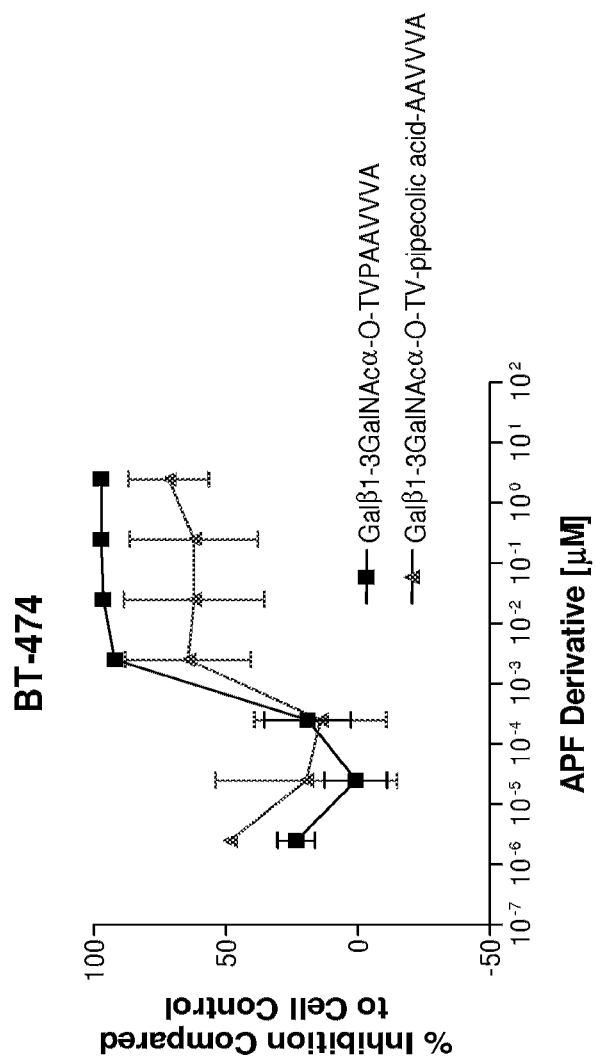
FIG. 65 illustrates inhibition of BT-474 cell proliferation with L-pipecolic acid APF derivative.
Figure 66:
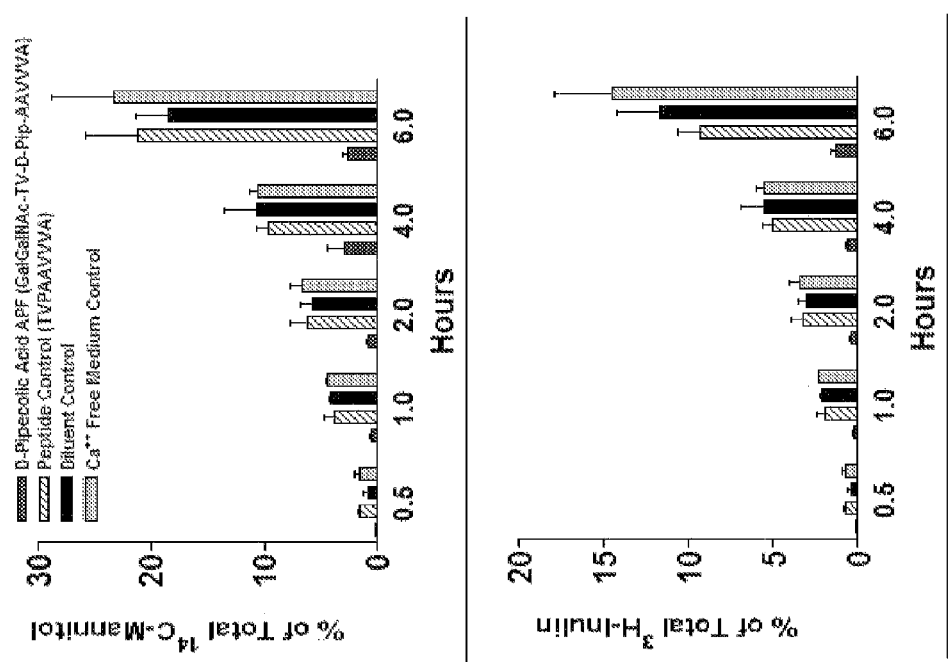
FIG. 66 shows that treatment with D-pipecolic acid APF significantly decreased paracellular permeability of both tracer molecules in IC/PBS cell monolayers grown on Transwell plates.

Although tight junction protein formation and tight junction formation had clearly normalized following treatment with the two proline-substituted APF derivatives, functional normalization of paracellular permeability remained to be demonstrated. Therefore, IC/PBS cells were treated with D-proline APF or D-pipecolic acid APF for 16 days, after which paracellular permeability to two radiolabeled tracers ($^3$H-inulin and $^{14}$C-mannitol) were determined. As shown in FIG. 57, and FIG. 66, respectively, treatment with D-proline APF or D-pipecolic acid significantly decreased paracellular permeability of both tracer molecules in IC/PBS cell monolayers grown on Transwell plates, restoring levels to those seen previously in normal bladder cells (Keay et al., 2000).

Significance of Certain Embodiments of the Invention

GalGalNAc-TV-(D-pipecolic acid)-AAVVVA (SEQ ID NO:14) and GalGalNAc-TV-(D-proline)-AAVVVA (SEQ ID NO:27) block APF's inhibitory effects on cell proliferation in both APF-treated primary normal bladder epithelial cells and bladder epithelial cells explanted from IC/PBS patients. Both APF derivatives also normalize tight junction protein expression of IC/PBS cells in vitro, and both also normalize IC/PBS cell paracellular permeability in vitro. All of these findings indicate that these small molecule APF inhibitors are useful for treatment of IC/PBS.

Example 14

Exemplary Materials and Methods for Example 13

Exemplary materials and methods from the studies described in Example 13 are provided below.

Patients

IC/PBS patients had previously undergone cystoscopy and fulfilled modified NIDDK diagnostic criteria for IC/PBS (without measurement of bladder capacity) (Keay et al., 2000; Keay et al., 2001; Keay et al., 2004; Keay et al., 2003); age- and gender-matched controls were asymptomatic for urinary tract disease. All participants were at least 18 years old and enrolled in accordance with guidelines of the Institutional Review Board of the University of Maryland School of Medicine.

Cell Culture

Cystoscopy was performed under general anesthesia, and 4-mm$^2$ pieces of transitional epithelium with submucosal bladder tissue were obtained from IC/PBS patients and controls for the growth of primary bladder epithelial cells, as previously described (Keay et al., 2000; Keay et al., 2001; Keay et al., 2004; Keay et al., 2003). Epithelial cells were propagated in DMEM-F12 (Media-Tech, Herndon Va.) with 10% heat-inactivated fetal bovine serum (FBS), 1% antibiotic/antimycotic solution, 1% L-glutamine, 0.25 units/ml insulin (all from Sigma, St. Louis, Mo.), and 5 ng/ml hEGF (R & D Systems, Minneapolis, Minn.) at 37° C. in a 5% $CO_2$ atmosphere and characterized by binding of AE-1/AE-3 pan-cytokeratin antibodies (Signet, Dedham, Mass.), as previously described.

Synthesis of APF Derivatives

D-proline APF and as-APF were synthesized as previously described (Kaczmarek et al., 2008). Synthesis of Galβ1-3GalNAcα-O-TV-(D-Pip)-AAVVVA (SEQ ID NO:14) is as follows. All glycopeptides were synthesized according to the procedure described earlier (Kaczmarek et al., 2008) with minor modifications. Briefly, the synthesis of Galβ1-3GalNAcα-O-TV-(D-Pip)-AAVVVA (SEQ ID NO:14) was performed manually using standard Fmoc solid-phase peptide chemistry on 2C1Trt resin. All Fmoc-protected amino acids (5 eq) were coupled using HATU (5 eq) and HOAt (5 eq) reagents in the presence of DIPEA (10 eq), but Fmoc-Thr (Ac$_4$Galβ1-3Ac$_2$GalNAcα-O—)—OH (0.5 eq), which was coupled using BEP/HOAt/DIPEA (0.5 eq:0.5 eq:1.5 eq) in NMP. The Fmoc group was removed with 20% piperidine in NMP, and the glycopeptide was cleaved from the resin with TFA:TIS:H2O (95:2.5:2.5). Acetyl groups were removed with NaOMe/MeOH. Preparative HPLC was performed on a Waters Prep LC 4000 System equipped with PDA detector (Waters 2996) on C18 column (mobile phase: Solvent A, 0.1% trifluoroacetic acid in $H_2O$; Solvent B, 0.1% trifluoroacetic acid in $CH_3CN$). All intermediates and final product were verified by HPLC-MS (Agilent 1200, Agilent Technologies, Inc., Santa Clara, Calif.). Purity of final product was confirmed by HPLC trace analysis with UV detection at 227 nm.

$^3$H-Thymidine Incorporation

Cell proliferation was measured by $^3$H-thymidine incorporation into explanted normal human bladder epithelial cells, as previously described (Keay et al., 2000; Keay et al., 2001; Keay et al., 2004; Keay et al., 2003; Saitoh et al., 2001). Significant inhibition of $^3$H-thymidine incorporation was defined as a mean decrease in counts per minute of greater than 2 standard deviations from the mean of control cells for each plate.

qRT-PCR

Total RNA was extracted from IC/PBS and normal control epithelial cell explants using the RNEasy Plus Mini Kit (Qiagen) according to the manufacturer's protocol. Quantitative real time RT-PCR for tight junction gene expression was performed using Quantitect Primers (Qiagen), SYBR Green RT-PCR kit reagents (Qiagen), and a Roche 480 Light-Cycler. Samples were tested in triplicate runs, and specific mRNA levels quantified and compared to mRNA levels for β-actin using LightCycler 480 real-time PCR analysis software (version 1.5).

Paracellular Permeability Assay

Flux assays were performed using 12-mm Transwell culture plates (Corning Incorporated, Corning, N.Y.), as previously described (Keay et al., 2000). Cells were plated at $4 \times 10^5$ cells/cm$^2$ on the insert and grown in DMEM-F12 medium containing 10% heat-inactivated FBS, 1% antibiotic solution, 1% L-glutamine, 0.25 units/ml insulin (all from Sigma, St. Louis, Mo.), and 5 ng/ml hEGF (R & D Systems, Minneapolis, Minn.) to establish tight monolayers. On day 2, the medium was changed to MEM (GIBCO/Invitrogen) containing 1% antibiotic/antimycotic solution and 1% L-glutamine (Sigma). On day 3, synthetic as-APF or its inactive unglycosylated peptide control was added to the medium; all cells were then cultured for an additional 48 hours.

Two different membrane impermeable molecules, [14C]-mannitol (molecular weight: 184 Daltons) and [$^3$H]-inulin (molecular weight: 5,200 Daltons), served as paracellular tracers. At the beginning of the flux assay, both sides of the bathing wells of Transwell filters were replaced with fresh medium containing either 5 mM unlabeled mannitol or 0.5 mM unlabeled inulin. Each tracer was added at a final concentration of 3.6 nM for [$^{14}$C]-mannitol and 0.36 nM for [$^3$H]-inulin to the apical bathing wells. The basal bathing well contained the same medium as the apical compartment but without tracers. Flux assays were performed at 37° C.; basal medium was collected at 0.5-6 hrs after addition of [$^{14}$C]-mannitol or [3H]-inulin, and the amount of radioactivity determined using a Beckman LS 5000 scintillation counter. Results were expressed as percentage of total counts for each tracer.

Immunofluresence Confocal Microscopy

For immunofluorescence, cells were fixed using ethanol/acetone (1:1) for 15 minutes at room temperature, washed 3 times with PBS and incubated with fluorescein isothiocyanate (FITC) labeled mouse monoclonal anti-ZO-1 (5 μg/ml); or unlabeled mouse monoclonal anti-occludin (5 μg/ml) or anti-claudin 4 (3 μg/ml); or unlabeled rabbit polyclonal anti-claudin 1 (3 μg/ml), anti-claudin 8 (8 μg/ml), or anti-claudin 12 (5 μg/ml from Zymed, South San Francisco, Calif.) diluted in PBS for 2 hours at 37 C. Cells incubated with unlabeled mouse monoclonal primary antibodies were then washed 3 times with PBS and further incubated with FITC-labeled secondary goat anti-mouse IgG antibody (Zymed) diluted in PBS, while cells incubated with unlabeled rabbit polyclonal primary antibodies were washed and further incubated for 2 hours at 37 C with goat anti-rabbit IgG (Zymed) diluted in PBS. Following an additional 5 washes with PBS, the cells were examined using an LSM510 confocal laser scanning microscope (Carl Zeiss, Oberkochen, Germany). Negative controls for the method included cells incubated without primary and secondary antibodies as well as cells incubated with secondary antibody alone.

Statistical Analysis

For the permeability assay, the percentage of total counts in the basal medium was determined in four experiments (using different IC/PBS cell donors), and expressed as mean±standard deviation. Crossover point analysis was performed for qRT-PCR data, and expression of each gene was quantified relative to β-actin; this value was expressed as mean±standard error of the mean for duplicate runs performed on two separate occasions. $^3$H-thymidine incorporation was determined in triplicate on two separate occasions, and the CPM expressed as mean±standard deviation.

The significance of the difference between mean values was determined by an analysis of variance for data expressed as noted above for each assay.

Example 15

L-Pipecolic Acid APF Derivative and Exemplary Cancer Studies

Although progress has been made in the prevention and management of certain human malignancies, many cancers remain prevalent and difficult to treat. For example, lung and bronchial cancers are the second most common malignancies and the most common cause of cancer deaths for both men and women in the U.S (Jemal et al., 2007). Bladder cancer is the fourth most common form of cancer in U.S. males and a major public health problem throughout the Western world (Jemal et al., 2007; Rosenberg et al,. 2005; Sengupta et al., 2004). Melanoma is the sixth most common form of cancer in both men and women in the U.S. and is increasing in incidence (Jemal et al., 2007; Ward et al., 2006). While ovarian and pancreatic cancers are less common, they are among the most fatal cancers in the U.S. (Jemal et al., 2007; Ward et al., 2006). All of these malignancies readily metastasize and can be difficult to treat, prompting the search for new or adjunctive treatments to improve outcomes.

Activation of Wnt/beta-catenin signaling appears to be critical for the development of many cancers including ovarian cancer, cervical cancer, transitional cell bladder cancer, lung cancer, pancreatic cancer and melanoma (Thievessen et al., 2003; Bates et al., 2005; Berx et al., 2001; Wakatski et al., 1996). An epithelial to mesenchymal transition (EMT) which is generally associated with decreased E-cadherin expression has been implicated in tumor progression and/or survival for these and other epithelial malignancies (Huber et al., 2005; Guarino et al., 2007), suggesting that they may respond to adjunctive therapy that inhibits Wnt signaling and stimulates E-cadherin production. Identification of such a factor has the potential to improve outcome by preventing recurrence and/or progression to invasive or metastatic disease.

APF appears to be made uniquely by bladder epithelial cells from patients with interstitial cystitis/painful bladder syndrome (IC/PBS), a poorly understood bladder disorder characterized by epithelial thinning and ulceration. APF is a small sialoglycopeptide (Keay et al., 2004) whose peptide backbone bears 100% homology to a segment from the 6th transmembrane segment of Frizzled 8, a receptor that functions in Wnt signalling (Saitoh et al., 2001). It was further determined that an asialo derivative (as-APF) had potent antiproliferative activity in both normal bladder epithelial cells and T24 transitional carcinoma cells (Keay et al., 2004), and that an L-pipecolic acid APF derivative also inhibited the proliferation of normal bladder epithelial cells (Kaczmarek et al., 2008).

APF profoundly inhibits cell proliferation and alters specific protein production in normal bladder epithelial cells in vitro [including the downstream effectors of Wnt signaling cyclin D1, JNK, and E-cadherin] (Keay et al., 2003). It was then determined whether as-APF and its derivative L-pipecolic acid APF could both also inhibit the proliferation of T24

(bladder), Caov-3 (ovarian), A549 (lung), PANC-1 (pancreatic), HeLa (cervical), WiDr (colon), BT-474 (breast) carcinoma cells, plus Hs839.T melanoma cells.

Materials and Methods

Cell Culture. Caov-3 ovarian carcinoma cells (HTB-75), A549 lung carcinoma cells (CCL-185), PANC-1 pancreatic carcinoma cells (CRL-1469), T24 bladder carcinoma cells (HTB-4), and melanoma cells (Hs839.T) were obtained from ATCC. HeLa cervical carcinoma cells (#153) were obtained from ERC Biosciences, NIAID. Caov-3, PANC-1, and HS839.T cells were grown in DMEM (Invitrogen) containing 10% heat inactivated fetal bovine serum, 1% antibiotic/antimycotic solution, 1% L-glutamine (all from Sigma), and 1.5 g/L sodium bicarbonate (Invitrogen). HeLa cells were grown in MEM (Invitrogen) containing 10% heat inactivated fetal bovine serum, 1% antibiotic/antimycotic solution, and 1% L-glutamine. A549 cells were grown in F-12 medium (Invitrogen) containing 10% heat inactivated fetal bovine serum, 1% antibiotic/antimycotic solution, and 1% L-glutamine. T24 cells were grown in McCoy's 5A medium (Invitrogen) containing 10% heat inactivated fetal bovine serum, 1% antibiotic/antimycotic solution, 1% L-glutamine, and 2.2 g/L sodium bicarbonate.

Synthesis of APF and its Derivatives as-APF, L-pipecolic acid APF, and inactive control nonglycosylated peptide were synthesized using standard Fmoc chemistry and purified as previously described (Kaczmarek et al., 2008).

$^3$H-Thymidine Cell Proliferation Assay

Cell proliferation was measured by $^3$H-thymidine incorporation into each cell type, plating cells in 150 ml of their respective medium (see above) onto a 96-well cell culture plate (Corning, N.Y.) at a predetermined optimal cell density for APF inhibition of cell proliferation: Caov-3, PANC-1, T24, HeLa, and HS839.T cells were plated at a density of $1.5 \times 10^3$ cells/well; A549 cells were plated at a density of $3 \times 103$ cells/well. On the next day, cell growth medium was removed and replaced with serum-free medium appropriate for each cell type. On the third day, APF was resuspended in acetonitrile/distilled water (1:1) and applied to the cells in the respective serum-free medium in varying concentrations; cell controls received acetonitrile/distilled water diluted in serum-free medium alone (at the same final dilution). Cells were then incubated at 37° C. in a 5% $CO_2$ atmosphere for 48 hours, after which cell contents were harvested, methanol-fixed onto glass fiber filter paper, and the amount of radioactivity incorporated determined. Each experiment was performed in triplicate at least twice.

Synthetic as-APF and its L-pipecolic acid derivative are potent inhibitors of nonurologic carcinoma as well as bladder carcinoma and melanoma cells, with $IC_{50}$'s in the low to mid nanomolar range for each cell type in vitro. (FIGS. 58-65). The markedly different dose-response curves for the melanoma cells (as compared to all normal epithelial or carcinoma cells tested to date) indicates there is a different APF receptor or inhibition of different signaling pathway(s) in cells of neuroectodermal vs. epithelial origin, in certain embodiments.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

PATENTS

U.S. Pat. No. 5,811,393
U.S. Pat. No. 5,916,871
U.S. Pat. No. 5,962,645
U.S. Pat. No. 6,156,522
U.S. Pat. No. 6,232,289
U.S. Pat. No. 6,376,197
U.S. Pat. No. 6,600,018

PUBLICATIONS

Ahn J M, Boyle N A, MacDonald M T, Janda K D Peptidomimetics and peptide backbone modifications. (2002) Mini Rev. Med. Chem., 2: 463-73

Aronov, O., Horowitz, A. T., Gabizon, A., Gibson, D. (2003) Bioconjug Chem 14(3):563-74.

Arya, P.; Barkley, A.; Randell, K. D.; Automated High-Throughput Synthesis of Artificial Glycopeptides. Small-Molecule Probes for Chemical Biology. J. Comb. Chem. 2002, 4, 193-198.

Auger, G., Blanot, D., van Heijenoort, J., Nadal, C., Gournay, M. F., Winchenne, J. J., Boffa, G. A., Lambin, P., Maes, P., & Tartar, A. (1989) J Cell Biochem 40, 439-451.

Bafico, A., Gazit, A., Pramila, T., Finch, P. W., Yaniv, A., & Aaronson, S. A. (1999) J Biol Chem 274, 16180-16187.

Bates R C, et al., Cancer Biol Ther 2005; 4: 365-370

Berx G, et al., Breast Cancer Res 2001; 3: 289-293

Brensinger, C., Matthews, Y. L., Abele, S. T., Kusek, J. W., et al. (2001) Urology 57, 67-81.

Clugston P A, Vistnes M D, Perry L C, Maxwell G P, Fisher J (1995) Ann Plast Surg. January; 34(1):12-5.

Conrads, T. P.; Tocci, G. M.; Hood, B. L.; Zhang, C.-O.; Guo, L.; Koch, K. R.; Michejda, C. J.; Veenstra, T. D.; Keay, S. K. CKAP4/p63 Is a Receptor for the Frizzled-8 Protein-Related Antiproliferative Factor from Interstitial Cystitis Patients. J. Biol. Chem. 2006, 281, 37836-37843.

Corzana, F; Busto, J. H.; Jiménez-Osés, G.; de Luis, M. G.; Asensio, J. L.; Jiménez-Barbero, J.; Peregrina, J. M.; Avenoza, A. Serine versus Threonine Glycosylation: The Methyl Group Causes a Drastic Alteration on the Carbohydrate Orientation and on the Surrounding Water Shell. J. Am. Chem. Soc. 2007, 129, 9458-9467.

Curhan, G. C., Speizer, F. E., Hunter, D. J., Curhan, S. G., & Stampfer, M. J. (1999) J Urol 161, 549-552.

Dawson, J. P.; Weinger, J. S.; Engelman, D. M. Motifs of Serine and Threonine can Drive Association of Transmembrane Helices. J. Mol. Biol. 2002, 316, 799-805.

Di Stefano, G., Tubaro, M., Lanza, M., Boga, C., Fiume, L., Traldi, P. Rapid Commun Mass Spectrom 17(22):2503-7.

Gimpelev, M.; Forrest, L. R.; Murray, D.; Honig, B. Helical Packing Patterns in Membrane and Soluble Proteins. Biophys. J. 2004, 87, 4075-4086.

Guarino M, et al., Pathology 2007; 39: 305-318

Heath, T. D. & Martin, F. J. (1986) Chem Phys Lipids 40(2-4):347-358.

Held, P. J.; Hanno, P. M.; Wein, A. J.; Pauly, M. V.; Cann, M. A. Epidemiology of Interstitial Cystitis: 2. In Interstitial Cystitis; Hanno, P. M., Staskin, D. R., Krane, R. J.; Wein, A. J., Eds.; Springer-Verlag: London, 1990, pp. 29-48.

Huber M A, et al., Curr Opin Cell Biol 2005; 17: 548-558

Jemal, et al., CA Cancer J Clin 2007; 57: 43-66

Johansson, S. L. & Fall, M. (1990) J Urol 143, 1118-1124.

Jones, S. E., Jomarcy, C., Grist, J., Stewart, H. J., & Neal, M. J. (2000) Neuroreport 11, 3963-3967.

Jones, S. E., Jomacy, C. (2002) BioEssays 24, 811-820.

Kaczmarek P, et al., J Med Chem 2008; 51: 5974-83

Keay, S., Zhang C-O, Shoenfelt J, Erickson D R, Whitmore K, Warren J W, Marvel R, & Chai T. (2001) Urology 57, 9-14.

Keay, S.; Tocci, G.; Zhang, C.-O.; Grkovic, D.; Michejda, C. The Frizzled 8-Related Antiproliferative Factor from IC Patients Inhibits Bladder and Kidney Carcinoma Cell Proliferation in vitro. 18*th EORTC-NCI-AACR Symposium: Molecular Targets and Cancer Therapeutics*. Nov. 7-10, 2006, Prague, Czech Republic.

Keay, S., Kleinberg, M., Zhang, C-O, Hise, M. K., & Warren, J. W. (2000) J Urol 64, 2112-2118.

Keay, S., Zhang, C-O., Shoenfelt, J. L., & Chai, T. C. (2003) Urology 61, 1278-1284.

Keay, S., Seillier-Moiseiwitsch, F., Zhang, C-O, Chai, T. C., & Zhang, J. (2003) Physiol Genomics 14, 107-115.

Keay, S., Zhang, C-O., Hise, M., Trifillis, A. L., Hebel, J. R., Jacobs, S. C., & Warren J W. (1996) J Urol 156, 2073-2078.

Keay, S., Zhang, C-O., Hise, M. K., Hebel, J. R., Jacobs, S. C., Gordon, D., Whitmore, K., Bodison, S., Gordon, N., & Warren, J. W. (1998) Urology 52, 974-978.

Keay, S.; Szekely, Z.; Conrads, T. P.; Veenstra, T. D.; Barchi, J. J. Jr.; Zhang, C.-O.; Koch, K. R.; Michejda, C. J. An Antiproliferative Factor from Interstitial Cystitis Patients is a Frizzled 8 Protein-Related Sialoglycopeptide. *Proc. Natl. Acad. Sci. USA* 2004, 101, 11803-11808.

Keller, M.; Sager, C.; Dumy, P.; Schutkowski, M.; Fisher, G. S.; Enhancing the Proline Effect: Pseudoprolines for Tailoring *Cis/Trans Isomerization*. *J. Am. Chem. Soc.* 1998, 120, 2714-2720.

Kleiger, G.; Grothe, R.; Mallick, P.; Eisenberg, D. GXXXG and AXXXA: Common α-Helical Interaction Motifs in Proteins, Particularly in Extremophiles. *Biochemistry* 2002, 41, 5990-5997.

Leuck, M., & Kunz, H. (1997) J PraktChemie/Chemiker Zeitung 339, 322-334.

Mandler, R., Kobayashi, H., Hinson, E. R., Brechbiel, M. W., Waldmann, T. A. (2004) Cancer Res 64(4):1460-1467.

Moos, P. J., Fattaey, H. K., & Johnson, T. C. (1995) J Cell Biochem 59, 79-90.

Ou, X. H., Kuang, A. R., Peng, X., Zhong, Y. G. (2003) World J Gastroenterol 9(8):1675-8.

Pandur, P., Maurus, D., Kuhl, M. (2002) Bioessays 24, 881-884.

Parson, C. L.; Lilly, J. D.; Stein, P. Epithelial Dysfunction in Nonbacterial Cystitis (Interstitial Cystitis). J. Urol. 1991, 145, 732-735.

Polo M, Smith P D, Kim Y J, Wang X, Ko F, Robson M C (1999) Ann Plast Surg. August; 43(2):185-90.

Qiu, D., Gandhi, S. S., & Koganty, R. R. (1996) Tetrahedron Letters 37, 595-598. Safavy, A., Bonner, J. A., Waksal, H. W., Buchsbaum, D. J., Gillespie, G. Y., Khazaeli, M. B., Arani, R., Chen, D. T., Carpenter, M., Raisch, K. P. (2003) Bioconjug Chem 14(2):302-10.

Rashid, H. H., Reeder, J. E., O'Connell, M. J., Zhang, C.-O., Messing, E. M., and Keay, S. K. (2004) BMC Urology 4:3, 1-5.

Ratliff, T. L.; Klutke, C. G.; McDougall, E. M. The Etiology of Interstitial Cystitis. *Urol. Clin. N. Am.* 1994, 21, 21-29.

Rosenberg J E, Carroll P R, Small E J. 2005. J Urol 174:14-20

Ruggieri, M. R.; Chelsky, M. J.; Rosen, S. I.; Shickley, T. J.; Hanno, P. M. Current Findings and Future Research Avenues in the Study of Interstitial Cystitis. *Urol. Clin. N. Am.* 1994, 21, 163-176.

Saitoh, T., Hirai, M., & Katoh, M. (2001) Int J Oncol 18, 991-996.

Schneider, D.; Engelman, D. M. Motifs of Two Small Residues can Assist but are not Sufficient to Mediate Transmembrane Helix Interactions. *J. Mol. Biol.* 2004, 343, 799-804.

Schon, M. P. (1999) J Invest Dermatol. September; 113(3): 427.

Schumann, H., Holtz, J., Zerkowski, H. R., & Hatzfield, M. (2000) Cardiovasc Res 45, 720-728.

Sengupta N, Siddiqui E, Mumtaz F H. 2004. J R Soc Health 124:228-229

Sharifi, B. G. & Johnson, T. C. (1987) J Biol Chem 262, 15752-15755

Skoluda, D., Wegner, K., & Lemmel, E-M. (1974) Urologe 13, 15-23.

Tomaszewski, J. E., Landis, J. R., Russack, V., Williams, T. M., Wang, L. P., Hardy, C., Svarovsky, S. A. &Barchi, J. J., Jr. (2003) Carbohydr Res 338, 1925-1935.

Thievessen, J., Seifert, H. H., Swiatkowski, S., Florl, A. R., & Schulz, W. A. (2003) Br J Cancer 88, 1932-1938.

Wakatsuki S, et al., Cancer Lett 1996; 103: 11-17

Ward E M, et al., Ann NY Acad Sci 2006; 1076: 29-53

Although the present invention and its advantages have been described in detail, it should be understood that various changes, substitutions and alterations can be made herein without departing from the invention as defined by the claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the claims are intended to include within their scope such processes, machines, manufacture, compositions of matter, means, methods, or steps.

What is claimed:

1. A composition comprising a derivative of antiproliferative factor (APF) having a disaccharide linked to a peptide moiety wherein:
 the peptide moiety is TVPAAVVVA (SEQ ID NO: 1), wherein the proline at position 3 is substituted with the proline mimetic D pipecolic acid, L-pipecolic acid, hydroxyproline, O-t-butyryl-trans-4-hydroxyproline, N-methylalanine, nipecotic acid, isonipecotic acid, 3-methylproline, 2-methylproline, or 2,4-CH$_2$-proline;
 the disaccharide comprises β-galactose and N-acetyl galactosamine; and
 the N-acetyl glactosamine is O-linked to the N-terminal threonine of the peptide moiety in the alpha configuration.

2. The composition of claim 1, wherein the proline at position 3 is substituted with the proline mimetic D pipecolic acid or L-pipecolic acid.

3. A pharmaceutical composition comprising the composition of claim 2 and one or more pharmaceutically acceptable excipients.

4. A kit, comprising the composition of claim 1.

5. A method of treating interstitial cystitis in an individual, comprising the step of administering to the individual a therapeutically effective amount of a composition comprising a derivative of antiproliferative factor (APF) having a disaccharide linked to a peptide moiety wherein:
 the peptide moiety is TVPAAVVVA (SEQ ID NO: 1), wherein the proline at position 3 substituted with D-pipecolic acid;
 the disaccharide comprises β-galactose and N-acetyl galactosamine, and
 the N-acetyl glactosamine is O-linked to the N-terminal threonine of the peptide moiety in the alpha configuration.

6. A method of treating bladder cancer in an individual, comprising the step of administering to the individual a therapeutically effective amount of a composition comprising a derivative of antiproliferative factor (APF) having a disaccharide linked to a peptide moiety wherein:
 the peptide moiety is TVPAAVVVA (SEQ ID NO: 1), wherein the proline at position 3 substituted with L-pipecolic acid;
 the disaccharide comprises β-galactose and N-acetyl galactosamine, and
 the N-acetyl glactosamine is O-linked to the N-terminal threonine of the peptide moiety in the alpha configuration.

7. A composition comprising a compound selected from the group consisting of:

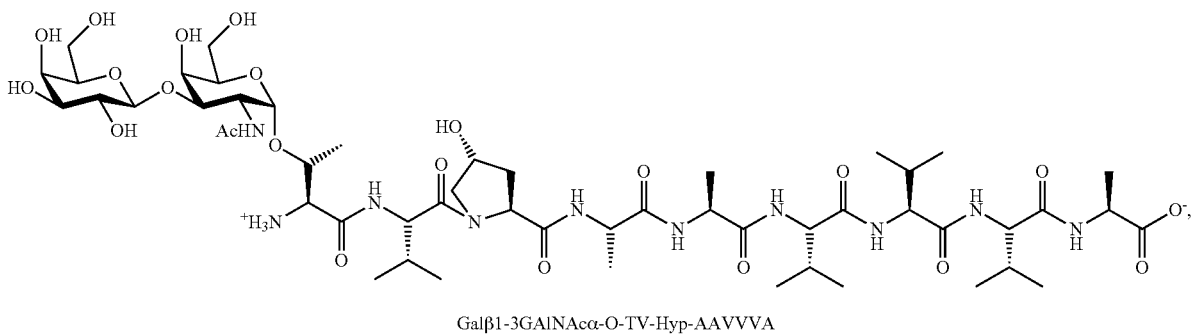

Galβ1-3GAlNAcα-O-TV-Hyp-AAVVVA

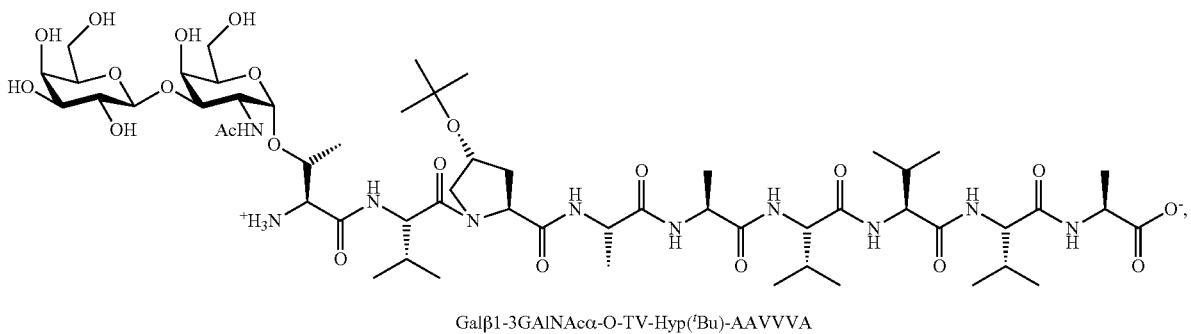

Galβ1-3GAlNAcα-O-TV-Hyp($^t$Bu)-AAVVVA and
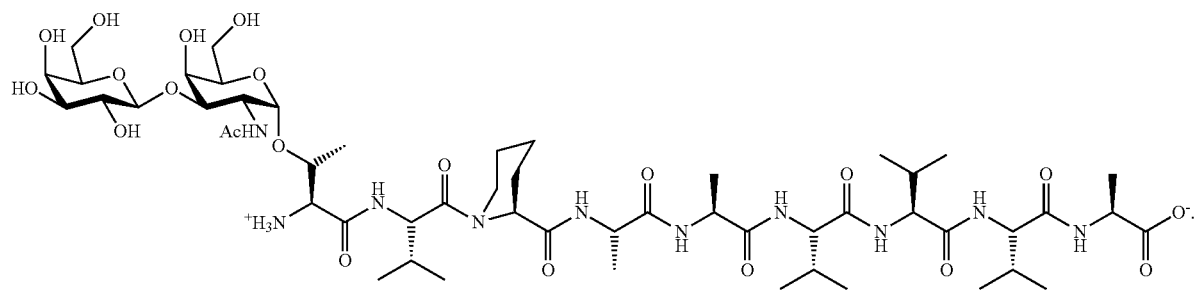
Galβ1-3GAlNAcα-O-TV-Pip-AAVVVA
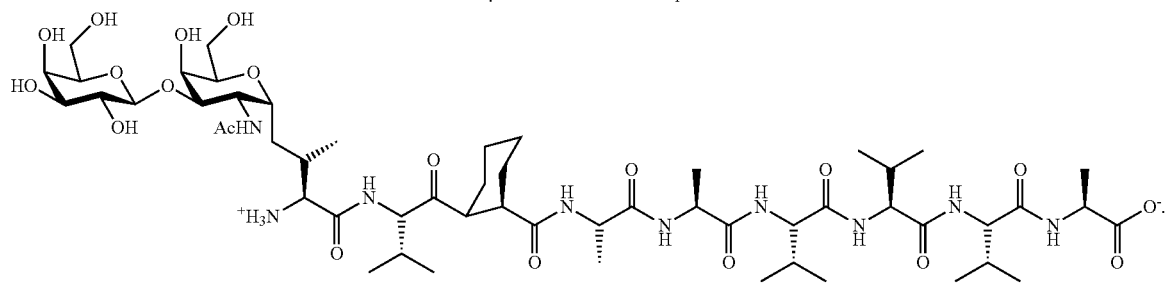
Galβ1-3GAlNAcα-O-TV-Pip-AAVVVA
* * * * *